(12) United States Patent
Geuijen et al.

(10) Patent No.: US 11,279,770 B2
(45) Date of Patent: Mar. 22, 2022

(54) ANTIBODY THAT BINDS ERBB-2 AND ERBB-3

(71) Applicant: Merus N.V., Utrecht (NL)

(72) Inventors: Cecilia Anna Wilhelmina Geuijen, Utrecht (NL); Cornelis Adriaan De Kruif, Utrecht (NL); Mark Throsby, Utrecht (NL); Ton Logtenberg, Utrecht (NL); Alexander Berthold Hendrik Bakker, Utrecht (NL)

(73) Assignee: Merus N.V., Utrecht (NL)

( * ) Notice: Subject to any disclaimer, the term of this patent is extended or adjusted under 35 U.S.C. 154(b) by 0 days.

(21) Appl. No.: 15/121,623

(22) PCT Filed: Feb. 27, 2015

(86) PCT No.: PCT/NL2015/050125
§ 371 (c)(1),
(2) Date: Aug. 25, 2016

(87) PCT Pub. No.: WO2015/130173
PCT Pub. Date: Sep. 3, 2015

(65) Prior Publication Data
US 2017/0037145 A1 Feb. 9, 2017

(30) Foreign Application Priority Data

Feb. 28, 2014 (EP) ..................................... 14157360
May 5, 2014 (EP) ..................................... 14167066

(51) Int. Cl.
| | | |
|---|---|---|
| A61K 39/00 | (2006.01) | |
| C07K 16/32 | (2006.01) | |
| A61K 31/185 | (2006.01) | |
| A61K 31/337 | (2006.01) | |
| A61K 31/436 | (2006.01) | |
| A61K 31/4375 | (2006.01) | |
| A61K 31/4439 | (2006.01) | |
| A61K 31/519 | (2006.01) | |
| A61K 39/395 | (2006.01) | |
| C07K 16/30 | (2006.01) | |

(52) U.S. Cl.
CPC ............ *C07K 16/32* (2013.01); *A61K 31/185* (2013.01); *A61K 31/337* (2013.01); *A61K 31/436* (2013.01); *A61K 31/4375* (2013.01); *A61K 31/4439* (2013.01); *A61K 31/519* (2013.01); *A61K 39/39558* (2013.01); *C07K 16/30* (2013.01); *A61K 2039/505* (2013.01); *C07K 2317/24* (2013.01); *C07K 2317/31* (2013.01); *C07K 2317/526* (2013.01); *C07K 2317/55* (2013.01); *C07K 2317/565* (2013.01); *C07K 2317/732* (2013.01); *C07K 2317/76* (2013.01); *C07K 2317/92* (2013.01)

(58) Field of Classification Search
CPC .................... A61K 39/39558; A61K 2039/505
See application file for complete search history.

(56) References Cited

U.S. PATENT DOCUMENTS

| | | | |
|---|---|---|---|
| 4,801,687 | A | 1/1989 | Ngo |
| 4,816,567 | A | 3/1989 | Cabilly et al. |
| 5,151,504 | A | 9/1992 | Croze |
| 5,731,168 | A | 3/1998 | Carter et al. |
| 7,642,228 | B2 | 1/2010 | Carter et al. |
| 7,705,103 | B2 | 4/2010 | Sherman et al. |
| 8,349,574 | B2 | 1/2013 | Bates et al. |
| 8,592,562 | B2 | 11/2013 | Kannan et al. |
| 8,628,774 | B2 | 1/2014 | Gurney et al. |
| 9,220,775 | B2 * | 12/2015 | Chowdhury ..... A61K 39/39558 |
| 9,248,181 | B2 | 2/2016 | De Kruif et al. |
| 9,248,182 | B2 | 2/2016 | De Kruif et al. |
| 9,358,286 | B2 | 6/2016 | De Kruif et al. |
| 9,551,208 | B2 | 1/2017 | Ma et al. |
| 2003/0078385 | A1 | 4/2003 | Arathoon et al. |
| 2004/0071696 | A1 | 4/2004 | Adams et al. |
| 2006/0212956 | A1 | 9/2006 | Crocker et al. |
| 2009/0182127 | A1 | 7/2009 | Kjaergaard et al. |
| 2009/0191559 | A1 | 7/2009 | Huang et al. |
| 2010/0015133 | A1 | 1/2010 | Igawa et al. |
| 2010/0183615 | A1 | 7/2010 | Kufer et al. |
| 2010/0286374 | A1 | 11/2010 | Kannan et al. |
| 2011/0077163 | A1 | 3/2011 | Doranz |
| 2011/0195454 | A1 | 8/2011 | Mcwhirter et al. |
| 2012/0107306 | A1 | 5/2012 | Elis et al. |

(Continued)

FOREIGN PATENT DOCUMENTS

| | | |
|---|---|---|
| EP | 0120694 A2 | 10/1984 |
| EP | 0314161 A1 | 5/1989 |

(Continued)

OTHER PUBLICATIONS

Robinson et al. (Br. J. Cancer. Nov. 4, 2008; 99 (9): 1415-25).*

(Continued)

*Primary Examiner* — Stephen L Rawlings
(74) *Attorney, Agent, or Firm* — Sterne, Kessler, Goldstein & Fox P.L.L.C.

(57) ABSTRACT

The invention relates among others to antibodies comprising a first antigen-binding site that binds Erb B-2 and a second antigen-binding site that binds Erb B-3. The antibodies can typically reduce a ligand-induced receptor function of Erb B-3 on a Erb B-2 and Erb B-3 positive cell. Also described are method for the treatment and use of the antibodies in imaging and in the treatment of subjects having an Erb B-2, Erb B-3 or Erb B-2/3 positive tumor.

17 Claims, 100 Drawing Sheets
Specification includes a Sequence Listing.

(56) References Cited

U.S. PATENT DOCUMENTS

| | | | |
|---|---|---|---|
| 2012/0270801 A1* | 10/2012 | Frejd | C07K 14/31 514/19.4 |
| 2012/0328623 A1* | 12/2012 | Takahashi | C07K 16/32 424/139.1 |
| 2013/0071859 A1 | 3/2013 | Bates et al. | |
| 2013/0115208 A1 | 5/2013 | Ho et al. | |
| 2013/0156779 A1* | 6/2013 | Clarke | C07K 16/32 424/139.1 |
| 2013/0185821 A1* | 7/2013 | Babb | A01K 67/0278 800/18 |
| 2013/0251703 A1* | 9/2013 | Elis | A61K 39/39558 424/133.1 |
| 2013/0259867 A1 | 10/2013 | Amler et al. | |
| 2013/0336981 A1 | 12/2013 | de Kruif et al. | |
| 2014/0072579 A1 | 3/2014 | De Kruif et al. | |
| 2014/0120096 A1 | 5/2014 | Bakker et al. | |
| 2014/0140999 A1 | 5/2014 | De Kruif et al. | |
| 2014/0141019 A1* | 5/2014 | Kharrat | C07K 16/32 424/172.1 |
| 2015/0013996 A1 | 1/2015 | Davies et al. | |
| 2015/0139996 A1 | 5/2015 | De Kruif et al. | |
| 2015/0196637 A1 | 7/2015 | De Kruif et al. | |
| 2016/0229920 A1* | 8/2016 | Ward | A61K 31/517 |
| 2017/0058035 A1* | 3/2017 | Logtenberg | A61P 35/04 |
| 2017/0166653 A1* | 6/2017 | Garner | A61K 39/39558 |

FOREIGN PATENT DOCUMENTS

| | | |
|---|---|---|
| EP | 0481790 A2 | 4/1992 |
| EP | 0523949 A1 | 1/1993 |
| EP | 1870459 A1 | 12/2007 |
| EP | 2604625 A1 | 6/2013 |
| JP | H 11-500915 A | 1/1999 |
| JP | 2011/508604 A | 3/2011 |
| JP | 2012509259 A | 4/2012 |
| WO | 1996027011 A1 | 9/1996 |
| WO | 1998050431 A2 | 11/1998 |
| WO | 00/63403 A2 | 10/2000 |
| WO | 03/004704 A2 | 1/2003 |
| WO | 2003/107218 A1 | 12/2003 |
| WO | 04/009618 A2 | 1/2004 |
| WO | 2004/061104 A1 | 7/2004 |
| WO | 2005/000894 A2 | 1/2005 |
| WO | 2005/118635 A2 | 12/2005 |
| WO | 2006/028936 A2 | 3/2006 |
| WO | WO 2006044908 A2 | 4/2006 |
| WO | 2006106905 A1 | 10/2006 |
| WO | 2007110205 A2 | 10/2007 |
| WO | 2007147901 A1 | 12/2007 |
| WO | 2008/027236 A2 | 3/2008 |
| WO | 2008/100624 A2 | 8/2008 |
| WO | 2008/119353 A1 | 10/2008 |
| WO | 2008/140493 A2 | 11/2008 |
| WO | 2009051974 A1 | 4/2009 |
| WO | 2009/080251 A1 | 7/2009 |
| WO | 2009/080252 A1 | 7/2009 |
| WO | 2009/080253 A1 | 7/2009 |
| WO | 2009/089004 A1 | 7/2009 |
| WO | 2009/098596 A2 | 8/2009 |
| WO | 2009/157771 A2 | 12/2009 |
| WO | WO 2010059315 A1 | 5/2010 |
| WO | 2010/084197 A1 | 7/2010 |
| WO | 2010/108127 A1 | 9/2010 |
| WO | 2010/129304 A2 | 11/2010 |
| WO | 2010/151792 A1 | 12/2010 |
| WO | 2011/028952 A1 | 3/2011 |
| WO | 2011/028953 A1 | 3/2011 |
| WO | 2011/143545 A1 | 11/2011 |
| WO | 2012023053 A2 | 2/2012 |
| WO | 2012/058768 A1 | 5/2012 |
| WO | 2012/125864 A2 | 9/2012 |
| WO | 2012/131555 A2 | 10/2012 |
| WO | 2013048883 A2 | 4/2013 |
| WO | WO 2013084151 A2 | 6/2013 |
| WO | 2013/107218 A1 | 7/2013 |
| WO | 2013/134686 A1 | 9/2013 |
| WO | 2013/157953 A1 | 10/2013 |
| WO | 2013/157954 A1 | 10/2013 |
| WO | 2014/051433 A1 | 4/2014 |
| WO | 2014/060365 A1 | 4/2014 |
| WO | 2014/159580 A1 | 10/2014 |
| WO | 2014/165855 A1 | 10/2014 |
| WO | 2014182970 A1 | 11/2014 |
| WO | 2015/130172 A1 | 9/2015 |
| WO | 2015/130173 A1 | 9/2015 |

OTHER PUBLICATIONS

Stancoviski et al. (Proceedings of the National Academy of Science USA. 1991; 88: 8691-8695).*
Xu et al. (Int. J. Cancer. 1993; 53: 401-408).*
Bettler et al. (Proc. Natl. Acad. Sci. USA. Sep. 1989; 86 (18): 7118-7122).*
Jiang et al. (J. Biol. Chem. Feb. 11, 2005; 280 (6): 4656-4662).*
Boyer et al. (Int. J. Cancer. 1999; 82: 525-531).*
Press et al. (J. Immunol. Dec. 15, 1988; 141 (12): 4410-4417).*
Riemer et al. (Mol. Immunol. 2005; 42: 1121-1124).*
Greenspan et al. (Nature Biotechnology. 1999; 7: 936-937).*
Pettersen et al. (J. Immunol. Jun. 15, 1999; 162 (12): 7031-7040).*
George et al. (Circulation. 1998; 97: 900-906).*
Bernard et al. (Human Immunol. 1986; 17: 388-405).*
Fu et al. (MAbs. 2014; 6 (4): 978-90).*
Edwards et al. (J. Mol. Biol. Nov. 14, 2003; 334 (1): 103-18).*
Klein et al. (MAbs. Nov.-Dec. 2012; 4 (6): 653-63).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Kang et al. (MAbs. Mar.-Apr. 2014; 6 (2): 340-53).*
Yu et al. (PLoS One. 2012; 7 (3): e33340; pp. 1-15).*
Chang et al. (Structure. Jan. 7, 2014; 22 (1): 9-21).*
Hathaway et al. (Breast Cancer Res. Nov. 3, 2011; 13 (5): R108; pp. 1-14).*
Jackson et al. (Int. J. Cell Biol. 2013; 2013: 973584; pp. 1-9).*
Volpi et al. (Sci. Rep. Mar. 5, 2019; 9 (1): 3545; pp. 1-12).*
Omenn et al. (J. Proteomics. 2014; 107: 103-112; pp. 1-22).*
Norde, WJ. et al., "Myeloid leukemic progenitor cells can be specifically targeted by minor histocompatibility antigen LRH-1-reactive cytotoxic T cells," Blood, vol. 113(10): 2312-2123 (2009).
Deisenhofer, J., "Crystallographic refinement and atomic models of a human Fc fragment and its complex with fragment B of protein A from *Staphylococcus aureus* at 2.9- and 2.8-A resolution," Biochemistry, vol. 20(9): 2361-2370 (1981).
Offner, S. et al., "Induction of regular cytolytic T cell synapses by bispecific single-chain antibody constructs on MHC class I-negative tumor cells," Molecular Immunology, vol. 43(6):763-771( 2006).
Oganesyan, V. et al., "Structural characterization of a human Fc fragment engineered for lack of effector functions," Acta Crystallogr D Biol Crystallogr., vol. 64(Pt. 6):700-704 (2008).
Demeule, B. et al., "Detection and characterization of protein aggregates by fluorescence microscopy," Int J Pharm, vol. 329(1-2):37-45 (2007).

(56) References Cited

OTHER PUBLICATIONS

Demeule, B., "Characterization of protein aggregation: the case of a therapeutic immunoglobulin," Biochim Biophys Acta, vol. 1774(1): 146-153 (2007).
Padlan, EA., "X-ray crystallography of antibodies," Adv Protein Chem, vol. 49: 57-133 (1996).
Papadea, EA, "Human immunoglobulin G and immunoglobulin G subclasses: biochemical, genetic, and clinical aspects.," Grit Rev Clin Lab Sci., vol. 27(1): 27-58 (1989).
Di, Z. et al., "Ultra High Content Image Analysis and Phenotype Profiling of 3D Cultured Micro-Tissues," PLoS One, PLoS ONE 9(10): e109688, 10 pages (2014).
Ellerson, JR. et al., "Structure and function of immunoglobulin domains. III. Isolation and characterization of a fragment corresponding to the Cgamma2 homology region of human immunoglobin G1," J. Immunol, vol. 116 (2):510-517 (1976).
Peng, R., et al., "Bleomycin Induces Molecular Changes Directly Relevant to Idiopathic Pulmonary Fibrosis: A Model for "Active'," Disease,"Plos One, 8(4): e59348, 15 pages (2013).
Farnan, D. et al., "Multiproduct high-resolution monoclonal antibody charge variant separations by pH gradient ion-exchange chromatography," Anal Chem, vol. 81(21): 8846-8857 (2009).
Raffen, R. et al . . . , "Reengineering immunoglobulin domain interactions by introduction of charged residues," Protein Eng., vol. 11(4): 303-309 (1998).
Reusch, U. et al., "Beyond mAbs with TandAbs," Innovations in Pharmaceutical Technology, pp. 51-60 (Jun. 2011).
Ridgway, JB. et al., "Knobs-into-holes' engineering of antibody CH3 domains for heavy chain heterodimerization," Protein Eng., vol. 9(7):617-621 (1996).
Logtenberg, T. "Hub for Organoids", Poster Presentation, www.innovationforhealth.nl/index.php/page/getFileUID/uid/82364b177dfed9754d785aafffb21363/cr_usedb/25, 29 pages, Mar. 22, 2016.
Carter, P., et al., "Toward the Production of Bispecific Antibody Fragments for Clinical Applications," Journal of Hematotherapy, vol. 4, pp. 463-470 (1995).
Sal-Man, N. et al., "Arginine Mutations within A Transmembrane Domain of Tar, an *Escherichia coli* Aspartate Receptor, Can Drive Homodimer Dissociation and Heterodimer Association in Vivo," Journal of Biochemistry, vol. 385: 29-36 (2005).
Sali, A. et al., "Comparative protein modelling by satisfaction of spatial restraints," J. Mol. Biol., vol. 234(3):779-815 (1993).
Sandercock, AM. et al., "Identification of anti-tumour biologies using primary tumour models, 3-D phenotypic screening and image-based multi-parametric profiling," Mol Cancer., vol. 14:147, 18 pages (2015).
Sato, T. et al., "Long-term Expansion of Epithelial Organoids From Human Colon, Adenoma, Adenocarcinoma, and Barrett's Epithelium," Gastroenterology, vol. 141: 1762-1772 (2011).
Schaefer, G. et al., "A two-in-one antibody against HER3 and EGFR has superior inhibitory activity compared with nonspecific antibodies," Cancer Cell, vol. 20(4): 472-486 (2011).
Schiffer, M. et al., "Analysis of Immunoglobulin Domain Interactions Evidence for a Dominant Role of Salt Bridges," JMB, vol. 203:799-802 (1988).
Chames, P. et al., "Bispecific antibodies for cancer therapy: the light at the end of the tunnel?," MAbs, vol. 1(6): 539-547 (2009).
Atwell,S. et al., "Stable heterodimers from remodeling the domain interface of a homodimer using a phage display library," J Mol Biol, vol. 270(1): 26-35 (1997).
Selzer, T. et al., "Rational design of faster associating and tighter binding protein complexes," Nature Structural Biology, vol. 7, p. 537-541 (2000).
Bargou, R. et al., "Tumor regression in cancer patients by very low doses of a T cell-engaging antibody," Science, vol. 321 (5891) 974-977 (2008).
Seshagiri, S., et al., "Recurrent R-spondin fusions in colon cancer," Nature, vol. 488(7413): 660-664 (2012).
Baeuerle, PA. et al., "Multiple myeloma and monoclonal gammopathy of undetermined significance: importance of whole-body versus spinal MR imaging," Cancer Research, vol. 252(2): 477-485 (2009).
Sheinerman, F., et al., "Electrostatic aspects of protein-protein interactions," Current Opinion in Structural Biology, vol. 10:153-159 (2000).
Sheridan, C., "Amgen swallows Micromet to BiTE into ALL market," Nat Biotechnol., vol. 30(4):300-301 (2012).
Shields, RL. et al., "High resolution mapping of the binding site on human IlgG1 for Fc gamma RI, Fc gamma RII, Fc gamma RIII, and FcRn and design of IgG1 variants with improved binding to the Fc gamma R," JBC, vol. 276(9): 6591-6604 (2001).
Sinha, N. et al., "Difference in Electrostatic Properties at Antibody-Antigen Binding Sites: Implications for Specificity and Cross-Reactivity," Biophysical Journal, vol. 83:2946-2968 (2002).
Sinha, N., et al. "Electrostatics in Protein Binding and Function," Current Protein and Peptide Science, vol. 3:601-614 (2002).
Sluijter, B.J., et al., "4-1BB-mediated expansion affords superior detection of in vivo primed effector memory CD8+ T cells from melanoma sentinel lymph nodes ," Clin Immunol, vol. 137(2): 221-233 (2010).
Von Horsten, HH. et al., "Production of non-fucosylated antibodies by co-expression of heterologous GDP-6-deoxy-D-lyxo-4-hexulose reductase," Glycobiology, vol. 20 (12):1607-1618 (2010).
Spiess, C., et al., "Alternative molecular formats and therapeutic applications for bispecific antibodies," Mol. Immunol., vol. 67(2 Pt A):95-106 (2015).
Staerz, UD. et al., "Hybrid hybridoma producing a bispecific monoclonal antibody that can focus effector T-cell activity," PNAS, vol. 83(5):1453-1457 (1986).
Strelkauskas, A. et al., "Human Monoclonal Antibody: 2. Simultaneous Expression of IgG and IgM with Similar Binding Specificities by a Human Hybrid Clone," Hybridoma, vol. 6 (5): 479-488 (1987).
Suntharalingam, G. et al., "Cytokine storm in a phase 1 trial of the anti-CD28 monoclonal antibody TGN1412," N Engl J Med, vol. 355 (10): 1018-10128 (2006).
Tahallah, N."The effect of the source pressure on the abundance of ions of noncovalent protein assemblies in an electrospray ionization orthogonal time-of-flight instrument," Rapid Commun Mass Spectrom, vol. 15(8):596-601 (2001).
Van Rhenen, A. et al., "The novel AML stem cell associated antigen CLL-1 aids in discrimination between normal and leukemic stem cells," Blood, vol. 110(7): 2659-2666 (2007).
Van De Wetering, M. et al., "Prospective Derivation of a Living Organoid Biobank of Colorectal Cancer Patients," Cell, vol. 161: 933-945 (2015).
Uberall, I. et al.,"The status and role of ErbB receptors in human cancer," Exp Mol Pathol., vol. 84:79-89 (2008).
UniProt Entry Q5QGZ9, UniProt, retrieved Jan. 21, 2015, from <http://www.uniprot.org/uniprotlQ5QGZ9.
U.S. Appl. No. 13/866,747, filed Apr. 19, 2013, Cornelis A. de Kruif.
U.S. Appl. No. 14/081,848, filed Nov. 15, 2013, Cornelis A. de Kruif.
U.S. Appl. No. 13/866,756, filed Apr. 19, 2013, Cornelis A. de Kruif.
U.S. Appl. No. 14/974,581, filed Dec. 18, 2015, Cornelis A. de Kruif.
U.S. Appl. No. 14/040,023, filed Sep. 27, 2013. Alexander Berthold Hendrik Bakker.
U.S. Appl. No. 14/395,330, filed Oct. 17, 2014, Cornelis A. de Kruif.
U.S. Appl. No. 14/395,325, filed Oct. 17, 2014, Cornelis A. de Kruif.
U.S. Appl. No. 15/205,629, filed Jul. 8, 2016, Alexander Berthold Hendrik Bakker.
U.S. Appl. No. 15/121,619, filed Aug. 25, 2016, Ton Logtenberg.
U.S. Appl. No. 13/866,747, Sep. 29, 2015.
U.S. Appl. No. 13/866,747, Oct. 4, 2015.
U.S. Appl. No. 14/081,848, Feb. 12, 2016.
U.S. Appl. No. 14/081,848, Apr. 10, 2015.
U.S. Appl. No. 13/866,756, Sep. 18, 2015.

(56) References Cited

OTHER PUBLICATIONS

U.S. Appl. No. 13/866,756, Apr. 13, 2015.
U.S. Appl. No. 14/974,581, Jan. 25, 2017.
U.S. Appl. No. 14/974,581, Sep. 28, 2016.
U.S. Appl. No. 14/974,581, May 10, 2016.
U.S. Appl. No. 14/040,023, Nov. 28, 2016.
U.S. Appl. No. 14/040,023, Dec. 3, 2015.
U.S. Appl. No. 14/395,330, Oct. 4, 2015.
U.S. Appl. No. 15/205,629, Nov. 1, 2016.
Almagro, JC et al., "Humanization of antibodies," Front Biosci., vol. 13:1619-1633 (2008).
Arteaga, CL et al., "Treatment of HER2-positive breast cancer: current status and future perspectives," Nat Rev Clin Oncol., vol. 9(1):16-32 (2011).
Balko, JM et al., "The receptor tyrosine kinase ErbB3 maintains the balance between luminal and basal breast epithelium," Proc Natl Acad Sci U S A., vol. 109(1):221-226 (2012).
Baselga, J. et al., "Pertuzumab plus Trastuzumab plus Docetaxel for Metastatic Breast Cancer," N Engl J Med. vol. 366(21):2018-2026 (2012).
Devash, Y. et al., "Vertical transmission of human immunodeficiency virus is correlated with the absence of high-affinity/avidity maternal antibodies to the gp120 principal neutralizing domain," Proc Natl Acad Sci USA, vol. 87, pp. 3445-3449(1990).
Ewer, MS, et al., "Cardiotoxicity of anticancer treatments: what the cardiologist needs to know," Nat Rev Cardiol., vol. 7(10):564-575 (2010).
Greco, WR et al., "The search for synergy: a critical review from a response surface perspective," Pharmacol Rev., vol. 47(2):331-385 (1995).
Jain, KK et al.,"A Prospective Randomized Comparison of Epirubicin and Doxorubicin in Patients With Advanced Breast Cancer," J Clin Oncol., vol. 3(6):818-820 (1985).
Junttila, TT., et al., "Ligand-Independent HER2/HER3/PI3K Complex Is Disrupted by Trastuzumab and Is Effectively Inhibited by the PI3K Inhibitor GDC-0941," Cancer Cell, vol. 15, 429-440 (2009).
Junttila, TT., et al,., "Superior In vivo Efficacy of Afucosylated Trastuzumab in the Treatment of HER2-Amplified Breast Cancer," Cancer Res; 70(11):4481-4489 (2010).
Kang, JC. et al., "Engineering multivalent antibodies to target heregulin-induced HER3 signaling in breast cancer cells," MAbs, vol. 6(2):340-353 (2014).
Landgraf, R., "HER2 therapy. HER2 (ERBB2): functional diversity from structurally conserved building blocks," Breast Cancer Res., vol. 9(1):202 (2007).
Liu, C. et al., "ADCC Enhancement Technologies for Next Generation Therapeutic Antibody," Trends in Bio/Pharmaceutcial Industry, 9 pages (2009).
Ocana, A. et al., "HER3 Overexpression and Survival in Solid Tumors; A Meta-analysis," J Natl Cancer Inst., vol. 105 (4):266-273 (2013).
Robinson, MK. et al., "Targeting ErbB2 and ErbB3 with a bispecific single-chain Fv enhances targeting selectivity and induces a therapeutic effect in vitro," Br J Cancer, vol. 99(9):1415-1425 (2008).
Schoeberl, B. et al., "An ErbB3 antibody, MM-121, is active in cancers with ligand dependent activation," Cancer Res., 70(6):2485-2494 (2010).
Sergina, NV. et al., "Escape from HER-family tyrosine kinase inhibitor therapy by the kinase-inactive HER3," Nature, vol. 445(7126):437-441 (2007).
Shames, DS. et al., "High Heregulin Expression Is Associated with Activated HER3 and May Define an Actionable Biomarker in Patients with Squamous Cell Carcinomas of the Head and Neck," PLoS One, vol. 8(2): e56765, 10 pages (2013).
Tanner, M. et al., "Characterization of a novel cell line established from a patient with Herceptin-resistant breast cancer," Mol Cancer Ther., vol. 3(12): 1585-1592 (2004).
Thery, JC. et al., "Resistance to human epidermal growth factor receptor type 2-targeted therapies," European Journal of Cancer, vol. 50: 892-901(2014).

Wadhwa, D. et al., "Trastuzumab mediated cardiotoxicity in the setting of adjuvant chemotherapy for breast cancer: a retrospective study," Breast Cancer Res Treat, vol. 117: 357-364 (2009).
Wehrman TS. et al., "A system for quantifying dynamic protein interactions defines a role for Herceptin in modulating ErbB2 interactions," Proc Natl Acad Sci USA, vol. 103(50): 19063-19068 (2006).
Weidle, UH. et al., "The Intriguing Options of Multispecific Antibody Formats for Treatment of Cancer," Cancer Genomics & Proteomics, vol. 10: 1-18 (2013).
Wilson TR. et al., "Widespread potential for growth-factor-driven resistance to anticancer kinase inhibitors," Nature, vol. 487(7408): 505-509 (2012).
Yarden, Y. et al., "The ERBB network: at last, cancer therapy meets systems biology," Nat Rev Cancer, vol. 12: 553-563 (2012).
Yonesaka, K. et al,., "Activation of ERBB2 signaling causes resistance to the EGFR directed therapeutic antibody cetuximab," Sci Transl Med., vol. 3(99): 19 pages (2011).
Zhang, H. et al., "ErbB receptors: from oncogenes to targeted cancer therapies," J. Clin. Invest. 117:2051-2058 (2007).
Buday, L. et al., "Epidermal Growth Factor Regulates the Exchange Rate of Guanine Nucleotides on p21ras in Fibroblasts," Molecular and Cellular Biology, vol. 13(3):1903-1910 (1993).
Cochran, JR. et al., "Domain-level antibody epitope mapping through yeast surface display of epidermal growth actor receptor fragments," J Immunol Methods, vol. 287(1-2): 147-158 (2004).
De Haard, HJ. et al., "A Large Non-immunized Human Fab Fragment Phage Library That Permits Rapid Isolation and Kinetic Analysis of High Affinity Antibodies*," The Journal of Biological Chemistry, vol. 274(26): 18218-18230 (1999).
Ferguson, KM., "A structure-based view of Epidermal Growth Factor Receptor regulation," Annu Rev Biophys., vol. 37: 353-373 (2008).
Gale, NW. et al., "Grb2 mediates the EGF-dependent activation of guanine nucleotide exchange on Ras," Nature, vol. 363(6424):88-92 (1993).
Garrett, TP. et al., "Crystal structure of a truncated epidermal growth factor receptor extracellular domain bound to transforming growth factor alpha," Cell, vol. 110 (6): 763-773 (2002).
Giard, DJ. et al., "In Vitro Cultivation of Human Tumors: Establishment of Cell Lines Derived From a Series of Solid Tumors," J Natl Cancer Inst., vol. 51, 1417-1423 (1973).
Gulli, LF. et al., "Epidermal growth factor-induced apoptosis in A431 cells can be reversed by reducing the tyrosine kinase activity,"Cell Growth Differ., vol. 7(2):173-178 (1996).
Jorissen, RN. et al., "Epidermal growth factor receptor: mechanisms of activation and signalling," Exp Cell Res. vol. 284(1):31-53 (2003).
Kubota, T. et al., "Engineered therapeutic antibodies with improved effector functions," Cancer Sci., vol. 100: 1566-1572 (2009).
Ledón, N. et al., "Comparative analysis of binding affinities to epidermal growth factor receptor of monoclonal antibodies nimotuzumab and cetuximab using different experimental animal models," Placenta, vol. 32: 531-534 (2011).
Lichtenberger, BM. et al., "Epidermal EGFR controls cutaneous host defense and prevents inflammation," Sci Transl Med., vol. 5 (199): 14 pages (2013).
Marks, JD. et al., "By-passing Immunization Human Antibodies from V-gene Libraries Displayed on Phage," J Mol Biol., vol. 222 :581-597 (1991).
Merlino, GT. et al., "Amplification and Enhanced Expression of the Epidermal Growth Factor Receptor Gene in A431 Human Carcinoma Cells," Science, vol. 224(4647): 417-419 (1984).
Meulemans, EV. et al., "Selection of phage-displayed antibodies specific for a cytoskeletal antigen by competitive elution with a monoclonal antibody," J Mol Biol., vol. 244(4):353-360 (1994).
Ogiso, H. et al., "Crystal Structure of the Complex of Human Epidermal Growth Factor and Receptor Extracellular Domains," Cell, vol. 110; 775-787 (2002).
Olayioye, MA et al., "The ErbB signaling network: receptor heterodimerization in development and cancer," EMBO J., vol. 19(13):3159-3167 (2000).

(56) References Cited

OTHER PUBLICATIONS

Pastore, S. et al., "ERK1/2 Regulates Epidermal Chemokine Expression and Skin Inflammation," J. Immunol., vol. 174:5047-5056 (2005).
Patel, DK., "Clinical use of anti-epidermal growth factor receptor monoclonal antibodies in metastatic colorectal cancer," Pharmacotherapy, vol. 28(11 Pt 2):31S-41S (2008).
Prigent, S et al., "Identification of c-erbB-3 binding sites for phosphatidylinositol 3'-kinase and SHC using an EGF receptor/c-erbB-3 chimera," EMBO J., vol. 13(12):2831-2841(1994).
Robertson, SC. et al., "RTK mutations and human syndromes when good receptors turn bad," Trends Genet., vol. 16(6):265-271 (2000).
Schmitz, K. et al., "Interaction of antibodies with ErbB receptor extracellular regions," Exp Cell Res., vol. 315(4): 659-670 (2009).
Soltoff, SP. et al., "ErbB3 Is Involved in Activation of Phosphatidylinositol 3-Kinase by Epidermal Growth Factor," Mol Cell Biol., vol. 14(6): 3550-3558 (1994).
Bendig, MM., The production of foreign proteins in mammalian cells, Genet Eng., vol. 7:91-127 (1988).
Bogan, AA. et al., "Anatomy of hot spots in protein interfaces," J Mol Biol, vol. 280 (1): 1-9 (1998).
Bostrom, J., "Variants of the antibody herceptin that interact with HER2 and VEGF at the antigen binding site," Science, vol. 323(5921):1610-1614 (2009).
Gunasekaran, K. et al., "Enhancing Antibody Fc Heterodimer Formation Through Electrostatic Steering Effects, Applications to Bispecific Molecules and Monovalent," JBC, vol. 285(25):19637-19646 (2010).
Gussow, D. et al., "Humanization of monoclonal antibodies," Methods Enzymol., vol. 203(5): 99-121 (1991).
Haagen, IA, et al., "The efficacy of CD3 x CD19 bispecific monoclonal antibody (BsAb) in a clonogenic assay: the effect of repeated addition of BsAb and interleukin-2," Blood, vol. 85(11): 3208-3212 (1995).
Han, Y. et al., "KLRL1, a novel killer cell lectinlike receptor, inhibits natural killer cell cytotoxicity," Blood, vol. 104(9): 2856-2866 (2004).
Hao, HX., et al., "ZNRF3 promotes Wnt receptor turnover in an R-spondin-sensitive manner," Nature, vol. 485 (7397):195-200 (2012).
Hendsch, Z. et al., "Preferential heterodimer formation via undercompensated electrostatic interactions," J Am Chem Soc, vol. 123(6): 1264-1265 (2001).
Idusogie, EE, "Mapping of the C1q binding site on rituxan, a chimeric antibody with a human IgG1 Fc," J Immunol., vol. 164(8):4178-4184 (2000).
Ionescu, RM. et al., "Contribution of variable domains to the; stability of humanized IgG1 monoclonal antibodies," J. Pharm Sci., vol. 97(4):1414-1426 (2008).
Capelle, MA et al., "Spectroscopic characterization of antibodies adsorbed to aluminium adjuvants: correlation with antibody vaccine immunogenicity," Vaccine, 23(14): 1686-1694 (2005).
Carmon, K. et al., "R-spondins function as ligands of the orphan receptors LGR4 and LGR5 to regulate Wnt/β-catenin signaling," PNAS, vol. 108(28): 11452-11457 (2011).
Carter, P. J.,"Bispecific Human IgG by Design," Immunol. Methods, vol. 248: 7-15 (2001).
Cartron, G. et al., "Therapeutic activity of humanized anti-CD20 monoclonal antibody and polymorphism in IgG Fc receptor FcγRIIIa gene," Blood, vol. 99(3): 754-758 (2002).
Kabat, EA., et al., "Identical V region amino acid; sequences and segments of sequences in antibodies of different specificities. Relative contributions of VH and VL genes, minigenes, and complementarity-determining regions to binding of antibody-combining sites," J Immunol., vol. 147(5): 1709-1719 (1991).
Coligan JE, "Commonly used detergents," Curr Protoc Protein Sci., Appendix 1:Appendix 1B (2001).
Kipriyanov, SM. et al., "Bispecific CD3 x CD19 diabody for T cell-mediated lysis of malignant human B cells," Int. J. Cancer, vol. 77(5): 763-772 (1998).

Kontermann, R.E.,"Dual targeting strategies with bispecific antibodies," MAbs, vol. 4(2): 182-197 (2012).
Davies, J. et al., "Antibody VH domains as small recognition units," Biotech., vol. 13(5): 475-479 (1995).
Kumar, R. et al., The Second PDZ Domain of INAD Is a Type 1 Domain Involved in Binding to Eye Protein Kinase C., J Biol Chem, vol. 276 (27): 24971-24977 (2001).
Lakowicz, JR., "Principles of Fluorescence Spectroscopy," 3rd edition, Kluwer Academic/Plenum Publisher, ISBN-10: 0-387-31278-1, 469 pages (2006).
Davis, JH. et al., "SEEDbodies: fusion proteins based on strand-exchange engineered domain (SEED) CH3 heterodimers in an Fc analogue platform for asymmetric binders or immunofusions and bispecific antibodies,", Protein Eng Des Sel., vol. 23(4):195-202 (2010).
Lanzavecchia, A. et al., "Lysis of nonnucleated red blood cells by cytotoxic T lymphocytes," Eur.J.Imm., vol. 17(7): 1073-1074 (1987).
De Kruif, J. et al., "Human immunoglobulin repertoires against Tetanus toxoid contain a large and diverse fraction of high-affinity VH genes" J. Mol. Biol., 387: 548-558 (2009).
Lee, B. et al., "The interpretation of protein structures: estimation of static accessibility," J Mol Biol., vol. 55(3), 379-400 (1971).
De Kruif, J. et al., "Generation of stable cell clones expressing mixtures of human antibodies," Biotechnol Bioeng, vol. 106(5): 741-750 (2010).
Armour, K.L. et al., "Differential binding to human FcgammaRIIa and FcgammaRIIb receptors by human IgG wildtype and mutant antibodies," Mol.Immunol., vol. 40(9): 585-593 (2003).
Liesveld, JL., "Expression of IgG Fc receptors in myeloid leukemic cell lines. Effect of colony-stimulating factors and cytokines," J. Immunol., vol. 140(5):1527-1533 (1988).
De Lau, W., et al., "The R-spondin/Lgr5/Rnf43 module: regulator of Wnt signal strength," Genes Dev, vol. 28:305-316 (2014).
Liu, H. et al., "Heterogeneity of Monoclonal Antibodies," J Pharm Sci. vol. 97(7): 2426-2447 (2008).
Liu, MA., et al., "Heteroantibody duplexes target cells for lysis by cytotoxic T lymphocytes," PNAS, vol. 82(24): 8648-8652 (1985).
Loeffler A. et al., "A recombinant bispecific single-chain antibody, CD19 X CD3, induces rapid and high lymphoma-directed cytotoxicity by unstimulated T lymphocytes," Blood, vol. 95(6) 2098-2103 (2000).
Bakker, AB et al., "C-type lectin-like molecule-1: a novel myeloid cell surface marker associated with acute myeloid eukemia," Cancer Research, vol. 64(22): 8443-8450 (2004).
Mariuzza, RA. et al., "The Structural Basis of Antigen-Antibody Recognition," Annu Rev Biophys Biophys Chem., vol. 116:139-159 (1987).
De Lau, W., et al.,"Lgr5 homologues associate with Wnt receptors and mediate R-spondin signalling," Nature, vol. 476:293-298 (2011).
Marshall, A.S. et al. "Identification and Characterization of a Novel Human Myeloidinhibitory C-type Lectin-like Receptor (MICL) That Is Predominantly Expressed on Granulocytes and Monocytes," J Biol Chem, vol. 279(15): 14792-14802 (2004).
Marvin, JS et al., "Redesigning an antibody fragment for faster association with its antigen," Biochemistry, vol. 42 (23): 7077-7083 (2003).
Mcphee, F. et al., "Engineering human immunodeficiency virus 1 protease heterodimers as macromolecular inhibitors of viral maturation," PNAS, vol. 93(21):11477-11481 (1996).
Merchant, AM. et al., "An efficient route to human bispecific IgC," Nat. Biotechn., vol. 16 : 677-681 (1998).
Bluemel, C. et al., "Epitope distance to the target cell membrane and antigen size determine the potency of T cell-mediated lysis by BiTE antibodies specific for a large melanoma surface antigen," Cancer Immunol.Immunother., vol. 59 (8):1197-1209 (2010).
Merus, Press Release Jun. 17, 2013.
Merus, Press Release Jan. 7, 2013.
De Vries, SJ. et al., The HADDOCK web server for data driven biomolecular docking, Nature Protocols, vol. 5 (5):883-897 (2010).
Miller, S., "Protein-protein recognition and the association of immunoglobulin constant domains," J Mol Biol., vol. 216(4):965-973 (1990).

(56) References Cited

OTHER PUBLICATIONS

Moore, PA. et al., "Application of dual affinity retargeting molecules to achieve optimal redirected T-cell killing of B-cell lymphoma," Blood, vol. 117(17):4542-4551 (2011).

Moshaver, B. et al., "Identification of a small subpopulation of candidate leukemia-initiating cells in the side population of patients with acute myeloid leukemia," Stem Cells, vol. 26(12): 3059-3067 (2008).

Nieba L. et al., "Disrupting the hydrophobic patches at the antibody variable/constant domain interface: improved in vivo folding and physical characterization of an engineered scFv fragment," Protein Eng., vol. 10(4): 435-444 (1997).

Nissim, A. et al., "Antibody fragments from a 'single pot' phage display library as immunochemical reagents," EMBO J., vol. 13(3): 692-698 (1994).

Nohaile, MJ. et al., "Altering dimerization specificity by changes in surface electrostatics," PNAS, USA, vol. 98(6): 3109-3114(2001).

Zhu, Z. et al., "Remodeling domain interfaces to enhance heterodimer formation," Protein Sci., vol. 6(4): 781-788 (1997).

Yarden, Y. et al., "The EGFR family and its ligands in human cancer: signalling mechanisms and therapeutic opportunities," European Journal of Cancer, vol. 37: S3-S8 (2001).

Chatenoud, L. et al., "In vivo cell activation following OKT3 administration. Systemic cytokine release and modulation by corticosteroids", Transplantation, vol. 49(4): 697-702 (1990).

Zebisch, M. et al., "Crystal structure of R-spondin 2 in complex with the ectodomains of its receptors LGR5 and ZNRF3," J Struct Biol., vol. 191: 149-155 (2015).

Zebisch, M et al., "ZNRF3/RNF43 e A direct linkage of extracellular recognition and E3 ligase activity to modulate cell surface signalling," Prog Biophys Mol Biol., vol. 118: 112-118 (2015).

Zeidler, R. et al., "Simultaneous activation of T cells and accessory cells by a new class of intact bispecific antibody results in efficient tumor cell killing,", J. Immunol., vol. 163(3): 1246-1252 (1999).

Zhang, W. et al., "*Homo sapiens* C-type lectin protein CLL-1 mRNA, complete cds," GenBank: AF247788.1, 1 page (2002).

Zhao, X., et.al., "Targeting C-type lectin-like molecule-1 for antibody-mediated immunotherapy in acute myeloid leukemia," Haematologica, vol. 95(1): 71-78 (2009).

Chen, C.H.et al., "Effect of Duration of Osmotherapy on blood-brain barrier disruption and regional cerebral edema after experiental stroke," Blood, Journal of Cerebral Blood Flow & Metabolism, vol. 26: 951-958 (2006).

Cui, H. et al., "Chemically Programmed Bispecific Antibodies That Recruit and Activate T Cells," The Journal of Biological Chemistry, vol. 287(34): 28206-28214 (2012).

Dewildt, RM et al.,"Analysis of Heavy and Light Chain Pairings Indicates the Receptor Editing Shapes the Human Antibody Repertoire," J. Mol. Biol., vol. 285: 895-901 (1999).

Dreier, T. et al., "Extremely potent, rapid and costimulation-independent cytotoxic T-cell response against lymphoma sells catalyzed by a single-chain bispecific antibody," Int. J.Canc., vol. 100(6): 690-697 (2002).

Geginat, J., A. et al., "Proliferation and differentiation potential of human CD8+ memory T-cell subsets in response to antigen or homeostatic cytokines," Blood, vol. 101(11): 4260-4266 (2003).

Dekruif, J. et al., "Selection and application of human single chain Fv antibody fragments from a semi-synthetic phage antibody display library with designed CDR3 regions," J. Mol Biol., vol. 248(1): 97-105 (1995.

Legall, F. et al., "Effect of linker sequences between the antibody variable domains on the formation, stability and biological activity of a bispecific tandem diabody," Protein Eng Des Sel., vol. 17(4):357-366 (2004).

Troise, F., et al., "A novel ErbB2 epitope targeted by human antitumor immunoagents," *FEBS Journal*, 278: 1156-1166, John Wiley & Sons, United States (2011).

\* cited by examiner

Fig. 16A(a)

SEQ ID NO: 7 MF2926: heavy chain variable region sequence of an erbB-2 binding antibody Nucleic acid sequence (underlined sequence encodes end of leader peptide):

```
  1   GGCCCAGCCG GCCATGGCCC AGGTCCAGCT GCAGCAGTCT GGACCTGAGC TGGTGAAACC
 61   TGGGGCTTCA GTGATGATTT CCTGCAAGGC TTCTGGTTAC TCATTCACTG GCTACCACAT
121   GAACTGGGTG AAGCAAAGTC CTGAAAAGAG CCTTGAGTGG ATTGGAGACA TAAATCCTAG
181   CATTGGTACG ACTGCCCACA ACCAGATTTT CAGGGCCAAG GCCACAATGA CTGTTGACAA
241   ATCCTCCAAC ACAGCCTACA TGCAGCTCAA GAGCCTGACA TCTGAAGACT CTGGAGTCTT
301   TTACTGTGTT AGAAGAGGGG ACTGGTCCTT CGATGTCTGG GGCACAGGGA CCACGGTCAC
361   CGTCTCCAGT
```

Amino acid sequence:

SEQ ID NO: 8 QVQLQQSGPELVKPGASVMISCKASGYSFTGYHMNWVKQSPEKSLEWIGDINPSIGT
TAHNQIFRAKATMTVDKSSNTAYMQLKSLTSEDSGVFYCVRRGDWSFDVWGTGTTV
TVSS

SEQ ID NO: 9  CDR1:    GYHMNWVKQSPEKSLE

SEQ ID NO: 10 CDR2:    NQIFRA

SEQ ID NO: 11 CDR3:    RGDWSFDV

Fig. 16A(b)

SEQ ID NO: 12 MF2930: heavy chain variable region sequence of an erbB-2 binding antibody Nucleic acid sequence (underlined sequence encodes end of leader peptide):

```
  1 GGCCCAGCCG GCCATGGCCG AGGTCCAGCT GCAGCAGTCT GGGGCTGAAC TGGTGAAGCC
 61 TGGAGCCTCA GTGATGATGT CCTGTAAGGT TTCTGGCTAC ACCTTCACTT CCTATCCTAT
121 AGCGTGGATG AAGCAGGTTC ATGGAAAGAG CCTAGAGTGG ATTGGAAATT TTCATCCTTA
181 CAGTGATGAT ACTAAGTACA ATGAAAACTT CAAGGGCAAG GCCACATTGA CTGTAGAAAA
241 ATCCTCTAGC ACAGTCTACT TGGAGCTCAG CCGATTAACA TCTGATGACT CTGCTGTTTA
301 TTACTGTGCA AGAAGTAACC CATTATATTA CTTTGCTATG GACTACTGGG GTCAAGGAAC
361 CTCGGTCACC GTCTCCAGT
```

Amino acid sequence:

SEQ ID NO: 13 EVQLQQSGAELVKPGASVMMSCKVSGYTFTSYPIAWMKQVHGKSLEWIGNFHPYSD
DTKYNENFKGKATLTVEKSSSTVYLELSRLTSDDSAVYYCARSNPLYYFAMDYWGQG
TSVTVSS

| | |
|---|---|
| SEQ ID NO: 14 CDR1: | SYPIAWMKQVHGKSLE |
| SEQ ID NO: 15 CDR2: | NENFKG |
| SEQ ID NO: 16 CDR3: | SNPLYYFAMDY |

Fig. 16A(c)

SEQ ID NO: 17 MF1849: heavy chain variable region sequence of an erbB-2 binding antibody Nucleic acid sequence (underlined sequence encodes end of leader peptide):

```
  1 GCCCCAGCCG GCCATGGCCC AGGTGCAGCT GGTGGAGTCT GGGGGAGGCG TGGTCCAGCC
 61 TGGGAGGTCC CTGAGACTCT CCTGTGCAGC CTCTGGATTC ACCTTCAGTA GCTATGGCAT
121 GCACTGGGTC CGCCAGGCTC CAGGCAAGGG GCTGGAGTGG GTGGCAGTTA TATCATATGA
181 TGGAAGTAAT AAATACTATG CAGACTCCGT GAAGGGCCGA TTCACCATCT CCAGAGACAA
241 TTCCAAGAAC ACGCTGTATC TGCAAATGAA CAGCCTGAGA GCTGAGGACA CGGCCGTGTA
301 TTACTGTGCA AAAGGTGACT ACGGTTCTTA CTCTTCTTAC GCCTTTGATT ATTGGGGCCA
361 AGGTACCCTG GTCACCGTCT CCAGT
```

Amino acid sequence:

SEQ ID NO: 18 QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKGDYGSYSSYAFDYWG
QGTLVTVSS

SEQ ID NO: 19 CDR1:      SYGMH

SEQ ID NO: 20 CDR2:      VISYDGSNKYYADSVKG

SEQ ID NO: 21 CDR3:      GDYGSYSSYAFDY

Fig. 16A(d)

SEQ ID NO: 22 MF2973: heavy chain variable region sequence of an erbB-2 binding antibody Nucleic acid sequence (underlined sequence encodes end of leader peptide):

```
  1 GGCCCAGCCG GCCATGGCCC AGGTGCAGCT GAAGCAGTCT GGGGCTGAGC TGGTGAGGCC
 61 TGGGGCTTCA GTGAAGTTGT CCTGCAAGGC TTCTGGCTAC ATTTTCACTG GCTACTATAT
121 AAACTGGTTG AGGCAGAGGC CTGGACAGGG ACTTGAATGG ATTGCAAAAA TTTATCCTGG
181 AAGTGGTAAT ACTTACTACA ATGAGAAGTT CAGGGCAAG GCCACACTGA CTGCAGAAGA
241 ATCCTCCAGC ACTGCCTACA TGCAGCTCAG CAGCCTGACA TCTGAGGACT CTGCTGTCTA
301 TTTCTGTGCA AGAGGGCCCC ACTATGATTA CGACGGCCCC TGGTTTGTTT ACTGGGGCCA
361 AGGGACTCTG GTCACCGTCT CCAGT
```

Amino acid sequence:

SEQ ID NO: 23 QVQLKQSGAELVRPGASVKLSCKASGYIFTGYYINWLRQRPGQGLEWIAKIYPGSGNT
YYNEKFRGKATLTAEESSSTAYMQLSSLTSEDSAVYFCARGPHYDYDGPWFVYWGQ
GTLVTVSS

| | | |
|---|---|---|
| SEQ ID NO: 24 | CDR1: | GYYINWLRQRPGQGLE |
| SEQ ID NO: 25 | CDR2: | NEKFRG |
| SEQ ID NO: 26 | CDR3: | GPHYDYDGPWFVY |

Fig. 16A(e)

SEQ ID NO: 27 MF3004: heavy chain variable region sequence of an erbB-2 binding antibody Nucleic acid sequence (underlined sequence encodes end of leader peptide):

```
  1 GGCCCAGCCG GCCATGGCCC AGGTGCAGCT GAAGCAGTCT GGGGCTGAGC TGGTGAGGCC
 61 TGGGGCTTCA GTGAAGCTGT CCTGCAAGGC TTCTGGCTAC ACTTTCACTG GCTACTATAT
121 AAACTGGGTG AAGCAGAGGC CTGGACAGGG ACTTGAGTGG ATTGCAAGGA TTTATCCTGG
181 AAGTGGTTAT ACTTACTACA ATGAGAAGTT CAAGGGCAAG GCCACACTGA CTGCAGAAGA
241 ATCCTCCAGC ACTGCCTACA TGCACCTCAG CAGCCTGACA TCTGAGGACT CTGCTGTCTA
301 TTTCTGTGCA AGACCCCACT ATGGTTACGA CGACTGGTAC TTCGGTGTCT GGGGCACAGG
361 CACCACGGTC ACCGTCTCCA GT
```

Amino acid sequence:

SEQ ID NO: 28 QVQLKQSGAELVRPGASVKLSCKASGYTFTGYYINWVKQRPGQGLEWIARIYPGSGY
TYYNEKFKGKATLTAEESSSTAYMHLSSLTSEDSAVYFCARPHYGYDDWYFGVWGT
GTTVTVSS

SEQ ID NO: 29 CDR1:    GYYINWVKQRPGQGLE

SEQ ID NO: 30 CDR2:    NEKFKG

SEQ ID NO: 31 CDR3:    PHYGYDDWYFGV

Fig. 16A(f)

SEQ ID NO: 32 MF2971: heavy chain variable region sequence of an erbB-2 binding antibody Nucleic acid sequence (underlined sequence encodes end of leader peptide):

```
  1 GGCCCAGCCG GCCATGGCCC AGGTGCAGCT GAAGCAGTCT GGGGCTGAGC TGGTGAGGCC
 61 TGGGGCTTCA GTGAAACTGT CCTGCAAGGC TTCTGGCTAC ACTTTCACTG CCTACTATAT
121 AAACTGGGTG AAGCAGAGGC CTGGACAGGG ACTTGAGTGG ATTGCAAGGA TTTATCCTGG
181 AAGTGGCTAT ACTTACTACA ATGAGATTTT CAAGGGCAGG GCCACACTGA CTGCAGACGA
241 ATCCTCCAGC ACTGCCTACA TGCAACTCAG CAGCCTGACA TCTGAGGACT CTGCTGTCTA
301 TTTCTGTGCA AGACCTCCGG TCTACTATGA CTCGGCCTGG TTTGCTTACT GGGGCCAAGG
361 GACTCTGGTC ACCGTCTCCA GT
```

Amino acid sequence:

SEQ ID NO: 33 QVQLKQSGAELVRPGASVKLSCKASGYTFTAYYINWVKQRPGQGLEWIARIYPGSGY
TYYNEIFKGRATLTADESSSTAYMQLSSLTSEDSAVYFCARPPVYYDSAWFAYWGQG
TLVTVSS

SEQ ID NO: 34 CDR1:    AYYINWVKQRPGQGLE

SEQ ID NO: 35 CDR2:    NEIFKG

SEQ ID NO: 36 CDR3:    PPVYYDSAWFAY

Fig. 16A(g)

SEQ ID NO: 37 MF3025: heavy chain variable region sequence of an erbB-2 binding antibody Nucleic acid sequence (underlined sequence encodes end of leader peptide):

```
  1 GGCCCAGCCG GCCATGGCCC AGGTGCAGCT GAAGCAGTCT GGGGCTGAGC TGGTGAGGCC
 61 TGGGACTTCA GTGAAGCTGT CCTGCAAGGC TTCTGGCTAC ACTTTCACTG GCTACTATAT
121 AAACTGGGTG AAGCAGAGGC CTGGACAGGG ACTTGAGTGG ATTGCAAGGA TTTATCCTGG
181 AAGTGGTTAT ACTTACTACA ATGAGAAGTT CAAGGGCAAG GCCACACTGA CTGCAGAAGA
241 ATCCTCCAAC ACTGCCTATA TGCACCTCAG CAGCCTGACA TCTGAGGACT CTGCTGTCTA
301 TTTCTGTGCA AGGCCCCACT ATGGTTACGA CGACTGGTAC TTCGCTGTCT GGGGCACAGG
361 GACCACGGTC ACCGTCTCCA GT
```

Amino acid sequence:

SEQ ID NO: 38 QVQLKQSGAELVRPGTSVKLSCKASGYTFTGYYINWVKQRPGQGLEWIARIYPGSGY
TYYNEKFKGKATLTAEESSNTAYMHLSSLTSEDSAVYFCARPHYGYDDWYFAVWGT
GTTVTVSS

| | | |
|---|---|---|
| SEQ ID NO: 39 | CDR1: | GYYINWVKQRPGQGLE |
| SEQ ID NO: 40 | CDR2: | NEKFKG |
| SEQ ID NO: 41 | CDR3: | PHYGYDDWYFAV |

Fig. 16A(h)

SEQ ID NO: 42 MF2916: heavy chain variable region sequence of an erbB-2 binding antibody Nucleic acid sequence (underlined sequence encodes end of leader peptide):

```
  1 GGCCCAGCCG GCCATGGCCC AGGTCCAGCT GCAGCAGTCT GGGGCTGAGC TGGTGAGGCC
 61 TGGGGCTTCA GTGAAGCTGT CCTGCAAGGC TTCTGGCTAC ACTTTCACTG GCTACTATAT
121 AAACTGGGTG AAGCAGAGGC CTGGACAGGG ACTTGAGTGG ATTGCAAGGA TTTATCCTGG
181 CAGTGGTCAT ACTTCCTACA ATGAGAAGTT CAAGGGCAAG GCCACACTGA CTACAGAAAA
241 ATCCTCCAGC ACTGCCTACA TGCAGCTCAG CAGCCTGACA TCTGAGGACT CTGCTGTCTA
301 TTTCTGTGCA AGACCTATCT ACTTTGATTA CGCAGGGGGG TACTTCGATG TCTGGGGCAC
361 AAGAACCTCG GTCACCGTCT CCAGT
```

Amino acid sequence:

SEQ ID NO: 43 QVQLQQSGAELVRPGASVKLSCKASGYTFTGYYINWVKQRPGQGLEWIARIYPGSGH
TSYNEKFKGKATLTTEKSSSTAYMQLSSLTSEDSAVYFCARPIYFDYAGGYFDVWGTR
TSVTVSS

SEQ ID NO: 44 CDR1:    GYYINWVKQRPGQGLE

SEQ ID NO: 45 CDR2:    NEKFKG

SEQ ID NO: 46 CDR3:    PIYFDYAGGYFDV

Fig. 16A(i)

SEQ ID NO: 47 MF3958: heavy chain variable region sequence of an erbB-2 binding antibody Nucleic acid sequence (underlined sequence encodes end of leader peptide):

```
  1 GGCCCAGCCG GCCATGGCCC AGGTGCAGCT GGTGCAGTCT GGCGCCGAAG TGAAGAAACC
 61 TGGCGCCAGC GTGAAGCTGA GCTGCAAGGC CAGCGGCTAC ACCTTCACCG CCTACTACAT
121 CAACTGGGTC CGACAGGCCC CAGGCCAGGG CCTGGAATGG ATCGGCAGAA TCTACCCCGG
181 CTCCGGCTAC ACCAGCTACG CCCAGAAGTT CCAGGGCAGA GCCACCCTGA CCGCCGACGA
241 GAGCACCAGC ACCGCCTACA TGGAACTGAG CAGCCTGCGG AGCGAGGATA CCGCCGTGTA
301 CTTCTGCGCC AGACCCCCCG TGTACTACGA CAGCGCTTGG TTTGCCTACT GGGGCCAGGG
361 CACCCTGGTC ACCGTCTCCA GT
```

Amino acid sequence:

SEQ ID NO: 48 QVQLVQSGAEVKKPGASVKLSCKASGYTFTAYYINWVRQAPGQGLEWIGRIYPGSGY
TSYAQKFQGRATLTADESTSTAYMELSSLRSEDTAVYFCARPPVYYDSAWFAYWGQG
TLVTVSS

SEQ ID NO: 49 CDR1:     AYYIN

SEQ ID NO: 50 CDR2:     RIYPGSGYTSYAQKFQG

SEQ ID NO: 51 CDR3:     PPVYYDSAWFAY

Fig. 16A(j)

SEQ ID NO: 52 MF3031: heavy chain variable region sequence of an erbB-2 binding antibody Nucleic acid sequence (underlined sequence encodes end of leader peptide):

```
  1 GGCCCAGCCG GCCATGGCCC AGGTCCAGCT GCAGCAGTCT GGGGCTGAGC TGGTGAGGCC
 61 TGGGGCTTCA GTGAAGCTGT CCTGCAAGGC TTCTGGCTAC ACTTTCACTG CCTACTATAT
121 AAACTGGGTG AAGCAGAGGC TGGACAGGG  ACTTGAGTGG ATTGCAAAGA TTTATCCTGG
181 AAGTGGTTAT ACTTACTACA ATGAGAATTT CAGGGGCAAG GCCACACTGA CTGCAGAAGA
241 ATCCTCCAGT ACTGCCTACA TACAACTCAG CAGCCTGACA TCTGAGGACT CTGCTGTCTA
301 TTTCTGTGCA AGAGGCGTCT ATGATTACGA CGGGGCCTGG TTTGCTTACT GGGGCCAAGG
361 GACTCTGGTC ACCGTCTCCA GT
```

Amino acid sequence:

SEQ ID NO: 53 QVQLQQSGAELVRPGASVKLSCKASGYTFTAYYINWVKQRPGQGLEWIAKIYPGSGY
TYYNENFRGKATLTAEESSSTAYIQLSSLTSEDSAVYFCARGVYDYDGAWFAYWGQG
TLVTVSS

SEQ ID NO: 54 CDR1:    AYYINWVKQRPGQGLE

SEQ ID NO: 55 CDR2:    NENFRG

SEQ ID NO: 56 CDR3:    GVYDYDGAWFAY

Fig. 16A(k)

SEQ ID NO: 57 MF3991: heavy chain variable region sequence of an erbB-2 binding antibody Nucleic acid sequence (underlined sequence encodes end of leader peptide):

```
  1 GGCCCAGCCG GCCATGGCCC AGGTGCAGCT GGTGCAGTCT GGCGCCGAAG TGAAGAAACC
 61 TGGCGCCAGC GTGAAGCTGA GCTGCAAGGC CAGCGGCTAC ACCTTCACCG CCTACTACAT
121 CAACTGGGTC CGACAGGCCC CAGGCCAGGG CCTGGAATGG ATCGGCAGAA TCTACCCCGG
181 CTCCGGCTAC ACCAGCTACG CCCAGAAGTT CCAGGGCAGA GCCACCCTGA CCGCCGACGA
241 GAGCACCAGC ACCGCCTACA TGGAACTGAG CAGCCTGCGG AGCGAGGATA CCGCCGTGTA
301 CTTCTGCGCC AGACCCCACT ACGGCTACGA CGACTGGTAC TTCGGCGTGT GGGGCCAGGG
361 CACCCTGGTC ACCGTCTCCA GT
```

Amino acid sequence:

SEQ ID NO: 58 QVQLVQSGAEVKKPGASVKLSCKASGYTFTAYYINWVRQAPGQGLEWIGRIYPGSGY
TSYAQKFQGRATLTADESTSTAYMELSSLRSEDTAVYFCARPHYGYDDWYFGVWGQ
GTLVTVSS

| | |
|---|---|
| SEQ ID NO: 59 CDR1: | AYYIN |
| SEQ ID NO: 60 CDR2: | RIYPGSGYTSYAQKFQG |
| SEQ ID NO: 61 CDR3: | PHYGYDDWYFGV |

Fig. 16B(a)

SEQ ID NO: 62 MF3178: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCTGTGTA
301 TTACTGTGCA AGAGATCATG GTTCTCGTCA TTTCTGGTCT TACTGGGGCT TGATTATTG
361 GGGCCAAGGT ACCCTGGTCA CCGTCTCCAG T
```

Amino acid sequence:

SEQ ID NO: 63 QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARDHGSRHFWSYWGF
DYWGQGTLVTVSS

SEQ ID NO: 64 CDR1: GYYMH

SEQ ID NO: 65 CDR2: WINPNSGGTNYAQKFQG

SEQ ID NO: 66 CDR3: DHGSRHFWSYWGFDY

Fig. 16B(b)

SEQ ID NO: 67 MF3176: heavy chain variable region sequence of an erbB-3 binding antibody Nucleic acid sequence (underlined sequence encodes end of leader peptide):

```
  1 GGCCCAGCCG GCCATGGCCG AGGTGCAGCT GTTGGAGTCT GGGGGAGGCT TGGTACAGCC
 61 TGGGGGGTCC CTGAGACTCT CCTGTGCAGC CTCTGGATTC ACCTTTAGCA GCTATGCCAT
121 GAGCTGGGTC CGCCAGGCTC CAGGGAAGGG GCTGGAGTGG GTCTCAGCTA TTAGTGGTAG
181 TGGTGGTAGC ACATACTACG CAGACTCCGT GAAGGGCCGG TTCACCATCT CCAGAGACAA
241 TTCCAAGAAC ACGCTGTATC TGCAAATGAA CAGCCTGAGA GCCGAGGACA CGGCTGTGTA
301 TTACTGTGCA AGAGATTGGT GGTACCCGCC GTACTACTGG GGCTTTGATT ATTGGGGCCA
361 AGGTACCCTG GTCACCGTCT CCAGT
```

Amino acid sequence:

SEQ ID NO: 68 EVQLLESGGGLVQPGGSLRLSCAASGFTFSSYAMSWVRQAPGKGLEWVSAISGSGGS
TYYADSVKGRFTISRDNSKNTLYLQMNSLRAEDTAVYYCARDWWYPPYYWGFDYWG
QGTLVTVSS

SEQ ID NO: 69 CDR1:      SYAMS

SEQ ID NO: 70 CDR2:      AISGSGGSTYYADSVKG

SEQ ID NO: 71 CDR3:      DWWYPPYYWGFDY

Fig. 16B(c)

SEQ ID NO: 72 MF3163: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AAAGATTCTT ACTCTCGTCA TTTCTACTCT TGGTGGGCCT TTGATTATTG
361 GGGCCAAGGT ACCCTGGTCA CCGTCTCCAG T
```

Amino acid sequence:

SEQ ID NO: 73 QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCAKDSYSRHFYSWWAF
DYWGQGTLVTVSS

SEQ ID NO: 74 CDR1:      GYYMH

SEQ ID NO: 75 CDR2:      WINPNSGGTNYAQKFQG

SEQ ID NO: 76 CDR3:      DSYSRHFYSWWAFDY

Fig. 16B(d)

SEQ ID NO: 77 MF3099: heavy chain variable region sequence of an erbB-3 binding antibody Nucleic acid sequence (underlined sequence encodes end of leader peptide):

```
  1 GGCCCAGCCG GCCATGGCCG AGGTCCAGCT GCAGCAGCCT GGGGCTGAGC TGGTGAGGCC
 61 TGGGACTTCA GTGAAGTTGT CCTGCAAGGC TTCTGGCTAC ACCTTCACCA GCTACTGGAT
121 GCACTGGGTA AAGCAGAGGC CTGGACAAGG CCTTGAGTGG ATCGGAATTC TTGATCCTTC
181 TGATAGTTAT ACTACCTACA ATCAAAAGTT CAAGGGCAAG GCCACATTAA CAGTAGACAC
241 ATCCTCCAGC ATAGCCTACA TGCAGCTCAG CAGCCTGACA TCTGAGGACT CTGCGCTCTA
301 TTACTGTGCA AGAGGGGAG ATTACGACGA GGGAGGTGCT ATGGACTACT GGGGTCAAGG
361 AACCTCGGTC ACCGTCTCCA GT
```

Amino acid sequence:

SEQ ID NO: 78 EVQLQQPGAELVRPGTSVKLSCKASGYTFTSYWMHWVKQRPGQGLEWIGILDPSDSY
TTYNQKFKGKATLTVDTSSSIAYMQLSSLTSEDSALYYCARGGDYDEGGAMDYWGQ
GTSVTVSS

SEQ ID NO: 79 CDR1:      SYWMH

SEQ ID NO: 80 CDR2:      ILDPSDSYTTYNQKFKG

SEQ ID NO: 81 CDR3:      GGDYDEGGAMDY

Fig. 16B(e)

SEQ ID NO: 82 MF3307: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 GCACTGGGTG CGACAGGCCC CTGGACAAGG GCTTGAGTGG ATGGGATGGA TCAACCCTAA
181 CAGTGGTGGC ACAAACTATG CACAGAAGTT TCAGGGCAGG GTCACGATGA CCAGGGACAC
241 GTCCATCAGC ACAGCCTACA TGGAGCTGAG CAGGCTGAGA TCTGACGACA CGGCCGTGTA
301 TTACTGTGCA AGAGGTTCTC GTAAACGTCT GTCTAACTAC TTCAACGCCT TTGATTATTG
361 GGGCCAAGGT ACCCTGGTCA CCGTCTCCAG T
```

Amino acid sequence:

SEQ ID NO: 83 QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARGSRKRLSNYFNAFDYWGQGTLVTVSS

SEQ ID NO: 84 CDR1:   GYYMH

SEQ ID NO: 85 CDR2:   WINPNSGGTNYAQKFQG

SEQ ID NO: 86 CDR3:   GSRKRLSNYFNAFDY

Fig. 16C a) Common Light Chain

SEQ ID NO: 87 DIQMTQSPSSLSASVGDRVTITCRASQSISSYLNWYQQKPGKAPKLLIYAASSLQSGVP
SRFSGSGSGTDFTLTISSLQPEDFATYYCQQSYSTPPTFGQGTKVEIKRTVAAPSVFIFP
PSDEQLKSGTASVVCLLNNFYPREAKVQWKVDNALQSGNSQESVTEQDSKDSTYSLS
STLTLSKADYEKHKVYACEVTHQGLSSPVTKSFNRGEC

Fig. 16D heavy chain for erbB-2 binding

SEQ ID NO: 88 QVQLVQSGAEVKKPGASVKLSCKASGYTFTAYYINWVRQAPGQGLEWIGRIYPGSGY
TSYAQKFQGRATLTADESTSTAYMELSSLRSEDTAVYFCARPPVYYDSAWFAYWGQG
TLVTVSSASTKGPSVFPLAPSSKSTSGGTAALGCLVKDYFPEPVTVSWNSGALTSGVH
TFPAVLQSSGLYSLSSVVTVPSSSLGTQTYICNVNHKPSNTKVDKRVEPKSCDKTHTC
PPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAK
GQPREPQVYTDPPSREEMTKNQVSLTCEVKGFYPSDIAVEWESNGQPENNYKTTPPV
LDSDGSFFLYSKLTVDKSRWQQGNVFSCSVMHEALHNHYTQKSLSLSPG heavy chain for erbB-3 binding SEQ ID NO: 89 QVQLVQSGAEVKKPGASVKVSCKASGYTFTGYYMHWVRQAPGQGLEWMGWINPNS
GGTNYAQKFQGRVTMTRDTSISTAYMELSRLRSDDTAVYYCARDHGSRHFWSYWGF
DYWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPI
EKTISKAKGQPREPQVYTKPPSREEMTKNQVSLKCLVKGFYPSDIAVEWESNGQPEN
NYKTTPPVLDSDGSFFLYSKLTVDKSRWQQGNVFSCSVMHEALHNHYTQKSLSLSPG

Fig. 16E(a)

HER2-specific Ab sequences

SEQ ID NO: 90 MF2889: heavy chain variable region sequence of an erbB-2 binding antibody Nucleic acid sequence (underlined sequence encodes end of leader peptide):

```
  1   GGCCCAGCCG GCCATGGCCG AGGTCCAGCT GCAGCAGTCT GGAGCTGAGC TGGTAAGGCC
 61   TGGGACTTCA GTGAAGGTGT CCTGCAAGGC TTCTGGATAC GCCTTCACTA ATTATTTGAT
121   AGAGTGGGTA AAGCAGAGGC CTGGCCAGGG CCTTGAGTGG ATTGGAGTGA TTTATCCTGA
181   AGGTGGTGGT ACTATCTACA ATGAGAAGTT CAAGGGCAAG GCAACACTGA CTGCAGACAA
241   ATCCTCCAGC ACTGCCTACA TGCAGCTCAG CGGCCTGACA TCTGAGGACT CTGCGGTCTA
301   TTTCTGTGCA AGAGGAGACT ATGATTACAA ATATGCTATG GACTACTGGG GTCAAGGAAC
361   CTCCGTCACC GTCTCCACT
```

Amino acid sequence:

SEQ ID NO: 91 EVQLQQSGAELVRPGTSVKVSCKASGYAFTNYLIEWVKQRPGQGLEWIGVIYPEGGG
TIYNEKFKGKATLTADKSSSTAYMQLSGLTSEDSAVYFCARGDYDYKYAMDYWGQG
TSVTVSS

SEQ ID NO: 92 CDR1:      NYLIE

SEQ ID NO: 93 CDR2:      VIYPEGGGTIYNEKFKG

SEQ ID NO: 94 CDR3:      GDYDYKYAMDY

Fig. 16E(b)

SEQ ID NO: 95 MF2913: heavy chain variable region sequence of an erbB-2 binding antibody Nucleic acid sequence (underlined sequence encodes end of leader peptide):

```
  1 GGCCCAGCCG GCCATGGCCG AGGTCAAGCT GCAGCAGTCT GGACCTGAGC TGGTGAAGCC
 61 TGGCGCTTCA GTGAAGATAT CCTGCAAGGC TTCTGGTTAC TCATTCACTG ACTACAAAAT
121 GGACTGGGTG AAGCAGAGCC ATGGAAAGAG CCTCGAATGG ATTGGAAATA TTAATCCTAA
181 CAGTGGTGGT GTTATCTACA ACCAGAAGTT CAGGGGCAAG GTCACATTGA CTGTTGACAG
241 GTCCTCCAGC GCAGCCTACA TGGAGCTCCG CAGCCTGACA TCTGAGGACA CTGCAGTCTA
301 TTATTGTTCA AGAGGACTGT GGGATGCTAT GGACTCCTGG GGTCAAGGAA CCTCGGTCAC
361 CGTCTCCAGT
```

Amino acid sequence:

SEQ ID NO: 96 EVKLQQSGPELVKPGASVKISCKASGYSFTDYKMDWVKQSHGKSLEWIGNINPNSGG
VIYNQKFRGKVTLTVDRSSSAAYMELRSLTSEDTAVYYCSRGLWDAMDSWGQGTSVT
VSS

SEQ ID NO: 97 CDR1:    DYKMDWVKQSHGKSLE

SEQ ID NO: 98 CDR2:    NQKFRG

SEQ ID NO: 99 CDR3:    GLWDAMDS

Fig. 16E(c)

SEQ ID NO: 100 MF1847: heavy chain variable region sequence of an erbB-2 binding antibody Nucleic acid sequence (underlined sequence encodes end of leader peptide):

```
  1   GGCCCAGCCG GCCATGGCCC AGGTGCAGCT GGTGGAGTCT GGGGGAGGCG TGGTCCAGCC
 61   TGGGAGGTCC CTGAGACTCT CCTGTGCAGC CTCTGGATTC ACCTTCAGTA GCTATGGCAT
121   GCACTGGGTC CGCCAGGCTC CAGGCAAGGG GCTGGAGTGG GTGGCAGTTA TATCATATGA
181   TGGAAGTAAT AAATACTATG CAGACTCCGT GAAGGGCCGA TTCACCATCT CCAGAGACAA
241   TTCCAAGAAC ACGCTGTATC TGCAAATGAA CAGCCTGAGA GCTGAGGACA CGGCCGTGTA
301   TTACTGTGCA AAAGGTTGGT GGCATCCCCT GCTGTCTGGC TTTGATTATT GGGGCCAAGG
361   TACCCTGGTC ACCGTCTCCA GT
```

Amino acid sequence:

SEQ ID NO: 101 QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKGWWHPLLSGFDYWG
QGTLVTVSS

| | | |
|---|---|---|
| SEQ ID NO: 102 | CDR1: | SYGMH |
| SEQ ID NO: 103 | CDR2: | VISYDGSNKYYADSVKG |
| SEQ ID NO: 104 | CDR3: | GWWHPLLSGFDY |

Fig. 16E(d)

SEQ ID NO: 105 MF3001: heavy chain variable region sequence of an erbB-2 binding antibody Nucleic acid sequence (underlined sequence encodes end of leader peptide):

```
  1  GGCCCAGCCG GCCATGGCCG AGGTCCAGCT GCAGCAGTCT GGGGCTGAAC TGGCAAAACC

61  TGGGGCCTCA GTGAAGCTGT CCTGCAACAC TTCTGGCTAC AACTTTCCTA TCTACTGGAT

121  GCACTGGGTA AAACAGAGGC CTGGACGGGG TCTGGAATGG ATTGGATACA TTAATCCTAG

181  TACTGGTTAT ATTAAGAACA ATCAGAAGTT CAAGGACAAG GCCACCTTGA CTGCAGACAA

241  ATCCTCCAAC ACAGCCTACA TGCAGCTGAA CAGCCTGACA TATGAGGACT CTGCAGTCTA

301  TTACTGTACA AGAGAAGGGA TAACTGGGTT TACTTACTGG GGCCAAGGGA CTCTGGTCAC

361  CGTCTCCAGT
```

Amino acid sequence:

SEQ ID NO: 106 EVQLQQSGAELAKPGASVKLSCKTSGYNFPIYWMHWVKQRPGRGLEWIGYINPSTGY
IKNNQKFKDKATLTADKSSNTAYMQLNSLTYEDSAVYYCTREGITGFTYWGQGTLVT
VSS

SEQ ID NO: 107 CDR1:        IYWMHWVKQRPGRGLE

SEQ ID NO: 108 CDR2:        NQKFKD

SEQ ID NO: 109 CDR3:        EGITGFTY

Fig. 16E(e)

SEQ ID NO: 110 MF1898: heavy chain variable region sequence of an erbB-2 binding antibody Nucleic acid sequence (underlined sequence encodes end of leader peptide):

```
  1  GGCCCAGCCG GCCATGGCCC AGGTGCAGCT GGTGGAGTCT GGGGGAGGCG TGGTCCAGCC

61  TGGGAGGTCC CTGAGACTCT CCTGTGCAGC CTCTGGATTC ACCTTCAGTA GCTATGGCAT

121  GCACTGGGTC CGCCAGGCTC CAGGCAAGGG GCTGGAGTGG GTGGCAGTTA TATCATATGA

181  TGGAAGTAAT AAATACTATG CAGACTCCGT GAAGGGCCGA TTCACCATCT CCAGAGACAA

241  TTCCAAGAAC ACGCTGTATC TGCAAATGAA CAGCCTGAGA GCTGAGGACA CGGCCGTGTA

301  TTACTGTGCA AAAGATGGTT TCCGTCGTAC TACTCTGTCT GGCTTTGATT ATTGGGGCCA

361  AGGTACCCTG GTCACCGTCT CCAGT
```

Amino acid sequence:

SEQ ID NO: 111 QVQLVESGGGVVQPGRSLRLSCAASGFTFSSYGMHWVRQAPGKGLEWVAVISYDGS
NKYYADSVKGRFTISRDNSKNTLYLQMNSLRAEDTAVYYCAKDGFRRTTLSGFDYW
GQGTLVTVSS

SEQ ID NO: 112 CDR1: SYGMH

SEQ ID NO: 113 CDR2: VISYDGSNKYYADSVKG

SEQ ID NO: 114 CDR3: DGFRRTTLSGFDY

Fig. 16E(f)

SEQ ID NO: 115 MF3003 heavy chain variable region sequence of an erbB-2 binding antibody Nucleic acid sequence (underlined sequence encodes end of leader peptide):

```
  1  GGCCCAGCCG GCCATGGCCC AGGTGCAGCT GAAGCAGTCT GGACCTGAGC TGGTGAAGCC
 61  TGGGGCCTCA GTGAAGATTT CCTGCAAGGC TTCTGGCGAC GCATTCAGTT ACTCCTGGAT
121  GAACTGGGTG AAGCAGAGGC CTGGAAAGGG TCTTGAGTGG ATTGGACGGA TTTATCCTGG
181  AGATGGAGAT ATTAACTACA ATGGAAGTT CAAGGGCAAG GCCACACTGA CTGCAGACAA
241  ATCCTCCAGC ACAGCCCACC TGCAACTCAA CAGCCTGACA TCTGAGGACT CTGCGGTCTA
301  CTTCTGTGCA AGAGGACAGC TCGGACTAGA GGCCTGGTTT GCTTATTGGG GCCAGGGGAC
361  TCTGGTCACC GTCTCCAGT
```

Amino acid sequence:

SEQ ID NO: 116 QVQLKQSGPELVKPGASVKISCKASGDAFSYSWMNWVKQRPGKGLEWIGRIYPGDG
DINYNGKFKGKATLTADKSSSTAHLQLNSLTSEDSAVYFCARGQLGLEAWFAYWGQ
GTLVTVSS

SEQ ID NO: 117 CDR1: YSWMNWVKQRPGKGLE

SEQ ID NO: 118 CDR2: NGKFKG

SEQ ID NO: 119 CDR3: GQLGLEAWFAY

Fig. 16E(g)

HER3-specific Ab sequences

SEQ ID NO: 120 MF6058: heavy chain variable region sequence of an erbB-3 binding antibody Nucleic acid sequence (underlined sequence encodes end of leader peptide):

```
  1 CCCCCAGCCG GCCATGGCCC ACCTGCACCT GGTCCACTCT GGGCTCACG TCAACAAGCC
 61 TGGGGCCTCA GTGAAGGTCA CGTGCAAGGC TTCTGGATAC ACCTTCACCG GCTACTATAT
121 GCACTGGGTG CGACAGGCCC CTGGACAAGC TCTTGAGTGG ATGGGATGGA TCAACCCTCA
181 AAGTCGTGGC ACAAACTATG CAAACAACTT TCACGGCAGG GTCTCTATGA CCACGCACAC
241 GTCCACAAGC ACAGCCTACA TGCAGCTGAG CAGGCTGAGA TCTGACGACA CGGCTACGTA
301 TTACTGTGCA AGAGATCATG GTTCTCGTCA TTTCTGGTCT TACTGGGGCT TGATTATTG
361 GGGCCAAGGT ACCCTGGTCA CCGTCTCCAG T
```

Amino acid sequence:

SEQ ID NO: 121 QVQLVQSGADVKKPGASVKVTCKASGYTFTGYYMHWVRQAPGQALEWMGWINPQS
GGTNYAKKFQGRVSMTRETSTSTAYMQLSRLRSDDTATYYCARDHGSRHFWSYWGF
DYWGQGTLVTVSS

| | | |
|---|---|---|
| SEQ ID NO: 122 CDR1: | GYYMH | |
| SEQ ID NO: 123 CDR2: | WINPQSGGTNYAKKFQG | |
| SEQ ID NO: 124 CDR3: | DHGSRHFWSYWGFDY | |

Fig. 16E(h)

SEQ ID NO: 125 MF6061: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCG GCTACTATAT
121 CCACTGGGTG CGACAGGCCC CTCCACAACG CCTTGACTGG ATGGGATGGA TCAACCCTCA
181 GAGTGGTGGC ACAAACTATG CACAGAAGTT TAAGGGCAGG GTCACGATGA CCAGGGACAC
241 GTCCACCAGC ACAGCCTACA TGGAGCTGAG CAGGCTGAGA TCTGACGACA CGGCTGTGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence:

SEQ ID NO: 126 QVQLVQSGAEVKKPGASVKVSCKASGYTFTGYYMHWVRQAPGQGLEWMGWINPQS
GGTNYAQKFKGRVTMTRDTSTSTAYMELSRLRSDDTAVYYCARDHGSRHFWSYWGF
DYWGQGTLVTVSS

| | | |
|---|---|---|
| SEQ ID NO: 127 | CDR1: | GYYMH |
| SEQ ID NO: 128 | CDR2: | WINPQSGGTNYAQKFKG |
| SEQ ID NO: 129 | CDR3: | DHGSRHFWSYWGFDY |

Fig. 16E(i)

SEQ ID NO: 130 MF6065: heavy chain variable region sequence of an erbB-3 binding antibody Nucleic acid sequence (underlined sequence encodes end of leader peptide):

```
  1 GGCCCAGCCG GCCATGGCCC AGGTGCAGCT GGTGCAGTCT GGGGCTGAGG TGAAGAAGCC
 61 TGGGGCCTCA GTGAAGGTCT CCTGCAAGGC TTCTGGATAC ACCTTCACCT CTTACTATAT
121 GCACTGGGTG CGACACGCCC CTCCACAACG CCTTGACTGG ATGGGATGGA TCAACCCTCA
181 GGGGGGTTCT ACAAACTATG CACAGAAGTT TCAGGGCAGG GTCACGATGA CCAGGGACAC
241 GTCCACCAGC ACAGTGTACA TGGAGCTGAG CAGGCTGAGA TCTGAGGACA CGGCTGTGTA
301 TTACTGTGCA AGAGATCATG GTTCTCGTCA TTTCTGGTCT TACTGGGGCT TTGATTATTG
361 GGGCCAAGGT ACCCTGGTCA CCGTCTCCAG T
```

Amino acid sequence:

SEQ ID NO: 131 QVQLVQSGAEVKKPGASVKVSCKASGYTFTSYYMHWVRQAPGQGLEWMGWINPQG
GSTNYAQKFQGRVTMTRDTSTSTVYMELSRLRSEDTAVYYCARDHGSRHFWSYWGF
DYWGQGTLVTVSS

SEQ ID NO: 132 CDR1:    SYYMH

SEQ ID NO: 133 CDR2:    WINPQGGSTNYAQKFQG

SEQ ID NO: 134 CDR3:    DHGSRHFWSYWGFDY 139 186
SEQ ID NO: 135 LCYQDTILWKD*IFHKNNQL*ALTLIDTNRSRACHPCSPMCKGSRCWGES

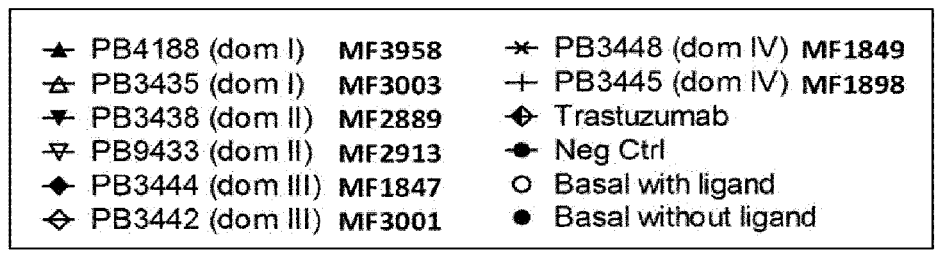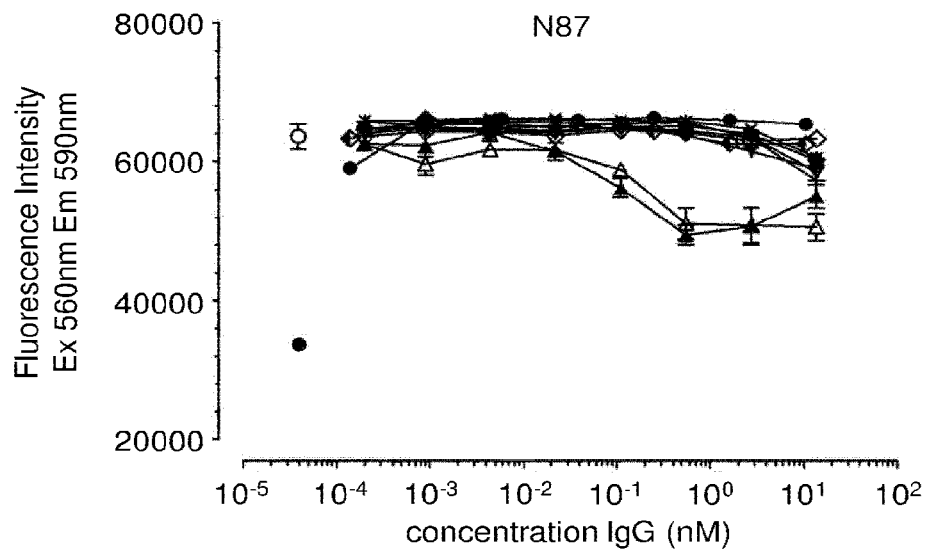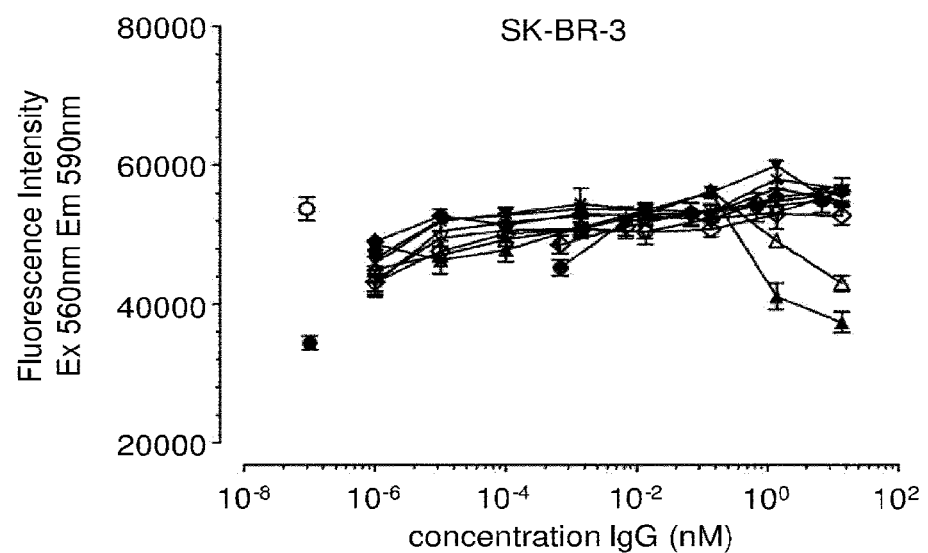
Fig. 28A

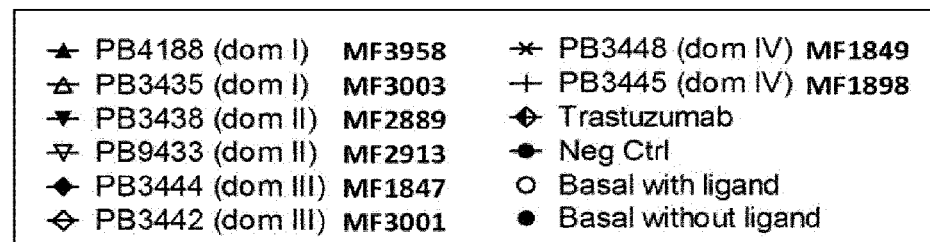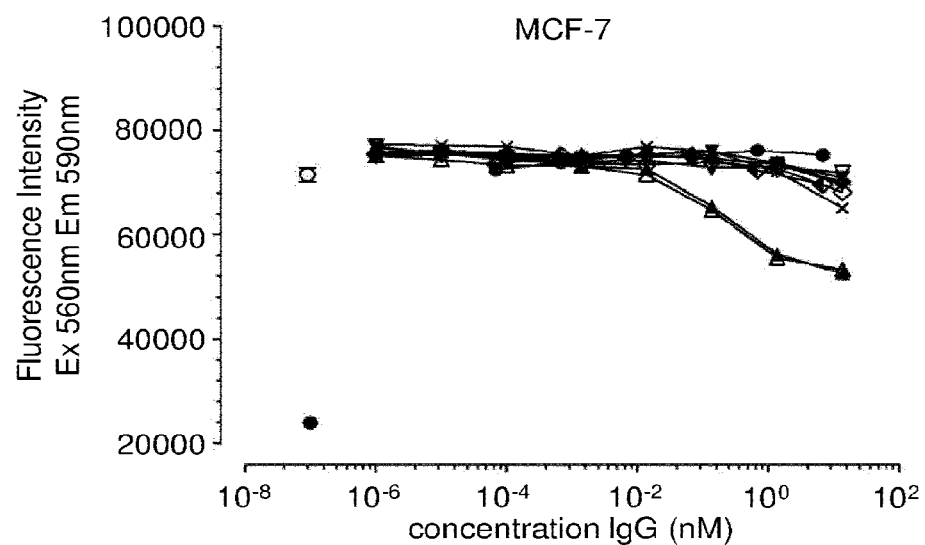
Fig. 28B

Fig. 37A

Amino acid alignment of MF3178 variants

```
                                              CDR1                            CDR2
               1         10        20        30        40        50        60
SEQ ID NO: 62  MF3178  QVQLVQSGAEVKKPGASVKVSCKASGYTFT GYYMH WVRQAPGQGLEWMG WINPNSGGTNYAQKFQG
SEQ ID NO: 136 MF6055  .........D....................      .....A.....   ....S.......K....
SEQ ID NO: 138 MF6056  .........D.........T..........      .....A.....   ....S.......K....
SEQ ID NO: 140 MF6057  .........D.........T..........      ...........   ....Q............
SEQ ID NO: 142 MF6058  .........D.........T..........      .....A.....   ....Q.......K....
SEQ ID NO: 144 MF6059  ..............................      ...........   ....G..S.........
SEQ ID NO: 146 MF6060  .........D....................      .....A.....   ....Q.......K....
SEQ ID NO: 148 MF6061  ..............................      ...........   ....Q...........K.
SEQ ID NO: 150 MF6062  ..............................      ...........   ....G..S.........
SEQ ID NO: 152 MF6063  ..............................      ...........   ....Q.......K....
SEQ ID NO: 154 MF6064  ..............................      .......K...   ....Q............
SEQ ID NO: 156 MF6065  .............................. S...  ...........   ....QG.S.........
SEQ ID NO: 158 MF6066  ..............................      ...........   ....Q..S.........
SEQ ID NO: 160 MF6067  ..............................      ...........   ....Q............
SEQ ID NO: 162 MF6068  ..............................      ...........   ....Q............
SEQ ID NO: 164 MF6069  ..............................      ...........   ....Q............
SEQ ID NO: 166 MF6070  .............................. S...  ...........   ....SG.S.........
SEQ ID NO: 168 MF6071  ..............................      ...........   ....S..S.........
SEQ ID NO: 170 MF6072  ..............................      ...........   ....S............
SEQ ID NO: 172 MF6073  ..............................      ...........   ....S............
SEQ ID NO: 174 MF6074  ..............................      ...........   ....S............

CDR3
               70        80        90        100       110       120
SEQ ID NO: 62  MF3178  RVTMTRDTSISTAYMELSRLRSDDTAVYYCAR DHGSRHFWSYWGFDY WGQGTLVTVSS
SEQ ID NO: 136 MF6055  ......E..T.................T.....                ...........
SEQ ID NO: 138 MF6056  ..S...E..T.....Q........T........                ...........
SEQ ID NO: 140 MF6057  ...............Q.................                ...........
SEQ ID NO: 142 MF6058  ..S...E..T.....Q........T........                ...........
SEQ ID NO: 144 MF6059  .................................                ...........
SEQ ID NO: 146 MF6060  ......E..T.................T.....                ...........
SEQ ID NO: 148 MF6061  .........T.......................                ...........
SEQ ID NO: 150 MF6062  .........T.......................                ...........
SEQ ID NO: 152 MF6063  .........T.......................                ...........
SEQ ID NO: 154 MF6064  .........T.......................                ...........
SEQ ID NO: 156 MF6065  .........T..V........E............               ...........
SEQ ID NO: 158 MF6066  .........T......S...E.............               ...........
SEQ ID NO: 160 MF6067  .........T..V...S.................               ...........
SEQ ID NO: 162 MF6068  .........T........................               ...........
SEQ ID NO: 164 MF6069  ..................................               ...........
SEQ ID NO: 166 MF6070  .........T..V........E............               ...........
SEQ ID NO: 168 MF6071  .........T......S...E.............               ...........
SEQ ID NO: 170 MF6072  .........T..V...S.................               ...........
SEQ ID NO: 172 MF6073  .........T........................               ...........
SEQ ID NO: 174 MF6074  ..................................               ...........
```

Fig. 37B

**Nucleic acid alignment of MF3178 variants (*without* end of leader sequence)**

```
SEQ ID NO: 62   MF3178   CAGGTGCAGCTGGTGCAGTCTGGGGCTGAGGTGAAGAAGCCTGGGGCCTCAGTGAAGGTCTCCTGCAAG
SEQ ID NO: 142  MF6058   ................................C............................A.G......
SEQ ID NO: 150  MF6061   .........................................................................
SEQ ID NO: 156  MF6065   .........................................................................

CDR1
SEQ ID NO: 62   MF3178   GCTTCTGGATACACCTTCACC  GGCTACTATATGCAC  TGGGTGCGACAGGCCCCTGGACAAGGGCTTG
SEQ ID NO: 142  MF6058   .....................  ...............  ..............................CT....
SEQ ID NO: 150  MF6061   .....................  ...............  .....................................
SEQ ID NO: 156  MF6065   .....................  TCT............  .....................................

CDR2
SEQ ID NO: 62   MF3178   AGTGGATGGGA  TGGATCAACCCTAACAGTGGTGGCACAAACTATGCACAGAAGTTTCAGGGC  AGGGT
SEQ ID NO: 142  MF6058   ...........  .............C.A....................A.................  .....
SEQ ID NO: 150  MF6061   ...........  .............C.G....................A.................  .....
SEQ ID NO: 156  MF6065   ...........  .............C.GG.G...TCT..............................  .....

SEQ ID NO: 62   MF3178   CACGATGACCAGGGACACGTCCATCAGCACAGCCTACATGGAGCTGAGCAGGCTGAGATCTGACGACAC
SEQ ID NO: 142  MF6058   .T.T.........G.......CA.................C...........................
SEQ ID NO: 150  MF6061   .....................C...............................................
SEQ ID NO: 156  MF6065   .....................C........TG................................G.....

CDR3
SEQ ID NO: 62   MF3178   GGCTGTGTATTACTGTGCAAGA  GATCATGGTTCTCGTCATTTCTGGTCTTACTGGGGCTTTGATTAT
SEQ ID NO: 142  MF6058   ....AC................  .............................................
SEQ ID NO: 150  MF6061   ......................  .............................................
SEQ ID NO: 156  MF6065   ......................  .............................................

SEQ ID NO: 62   MF3178   TGGGGCCAAGGTACCCTGGTCACCGTCTCCAGT
SEQ ID NO: 142  MF6058   .................................
SEQ ID NO: 150  MF6061   .................................
SEQ ID NO: 156  MF6065   .................................
```

Fig. 37C

DNA sequences of MF3178 variants (without end of leader sequence)

SEQ ID NO: 136 MF6055

```
>MF6055_VH
caggtgcagctggtgcagtctggggctgacgtgaagaagcctggggcctcagtgaaggtctcctgcaagg
cttctggatacaccttcaccggctactatatgcactgggtgcgacaggcccctggacaagctcttgagtg
gatgggatggatcaacccttctagtggtggcacaaactatgcaaagaagtttcagggcagggtcacgatg
accagggagacgtccacaagcacagcctacatggagctgagcaggctgagatctgacgacacggctacgt
attactgtgcaagagatcatggttctcgtcatttctggtcttactgggctttgattattggggccaagg
tacctggtcaccgtctccagt
```

SEQ ID NO: 138 MF6056

```
>MF6056_VH
caggtgcagctggtgcagtctggggctgacgtgaagaagcctggggcctcagtgaaggtcacgtgcaagg
cttctggatacaccttcaccggctactatatgcactgggtgcgacaggcccctggacaagctcttgagtg
gatgggatggatcaacccttctagtggtggcacaaactatgcaaagaagtttcagggcagggtctctatg
accagggagacgtccacaagcacagcctacatgcagctgagcaggctgagatctgacgacacggctacgt
attactgtgcaagagatcatggttctcgtcatttctggtcttactgggctttgattattggggccaagg
tacctggtcaccgtctccagt
```

SEQ ID NO: 140 MF6057

```
>MF6057_VH
caggtgcagctggtgcagtctggggctgatgtgaagaagcctggggcctcagtgaaggtcacgtgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccatcagcacagcctacatgcagctgagcaggctgagatctgacgacacggctgtgt
attactgtgcaagagatcatggttctcgtcatttctggtcttactgggctttgattattggggccaagg
tacctggtcaccgtctccagt
```

SEQ ID NO: 142 MF6058

```
>MF6058_VH
caggtgcagctggtgcagtctggggctgacgtgaagaagcctggggcctcagtgaaggtcacgtgcaagg
cttctggatacaccttcaccggctactatatgcactgggtgcgacaggcccctggacaagctcttgagtg
gatgggatggatcaaccctcaaagtggtggcacaaactatgcaaagaagtttcagggcagggtctctatg
accagggagacgtccacaagcacagcctacatgcagctgagcaggctgagatctgacgacacggctacgt
attactgtgcaagagatcatggttctcgtcatttctggtcttactgggctttgattattggggccaagg
tacctggtcaccgtctccagt
```

Fig. 37D

SEQ ID NO: 144 MF6059

>MF6059_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctggcagtggttctacaaactatgcacagaagtttcagggcagggtcacgatg
accagggacacgtccatcagcacagcctacatggagctgagcaggctgagatctgacgacacggctgtgt
attactgtgcaagagatcatggttctcgtcatttctggtcttactgggctttgattattggggccaagg
taccctggtcaccgtctccagt

SEQ ID NO: 146 MF6060

>MF6060_VH
caggtgcagctggtgcagtctggggctgacgtgaagaagcctggggcctcagtgaaggtctcctgcaagg
cttctggatacaccttcaccggctactatatgcactgggtgcgacaggcccctggacaagctcttgagtg
gatgggatggatcaaccctaaagtggtggcacaaactatgcaaagaagtttcagggcagggtcacgatg
accagggagacgtccacaagcacagcctacatggagctgagcaggctgagatctgacgacacggctacgt
attactgtgcaagagatcatggttctcgtcatttctggtcttactgggctttgattattggggccaagg
taccctggtcaccgtctccagt

SEQ ID NO: 148 MF6061

>MF6061_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttaagggcagggtcacgatg
accagggacacgtccaccagcacagcctacatggagctgagcaggctgagatctgacgacacggctgtgt
attactgtgcaagagatcatggttctcgtcatttctggtcttactgggctttgattattggggccaagg
taccctggtcaccgtctccagt

SEQ ID NO: 150 MF6062

>MF6062_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctggcagtggttctacaaactatgcacagaagtttcagggcagggtcacgatg
accagggacacgtccacaagcacagcctacatggagctgagcaggctgagatctgacgacacggctgtgt
attactgtgcaagagatcatggttctcgtcatttctggtcttactgggctttgattattggggccaagg
taccctggtcaccgtctccagt

Fig. 37E

SEQ ID NO: 152 MF6063

>MF6063_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcaaagaagtttcagggcagggtcacgatg
accagggacacgtccaccagcacagcctacatggagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 154 MF6064

>MF6064_VH
caggtgcagctggtgcagtctggggctgaggtgaagaagcctggggcctcagtgaaggtctcctgcaagg
cttctggatacaccttcaccggctactatatgcactgggtgcgacaggcccctggaaagggcttgagtg
gatgggatggatcaaccctcagagtggtggcacaaactatgcacagaagtttcagggcagggtcacgatg
accagggacacgtccacgagcacagcctacatggagctgagcaggctgagatctgacgacacggctgtgt
attactgtgcaagagatcatggttctcgtcatttctggtcttactggggctttgattattggggccaagg
taccctggtcaccgtctccagt

SEQ ID NO: 156 MF6065

>MF6065_VH
caggtgcagctggtgcagtctggggctgaggtgaagaagcctggggcctcagtgaaggtctcctgcaagg
cttctggatacaccttcacctcttactatatgcactgggtgcgacaggcccctggacaagggcttgagtg
gatgggatggatcaaccctcaggggggttctacaaactatgcacagaagtttcagggcagggtcacgatg
accagggacacgtccaccagcacagtgtacatggagctgagcaggctgagatctgaggacacggctgtgt
attactgtgcaagagatcatggttctcgtcatttctggtcttactggggctttgattattggggccaagg
taccctggtcaccgtctccagt

SEQ ID NO: 158 MF6066

>MF6066_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggttctacaaactatgcacagaagtttcagggcagggtcacgatg
accagggacacgtccaccagcacagcctacatggagctgagctctgagatctgaggacacggctgtgt
attactgtgcaagagatcatggttctcgtcatttctggtcttactggggctttgattattggggccaagg
taccctggtcaccgtctccagt

Fig. 37F

SEQ ID NO: 160 MF6067

>MF6067_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccaccagcacagtctacatggagctgagctctctgagatctgacgacacggctgtgt
attactgtgcaagagatcatggttctcgtcatttctggtcttactggggcttttgattattggggccaagg
taccctggtcaccgtctccagt

SEQ ID NO: 162 MF6068

>MF6068_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccaccagcacagcctacatggagctgagcaggctgagatctgacgacacggctgtgt
attactgtgcaagagatcatggttctcgtcatttctggtcttactgggctttgattattgggccaagg
taccctggtcaccgtctccagt

SEQ ID NO: 164 MF6069

>MF6069_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctcagagtggtggcacaaactatgcacagaagtttcagggcagggtcacgatg
accagggacacgtccatcagcacagcctacatggagctgagcaggctgagatctgacgacacggctgtgt
attactgtgcaagagatcatggttctcgtcatttctggtcttactggggctttgattattgggccaagg
taccctggtcaccgtctccagt

SEQ ID NO: 166 MF6070

>MF6070_VH
caggtgcagctggtgcagtctggggctgaggtgaagaagcctggggcctcagtgaaggtctcctgcaagg
cttctggatacaccttcacctcttactatatgcactgggtgcgacaggcccctggacaagggcttgagtg
gatgggatggatcaaccttctgggggttctacaaactatgcacagaagtttcagggcagggtcacgatg
accagggacacgtccaccagcacagtgtacatggagctgagcaggctgagatctgaggacacggctgtgt
attactgtgcaagagatcatggttctcgtcatttctggtcttactggggctttgattattgggccaagg
taccctggtcaccgtctccagt

Fig. 37G

SEQ ID NO: 168 MF6071

>MF6071_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccttctagtggttctacaaactatgcacagaagtttcagggcagggtcacgatg
accagggacacgtccaccagcacagcctacatggagctgagctctctgagatctgaggacacggctgtgt
attactgtgcaagagatcatggttctcgtcatttctggtcttactgggcttt gattattggggccaagg
taccctggtcaccgtctccagt

SEQ ID NO: 170 MF6072

>MF6072_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccctctagtggtggcacaaactatgcacagaagtttcagggcagggtcacgatg
accagggacacgtccaccagcacagtctacatggagctgagctctctgagatctgacgacacggctgtgt
attactgtgcaagagatcatggttctcgtcatttctggtcttactgggcttt gattattggggccaagg
taccctggtcaccgtctccagt

SEQ ID NO: 172 MF6073

>MF6073_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccttctagtggtggcacaaactatgcacagaagtttcagggcagggtcacgatg
accagggacacgtccaccagcacagcctacatggagctgagcaggctgagatctgacgacacggctgtgt
attactgtgcaagagatcatggttctcgtcatttctggtcttactgggcttt gattattggggccaagg
taccctggtcaccgtctccagt

SEQ ID NO: 174 MF6074

>MF6074_VH
caggtgcagctggtgcagtctggggctgaggtgaagaagcctggggcctcagtgaaggtctcctgcaagg
cttctggatacaccttcaccggctactatatgcactgggtgcgacaggcccctggacaagggcttgagtg
gatgggatggatcaaccttctagtggtggcacaaactatgcacagaagtttcagggcagggtcacgatg
accagggacacgtccatcagcacagcctacatggagctgagcaggctgagatctgacgacacggctgtgt
attactgtgcaagagatcatggttctcgtcatttctggtcttactgggcttt gattattggggccaagg
taccctggtcaccgtctccagt

ANTIBODY THAT BINDS ERBB-2 AND ERBB-3

REFERENCE TO SEQUENCE LISTING SUBMITTED ELECTRONICALLY

The content of the electronically submitted sequence listing (Name 4096.0100002_ST25.txt: Size: 172032 bytes; and Date of Creation: Apr. 10, 2018) is incorporated herein by reference in its entirety.

The invention relates to the field of antibodies. In particular it relates to the field of therapeutic (human) antibodies for the treatment of diseases involving aberrant cells. More in particular it relates to antibodies that bind ErbB-2 and ErbB-3 and their use in the binding of ErbB-2 and ErbB-3 positive cells, particularly tumor cells.

The human epidermal growth factor receptor family (HER, also collectively referred to as the ErbB signaling network) is a family of transmembrane receptor tyrosine kinases (RTK). The family includes the epidermal growth factor receptor (EGFR), also known as ErbB-1 (or HER1), and the homologous receptors ErbB-2 (HER2), ErbB-3 (HER3) and ErbB-4 (HER4). The receptors (reviewed in Yarden and Pines 2012) are widely expressed on epithelial cells. Upregulation of HER receptors or their ligands, such as heregulin (HRG) or epidermal growth factor (EGF), is a frequent event in human cancer (Wilson, Fridlyand et al. 2012). Overexpression of ErbB-1 and ErbB-2 in particular occurs in epithelial tumors and is associated with tumor invasion, metastasis, resistance to chemotherapy, and poor prognosis (Zhang, Berezov et al. 2007). In the normal breast, ErbB-3 has been shown to be important in the growth and differentiation of luminal epithelium. For instance, loss/inhibition of ErbB-3 results in selective expansion of the basal over the luminal epithelium (Balko, Miller et al. 2012). Binding of ligand to the extracellular domain of the RTKs induces receptor dimerization, both between the same (homodimerization) and different (heterodimerization) receptor subtypes. Dimerization can activate the intracellular tyrosine kinase domains, which undergo autophosphorylation and, in turn, can activate a number of downstream pro-proliferative signaling pathways, including those mediated by mitogen-activated protein kinases (MAPK) and the prosurvival pathway Akt (reviewed in Yarden and Pines, 2012). No specific endogenous ligand has been identified for ErbB-2, which is therefore assumed to normally signal through heterodimerization (Sergina, Rausch et al. 2007). ErbB-3 can be activated by engagement of its ligands. These ligands include but are not limited to neuregulin (NRG) and heregulin (HRG).

Various modes of activation of signaling of the ErbB receptor family have been identified. Among these are ligand dependent and ligand independent activation of signaling. Over-expressed ErbB-2 is able to generate oncogenic signaling through the ErbB-2:ErbB-3 heterodimer even in the absence of the ErbB-3 ligand (Junttila, Akita et al. 2009). ErbB-2 activity can be inhibited by ErbB-2 specific antibodies. Such ErbB-2 specific antibodies are for instance used in the treatment of ErbB-2 positive (HERH2+) tumors. A problem with such treatments is that often tumors escape the ErbB-2 specific treatment and continue to grow even in the presence of the inhibiting antibody. It has been observed that ErbB-2 positive tumors, such as breast, ovarian, cervical and gastric tumors can escape treatment by the selective outgrowth of a subpopulation of tumor cells that exhibit upregulated ErbB-3 expression (Ocana, Vera-Badillo et al. 2013) and/or ErbB-3 ligand expression (Wilson. Fridlyand et al. 2012). Also activating mutations in the ErbB-3 receptor have been identified.

The anti-ErbB-2 monoclonal antibody trastuzumab (HERCEPTINS) and the ErbB-1 specific cetuximab (Erbitux) are among several monoclonal antibodies approved for clinical application. Trastuzumab has a proven survival benefit in metastatic breast cancer (Arteaga, Sliwkowski et al. 2011). The precise mechanism of action of trastuzumab has not been unequivocally established. Suggested modes of action are the inhibition of RTK signaling and the recruitment of antibody dependent cellular cytotoxicity (ADCC). Other mechanisms of action that have been described include blocking proteolytic cleavage of the ErbB-2 extracellular domain, inhibition of angiogenic factors and enhancement of receptor endocytosis. Other agents that interfere with ErbB-2 signaling have been approved or are under development for treatment of breast and other ErbB-2 overexpression cancers. For example, the chemical compound lapatinib inhibits both ErbB-1 and ErbB-2 tyrosine kinase activity and is used in first line treatment of ErbB-2 amplified breast cancer.

In patients with HER2+ metastatic breast cancer, resistance to trastuzumab either as single-agent or in combination with chemotherapy, commonly occurs within months of starting therapy. Only a fraction of patients with HER2+ metastatic breast cancer respond to single agent trastuzumab, suggesting de novo mechanisms of resistance in advanced cancers. These mechanisms include, among others, signaling from other HER family of receptors and compensatory signaling from RTKs outside of the HER family (Thery et al., Resistance to human epidermal growth factor receptor type 2-targeted therapies, Eur J Cancer (2014). Vol. 50, Issue 5, pages 892-901 (ttp://dx.doi.org/10.1016/j.ejca.2014.01.003)). For example, overexpression of HER3 or its ligands along with HER2 leads to the formation of HER-2/HER-3 heterodimers and acquired resistance to trastuzumab. Thus, the antibody trastuzumab is thought to be ineffective in blocking signaling driven by ErbB-3 ligands (Wehrman, Raab et al. 2006, Junttila, Akita et al. 2009, Thery et al. 2014).

Recently the monoclonal antibody pertuzumab was approved for use in combination with trastuzumab on the basis of an extra 5 months progression-free survival benefit (Baselga, Cortes et al. 2012). Pertuzumab also binds ErbB-2 but at a different position than trastuzumab.

Other strategies to treat ErbB-2 positive tumors are directed towards ErbB-3, ErbB-3 binding monoclonal antibodies have demonstrated activity in preclinical studies (Schoeberl, Faber et al. 2010). Some ErbB-3 binding monoclonal antibodies can inhibit proliferation and growth of a variety of cancers.

Another strategy involves binding of both the ErbB-2 and ErbB-3 receptor. The molecule MM-111, is an artificial biological molecule containing two single chain Fv (scFv) fragments that bind ErbB-2 and ErbB-3. The two scFv are associated with a mutated human serum albumin (HSA) protein to increase the half-life of the molecule. In preclinical testing the molecule was shown to inhibit ErbB-3 signaling and proliferation. This effect was predominantly measured on ErbB-3 positive cell lines that expressed relatively high amounts of ErbB-2.

SUMMARY OF THE INVENTION

The invention provides a bispecific antibody comprising a first antigen-binding site that binds ErbB-2 and a second antigen-binding site that binds ErbB-3, and wherein the antibody can reduce a ligand-induced receptor function of ErbB-3 on a ErbB-2 and ErbB-3 positive cell. Said first antigen-binding site is preferably present in a variable domain comprising a VH chain with the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001; MF3003 or MF1898 as depicted in FIG. 16A or FIG. 16E. Said second antigen-binding site is preferably present in a variable domain comprising a VH chain with the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 as depicted in FIG. 16B or FIG. 16E or FIG. 37. The immunoglobulin light chain in the variable domain preferably comprises the amino acid sequence of FIG. 16C.

An antibody of the invention is, unless otherwise specifically specified, preferably a bispecific antibody.

The invention further provides a pharmaceutical composition comprising an antibody according to the invention.

Further provided is an antibody according to the invention that further comprises a label, preferably a label for in vivo imaging.

The invention also provides a method for the treatment of a subject having a ErbB-2, ErbB-3 or ErbB-2/ErbB-3 positive tumor or at risk of having said tumor comprising administering to the subject a bispecific antibody according to the invention. Also provided is a bispecific antibody according to the invention for use in the treatment of a subject having or at risk of having an ErbB-2, ErbB-3 or ErbB-2/ErbB-3 positive tumor.

DETAILED DESCRIPTION OF THE INVENTION

The invention provides a bispecific antibody comprising a first antigen-binding site that binds ErbB-2 and a second antigen-binding site that binds ErbB-3, wherein the bispecific antibody reduces or can reduce a ligand-induced receptor function of ErbB-3 on a ErbB-2 and ErbB-3 positive cell.

As used herein, the term "antigen-binding site" refers to a site derived from and preferably as present on a bispecific antibody which is capable of binding to antigen. An unmodified antigen-binding site is typically formed by and present in the variable domain of the antibody. The variable domain contains said antigen-binding site. A variable domain that binds an antigen is a variable domain comprising an antigen-binding site that binds the antigen.

In one embodiment an antibody variable domain of the invention comprises a heavy chain variable region (VH) and a light chain variable region (VL). The antigen-binding site can be present in the combined VH/VL variable domain, or in only the VH region or only the VL region. When the antigen-binding site is present in only one of the two regions of the variable domain, the counterpart variable region can contribute to the folding and/or stability of the binding variable region, but does not significantly contribute to the binding of the antigen itself.

As used herein, antigen-binding refers to the typical binding capacity of an antibody to its antigen. An antibody comprising an antigen-binding site that binds to ErbB-2, binds to ErbB-2 and, under otherwise identical conditions, at least 100-fold lower to the homologous receptors ErbB-1 and ErbB-4 of the same species. An antibody comprising an antigen-binding site that binds to ErbB-3, binds to ErbB-3 and, under otherwise identical conditions, not to the homologous receptors ErbB-1 and ErbB-4 of the same species. Considering that the ErbB-family is a family of cell surface receptors, the binding is typically assessed on cells that express the receptor(s). Binding of an antibody to an antigen can be assessed in various ways. One way is to incubate the antibody with the antigen (preferably cells expressing the antigen), removing unbound antibody (preferably by a wash step) and detecting bound antibody by means of a labeled antibody that binds to the bound antibody.

Antigen binding by an antibody is typically mediated through the complementarity regions of the antibody and the specific three-dimensional structure of both the antigen and the variable domain allowing these two structures to bind together with precision (an interaction similar to a lock and key), as opposed to random, non-specific sticking of antibodies. As an antibody typically recognizes an epitope of an antigen, and as such epitope may be present in other compounds as well, antibodies according to the present invention that bind ErbB-2 and/or ErbB-3 may recognize other proteins as well, if such other compounds contain the same epitope. Hence, the term "binding" does not exclude binding of the antibodies to another protein or protein(s) that contain the same epitope. Such other protein(s) is preferably not a human protein. An ErbB-2 antigen-binding site and an ErbB-3 antigen-binding site as defined in the present invention typically do not bind to other proteins on the membrane of cells in a post-natal, preferably adult human. A bispecific antibody according to the present invention is typically capable of binding ErbB-2 and ErbB-3 with a binding affinity of at least $1 \times 10e-6$ M, as outlined in more detail below.

The term "interferes with binding" as used herein means that the antibody is directed to an epitope on ErbB-3 and the antibody competes with ligand for binding to ErbB-3. The antibody may diminish ligand binding, displace ligand when this is already bound to ErbB-3 or it may, for instance through steric hindrance, at least partially prevent that ligand can bind to ErbB-3.

The term "antibody" as used herein means a proteinaceous molecule, preferably belonging to the immunoglobulin class of proteins, containing one or more variable domains that bind an epitope on an antigen, where such domains are derived from or share sequence homology with the variable domain of an antibody. Antibodies for therapeutic use are preferably as close to natural antibodies of the subject to be treated as possible (for instance human antibodies for human subjects). Antibody binding can be expressed in terms of specificity and affinity. The specificity determines which antigen or epitope thereof is specifically bound by the binding domain. The affinity is a measure for the strength of binding to a particular antigen or epitope. Specific binding, is defined as binding with affinities (KD) of at least $1 \times 10e-6$ M, more preferably $1 \times 10e-7$ M, more preferably higher than $1 \times 10e-9$ M. Typically, antibodies for therapeutic applications have affinities of up to $1 \times 10e-10$ M or higher. Antibodies such the bispecific antibodies of the present invention comprise the constant domains (Fc part) of a natural antibody. An antibody of the invention is typically a bispecific full length antibody, preferably of the human IgG subclass. Preferably, an antibody of the present invention is of the human IgG1 subclass. Such antibodies of the invention have good ADCC properties, have favorable half life upon in vivo administration to humans and CH3 engineering technology exists that can provide for modified heavy chains that preferentially form heterodimers over homodimers upon co-expression in clonal cells.

An antibody of the invention is preferably a "full length" antibody. The term 'full length' according to the invention is defined as comprising an essentially complete antibody, which however does not necessarily have all functions of an intact antibody. For the avoidance of doubt, a full length antibody contains two heavy and two light chains. Each chain contains constant (C) and variable (V) regions, which can be broken down into domains designated CH1, CH2, CH3, VH, and CL, VL. An antibody binds to antigen via the variable domains contained in the Fab portion, and after binding can interact with molecules and cells of the immune system through the constant domains, mostly through the Fc portion. The terms 'variable domain', 'VH/VL pair'. 'VH/VL' are used herein interchangeably. Full length antibodies according to the invention encompass antibodies wherein mutations may be present that provide desired characteristics. Such mutations should not be deletions of substantial portions of any of the regions. However, antibodies wherein one or several amino acid residues are deleted, without, essentially altering the binding characteristics of the resulting antibody are embraced within the term "full length antibody". For instance, an IgG antibody can have 1-20 amino acid residue insertions, deletions or a combination thereof in the constant region. For instance. ADCC activity of an antibody can be improved when the antibody itself has a low ADCC activity, by slightly modifying the constant region of the antibody (dunttila. T. T., K. Parsons, et al. (2010). "Superior In vivo Efficacy of Afucosylated Trastuzumab in the Treatment of HER2-Amplified Breast Cancer." Cancer Research 70(11): 4481-4489)

Full length IgG antibodies are preferred because of their favourable half life and the need to stay as close to fully autologous (human) molecules for reasons of immunogenicity. An antibody of the invention is preferably a bispecific IgG antibody, preferably a bispecific full length IgG1 antibody. IgG1 is favoured based on its long circulatory half life in man. In order to prevent any immunogenicity in humans it is preferred that the bispecific IgG antibody according to the invention is a human IgG1.

The term 'bispecific' (bs) means that one part of the antibody (as defined above) binds to one epitope on an antigen whereas a second part binds to a different epitope. The different epitope is typically present on a different antigen. According to the present invention, said first and second antigens are in fact two different proteins. A preferred bispecific antibody is an antibody that comprises parts of two different monoclonal antibodies and consequently binds to two different types of antigen. One arm of the bispecific antibody typically contains the variable domain of one antibody and the other arm contains the variable domain of another antibody. The heavy chain variable regions of the bispecific antibody of the invention are typically different from each other, whereas the light chain variable regions are preferably the same in the bispecific antibodies of the invention. A bispecific antibody wherein the different heavy chain variable regions are associated with the same, or a common, light chain is also referred to as a bispecific antibody with a common light chain. Further provided is therefore a bispecific antibody according to the invention, wherein both arms comprise a common light chain.

Preferred bispecific antibodies can be obtained by co-expression of two different heavy chains and a common light chain in a single cell. When wildtype CH3 domains are used, co-expression of two different heavy chains and a common light chain will result in three different species, AA, AB and BB. To increase the percentage of the desired bispecific product (AB) CH3 engineering can be employed, or in other words, one can use heavy chains with compatible heterodimerization domains, as defined hereunder.

The term 'compatible heterodimerization domains' as used herein refers to protein domains that are engineered such that engineered domain A' will preferentially form heterodimers with engineered domain B' and vice versa, whereas homodimerization between A'-A' and B'-B' is diminished.

The term 'common light chain' according to the invention refers to light chains which may be identical or have some amino acid sequence differences while the binding specificity of the full length antibody is not affected. It is for instance possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. The terms 'common light chain', 'common VL', 'single light chain', 'single VL', with or without the addition of the term 'rearranged' are all used herein interchangeably. It is an aspect of the present invention to use as common light chain a human light chain that can combine with different heavy chains to form antibodies with functional antigen binding domains (WO2004/009618, WO2009/157771, Merchant et al. 1998 and Nissim et al. 1994). Preferably, the common light chain has a germline sequence. A preferred germline sequence is a light chain variable region that is frequently used in the human repertoire and has good thermodynamic stability, yield and solubility. A preferred germline light chain is O12, preferably the rearranged germline human kappa light chain IgVκ1-39*01/IGJκ1*01 or a fragment or a functional equivalent (i.e. same IgVκ1-39 gene segment but different IGJκ gene segment) thereof (nomenclature according to the IMGT database worldwide web at imgt.org). Further provided is therefore a bispecific antibody according to the invention, wherein said common light chain is a germline light chain, preferably a rearranged germline human kappa light chain comprising the IgVK1-39 gene segment, most preferably the rearranged germline human kappa light chain igVK1-39*01/IGJK1*01. The terms rearranged germline human kappa light chain IgVK1-39*01/IGJK1*01, IGKV1-39/IGKJ1, huVK1-39 light chain or in short huVK1-39 are used interchangeably throughout the application. Obviously, those of skill in the art will recognize that "common" also refers to functional equivalents of the light chain of which the amino acid sequence is not identical. Many variants of said light chain exist wherein mutations (deletions, substitutions, additions) are present that do not materially influence the formation of functional binding regions. The light chain of the present invention can also be a light chain as specified herein above, having 1-5 amino acid insertions, deletions, substitutions or a combination thereof.

Also contemplated are antibodies wherein a VH is capable of specifically recognizing a first antigen and the VL, paired with the VH in a immunoglobulin variable domain, is capable of specifically recognizing a second antigen. The resulting VH/VL pair will bind either antigen 1 or antigen 2. Such so called "two-in-one antibodies", described in for instance WO 2008/027236. WO 2010/108127 and Schaefer et al (Cancer Cell 20, 472-486, October 2011), are different from bispecific antibodies of the invention and are further referred to as "two-in-one" antibodies. Such "two-in-one" antibodies have identical arms and are not antibodies of the present invention.

The term 'ErbB-2' as used herein refers to the protein that in humans is encoded by the ERBB-2 gene. Alternative names for the gene or protein include CD340; HER-2; HER-2/neu; MLN 19: NEU; NGL; TKR1. The ERBB-2 gene is frequently called HER2 (from human epidermal growth factor receptor 2). Where reference is made herein to ErbB-2, the reference refers to human ErbB-2. An antibody comprising an antigen-binding site that binds ErbB-2, binds human ErbB-2. The ErbB-2 antigen-binding site may, due to sequence and tertiary structure similarity between human and other mammalian orthologs, also bind such an ortholog but not necessarily so. Database accession numbers for the human ErbB-2 protein and the gene encoding it are (NP_001005862.1, NP_004439.2 NC_000017.10 NT_010783.15 NC_018928.2). The accession numbers are primarily given to provide a further method of identification of ErbB-2 as a target, the actual sequence of the ErbB-2 protein bound the antibody may vary, for instance because of a mutation in the encoding gene such as those occurring in some cancers or the like. The ErbB-2 antigen binding site binds ErbB-2 and a variety of variants thereof, such as those expressed by some ErbB-2 positive tumor cells.

The term 'ErbB-3' as used herein refers to the protein that in humans is encoded by the ERBB-3 gene. Alternative names for the gene or protein are HER3; LCCS2; MDA-BF-1; c-ErbB-3; c-erbb-3; erbb-3-S; p180-Erbb-3; p45-sErbb-3: and p85-sErbb-3. Where reference is made herein to ErbB-3, the reference refers to human ErbB-3. An antibody comprising an antigen-binding site that binds ErbB-3, binds human ErbB-3. The ErbB-3 antigen-binding site, may, due to sequence and tertiary structure similarity between human and other mammalian orthologs, also bind such an ortholog but not necessarily so. Database accession numbers for the human ErbB-3 protein and the gene encoding it are (NP_001005915.1 NP_001973.2, NC_000012.11 NC_018923.2 NT_029419.12). The accession numbers are primarily given to provide a further method of identification of ErbB-3 as a target, the actual sequence of the ErbB-3 protein bound by an antibody may vary, for instance because of a mutation in the encoding gene such as those occurring in some cancers or the like. The ErbB-3 antigen binding site binds ErbB-3 and a variety of variants thereof, such as those expressed by some ErbB-2 positive tumor cells.

A bispecific antibody of the invention that comprises a first antigen-binding site that binds ErbB-2 and a second antigen-binding site that binds ErbB-3, can reduce or reduces a ligand-induced receptor function of ErbB-3 on an ErbB-2 and ErbB-3 positive cell. In the presence of excess ErbB-2, ErbB-2/ErbB-3 heterodimers may provide a growth signal to the expressing cell in the absence of detectable ligand for the ErbB-3 chain in the heterodimer. This ErbB-3 receptor function is herein referred as a ligand-independent receptor function of ErbB-3. The ErbB-2/ErbB-3 heterodimer also provide a growth signal to the expressing cell in the presence of an ErbB-3 ligand. This ErbB-3 receptor function is herein referred to as a ligand-induced receptor function of ErbB-3.

The term "ErbB-3 ligand" as used herein refers to polypeptides which bind and activate ErbB-3. Examples of ErbB-3 ligands include, but are not limited to neuregulin 1 (NRG) and neuregulin 2, betacellulin, heparin-binding epidermal growth factor, and epiregulin. The term includes biologically active fragments and/or variants of a naturally occurring polypeptide.

In a preferred embodiment of the invention the ligand-induced receptor function of ErbB-3 is ErbB-3 ligand-induced growth of an ErbB-2 and ErbB-3 positive cell. In a preferred embodiment said cell is an MCF-7 cell (ATCC® HTB-22™); an SKBR3 (ATCC® ITB-30™) cell; an NCI-87 (ATCCS CRL-5822™) cell; a BxPC-3-luc2 cell (Perkin Elmer 125058), a BT-474 cell (ATCC® HTB-20™) or a JIMT-1 cell (DSMZ no.: ACC 589).

In a preferred embodiment the ErbB-2 and ErbB-3 positive cell comprises at least 50.000 ErbB-2 receptors on the cell surface. In a preferred embodiment at least 100.000 ErbB-2 receptors. In one preferred embodiment, the ErbB-2 and ErbB-3 positive cell comprises at least 1.000.000 ErbB-2 receptors on the cell surface. In another preferred embodiment the ErbB-2 and ErbB-3 positive cell comprises no more than 1.000.000 ErbB-2 receptors on the cell surface. Currently used therapies such as trastuzumab (HERCEPTIN®) and pertuzumab are only prescribed for patients with malignant ErbB-2 positive cells that have more than 1.000.000 ErbB-2 receptors on their cell surface, in order to obtain a clinical response. Patients with ErbB-2 positive tumor cells with more than 1.000.000 ErbB-2 receptors on their cell surface are typically classified as ErbB-2 [+++]. Patients are for instance classified using the HERCEPT-EST™ and/or HER2 FISH (PHARMDX™), marketed both by Dako Denmark A/S, and/or using a HERMARK® assay, marketed by Monogram Biosciences. Trastuzumab and pertuzumab are only prescribed to ErbB-2 [+++] patients because patients with lower ErbB-2 concentrations typically do not exhibit a sufficient clinical response when treated with trastuzumab and pertuzumab. The invention, however, provides bispecific antibodies that also have an improved binding affinity for cells with a lower ErbB-2 receptor concentration, as compared to trastuzumab. As shown in the Examples, proliferation of such cells with lower ErbB2 expression is effectively counteracted with an antibody according to the invention. Such lower ErbB-2 receptor concentration is present on malignant cells of patients that are classified as ErbB-2 [++] or ErbB-2 [+]. Also, relapsed ErbB-2 positive tumors often have an ErbB-2 receptor concentration of lower than 1.000.000 receptors per cell. Such ErbB-2 [++] or ErbB-2 [+] patients, as well as patients with a relapsed ErbB-2 positive tumor, are therefore preferably treated with a bispecific antibody according to the present, invention. Further provided is therefore a bispecific antibody comprising a first antigen-binding site that binds ErbB-2 and a second antigen-binding site that binds ErbB-3, wherein the antibody can reduce ligand-induced growth of an ErbB-2 and ErbB-3 positive cell that has less than 1.000.000 ErbB-2 cell-surface receptors. Also provided is a method for the treatment of a subject having a ErbB-2, ErbB-3 or ErbB-2/ErbB-3 positive tumor or at risk of having said tumor, wherein said tumor has less than 1.000.000 ErbB-2 cell-surface receptors per cell, the method comprising administering to the subject a bispecific antibody or pharmaceutical composition according to the invention. A bispecific antibody according to the invention for use in the treatment of a subject having or at risk of having an ErbB-2, ErbB-3 or ErbB-2/ErbB-3 positive tumor, wherein said tumor has less than 1.000.000 ErbB-2 cell-surface receptors per cell, is also herewith provided. Said antibody according to the present invention is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain 1 of ErbB-2 and a second antigen-binding site that binds domain III of ErbB-3. In one preferred embodiment, the affinity of said second antigen-binding site for an ErbB-3 positive cell is equal to, or higher than, the affinity of said first antigen-binding site for an ErbB-2 positive cell, as explained herein below in more detail. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment, said antibody according to the invention comprises an antigen-binding site that binds at least one amino acid of domain I of ErbB-2 selected from the group consisting of T144, T164, R166, P172, (179, S180 and R181, and surface-exposed amino acid residues that are located within about 5 amino acid positions from T144, T164, R166, P172, G179, S180 or R181. In one preferred embodiment, said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

To establish whether a tumor is positive for ErbB-3 the skilled person can for instance determine the ErbB-3 amplification and/or staining in immunohistochemistry. At least 10% tumor cells in a biopt should be positive. The biopt can also contain 20%, 30% 40% 50% 60% 70% or more positive cells.

As used herein the ligand-induced receptor function is reduced by at least 20%, preferably at least 30, 40, 50 60, or at least 70% in a particularly preferred embodiment the ligand-induced receptor function is reduced by 80, more preferably by 90%. The reduction is preferably determined by determining a ligand-induced receptor function in the presence of a bispecific antibody of the invention, and comparing it with the same function in the absence of the antibody, under otherwise identical conditions. The conditions comprise at least the presence of an ErbB-3 ligand. The amount of ligand present is preferably an amount that induces half of the maximum growth of an ErbB-2 and ErbB-3 positive cell line. The ErbB-2 and ErbB-3 positive cell line for this test is preferably the MCF-7 cell line (ATCC® HIT13-22™), the SK3R3 cell line (ATCC® HTB-30™) cells, the JIMT-1 cell line (DSMZ ACC 589) or the NCI-87 cell line (ATCC® CRL-5822™). The test and/or the ligand for determining ErbB-3 ligand-induced receptor function is preferably a test for ErbB-3 ligand induced growth reduction as specified in the examples.

The ErbB-2 protein contains several domains (see for reference FIG. 1 of Landgraf, R Breast Cancer Res. 2007; 9(1): 202-). The extracellular domains are referred to as domains I-IV. The place of binding to the respective domains of antigen-binding sites of antibodies described herein has been mapped (see examples). A bispecific antibody of the invention with an antigen-binding site (first antigen-binding site) that binds domain I or domain IV of ErbB-2 (first antigen-binding site) comprises a heavy chain variable region that maintains significant binding specificity and affinity for ErbB-2 when combined with various light chains. Bispecific antibodies with an antigen-binding site (first antigen-binding site) that binds domain I or domain IV of ErbB-2 (first antigen-binding site) and an antigen-binding site for ErbB-3 (second antigen-binding site) were found to be more effective in reducing a ligand-induced receptor function of ErbB-3 when compared to a bispecific antibody comprising an antigen-binding site (first antigen-binding site) that binds to another extra-cellular domain of ErbB-2. A bispecific antibody comprising an antigen-binding site (first antigen-binding site) that binds ErbB-2, wherein said antigen-binding site binds to domain I or domain IV of ErbB-2 is preferred. Preferably said antigen-binding site binds to domain IV of ErbB-2. A bispecific antibody with an antigen-binding site (first antigen-binding site) that binds ErbB-2, and that further comprises ADC(C was found to be more effective than other ErbB-2 binding antibodies that did not have significant ADCC activity, particularly in vivo. A bispecific antibody according to the invention which exhibits ADCC is therefore preferred. It was found that antibodies wherein said first antigen-binding site binds to domain IV of ErbB-2 had intrinsic ADCC activity. A domain I binding ErbB-2 binding antibody that has low intrinsic ADCC activity can be engineered to enhance the ADCC activity Fe regions mediate antibody function by binding to different receptors on immune effector cells such as macrophages, natural killer cells, B-cells and neutrophils. Some of these receptors, such as CD16A (FcγRIIIA) and CD32A (FcγRIIA), activate the cells to build a response against antigens. Other receptors, such as CD32B, inhibit the activation of immune cells. By engineering Fc regions (through introducing amino acid substitutions) that bind to activating receptors with greater selectivity, antibodies can be created that have greater capability to mediate cytotoxic activities desired by an anti-cancer Mab.

One technique for enhancing ADCC of an antibody is afucosylation. (See for instance Junttila. T. T., K. Parsons, et al. (2010). "Superior In vivo Efficacy of Afucosylated Trastuzumab in the Treatment of HER2-Amplified Breast Cancer." Cancer Research 70(11): 4481-4489). Further provided is therefore a bispecific antibody according to the invention, which is afucosylated. Alternatively, or additionally, multiple other strategies can be used to achieve ADCC enhancement, for instance including glycoengineering (Kyowa Hakko/Biowa. GlycArt (Roche) and Eureka Therapeutics) and mutagenesis (Xencor and Macrogenics), all of which seek to improve Fe binding to low-affinity activating FcγRIIIa, and/or to reduce binding to the low affinity inhibitory FcγRIIb.

Several in vitro methods exist for determining the efficacy of antibodies or effector cells in eliciting ADCC. Among these are chromium-51 [Cr51] release assays, europium [Eu] release assays, and sulfur-35 [S35] release assays. Usually, a labeled target cell line expressing a certain surface-exposed antigen is incubated with antibody specific for that antigen. After washing, effector cells expressing Fe receptor CD16 are typically co-incubated with the antibody-labeled target cells. Target cell lysis is subsequently typically measured by release of intracellular label, for instance by a scintillation counter or spectrophotometry. A preferred test is detailed in the Examples.

One advantage of the present invention is the fact that binding of antibodies according to the invention such as for instance PB4188 to ErbB-2 and ErbB-3 positive cells results in internalization that is to the same extent as compared to trastuzumab. If a combination of trastuzumab and pertuzumab is used, internalization of these antibodies is enhanced. This enhanced internalization, however, results in reduced ADCC. An antibody according to the present invention resulting in internalization that is essentially to the same extent as compared to trastuzumab is, therefore, preferred over a combination of trastuzumab and pertuzumab because with such antibody the ADCC activity is better maintained.

An antibody of the invention comprising an antigen-binding site that binds ErbB-3, interferes with binding of an ErbB-3 ligand to ErbB-3. Such antibodies are more effective in reducing a ligand-induced receptor function of ErbB-3 on an ErbB-2 and ErbB-3 positive cell line, particularly in the context of an bi-specific antibody that also comprises an antigen-binding site that binds ErbB-2.

Preferred embodiments of the current invention provide a bispecific antibody comprising a first antigen-binding site that binds ErbB-2 and a second antigen-binding site that binds ErbB-3, wherein said first antigen-binding site binds domain I of ErbB-2. As shown in the Examples, bispecific antibodies having these characteristics are well capable of binding ErbB-2 and ErbB-3 positive cells and counteracting their activity (such as the ligand-induced receptor function of ErbB-3 and the ligand-induced growth of an ErbB-2 and ErbB3 positive cell). Moreover, bispecific antibodies according to the invention comprising a first antigen-binding site that binds domain I of ErbB-2 are particularly suitable for use in combination with existing anti-ErbB-2 therapies like trastuzumab and pertuzumab, because trastuzumab and pertuzumab bind different domains of ErbB-2. Trastuzumab binds domain IV of ErbB-2 and pertuzumab binds domain II of ErbB-2. Hence, bispecific antibodies according to the invention that bind domain 1 of ErbB-2 are preferred because they do not compete with trastuzumab and pertuzumab for the same epitope.

Another preferred embodiment provides a bispecific antibody comprising a first antigen-binding site that binds ErbB-2 and a second antigen-binding site that binds ErbB-3, wherein said second antigen-binding site binds domain III of ErbB-3. Such antibody according to the invention is particularly suitable for combination therapy with currently used anti-ErbB-3 binding molecules that do not bind domain III of ErbB-3, such as MM-121 (Merrimack Pharmaceuticals: also referred to as #Ab6) and RG7116 (Roche) that bind domain I of ErbB-3, because then the different binding molecules do not compete with each other for the same epitope.

Preferably, a bispecific antibody is provided that comprises a first antigen-binding site that binds ErbB-2 and a second antigen-binding site that binds ErbB-3, wherein said first antigen-binding site binds domain I of ErbB-2 and said second antigen-binding site binds domain III of ErbB-3. Such antibody is particularly suitable for combination therapy with anti-ErbB-2 binding molecules that do not bind domain I of ErbB-2, such as trastuzumab and pertuzumab, and with anti-ErbB-3 binding molecules that do not bind domain III of ErbB-3, such as MM-121 (#Ab6) and RG7116.

One preferred embodiment provides a bispecific antibody that comprises a first antigen-binding site that binds ErbB-2 and a second antigen-binding site that binds ErbB-3, wherein said first antigen-binding site binds domain I of ErbB-2 and said second antigen-binding site binds domain III of ErbB-3 and wherein the antibody can reduce a ligand-induced receptor function of ErbB-3 on a ErbB-2 and ErbB-3 positive cell. Said antibody can preferably reduce ligand-induced growth of an ErbB-2 and ErbB-3 positive cell.

Further embodiments of the invention provide a bispecific antibody comprising a first antigen-binding site that binds ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell. Contrary to prior art bispecific compounds such as for instance MM-111 from Merrimack Pharmaceuticals, which have a higher affinity for ErbB-2 than for ErbB-3, the present invention provides bispecific antibodies which have an ErbB-3-specific arm with an affinity for ErbB-3 on cells that is higher than the affinity of the ErbB-2-specific arm for ErbB-2 on cells. Such bispecific antibodies are better capable of binding ErbB-3, despite the low cell surface concentration of ErbB-3. This provides the advantage that the functional activity against ErbB-3 is enhanced as compared to prior art compounds, meaning that these bispecific antibodies according to the invention are better capable of counteracting ErbB-3 activity (such as ligand-induced growth).

As used herein, the term "affinity" refers to the KD value.

The affinity (KD) of said second antigen-binding site for an ErbB-3 positive cell is preferably lower than or equal to 2.0 nM, more preferably lower than or equal to 1.5 nM, more preferably lower than or equal to 1.39 nM, more preferably lower than or equal to 0.99 nM. In one preferred embodiment, the affinity of said second antigen-binding site for ErbB-3 on SK-BR-3 cells is lower than or equal to 2.0 nM, more preferably lower than or equal to 1.5 nM, more preferably lower than or equal to 1.39 nM, preferably lower than or equal to 0.99 nM. In one embodiment, said affinity is within the range of 1.39-0.59 nM. In one preferred embodiment, the affinity of said second antigen-binding site for ErbB-3 on BT-474 cells is lower than or equal to 2.0 nM, more preferably lower than or equal to 1.5 nM, more preferably lower than or equal to 1.0 nM, more preferably lower than 0.5 nM, more preferably lower than or equal to 0.31 nM, more preferably lower than or equal to 0.23 nM. In one embodiment, said affinity is within the range of 0.31-0.15 nM. The above-mentioned affinities are preferably as measured using steady state cell affinity measurements, wherein cells are incubated at 4° C. using radioactively labeled antibody, where after cell-bound radioactivity is measured, as described in the Examples.

The affinity (KD) of said first antigen-binding site for an ErbB-2 positive cell is preferably lower than or equal to 5.0 nM, more preferably lower than or equal to 4.5 nM, more preferably lower than or equal to 3.9 nM. In one preferred embodiment, the affinity of said first antigen-binding site for ErbB-2 on SK-BR-3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, more preferably lower than or equal to 2.3 nM. In one embodiment, said affinity is within the range of 3.0-1.6 nM. In one preferred embodiment, the affinity of said first antigen-binding site for ErbB-2 on BT-474 cells is lower than or equal to 5.0 nM, preferably lower than or equal to 4.5 nM, more preferably lower than or equal to 3.9 nM. In one embodiment, said affinity is within the range of 4.5-3.3 nM. The above-mentioned affinities are preferably as measured using steady state cell affinity measurements, wherein cells are incubated at 4° C. using radioactively labeled antibody, where after cell-bound radioactivity is measured, as described in the Examples.

In one preferred embodiment, a bispecific antibody according to the invention is provided, wherein the affinity (KD) of said bispecific antibody for BT-474 cells is lower than or equal to 5.0 nM, preferably lower than or equal to 4.5 nM, more preferably lower than or equal to 4.0 nM, more preferably lower than or equal to 3.5 nM, more preferably lower than or equal to 3.7 nM, preferably lower than or equal to 3.2 nM. In one embodiment, said affinity is within the range of 3.7-2.7 nM. In one preferred embodiment, a bispecific antibody according to the invention is provided, wherein the affinity of said bispecific antibody for SK-BR-3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, preferably lower than or equal to 2.5 nM, more preferably lower than or equal to 2.0 nM. In one embodiment, said affinity is within the range of 2.4-1.6 nM. Again, the above-mentioned affinities are preferably as measured using steady state cell affinity measurements, wherein cells are incubated at 4° C. using radioactively labeled antibody, where after cell-bound radioactivity is measured, as described in the Examples.

Further preferred embodiments of the invention provide a bispecific antibody comprising a first antigen-binding site that binds ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell, and wherein the antibody can reduce a ligand-induced receptor function of ErbB-3 on a ErbB-2 and ErbB-3 positive cell. Said antibody can preferably reduce ligand-induced growth of an ErbB-2 and ErbB-3 positive cell.

The above-mentioned antibodies according to the invention with a high affinity for ErbB-3 preferably bind domain I of ErbB2 and/or domain III of ErbB-3. Further provided is, therefore, a bispecific antibody according to the invention that comprises a first antigen-binding site that binds domain 1 of ErbB-2 and a second antigen-binding site that binds ErbB-3, wherein the affinity (KD) of said second antigen-binding site for an ErbB-3 positive cell is equal to, or higher than, the affinity of said first antigen-binding site for an ErbB-2 positive cell. Also provided is a bispecific antibody according to the invention that comprises a first antigen-binding site that binds ErbB-2 and a second antigen-binding site that binds domain III of ErbB-3, wherein the affinity of said second antigen-binding site for an ErbB-3 positive cell is equal to, or higher than, the affinity of said first antigen-binding site for an ErbB-2 positive cell. In a particularly preferred embodiment a bispecific antibody according to the invention is provided that comprises a first antigen-binding site that binds domain I of ErbB-2 and a second antigen-binding site that binds domain III of ErbB-3, wherein the affinity of said second antigen-binding site for an ErbB-3 positive cell is equal to, or higher than, the affinity of said first antigen-binding site for an ErbB-2 positive cell.

Said second antigen-binding site preferably binds domain III of ErbB-3 and has an affinity (KD) for an ErbB-3 positive cell that is lower than or equal to 2.0 nM, more preferably lower than or equal to 1.5 nM, preferably lower than or equal to 1.39 nM, more preferably lower than or equal to 0.99 nM. In one preferred embodiment, said second antigen-binding site binds domain III of ErbB-3 and has an affinity for ErbB-3 on SK-BR-3 cells that is lower than or equal to 2.0 nM, more preferably lower than or equal to 1.5 nM, preferably lower than or equal to 1.39 nM, more preferably lower than or equal to 0.99 nM. In one embodiment, said affinity is within the range of 1.39-0.59 nM. In one preferred embodiment, said second antigen-binding site binds domain III of ErbB-3 and has an affinity for ErbB-3 on BT-474 cells that is lower than or equal to 2.0 nM, more preferably lower than or equal to 1.5 nM, more preferably lower than or equal to 1.0 nM, more preferably lower than or equal to 0.5 nM, more preferably lower than or equal to 0.31 nM, more preferably lower than or equal to 0.23 nM. In one embodiment, said affinity is within the range of 0.31-0.15 nM.

Said first antigen-binding site preferably binds domain I of ErbB-2 and has an affinity (KD) for an ErbB-2 positive cell that is lower than or equal to 5.0 nM, more preferably lower than or equal to 4.5 nM, more preferably lower than or equal to 3.9 nM. In one preferred embodiment, said first antigen-binding site binds domain I of ErbB-2 and has an affinity for ErbB-2 on SK-BR-3 cells that is lower than or equal to 5.0 nM, more preferably lower than or equal to 4.5 nM, more preferably lower than or equal to 4.0 nM, more preferably lower than or equal to 3.5 nM, more preferably lower than or equal to 3.0 nM, more preferably lower than or equal to 2.5 nM, more preferably lower than or equal to 2.3 nM. In one embodiment, said affinity is within the range of 3.0-1.6 nM. The affinity of said bispecific antibody for SK-BR-3 cells is preferably lower than or equal to 5.0 nM, more preferably lower than or equal to 4.5 nM, more preferably lower than or equal to 4.0 nM, more preferably lower than or equal to 3.5 nM, more preferably lower than or equal to 3.0 nM, more preferably lower than or equal to 2.5 nM, more preferably lower than or equal to 2.4 nM, more preferably lower than or equal to 2.0 nM. In one embodiment, said affinity is within the range of 2.4-1.6 nM.

In one preferred embodiment, said first antigen-binding site binds domain I of ErbB-2 and has an affinity (KD) for ErbB-2 on BT-474 cells that is lower than or equal to 5.0 nM, more preferably lower than or equal to 4.5 nM, preferably lower than or equal to 3.9 nM. In one embodiment, said affinity is within the range of 4.5-3.3 nM. The affinity of said bispecific antibody for BT-474 cells is preferably lower than or equal to 5.0 nM, more preferably lower than or equal to 4.5 nM, more preferably lower than or equal to 4.0 nM, more preferably lower than or equal to 3.7 nM, more preferably lower than or equal to 3.2 nM. In one embodiment, said affinity is within the range of 3.7-2.7 nM.

Again, the above-mentioned affinities are preferably as measured using steady state cell affinity measurements, wherein cells are incubated at 4° C. using radioactively labeled antibody, where after cell-bound radioactivity is measured, as described in the Examples.

Another preferred embodiment provides a bispecific antibody according to the invention comprising a first antigen-binding site that binds ErbB-2 and a second antigen-binding site that binds ErbB-3, wherein the antibody can reduce a ligand-induced receptor function of ErbB-3 on a ErbB-2 and ErbB-3 positive cell, wherein said bispecific antibody does not significantly affect the survival of cardiomyocytes. Cardiotoxicity is a known risk factor in ErbB-2 targeting therapies and the frequency of complications is increased when trastuzumab is used in conjunction with anthracyclines thereby inducing cardiac stress. For instance, the combination of doxycycline (DOX) with trastuzumab induces severe cardiac side effects. Clinical studies have estimated that 5% to 10% of patients who receive trastuzumab in the adjuvant setting of breast cancer develop cardiac dysfunction (Guarneri et al., J Clin Oncol., 1985, 3:818-26: Ewer M S et al. Nat Rev Cardiol 2010:7:564-75). However, in a retrospective study, it was demonstrated that the risk for developing asymptomatic cardiac dysfunction is actually as high as about 25% when trastuzumab is used in the adjuvant setting with DOX (Wadhwa et al. Breast Cancer Res Treat 2009:117:357-64). As shown in the Examples, the present invention provides antibodies that target ErbB-2 and that do not, or to a significantly lesser extent as compared to trastuzumab and pertuzumab, affect the survival of cardiomyocytes. This provides an important advantage since cardiotoxicity is reduced. This is already advantageous for people who do not suffer from an impaired cardiac function, and even more so for people who do suffer from an impaired cardiac function, or who are at risk thereof, such as for instance subjects suffering from congestive heart failure (CHF), left ventricular dysfunction (LVD) and/or a ≥10% decreased Left Ventricular Ejection Fraction (LVEF), and/or subjects who have had a myocardial infarction. Antibodies according to the invention that do not significantly affect the survival of cardiomyocytes are, therefore, preferred. In vitro, the function of cardiomyocytes is for instance measured by determining the viability of cardiomyocytes, by determining BNP (B-type natriuretic peptide, which is a cardiac biomarker), by determining QT prolongation, and/or by determining mitochondrial membrane potential.

Said antibody according to the invention preferably comprises a first antigen-binding site that binds domain I of ErbB-2 and a second antigen-binding site that binds domain III of ErbB-3. One embodiment provides an antibody according to the invention that does not significantly affect the survival of cardiomyocytes, comprising a first antigen-binding site that binds ErbB-2 and a second antigen-binding site that binds ErbB-3, wherein the affinity of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.:39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment said antibody that does not significantly affect the survival of cardiomyocytes comprises:
  at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences; and/or
  at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences. In one preferred embodiment, said antibody is PB4188.

Another aspect of the present invention provides an antibody according to the invention, comprising a first antigen-binding site that binds ErbB-2 and a second antigen-binding site that binds ErbB-3, wherein said antibody comprises an antigen-binding site that binds at least one amino acid residue of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181. The amino acid residue numbering is that of Protein Data Bank (PDB) ID #1S78. As shown in the Examples, antibodies binding this region of domain I of ErbB-2 exhibit particularly good binding characteristics and they are capable of counteracting the activity of ErbB-2 positive cells (such as ligand-induced receptor function of ErbB-3 on a ErbB-2 and ErbB-3 positive cell, and/or ligand-induced growth of such cell). Moreover, such antibodies are particularly suitable for combination therapy with currently known anti-ErbB-2 monoclonal antibodies like trastuzumab (that binds domain IV of ErbB-2) and pertuzumab (that binds domain II of ErbB-2) because they bind different domains of ErbB-2. Hence, these antibodies can be used simultaneously without competition for the same epitope. The term "surface-exposed amino acid residues that are located within about 5 amino acid positions from T144, T164, R166, P172, G179, S180 or R181" refers to amino acid residues that are in the primary amino acid sequence located within about the first five amino acid residues adjacent to the recited residues and that are at least in part exposed to the outside of the protein, so that they can be bound by antibodies (see for instance FIG. 21B). Preferably, said amino acid residue located within about 5 amino acid positions from T144, T164, R166, P172, G1179, S180 or R181 is selected from the group consisting of L139, C140, Y141, Q142, D143, I145, L146, W147, K148, D149, L159, T160, L161, 1162, D163, N165, S167, R168, A169, C170, H171, C173, S174, P175, M176, C177, K178, C182, W183, G184, E185 and S186. Preferably, said antibody comprises an antigen-binding site that binds at least 2 or at least 3 amino acid residues of domain I of ErbB-2 selected from the group consisting of T144, T164, R166, P172, G179, S180 and R181, and surface-exposed amino acid residues that are located within 5 amino acid positions from T144, T164, R166, P172, G179, S180 or R181.

In one preferred embodiment, a bispecific antibody according to the invention is provided, wherein said antibody comprises an antigen-binding site that binds at least T144, R166 and R181 of domain I of ErbB-2. Another embodiment provides a bispecific antibody according to the invention, wherein said antibody comprises an antigen-binding site that binds at least T144, R166, P172, G179 and R181 of domain I of ErbB-2. Another embodiment provides a bispecific antibody according to the invention, wherein said antibody comprises an antigen-binding site that binds at least T144, T164, R166, P172, G179, S180 and R181 of domain I of ErbB-2.

Another aspect of the present invention provides an antibody comprising a first antigen-binding site that binds ErbB-2 and a second antigen-binding site that binds ErbB-3, wherein said antibody comprises an antigen-binding site that binds at least one amino acid of domain III of ErbB-3 selected from the group consisting R426 and surface-exposed amino acid residues that are located within 11.2 Å from R426 in the native ErbB-3 protein. The amino acid residue numbering is that of Protein Data Bank (PDB) ID #4P59. As shown in the Examples, antibodies binding this region of domain III of ErbB-3 exhibit particularly good binding characteristics and they are capable of counteracting the activity of ErbB-3 positive cells (such as ligand-induced receptor function of ErbB-3 on a ErbB-2 and ErbB-3 positive cell, and/or ligand-induced growth of such cell). The term "surface-exposed amino acid residues that are located within 11.2 Å from R426 in the native ErbB-3 protein" refers to amino acid residues that are in the tertiary structure of the ErbB-3 protein spationally positioned within 11.2 Å from R426 and that are at least in part exposed to the outside of the protein, so that they can be bound by antibodies. Preferably, said amino acid residues that are located within 11.2 Å from R426 in the native ErbB-3 protein are selected from the group consisting of L423, Y424, N425, G427, G452, R453, Y455, E480, R481, L482, D483 and K485 (see for instance FIG. 21C and Table 15). In one preferred embodiment, a bispecific antibody according to the invention is provided, wherein said antibody comprises an antigen-binding site that binds at least R426 of domain III of ErbB-3. Preferably, said antibody comprises an antigen-binding site that binds at least R426 of domain III of ErbB-3.

A bispecific antibody of the invention is preferably afucosylated in order to enhance ADCC activity. A bispecific antibody of the invention preferably comprises a reduced amount of fucosylation of the N-linked carbohydrate structure in the Fc region, when compared to the same antibody produced in a normal CHO cell.

A bispecific antibody of the present invention is preferably used in humans. To this end a bispecific antibody of the invention is preferably a human or humanized antibody. Tolerance of a human to a polypeptide is governed by many different aspects. Immunity, be it T-cell mediated, B-cell mediated or other is one of the variables that are encompassed in tolerance of the human for a polypeptide. The constant region of a bispecific antibody of the present invention is preferably a human constant region. The constant region may contain one or more, preferably not more than 10, preferably not more than 5 amino-acid differences with the constant region of a naturally occurring human antibody. It is preferred that the constant part is entirely derived from a naturally occurring human antibody. Various antibodies produced herein are derived from a human antibody variable domain library. As such these variable domains are human. The unique CDR regions may be derived from humans, be synthetic or derived from another organism. The variable region is considered a human variable region when it has an amino acid sequence that is identical to an amino acid sequence of the variable region of a naturally occurring human antibody, but for the CDR region. The variable region of an ErbB-2 binding VH, an ErbB-3 binding VH, or a light chain in an antibody of the invention may contain one or more, preferably not more than 10, preferably not more than 5 amino-acid differences with the variable region of a naturally occurring human antibody, not counting possible differences in the amino acid sequence of the CDR regions. Such mutations occur also in nature in the context of somatic hypermutation.

Antibodies may be derived from various animal species, at least with regard to the heavy chain variable region. It is common practice to humanize such e.g. murine heavy chain variable regions. There are various ways in which this can be achieved among which there are CDR-grafting into a human heavy chain variable region with a 3D-structure that matches the 3-D structure of the murine heavy chain variable region: deimmunization of the murine heavy chain variable region, preferably done by removing known or suspected T- or B-cell epitopes from the murine heavy chain variable region. The removal is typically by substituting one or more of the amino acids in the epitope for another (typically conservative) amino acid, such that the sequence of the epitope is modified such that it is no longer a T- or B-cell epitope. Such deimmunized murine heavy chain variable regions are less immunogenic in humans than the original murine heavy chain variable region. Preferably a variable region or domain of the invention is further humanized, such as for instance veneered. By using veneering techniques, exterior residues which are readily encountered by the immune system are selectively replaced with human residues to provide a hybrid molecule that comprises either a weakly immunogenic or substantially non-immunogenic veneered surface. An animal as used in the invention is preferably a mammal, more preferably a primate, most preferably a human.

A bispecific antibody according to the invention preferably comprises a constant region of a human antibody. According to differences in their heavy chain constant domains, antibodies are grouped into five classes, or isotypes: IgG, IgA, IgM, IgD, and IgE. These classes or isotypes comprise at least one of said heavy chains that is named with a corresponding Greek letter. In a preferred embodiment the invention provides an antibody according to the invention wherein said constant region is selected from the group of IgG, IgA, IgM, IgD, and IgE constant regions, more preferably said constant region comprises an IgG constant region, more preferably an IgG1 constant region, preferably a mutated IgG1 constant region. Some variation in the constant region of IgG1 occurs in nature, such as for instance the allotypes G1m1, 17 and G1m3, and/or is allowed without changing the immunological properties of the resulting antibody. Typically between about 1-10 amino acid insertions, deletions, substitutions or a combination thereof are allowed in the constant region.

The invention in one embodiment provides an antibody comprising a variable domain that binds ErbB-2, wherein said antibody comprises at least the CDR3 sequence of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or wherein said antibody comprises a heavy chain CDR3 sequence that differs in at most three, preferably in at most two, preferably in no more than one amino acid from a CDR3 sequence of a VH selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E. Said antibody preferably comprises at least the CDR3 sequence of MF1849, MF2971, MF3958, MF3004 or MF3991, most preferably at least the CDR3 sequence of MF3958.

Said antibody preferably comprises at least the CDR1, CDR2 and CDR3 sequences of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or heavy chain CDR1, CDR2 and CDR3 sequences that differ in at most three, preferably in at most two, preferably in at most one amino acid from the CDR1, CDR2 and CDR3 sequences of MF2926, MF2930, MF1849; MF2973, MF3004, MF3958, MF2971, MF3025, MF2916, MF3991, MF3031, MF2889, MF2913, MF1847, MF3001, MF3003 or MF1898. Said antibody preferably comprises at least the CDR1, CDR2 and CDR3 sequences of MF1849, MF2971, MF3958, MF3004 or MF3991, most preferably at least the CDR1, CDR2 and CDR3 sequences of MF3958.

The invention also provides an antibody comprising a variable domain that binds ErbB-3, wherein said antibody comprises at least the CDR3 sequence of an ErbB-3 specific heavy chain variable region selected from the group consisting of MF3178; MF3176; MF3163; MF3099; N3307; MF6055; MF6056; N6057; MF6058; MF6059; MF6060; MF6061; MF6062; MF6063; MF6064; MF6065; MHF6066; MF6067; MF6068; MF6069; MF6070; MF6071; MF6072; MF6073 and MF6074 as depicted in FIG. 16B or FIG. 16E or FIG. 37, or wherein said antibody comprises a heavy chain CDR3 sequence that differs in at most three, preferably in at most two, preferably in no more than one amino acid from a CDR3 sequence of a VH selected from the group consisting of MF3178; MF3176; MF3163; MvNF3099; MF3307; MF6055; MHF6056; MF6057; MF6058; MHF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37. Said antibody preferably comprises at least the CDR3 sequence of MF3178, MF3176, MF3163, MF6058, MF6061 or MF6065, most preferably at least the CDR3 sequence of MF3178.

Said antibody preferably comprises at least the CDR1, CDR2 and CDR3 sequences of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; N6068; MF6069; MF6070; N6071; MF6072; MF6073 and MF6074 as depicted in FIG. 16B or FIG. 16E or FIG. 37, or heavy chain CDR1, CDR2 and CDR3 sequences that differ in at most three, preferably in at most two, preferably in at most one amino acid from the CDR1, CDR2 and CDR3 sequences of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074. Said antibody preferably comprises at least the CDR1. CDR2 and CDR3 sequences of MF3178, MF3176, MF3163, MF6058, MF6061 or MF6065, most preferably at least the CDR1, CDR2 and CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR3 sequence of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MHF3001, MF3003 and MF1898 as depicted in FIG. 16A or FIG. 16E, or a heavy chain CDR3 sequence that differs in at most three, preferably in at most two, preferably in no more than one amino acid from a CDR3 sequence of a VH selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, and wherein said second antigen-binding site comprises at least the CDR3 sequence of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 and MF6074 as depicted in FIG. 16B or FIG. 16E or FIG. 37, or a heavy chain CDR3 sequence that differs in at most three, preferably in at most two, preferably in no more than one amino acid from a CDR3 sequence of a VH selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37. Said first antigen-binding site preferably comprises at least the CDR3 sequence of MF1849, MF2971, MF3958, MF3004 or MF3991, most preferably at least the CDR3 sequence of MF3958 and said second antigen-binding site preferably comprises at least the CDR3 sequence of MF3178, MF3176, MF3163, MF6058, MF6061 or MF6065, most preferably at least the CDR3 sequence of MF3178.

Said first antigen-binding site preferably comprises at least the CDR1, CDR2 and CDR3 sequences of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or heavy chain CDR1, CDR2 and CDR3 sequences that differ in at most three, preferably in at most two, preferably in at most one amino acid from the CDR1, CDR2 and CDR3 sequences of MF2926, MF2930, MF1849; MF2973, MF3004, MF3958, MF2971, MF3025, MF2916, MF3991, MF3031, MF2889, MIF2913, MF1847, MF3001, MF3003 or MF1898, and said second antigen-binding site preferably comprises at least the CDR1, CDR2 and CDR3 sequences of an ErbB-3 specific heavy chain variable region selected from the group consisting of MF3178; MF3176; MF3163; MF3099; MF3307; MF6055; MF6056; MF6057; MF6058; MF6059; MF6060; MF6061; MIF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37, or heavy chain CDR1, CDR2 and CDR3 sequences that differ in at most three, preferably in at most two, preferably in at most one amino acid from the CDR1, CDR2 and CDR3 sequences of MF3178; MF3176; MF3163; MF3099; MF3307; MF6055; MF6056; MF6057; MF6058; MF6059; MF6060; MF6061; MF6062; MF6063; MF6064; MF 6065; MF6066; MF6067; MF6068; MF6069; MF6070; MF6071; MF6072; MF6073 or MF6074 as depicted in FIG. 16B or FIG. 16E or FIG. 37. Said first antigen-binding site preferably comprises at least the CDR1, CDR2 and CDR3 sequences of MF1849, MF2971, MF3958, MF3004 or MF3991, most preferably at least the CDR1, CDR2 and CDR3 sequences of MF3958, and said second antigen-binding site preferably comprises at least the CDR1, CDR2 and CDR3 sequences of MF3178, MF3176, MF3163, MF6058, MF6061 or MF6065, most preferably at least the CDR1, CDR2 and CDR3 sequence of MF3178.

One preferred embodiment provides a bispecific antibody comprising a first antigen-binding site that binds ErbB-2 and a second antigen-binding site that binds ErbB-3, wherein said first antigen-binding site comprises at least the CDR3 sequence of MF3958, or a CDR3 sequence that differs in at most three, preferably in at most two, preferably in no more than one amino acid from the CDR3 sequence of MF3958, and wherein said second antigen-binding site comprises at least the CDR3 sequence of MF3178, or a CDR3 sequence that differs in at most three, preferably in at most two, preferably in no more than one amino acid from the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF3958, or CDR1, CDR2 and CDR3 sequences that differ in at most three, preferably in at most two, preferably in at most one amino acid from the CDR1, CDR2 and CDR3 sequences of MF3958, and wherein said second antigen-binding site comprises at least the CDR1, CDR2 and CDR3 sequence of MF3178, or CDR1, CDR2 and CDR3 sequences that differ in at most three, preferably in at most two, preferably in at most one amino acid from the CDR1, CDR2 and CDR3 sequences of MF3178.

The invention in one embodiment provides a bispecific antibody comprising a first antigen-binding site that binds ErbB-2 and a second antigen-binding site that binds ErbB-3, wherein said first antigen-binding site comprises at least the CDR3 sequence of MF3958 and wherein said second antigen-binding site comprises at least the CDR3 sequence of MF3178.

The invention in one embodiment provides a bispecific antibody comprising a first antigen-binding site that binds ErbB-2 and a second antigen-binding site that binds ErbB-3, wherein said first antigen-binding site comprises at least the CDR1, CDR2 and CDR3 sequences of MF3958 and wherein said second antigen-binding site comprises at least the CDR1, CDR2 and CDR3 sequence of MF3178.

CDR sequences are for instance varied for optimization purposes, preferably in order to improve binding efficacy or the stability of the antibody. Optimization is for instance performed by mutagenesis procedures where after the stability and/or binding affinity of the resulting antibodies are preferably tested and an improved ErbB-2 or ErbB-3-specific CDR sequence is preferably selected. A skilled person is well capable of generating antibody variants comprising at least one altered CDR sequence according to the invention. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for aspartic acid, or glutamine for asparagine.

The invention in one embodiment provides an antibody comprising a variable domain that binds ErbB-2, wherein the VH chain of said variable domain comprises the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 16A or FIG. 16E; or comprises the amino acid sequence of VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 16A or FIG. 16E having at most 15, preferably 1, 2, 3, 4, 5, 6, 7, 8, 9 or 10 more preferably at most 1, 2, 3, 4 or 5, amino acid insertions, deletions, substitutions or a combination thereof with respect to the above mentioned VH chain sequence of FIG. 16A or FIG. 16E. The VH chain of the variable domain that binds ErbB-2 preferably comprises the amino acid sequence of MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991;

as depicted in FIG. 16A. In one embodiment, the VH chain of the variable domain that binds ErbB-2 comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991, wherein the recited VH sequences have at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A. In a preferred embodiment the VH chain of the variable domain that binds ErbB-2 comprises the amino acid sequence of MF3958; or comprises the amino acid sequence of MF3958 depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. The antibody comprising a variable domain that binds ErbB-2 is preferably a bispecific antibody that preferably further comprises a variable domain that binds ErbB-3. The VH chain of the variable domain that binds Erb-133 preferably comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; N6072; MF6073 or MF6074 as depicted in FIG. 16B or FIG. 16E or FIG. 37; or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 as depicted in FIG. 16B or FIG. 16E or FIG. 37 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence of FIG. 16B or FIG. 16E or FIG. 37. The VH chain of the variable domain that binds Erb-B3 preferably comprises the amino acid sequence of MF3178, MF3176, MF3163, MF6058, MF6061 or MF6065; or comprises the amino acid sequence of MF3178, MF3176, MF3163, MF6058, MF6061 or MF6065 having at most 15, preferably 1, 2, 3, 4, 5, 6, 7, 8, 9 or 10, more preferably in at most 1, 2, 3, 4 or 5, amino acid insertions, deletions, substitutions or a combination thereof with respect to the respective VH chain sequence of FIG. 16B or FIG. 37. In a preferred embodiment the VH chain of the variable domain that binds ErbB-3 comprises the amino acid sequence of MF3178; or comprises the amino acid sequence of MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. Preferably, the above-mentioned amino acid insertions, deletions and substitutions are not present in the CDR3 region. The above-mentioned amino acid insertions, deletions and substitutions are also preferably not present in the CDR1 and CDR2 regions. The above-mentioned amino acid insertions, deletions and substitutions are also preferably not present in the FR4 region.

The invention further provides an antibody comprising a variable domain that binds ErbB-3, wherein the VH chain of said variable region comprises the amino acid sequence of VH chain MF3178; MF3176; MF3163; MF3099; MF3307; MF6055; MF6056; MF6057; MF6058; MIF6059; MF6060; MF6061; MIF6062; MF6063; MF6064; MF6065; MF6066; MF6067; MF6068; MF6069; MF6070; MF6071; MF6072; MF607; 3 or MF6074 as depicted in FIG. 16B or FIG. 16E or FIG. 37, or comprises the amino acid sequence of VH chain MF3178; MF3176; MF3163; MF3099; MF3307; MF6055; N6056; MF6057; MF6058; MF6059; MF6060; MF6061; MF6062; MF6063; MF6064; MF6065; MF6066; MF6067; MF6068; MF6069; MF6070; MF6071; MF6072; MIF6073 or MF6074 as depicted in FIG. 16B or FIG. 16E or FIG. 37 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to said VH chain sequence. The VH chain of the variable domain that binds ErbB3 preferably comprises the amino acid sequence of VH chain MF3178, MF3176, MF3163, MF6058, MF6061 or MF6065; or comprises the amino acid sequence of VH chain MF3178, MF3176, MF3163, MF6058, MF6061 or MF6065 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to said VH chain sequence. In a preferred embodiment the VH chain of the variable domain that binds ErbB-3 comprises the amino acid sequence of VH chain MF3178 depicted in FIG. 16B; or comprises the amino acid sequence of VH chain MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence. The antibody comprising a variable domain that binds ErbB-3, is preferably a bispecific antibody that preferably further comprises a variable domain that binds ErbB-2. The VH chain of the variable domain that binds ErbB-2 preferably comprises the amino acid sequence of a VH chain of FIG. 16A or FIG. 16E. The VH chain of the variable domain that binds ErbB-2 preferably comprises the amino acid sequence of MF1849; or MIF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 16A. In one embodiment, the recited Erb-132 binding VH sequences have at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A. In one preferred embodiment, said ErbB-2 binding VH chain of FIG. 16A comprises the amino acid sequence of MF3958; or comprises the amino acid sequence of MF3958 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VI chain sequence. Preferably, the above-mentioned amino acid insertions, deletions and substitutions are not present in the CDR3 region. The above-mentioned amino acid insertions, deletions and substitutions are also preferably not present in the CDR1 and CDR2 regions. The above-mentioned amino acid insertions, deletions and substitutions are also preferably not present in the FR4 region.

Further provided is an antibody according to the invention, wherein said antibody comprises an ErbB-2 specific heavy chain variable region sequence selected from the group consisting of the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or wherein said antibody comprises a heavy chain variable region sequence that differs in at most 15, preferably in 1, 2, 3, 4, 5, 6, 7, 8, 9 or 10, more preferably in at most 1, 2, 3, 4 or 5, amino acids from the heavy chain variable region sequences of MF2926, MF2930, MF1849; MF2973, MF3004, MF3958, MF2971, MF3025, MF2916, MF3991, MF3031, MF2889, MF2913, MF1847, MF3001, MF3003 or MF1898.

Further provided is an antibody according to the invention, wherein said antibody comprises an ErbB-3 specific heavy chain variable region sequence selected from the group consisting of the heavy chain variable region sequences of MF3178; MF3176; MF3163; MF3099; MF3307; MF6055; MF6056; MF6057; MF6058; MF6059; MF6060; MF6061; NF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37, or wherein said antibody comprises a heavy chain variable region sequence that differs in at most 15, preferably in 1, 2, 3, 4, 5, 6, 7, 8, 9 or 10, more preferably in at most 1, 2, 3, 4 or 5, amino acids from the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074.

The invention in one embodiment provides an antibody comprising two antigen-binding sites that bind ErbB-2, wherein at least one of said antigen-binding sites binds domain I of ErbB-2. Preferably, both antigen-binding sites bind domain I of ErbB-2. Such antibody according to the invention is particularly suitable for combination therapy with currently used anti-ErbB-2 binding molecules that do not bind domain I of ErbB-2, such as trastuzumab that binds domain IV of ErbB-2 and pertuzumab that binds domain II of ErbB-2, because then the different binding molecules do not compete with each other for the same epitope.

Further provided is an antibody comprising two antigen-binding sites that bind ErbB-2, wherein at least one of said antigen-binding sites binds domain I of ErbB-2 and wherein the affinity (KD) of said at least one antigen-binding site for an ErbB-2 positive cell is lower than or equal to 5.0 nM, preferably lower than or equal to 4.5 nM, more preferably lower than or equal to 3.9 nM. Preferably, both antigen-binding sites bind domain I of ErbB-2. In one preferred embodiment, the affinity of said at least one antigen-binding site for ErbB-2 on SK-BR-3 cells is lower than or equal to 5.0 nM, preferably lower than or equal to 4.5 nM, more preferably lower than or equal to 4.0 nM, more preferably lower than or equal to 3.5 nM, more preferably lower than or equal to 3.0 nM, more preferably lower than or equal to 2.3 nM. In one embodiment, said affinity is within the range of 3.0-1.6 nM. In one preferred embodiment, the affinity of said at least one antigen-binding site for ErbB-2 on BT-474 cells is lower than or equal to 5.0 nM, preferably lower than or equal to 4.5 nM, more preferably lower than or equal to 3.9 nM. In one embodiment, said affinity is within the range of 4.5-3.3 nM.

The above-mentioned affinities are preferably as measured using steady state cell affinity measurements, wherein cells are incubated at 4° C. using radioactively labeled antibody, where after cell-bound radioactivity is measured, as described in the Examples.

The invention further provides an antibody comprising two variable domains that bind ErbB-2, wherein a VH chain of said variable domains comprises the amino acid sequence of the VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 as depicted in FIG. 16A or FIG. 16E; or the amino acid sequence of the VH chain MF2926; MF2930; MF1849; MF2973; MF3004; MF3958 (is humanized MF2971); MF2971; MF3025; MF2916; MF3991 (is humanized MF3004); MF3031; MF2889; MF2913; MF1847; MF3001, MF3003 or MF1898 VH-chains as depicted in FIG. 16A or FIG. 16E, having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A or FIG. 16E. Said VH preferably comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 16A; or comprises the amino acid sequence of VH chain MF1849; or MF2971 or a humanized version thereof, wherein said humanized version preferably comprises the amino acid sequence of MF3958; or MF3004 or a humanized version thereof, wherein said humanized version preferably comprises the amino acid sequence of MF3991 as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the respective sequence depicted in FIG. 16A. The variable domains of the antibody preferably comprise identical VH chains, preferably having a sequence as depicted in FIG. 16A or FIG. 16E. An antibody with variable domains with identical VH chains is not a bispecific antibody. VHI chains are identical for the present invention if they comprise the same VH chain sequence as depicted in FIG. 16A or FIG. 16E or FIG. 37, or the same VH chain sequence but for 1, 2, 3, 4 or 5 amino acid insertions, deletions, substitutions or a combination thereof with respect to the respective sequence depicted in FIG. 16A or FIG. 16E or FIG. 37.

The invention in one embodiment provides an antibody comprising two antigen-binding sites that bind ErbB-3, wherein at least one of said antigen-binding sites binds domain III of ErbB-3. Preferably, both antigen-binding sites bind domain III of ErbB-3. Such antibody according to the invention is particularly suitable for combination therapy with currently used anti-ErbB-3 binding molecules that do not bind domain III of ErbB-3, such as MM-121 (#Ab6) and RG7116 that bind domain I of ErbB-3, because then the different binding molecules do not compete with each other for the same epitope.

Further provided is an antibody comprising two antigen-binding sites that bind ErbB-3, wherein at least one of said antigen-binding sites binds domain III of ErbB-3 and wherein the affinity (I) of said at least one antigen-binding site for an ErbB-3 positive cell is lower than or equal to 2.0 nM, preferably lower than or equal to 1.5 nM, more preferably lower than or equal to 1.39 nM, more preferably lower than or equal to 0.99 nM. Preferably, both antigen-binding sites bind domain III of ErbB-3. In one preferred embodiment, the affinity of said at least one antigen-binding site for ErbB-3 on SK-BR-3 cells is lower than or equal to 2.0 nM, preferably lower than or equal to 1.5 nM, more preferably lower than or equal to 1.39 nM, more preferably lower than or equal to 0.99 nM. In one embodiment, said affinity is within the range of 1.39-0.59 nM. In one preferred embodiment, the affinity of said at least one antigen-binding site for ErbB-3 on BT-474 cells is lower than or equal to 2.0 nM, more preferably lower than or equal to 1.5 nM, more preferably lower than or equal to 1.0 nM, more preferably lower than or equal to 0.5 nM, more preferably lower than or equal to 0.31 nM, more preferably lower than or equal to 0.23 nM. In one embodiment, said affinity is within the range of 0.31-0.15 nM.

Again, the above-mentioned affinities are preferably as measured using steady state cell affinity measurements, wherein cells are incubated at 4° C. using radioactively labeled antibody, where after cell-bound radioactivity is measured, as described in the Examples.

The invention further provides an antibody comprising two variable domains that each bind ErbB3 wherein a VH of the variable domains comprises the amino acid sequence of VI chain MIF3178; MF3176; MF3163; MF3099; MF3307; MF6055; MF6056; MF6057; MF6058; MF6059; MF6060; MF6061; MF6062; MF6063; MF6064; MF6065; MF6066; N6067; MF6068; MF6069; MF6070; MF6071; MF6072; MF6073 or MF6074 as depicted in FIG. 16B or FIG. 16E or FIG. 37; or comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences. Said VH preferably comprises the amino acid sequence of VH chain MF3178, MF3176, MF3163, MF6058, MF6061 or MF6065; or comprises the amino acid sequence of VH chain MF3178, MF3176, MF3163, MF6058, MF6061 or MF6065 having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences. Said VH preferably comprises the amino acid sequence of VH chain MF3178; or comprises the amino acid sequence of VH chain MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the MF3178 VH chain sequence. The variable domains of the antibody preferably comprise identical VH chains, preferably having a sequence as depicted in FIG. 16B or FIG. 16E or FIG. 37. An antibody with variable domains with identical VH chains is not a bispecific antibody. The VH chains are identical if they comprise the same VH chain sequence as depicted in FIG. 16B or FIG. 16E or FIG. 37, or the same VH chain sequence but for 1, 2, 3, 4 or 5 amino acid insertions, deletions, substitutions or a combination thereof with respect to the VH chain sequence of FIG. 16B or FIG. 16E or FIG. 37.

Monospecific antibodies according to the present invention that are specific for ErbB-3 have the advantage that they have a better functional activity against ErbB-3, as compared to prior art compounds such as for instance MM-121 (#Ab6), meaning that these antibodies according to the invention are better capable of counteracting ErbB-3 activity (such as a ligand-induced receptor function of ErbB-3 and/or ligand-induced growth of an ErbB-2 and ErbB-3 positive cell). This is for instance shown in Table 7 and FIG. 38.

In a preferred embodiment the invention provides a bispecific antibody comprising a variable domain that binds ErbB-2, wherein the VH chain of said variable domain comprises
the amino acid sequence of VH chain MF1849; or MF2971 or a humanized version thereof, wherein said humanized version preferably comprises the amino acid sequence of MF3958: or MF3004 or a humanized version thereof, wherein said humanized version preferably comprises the amino acid sequence of MF3991, as depicted in FIG. 16A; or comprises
the amino acid sequence of VH chain MF1849 or MF2971 or a humanized version thereof, wherein said humanized version preferably comprises the amino acid sequence of MF3958; or MF3004 or a humanized version thereof, wherein said humanized version preferably comprises the amino acid sequence of MF3991, as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect to said VH. Such bispecific antibody according to this embodiment further preferably comprises a variable domain that binds ErbB-3. The VH chain of the variable domain that binds ErbB-3 preferably comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 as depicted in FIG. 16B or FIG. 16E or FIG. 37, or most preferably comprises the amino acid sequence of VH chain MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074 as depicted in FIG. 16B or FIG. 16E or FIG. 37, having at most 15, preferably 1, 2, 3, 4, 5, 6, 7, 8, 9 or 10, more preferably at most 1, 2, 3, 4 or 5, amino acid insertions, deletions, substitutions or a combination thereof with respect to any of said VH chain sequences of FIG. 16B or FIG. 16E or FIG. 37. The VH chain of the variable domain that binds ErbB-3 preferably comprises the amino acid sequence of VH chain MF3178 as depicted in FIG. 16B or comprises the amino acid sequence of VH chain MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VI chain sequence of FIG. 16B.

The invention preferably provides a bispecific antibody comprising a variable domain that binds ErbB-2 and a variable domain that binds ErbB-3, wherein the VH chain of the variable domain that binds ErbB-2 comprises
the amino acid sequence of VH chain MF3958 as depicted in FIG. 16A; or
the amino acid sequence of VH chain MF3958 as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH: and
wherein the VIH chain of the variable domain that binds ErbB-3 comprises
the amino acid sequence of VH chain MF3178 as depicted in FIG. 16B; or
the amino acid sequence of VH chain MF3178 depicted in FIG. 16B having at most 15, preferably 1, 2, 3, 4, 5, 6, 7, 8, 9 or 10 more preferably at most 1, 2, 3, 4 or 5, amino acid insertions, deletions, substitutions or a combination thereof with respect to the VH chain sequence of FIG. 16B.

The invention preferably provides a bispecific antibody comprising a variable domain that binds ErbB-2 and a variable domain that binds ErbB-3, wherein the VH chain of the variable domain that binds ErbB-2 comprises
the amino acid sequence of VH chain MF3991 as depicted in FIG. 16A: or
the amino acid sequence of VH chain MF3991 as depicted in FIG. 16A having at most 15, preferably 1, 2, 3, 4, 5, 6, 7, 8, 9 or 10, more preferably at most 1, 2, 3, 4 or 5, amino acid insertions, deletions, substitutions or a combination thereof with respect said VH and
wherein the VH chain of the variable domain that binds ErbB-3 comprises
the amino acid sequence of VH chain MF3178 as depicted in FIG. 16B; or
the amino acid sequence of VH chain MF3178 depicted in FIG. 16B having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the VH chain sequence of FIG. 16B.

When compared to the sequence in FIG. 16, the behavior of a XII chain typically starts to become noticeably different when it has more than 15 amino acid changes with respect to the amino acid sequence of a VH chain as depicted in FIG. 16. A VH chain having at most 15, preferably 1, 2, 3, 4, 5, 6, 7, 8, 9 or 10 amino acid insertions, deletions, substitutions or a combination thereof with respect to the VH chain depicted in FIG. 16, preferably has 1, 2, 3, 4 or 5 amino acid insertions, deletions, substitutions or a combination thereof with respect to the XII chain depicted in FIG. 16, preferably 1, 2, 3 or 4 insertions, deletions, substitutions or a combination thereof, preferably 1, 2 or 3 insertions, deletions, substitutions or a combination thereof, more preferably 1 or 2 insertions, deletions, substitutions or a combination thereof, and preferably 1 insertion, deletion, substitution or a combination thereof with respect to the VH chain depicted in FIG. 16. The one or more amino acid insertions, deletions, substitutions or a combination thereof are preferably not in the CDR1, CDR2 and CDR3 region of the XII chain. They are also preferably not present in the FR4 region. An amino acid substitution is preferably a conservative amino acid substitution.

In a preferred embodiment the invention provides a bispecific antibody comprising an amino acid sequence as depicted in FIG. 16D, or a bispecific antibody of FIG. 16D having at most 15, preferably 1, 2, 3, 4, 5, 6, 7, 8, 9 or 10, more preferably at most 1, 2, 3, 4 or 5, amino acid insertions, deletions, substitutions or a combination thereof with respect to the sequence of FIG. 16D, wherein the at most 15, preferably 1, 2, 3, 4, 5, 6, 7, 8, 9 or 10 amino acid substitutions are preferably conservative amino acid substitutions. The insertions, deletions, substitutions or a combination thereof are preferably not in the CDR3 region of the VH chain, preferably not in the CDR1, CDR2 and CDR3 region of the Vl chain, and preferably not in the FR4 region.

Rational methods have evolved toward minimizing the content of non-human residues in the human context. Various methods are available to successfully graft the antigen-binding property of a bispecific antibody onto another antibody. The binding properties of antibodies rest predominantly in the exact sequence of the CDR3 region, often supported by the sequence of the CDR1 and CDR2 regions in the variable domain combined with the appropriate structure of the variable domain as a whole. Various methods are presently available to graft CDR regions onto a suitable variable domain of another antibody. Some of these methods are reviewed in J. C. Almagrol and J. Fransson (2008) Frontiers in Bioscience 13, 1619-1633, which is included by reference herein. The invention therefore further provides a human or humanized bispecific antibody comprising a first antigen-binding site that binds ErbB-2 and a second antigen-binding site that binds ErbB-3, wherein the variable domain comprising the ErbB-2 binding site comprises a VH CDR3 sequence as depicted in FIG. 16A or FIG. 16E, and wherein the variable domain comprising the ErbB-3 binding site comprises a VH CDR3 region as depicted in FIG. 16B or FIG. 16E or FIG. 37. The VH variable region comprising the ErbB-2 binding site preferably comprises the sequence of the CDR1 region. CDR2 region and the CDR3 region of a VH chain in FIG. 16A or FIG. 16E. The VH variable region comprising the ErbB-3 binding site preferably comprises the sequence of the CDR1 region, CDR2 region and the CDR3 region of a VH chain in FIG. 16B or FIG. 16E or FIG. 37. CDR grafting may also be used to produce a VH chain with the CDR regions of a VH of FIG. 16 or FIG. 37, but having a different framework. The different framework may be of another human VH, or a different mammal.

The mentioned at most 15, preferably 1, 2, 3, 4, 5, 6, 7, 8, 9 or 10 amino acid substitutions are preferably conservative amino acid substitutions. The insertions, deletions, substitutions or a combination thereof are preferably not in the CDR3 region of the VH chain, preferably not in the CDR1, CDR2 or CDR3 region of the VH chain and preferably not in the FR4 region.

The light chain of a variable domain comprising a variable heavy chain sequence as depicted in FIG. 16 or FIG. 37, is preferably germline light chain O12, preferably the rearranged germline human kappa light chain IgVκ1-39*01/IGJκ1*01 or a fragment or a functional derivative thereof (nomenclature according to the IMGT database worldwide web at imgt.org). The terms rearranged germline human kappa light chain IgVκ1·39*01/IGJκ1*01. IGKV1·39/IGKJ1, huVκ1·39 light chain or in short huVκ1·39 are used. The light chain can have 1, 2, 3, 4 or 5 amino acid insertions, deletions, substitutions or a combination thereof. The mentioned 1, 2, 3, 4 or 5 amino acid substitutions are preferably conservative amino acid substitutions, the insertions, deletions, substitutions or a combination thereof are preferably not in the CDR3 region of the VL chain, preferably not in the CDR1, CDR2 or CDR3 region or FR4 region of the VL chain.

Various methods are available to produce bispecific antibodies. One method involves the expression of two different heavy chains and two different light chains in a cell and collecting antibody that is produced by the cell. Antibody produced in this way will typically contain a collection of antibodies with different combinations of heavy and light chains, some of which are the desired bispecific antibody. The bispecific antibody can subsequently be purified from the collection. The ratio of bispecific to other antibodies that are produced by the cell can be increased in various ways. In a preferred embodiment of the invention, the ratio is increased by expressing not two different light chains but two essentially identical light chains in the cell. This concept is in the art also referred to as the "common light chain" method. When the essentially identically light chains work together with the two different heavy chains allowing the formation of variable domains with different antigen-binding sites and concomitant different binding properties, the ratio of bispecific antibody to other antibody that is produced by the cell is significantly improved over the expression of two different light chains. The ratio of bispecific antibody that is produced by the cell can be further improved by stimulating the pairing of two different heavy chains with each other over the pairing of two identical heavy chains. The art describes various ways in which such heterodimerization of heavy chains can be achieved. One way is to generate 'knob into hole' bispecific antibodies. See US Patent Application 20030078385 (Arathoon et al.—Genentech). Another and preferred method is described in U.S. provisional application 61/635,935, which has been followed up by US regular application Ser. No. 13/866,747 and PCT application No. PCT/NL2013/050294 (WO 2013/157954 A1), which are incorporated herein by reference. Methods and means are disclosed for producing bispecific antibodies from a single cell, whereby means are provided that favor the formation of bispecific antibodies over the formation of monospecific antibodies. These methods can also be favorably employed in the present invention. Thus the invention provides a method for producing a bispecific antibody according to the invention (from a single cell), wherein said bispecific antibody comprises two CH-3 domains that are capable of forming an interface, said method comprising providing in said cell a) a first nucleic acid molecule encoding a 1st CH3 domain comprising heavy chain, b) a second nucleic acid molecule encoding a 2nd (113 domain comprising heavy chain, wherein said nucleic acid molecules are provided with means for preferential pairing of said 1st and 2nd CH3 domain comprising heavy chains, said method further comprising the step of culturing said host cell and allowing for expression of said two nucleic acid molecules and harvesting said bispecific antibody from the culture. Said first and second nucleic acid molecules may be part of the same nucleic acid molecule, vector or gene delivery vehicle and may be integrated at the same site of the host cell's genome. Alternatively, said first and second nucleic acid molecules are separately provided to said cell.

A preferred embodiment provides a method for producing a bispecific antibody according to the invention (from a single cell), wherein said bispecific antibody comprises two CH3 domains that are capable of forming an interface, said method comprising providing:

a cell having a) a first nucleic acid molecule encoding a heavy chain comprising an antigen binding site that binds ErbB-2 and that contains a 1st CH3 domain, and b) a second nucleic acid molecule encoding a heavy chain comprising an antigen-binding site that binds ErbB-3 and that contains a 2nd CH3 domain, wherein said nucleic acid molecules are provided with means for preferential pairing of said 1st and 2nd CH3 domains.

said method further comprising the step of culturing said cell and allowing for expression of said two nucleic acid molecules and harvesting said bispecific IgG antibody from the culture. In a particularly preferred embodiment, said cell also has a third nucleic acid molecule encoding a common light chain. Said first, second and third nucleic acid molecule may be part of the same nucleic acid molecule, vector or gene delivery vehicle and may be integrated at the same site of the host cell's genome. Alternatively, said first, second and third nucleic acid molecules are separately provided to said cell. A preferred common light chain is O12, preferably the rearranged germline human kappa light chain IgVκ1 39*01/IGJκ1*01, as described above. Means for preferential pairing of said $1^{st}$ and said $2^{nd}$ CH3 domain are preferably the corresponding mutations in the CH3 domain of the heavy chain coding regions. The preferred mutations to produce essentially only bispecific antibodies are the amino acid substitutions L351K and T366K (numbering according to Kabat) in the first CH3 domain and the amino acid substitutions L351D and L368E in the second CH3 domain, or vice versa. Further provided is therefore a method according to the invention for producing a bispecific antibody, wherein said first CH3 domain comprises the amino acid substitutions L351K and T366K (numbering according to Kabat) and wherein said second CH3 domain comprises the amino acid substitutions L351D and L368E, said method further comprising the step of culturing said cell and allowing for expression of said nucleic acid molecules and harvesting said bispecific antibody from the culture. Also provided is a method according to the invention for producing a bispecific antibody, wherein said first CH3 domain comprises the amino acid substitutions L351D and L368E (numbering according to Kabat) and wherein said second (113 domain comprises the amino acid substitutions L351K and T366K, said method further comprising the step of culturing said cell and allowing for expression of said nucleic acid molecules and harvesting said bispecific antibody from the culture. Antibodies that can be produced by these methods are also part of the present invention. The CH3 heterodimerization domains are preferably IgG1 heterodimerization domains. The heavy chain constant regions comprising the CH3 heterodimerization domains are preferably IgG1 constant regions.

In one embodiment the invention provides a nucleic acid molecule encoding an antibody heavy chain variable region according to the invention. The nucleic acid molecule (typically an in vitro, isolated or recombinant nucleic acid) preferably encodes a heavy chain variable region as depicted in FIG. 16A or FIG. 16B or FIG. 37, or a heavy chain variable region as depicted in FIG. 16A or FIG. 16B or FIG. 37 having 1, 2, 3, 4 or 5 amino acid insertions, deletions, substitutions or a combination thereof. In a preferred embodiment the nucleic acid molecule comprises a sequence as depicted in FIG. 16 or FIG. 37. In another preferred embodiment the nucleic acid molecule encodes the same amino acid sequence as the nucleic acid depicted in FIG. 16 or FIG. 37, but has a different sequence because it encodes one or more different codons. For instance, such nucleic acid molecule is codon optimized for antibody producer cells, such as for instance Chinese hamster ovary (CHO) cells, NS0 cells or PER-C6™ cells. The invention further provides a nucleic acid sequence encoding a heavy chain of FIG. 16D or FIG. 37.

A nucleic acid molecule as used in the invention is typically but not exclusively a ribonucleic acid (RNA) or a deoxyribonucleic acid (DNA). Alternative nucleic acids are available for a person skilled in the art. A nucleic acid according to the invention is for instance comprised in a cell. When said nucleic acid is expressed in said cell, said cell produces an antibody according to the invention. Therefore, the invention in one embodiment provides a cell comprising an antibody according to the invention and/or a nucleic acid according to the invention. Said cell is preferably an animal cell, more preferably a mammal cell, more preferably a primate cell, most preferably a human cell. For the purposes of the invention a suitable cell is any cell capable of comprising and preferably of producing an antibody according to the invention and/or a nucleic acid according to the invention.

The invention further provides a cell comprising an antibody according to the invention. Preferably said cell (typically an in vitro, isolated or recombinant cell) produces said antibody. In a preferred embodiment said cell is a hybridoma cell, a CHO cell, an NS0 cell or a PER-C6™ cell. In a particularly preferred embodiment said cell is a CHO cell. Further provided is a cell culture comprising a cell according to the invention. Various institutions and companies have developed cell lines for the large scale production of antibodies, for instance for clinical use. Non-limiting examples of such cell lines are CHO cells, NS0 cells or PER.C6™ cells. These cells are also used for other purposes such as the production of proteins. Cell lines developed for industrial scale production of proteins and antibodies are herein further referred to as industrial cell lines. Thus in a preferred embodiment the invention provides the use of a cell line developed for the large scale production of antibody for the production of an antibody of the invention.

The invention further provides a method for producing an antibody comprising culturing a cell of the invention and harvesting said antibody from said culture. Preferably said cell is cultured in a serum free medium. Preferably said cell is adapted for suspension growth. Further provided is an antibody obtainable by a method for producing an antibody according to the invention. The antibody is preferably purified from the medium of the culture. Preferably said antibody is affinity purified.

A cell of the invention is for instance a hybridoma cell line, a CHO cell, an NS0 cell or another cell type known for its suitability for antibody production for clinical purposes. In a particularly preferred embodiment said cell is a human cell.

Preferably a cell that is transformed by an adenovirus E1 region or a functional equivalent thereof. A preferred example of such a cell line is the PER.C6™ cell line or equivalent thereof. In a particularly preferred embodiment said cell is a CHO cell or a variant thereof. Preferably a variant that makes use of a Glutamine synthetase (GS) vector system for expression of an antibody.

The invention further provides a composition, preferably a pharmaceutical composition, comprising an antibody according to the invention. The pharmaceutical composition preferably comprises a (pharmaceutically acceptable) excipient or carrier. In a preferred embodiment the pharmaceutical composition comprises 5-50 mM Histidine, 100-300 mM Trehalose, 0.1-03 g/L PolySorbate20 or a combination thereof. The pH is preferably set at pH=5.5-6.5. In a preferred embodiment the pharmaceutical composition comprises 25 mM Histidine, 220 mM Trehalose, 0.2 g/L Poly-Sorbate20 or a combination thereof. The pH is preferably set at pH=5.5-6.5, most preferably at pH=6.

An antibody of the invention preferably further comprises a label, preferably a label for in vivo imaging. Such a label is typically not necessary for therapeutic applications. In for instance a diagnostic setting, a label can be helpful. For instance in visualizing target cells in the body. Various labels are suited and many are well known in the art. In a preferred embodiment the label is a radioactive label for detection. In another preferred embodiment, the label is an infrared label. Preferably the infrared label is suited for in vivo imaging. Various infrared labels are available to the person skilled in the art. Preferred infrared labels are for instance, IRDye 800: IRDye 680RD: IRDye 680LT: IRDye 750; IRDye 700DX; IRDye 800RS IRDye 650: IRDye 700 phosphoramidite: IRDye 800 phosphoramidite (LI-COR USA; 4647 Superior Street; Lincoln, Nebr.).

The invention further provides a method for the treatment of a subject having a ErbB-2, ErbB-3 or ErbB-2/ErbB-3 positive tumor or at risk of having said tumor comprising administering to the subject an antibody or pharmaceutical composition according to the invention. Before start of said treatment, the method preferably comprises determining whether said subject has, or is at risk of, such ErbB-2, ErbB-3 or ErbB-2/ErbB-3 positive tumor. In some embodiments, the subject is classified as 1+1 or [++] for ErbB-2. In another embodiment the subject is classified as [+++] for ErbB-2. The invention further provides an antibody of the invention for use in the treatment of a subject having or at risk of having an ErbB-2, ErbB-3 or ErbB-2/ErbB-3 positive tumor. Alternatively formulated, the invention provides a use of an antibody according to the invention for the manufacture of a medicament or prophylactic agent for the treatment of an ErbB-2, ErbB-3 or ErbB-2/ErbB-3 positive tumor. As used herein, the term treatment encompasses prophylaxis.

The tumor is preferably an ErbB-2, ErbB-3 or ErbB-2/ErbB-3 positive cancer. Preferably said positive cancer is a breast cancer, such as early-stage breast cancer. However, the invention can be applied to a wide range of ErbB-2, ErbB-3 or ErbB-2/ErbB-3 positive cancers, like gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, melanoma, and the like. Said antibody according to the present invention is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity (I) of said second antigen-binding site for an ErbB-3 positive cell is equal to, or higher than, the affinity of said first antigen-binding site for an ErbB-2 positive cell. Further provided is therefore an antibody comprising a first antigen-binding site that binds ErbB-2 and a second antigen-binding site that binds ErbB-3 for use in the treatment of a subject having or at risk of having an ErbB-2, ErbB-3 or ErbB-2/ErbB-3 positive tumor, preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, wherein the affinity of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM. In one preferred embodiment, said antibody is antibody PB4188.

In one preferred embodiment, said antibody according to the invention comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, said antibody according to the invention preferably comprises an antigen-binding site that binds at least one amino acid of domain III of ErbB-3 selected from the group consisting R426 and surface-exposed amino acid residues that are located within 11.2 Å from R426 in the native ErbB-3 protein.

Further provided is therefore an antibody comprising a first antigen-binding site that binds ErbB-2 and a second antigen-binding site that binds ErbB-3 for use in the treatment of a subject having or at risk of having an ErbB-2, ErbB-3 or ErbB-2/ErbB-3 positive tumor, preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, wherein said antibody according to the invention comprises an antigen-binding site that binds at least one amino acid of domain I of ErbB-2 selected from the group consisting of T144, T164, R166, P1172, G179, S180 and R181, and surface-exposed amino acid residues that are located within about 5 amino acid positions from T144, T164, R166, P172, G179, S180 or R181, and/or wherein said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

The subject is preferably a human subject. The subject is preferably a subject eligible for monoclonal antibody therapy using an ErbB-2 specific antibody such as trastuzumab. In a preferred embodiment the subject comprises a tumor, preferably an ErbB-2/ErbB-3 positive cancer, preferably a tumor/cancer with an ErbB-2 therapy resistant phenotype and/or a heregulin resistance phenotype, preferably a monoclonal antibody resistant phenotype. A tumor involving such phenotype can escape treatment with a current anti-HER2 regimen, such as (but not limited to) monoclonal antibody therapy against ErbB-2.

The amount of antibody according to the invention to be administered to a patient is typically in the therapeutic window, meaning that a sufficient quantity is used for obtaining a therapeutic effect, while the amount does not exceed a threshold value leading to an unacceptable extent of side-effects. The lower the amount of antibody needed for obtaining a desired therapeutic effect, the larger the therapeutic window will typically be. An antibody according to the invention exerting sufficient therapeutic effects at low dosage is, therefore, preferred. The dosage can be in the range of the dosing regime for trastuzumab or lower.

The present invention describes among others antibodies that target the ErbB-2 and ErbB-3 receptors and result in potent proliferation inhibition of cancer cell lines in vitro and tumor growth inhibition in vivo, even in the presence of an escape mechanism such as for instance upregulation of NRG1-β1. A diverse panel of human and murine Fab binding arms specific for either ErbB-2 or ErbB-3 were identified. These were produced as bispecific antibodies by cloning them into complementary expression vectors that contain mutations in the CH3 region that drives heterodimerization of heavy chains. More than 500 bispecific antibodies were produced at small scale and tested in binding and functional assays on three different cancer cell lines. Various bispecific antibodies were selected and tested in an orthotopic xenograft model using the BxPC3 cell line. This cell line expresses both the ErbB-2 and ErbB-3 receptors and is partially dependent on the ErbB-3 ligand for growth. BxPC3 models are a robust and stringent screening model. Furthermore, a strong anti-tumor activity in vivo has been confirmed using a xenograft model using the JIMT-1 cell line. JIMT-1 cells are derived from a pleural metastasis of a 62-year old patient with breast cancer who was clinically resistant to trastuzumab. JIMT-1 cells grow as an adherent monolayer and form xenograft tumors in nude mice. JIMT-1 cells have an amplified HER-2 oncogene, which showed no identifiable mutations in its coding sequence. JIMT-1 cells overexpress HER-2 mRNA and protein, and the levels of HER-1, HER-3, and HER-4 mRNA and protein are similar to the trastuzumab-sensitive cell line SKBR-3 (Tanner et al, Mol Cancer Ther 2004).

Importantly, a better anti-tumor effect was obtained using an antibody according to the invention as compared to the currently used monoclonal antibodies trastuzumab and pertuzumab, as well as the chemical compound lapatinib.

Antibodies of the invention can be produced at levels >50 mg/L after transient transfection in suspension 293F cells. The bispecific antibodies can be purified to greater than 98% purity with yields >70%. Analytical characterization studies show bispecific IgG1 antibody profiles that are comparable to bivalent monospecific IgG1. In terms of functional activity a bispecific antibody of the invention can demonstrate superior potency compared to trastuzumab+pertuzumab in vitro and in vivo.

Preferred embodiments of the invention provide combination therapy. In one embodiment, an antibody according to the invention is combined with trastuzumab or pertuzumab, since these antibodies bind different ErbB-2 epitopes so that they do not compete for the same epitope with an antibody according to the invention, as shown in the Examples. In another embodiment, an antibody according to the invention is combined with MM-121 (#Ab6) or RG7116 (Roche), since these antibodies bind different ErbB-3 epitopes so that they do not compete for the same epitope with an antibody according to the invention, as shown in the Examples.

In another preferred embodiment, a binding compound that is specific for ErbB-2 and ErbB-3 is combined with an inhibitor of a component of the PI3Kinase pathway and/or with an inhibitor of a component of the MAPK pathway, such as for instance with a tyrosine kinase inhibitor, a PI3Ka inhibitor, an Akt inhibitor, an mTOR inhibitor or an Src inhibitor. In one embodiment a binding compound that is specific for ErbB-2 and ErbB-3 is combined with a microtubuli disrupting drug or with an inhibitor of a histone deacetylase (HDAC). Surprisingly, the inventors have found a synergistic effect when these combinations are used. Further provided is therefore a method for the treatment of a subject having a ErbB-2, ErbB-3 or ErbB-2/ErbB-3 positive tumor or at risk of having said tumor, the method comprising administering to the subject:
a binding compound that is specific for ErbB-2 and ErbB-3, and
one or more compounds selected from the group consisting of an inhibitor of a component of the PI3Kinase pathway, an inhibitor of a component of the MAPK pathway, a microtubuli disrupting drug, and an inhibitor of a histone deacetylase (HDAC). Said inhibitor preferably comprises a tyrosine kinase inhibitor, a PI3Ka inhibitor, an Akt inhibitor, an mTOR inhibitor or an Src inhibitor. Said tyrosine kinase inhibitor is preferably afatinib, lapatinib and/or neratinib. Said PI3Ka inhibitor is preferably BYL719. In one embodiment, said Akt inhibitor is MK-2206. In one preferred embodiment, said mTOR inhibitor is everolimus. In one preferred embodiment, said Src inhibitor is saracatinib. In one preferred embodiment, said microtubuli disrupting drug is paclitaxel. In one preferred embodiment, said HDAC inhibitor is vorinostat. In one preferred embodiment, said binding compound that is specific for ErbB-2 and ErbB-3 is MM-111 (Merrimack Pharmaceuticals). In one preferred embodiment, said binding compound that is specific for ErbB-2 and ErbB-3 is a bispecific antibody. In one preferred embodiment., said binding compound that is specific for ErbB-2 and ErbB-3 is a bispecific antibody according to the invention.

Further provided is therefore a method for the treatment of a subject having a ErbB-2, ErbB-3 or ErbB-2/ErbB-3 positive tumor or at risk of having said tumor, the method comprising administering to the subject:
a bispecific antibody comprising a first antigen-binding site that binds ErbB-2 and a second antigen-binding site that binds ErbB-3, and
one or more compounds selected from the group consisting of an inhibitor of a component of the PI3Kinase pathway, an inhibitor of a component of the MAPK pathway, a microtubuli disrupting drug, and an HDAC inhibitor.

Also provided is a bispecific antibody comprising a first antigen-binding site that binds ErbB-2 and a second antigen-binding site that binds ErbB-3 for use in the treatment of a ErbB-2, ErbB-3 or ErbB-2/ErbB-3 positive tumor, wherein said treatment comprises administering said bispecific antibody and at least one compound selected from the group consisting of an inhibitor of a component of the PI3Kinase pathway, an inhibitor of a component of the MAPK pathway, a microtubuli disrupting drug, and an HDAC inhibitor to a subject having a ErbB-2, ErbB-3 or ErbB-2/ErbB-3 positive tumor. Preferably, a bispecific antibody according to the invention having a first antigen-binding site that binds domain I of ErbB-2 and a second antigen-binding site that binds domain III of ErbB-3 is combined with one or more compounds selected from the group consisting of an inhibitor of a component of the PI3Kinase pathway, an inhibitor of a component of the MAPK pathway, a microtubuli disrupting drug, and an HDAC inhibitor. Said inhibitor preferably comprises a tyrosine kinase inhibitor, a PI3Ka inhibitor, an Akt inhibitor, an mTOR inhibitor or an Src inhibitor. Said tyrosine kinase inhibitor is preferably afatinib, lapatinib and/or neratinib. Said PI3Ka inhibitor is preferably BYL719. In one embodiment, said Akt inhibitor is MK-2206. In one preferred embodiment, said mTOR inhibitor is everolimus. In one preferred embodiment, said Src inhibitor is saracatinib. In one preferred embodiment, said microtubuli disrupting drug is paclitaxel. In one preferred embodiment, said HDAC inhibitor is vorinostat.

Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. In one embodiment, said ErbB-2, ErbB-3 or ErbB-2/ErbB-3 positive tumor has less than 1.000.000 ErbB-2 cell-surface receptors per tumor cell.

In one embodiment, an antibody according to the present invention that is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel, is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity (KD) of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment, an antibody according to the invention that is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a P3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel, comprises an antigen-binding site that binds at least one amino acid of domain 1 of ErbB-2 selected from the group consisting of T144, T164, R166, P172, G179, S180 and R181, and surface-exposed amino acid residues that are located within about 5 amino acid positions from T144, T164, R166, P172, G179, S180 or R181.

In one preferred embodiment, an antibody according to the invention that is combined with one or more compounds selected from the group consisting of an inhibitor of a component of the PI3Kinase pathway, an inhibitor of a component of the MAPK pathway, a microtubui disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib. BYL719, MK-2206, everolimus, saracatinib, vorinostat and paclitaxel, comprises an antigen-binding site that binds at least one amino acid of domain III of ErbB-3 selected from the group consisting of R426 and surface-exposed amino acid residues that are located within 11.2 Å from R426 in the native ErbB-3 protein.

Preferably, a bispecific antibody according to the invention comprising at least the CDR3 sequence, preferably at least the CDR1, CDR2 and CDR3 sequences, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF300, MF3003 and MF1898 as depicted in FIG. 16A or FIG. 16E, and/or comprising at least the CDR3 sequence, preferably at least the CDR1, CDR2 and CDR3 sequences, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37 is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and pactitaxel, more preferably with at least one compound selected from the group consisting of afatinib, lapatinib, neratinib, BYL719, MK-2206, everolimus, saracatinib, vorinostat and pacitaxel In one preferred embodiment a bispecific antibody according to the invention comprising:
an ErbB-2 specific heavy chain variable region sequence selected from the group consisting of the heavy chain variable region sequences of MF2926, MF2930, MF1849; MF2973, MF3004, MF3958, N2971, MF3025, MF2916, N3991, MF3031, MF2889, MF2913, MF1847, MF3001, MF3003 and MF1898 as depicted in FIG. 16A or FIG. 16E, or comprising an ErbB-2 specific heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the heavy chain variable region sequences of MF2926, MF2930.

MF1849; MF2973, MF3004, MF3958, MF2971, MF3025, MF2916, MF3991, MF3031, MF2889, MF2913, MF1847, MF3001, MF3003 or MF1898, and
an ErbB-3 specific heavy chain variable region sequence selected from the group consisting of the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37, or comprising an ErbB-3 specific heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the heavy chain variable region sequences of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 or MF6074, is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel. In one preferred embodiment, antibody PB4188 is combined with one or more compounds selected from the group consisting of an inhibitor of a component of the PI3Kinase pathway, an inhibitor of a component of the MAPK pathway, a microtubuli disrupting drug and an HDAC inhibitor, preferably with at least one compound selected from the group consisting of a tyrosine kinase inhibitor, a PI3Ka inhibitor, an Akt inhibitor, an mTOR inhibitor, an Src inhibitor, vorinostat and paclitaxel, more preferably with at least one compound selected from the group consisting of afatinib, lapatinib, neratinib, BYL719, MK-2206, everolimus, saracatinib, vorinostat and paclitaxel.

Preferred embodiments of the invention provide uses of antibodies according to the invention under heregulin stress conditions. Heregulin is a growth factor that is involved in growth of ErbB-3 positive tumor cells. Typically, when the tumor cells express high levels of heregulin (referred to as heregulin stress), currently known therapies like trastuzumab, pertuzumab and lapatinib are no longer capable of inhibiting tumor growth. This phenomenon is called heregulin resistance. Surprisingly, however, an antibody according to the invention is also capable of counteracting growth of tumor cells that express high levels of heregulin. As used herein, an expression level of heregulin is considered high if a cell has a heregulin expression level that is at least 60%, preferably at least 70%, more preferably at least 80%, more preferably at least 85%, more preferably at least 90% or 95% of the heregulin expression level of BXPC3 or MCF7 cells. Heregulin expression levels are for instance measured using qPCR with tumor RNA (such as for instance described in Shames et al. PLOS ONE, February 2013, Vol. 8, Issue 2, pp 1-10 and in Yonesaka et al., Sci. transl. Med., Vol. 3. Issue 99 (2011); pp 1-11), or using protein detection methods, like for instance ELISA, preferably using blood, plasma or serum samples (such as for instance described in Yonesaka et al., Sci. transl. Med., Vol. 3, Issue 99 (2011); pp 1-11). Further provided is therefore an antibody according to the invention for use in the treatment of a subject having or at risk of having an ErbB-2, ErbB-3 or ErbB-2/ErbB-3 positive tumor, wherein said cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the invention preferably comprises a first antigen-binding site that binds domain I of ErbB-2. Also provided is a method for the treatment of a subject having a ErbB-2, ErbB-3 or ErbB-2/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, the method comprising administering to the subject an antibody or pharmaceutical composition according to the invention. One preferred embodiment provides a use of an antibody according to the invention for the preparation of a medicament for the treatment of an ErbB-2, ErbB-3 or ErbB-2/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore an antibody according to the invention for use in the treatment of a subject having or at risk of having breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma, preferably breast cancer, wherein cells of said cancer have a heregulin expression level that is at least 60%, preferably at least 70%, more preferably at least 80%, more preferably at least 85%, more preferably at least 90% or 95% of the heregulin expression level of BXPC3 or MCF7 cells. Said antibody according to the invention preferably comprises a first antigen-binding site that binds domain I of ErbB-2.

High heregulin levels are typically present during the formation of metastases (i.e, the migration, invasion, growth and/or differentiation of tumor cells or tumor initiating cells). Typically, tumor initiating cells are identified based on stem cell markers such as for instance CD44, CD24, CD133 and/or ALDH1. These processes can therefore barely be counteracted with currently known therapies like trastuzumab and pertuzumab. Since an antibody according to the invention is capable of counteracting growth and/or differentiation of tumor cells or tumor initiating cells that express high levels of heregulin, such antibody according to the invention is also particularly suitable for counteracting the formation of metastases. Further provided is therefore a method for counteracting the formation of a metastasis in a subject having a ErbB-2, ErbB-3 or ErbB-2/ErbB-3 positive tumor, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells, comprising administering to the subject a bispecific antibody comprising a first antigen-binding site that binds ErbB-2 and a second antigen-binding site that binds ErbB-3. Also provided is a bispecific antibody comprising a first antigen-binding site that binds ErbB-2 and a second antigen-binding site that binds ErbB-3 for use in the treatment or prevention of the formation of metastases, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Further provided is a use of a bispecific antibody according to the invention for the preparation of a medicament for the treatment or prevention of the formation of metastases, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells. Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Further provided is therefore a bispecific antibody according to the invention comprising a first antigen-binding site that binds ErbB-2 and a second antigen-binding site that binds ErbB-3 for use in the treatment or prevention of the formation of metastases of breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma cells, preferably breast cancer cells, wherein said cells have a heregulin expression level that is at least 60%, preferably at least 70%, more preferably at least 80%, more preferably at least 85%, more preferably at least 90% or 95% of the heregulin expression level of BXPC3 or MCF7 cells. Said antilxxdy according to the present invention is typically capable of reducing a ligand-induced receptor function, preferably ligand induced growth, of ErbB-3 on a ErbB-2 and ErbB-3 positive cell. Said antibody according to the invention preferably comprises a first antigen-binding site that binds domain I of ErbB-2 and a second antigen-binding site that binds domain III of ErbB-3. In one preferred embodiment, the affinity (KD) of said second antigen-binding site for an ErbB-3 positive cell is equal to, or higher than, the affinity of said first antigen-binding site for an ErbB-2 positive cell. The affinity of said second antigen-binding site for an ErbB-3 positive cell is preferably lower than or equal to 2.0 nM, more preferably lower than or equal to 1.39 nM, more preferably lower than or equal to 0.99 nM. The affinity of said first antigen-binding site for an ErbB-2 positive cell is preferably lower than or equal to 5.0 nM, preferably lower than or equal to 4.5 nM preferably lower than or equal to 4.0 nM.

In one preferred embodiment, said antibody according to the invention comprises an antigen-binding site that binds at least one amino acid of domain I of ErbB-2 selected from the group consisting of T144, T164, R166, P172, G179, S180 and R181, and surface-exposed amino acid residues that are located within about 5 amino acid positions from T144, T164, R166, P172, G179. S180 or R181.

In one preferred embodiment, said antibody according to the invention preferably comprises an antigen-binding site that binds at least one amino acid of domain III of ErbB-3 selected from the group consisting of R426 and surface-exposed amino acid residues that are located within 11.2 Å from R426 in the native ErbB-3 protein.

One preferred embodiment provides a method according to the invention for the treatment of a subject having a ErbB-2, ErbB-3 or ErbB-2/ErbB-3 positive tumor wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, or an antibody according to the invention for use in such treatment, wherein said antibody comprises at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E.

One preferred embodiment provides a method according to the invention for the treatment of a subject having a ErbB-2, ErbB-3 or ErbB-2/ErbB-3 positive tumor wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, or an antibody according to the invention for use in such treatment, wherein said antibody comprises at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37. One embodiment provides antibody PB4188 for use in the treatment of a subject having a ErbB-2, ErbB-3 or ErbB-2/ErbB-3 positive tumor, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells.

As already described, antibodies according to the present invention are particularly suitable for treating ErbB-2 positive tumor cells with less than 1.000.000 ErbB-2 receptors on their cell surface. Patients with such tumors, who are typically classified as ErbB-2 [++] or ErbB-2 [+], include patients with primary tumors as well as patients with relapsed ErbB-2 positive tumors. Currently used therapies such as trastuzumab (HERCEPTIN®) and pertuzumab are only prescribed for patients with malignant ErbB-2 positive cells that have more than 1.000.000 ErbB-2 receptors on their cell surface, which are classified as ErbB-2 [+++]. Patients that are classified as ErbB-2 [++] or ErbB-2 [+] are therefore preferably treated with an antibody according to the present invention. Further provided is therefore a method or antibody for use according to the invention, wherein said subject has an ErbB-2 or ErbB-2/ErbB-3 positive tumor that has less than 1.000.000 ErbB-2 cell-surface receptors per tumor cell. One preferred embodiment provides a bispecific antibody according to the invention comprising a first antigen-binding site that binds ErbB-2 and a second antigen-binding site that binds ErbB-3 for use in the treatment or prevention of the formation of metastases, wherein said ErbB-2, ErbB-3 or ErbB-2/ErbB-3 positive tumor cell has a heregulin expression level that is at least 60%, preferably at least 70%, more preferably at least 80%, more preferably at least 85%, more preferably at least 90% or 95% of the heregulin expression level of BXPC3 or MCF7 cells, and wherein said tumor cell has less than 1.000.000 ErbB-2 cell-surface receptors.

In another preferred embodiment, an antibody according to the invention is used for counteracting an ErbB-2, ErbB-3 or ErbB-2/ErbB-3 positive tumor in a subject who has an impaired cardiac function, or who is at risk thereof. With an impaired cardiac function is meant that the subject has a cardiac function, such as for instance the left ventricular ejection fraction (LVEF), that is lower than 90%, preferably lower than 85% or lower than 80%, preferably lower than 75% or lower than 70%, as compared to a healthy cardiac function. Said healthy cardiac function is, for instance, the average cardiac function (such as for instance the average LVEF) of the healthy population. Alternatively, said healthy cardiac function is the function (such as the LVEF) as measured in a patient before the start of anti-tumor therapy with an antibody according to the invention.

Cardiac function is for instance monitored by a physical examination of the subject and by an examination of the LVEF, using for instance an echocardiogram or a MUGA scan.

ErbB-2 is involved in growth, repair, and survival of adult cardiomyocytes as part of a signalling network that involves the heregulin receptor complex HER2:HER4. As described herein before, cardiotoxicity is a known risk factor in ErbB-2 targeting therapies and the frequency of complications is increased when trastuzumab is used in conjunction with anthracyclines thereby inducing cardiac stress. For instance, the combination of doxycycline with trastuzumab induces severe cardiac side effects. Despite the increasing number of clinical cases of trastuzumab-induced cardiac dysfunction, its mechanism of action is unknown. In view of the cardiotoxicity of currently known therapies against ErbB-2, ErbB-3 or ErbB-2/ErbB-3 positive tumors, it is of particular advantage to use an antibody according to the invention. As shown in the Examples, antibodies have now been provided that do not, or to a significantly lesser extent as compared to trastuzumab and pertuzumab, affect the survival of cardiomyocytes. This provides an important advantage since cardiotoxicity is reduced. This is already advantageous for people who do not suffer from an impaired cardiac function, and even more so for people who do suffer from an impaired cardiac function, such as for instance subjects suffering from congestive heart failure (CHF), left ventricular dysfunction (LVD) and/or a decreased Left Ventricular Ejection Fraction (LVEF), and/or subjects who have had a myocardial infarction. Further provided is therefore a bispecific antibody according to the invention for use in the treatment of a subject having or at risk of having an ErbB-2, ErbB-3 or ErbB-2/ErbB-3 positive tumor, wherein said subject has a cardiac function that is lower than 90%, preferably lower than 85% or lower than 80% or lower than 75% or lower than 70%, as compared to a healthy cardiac function. Said cardiac function preferably includes the LVEF. Said ErbB-2. ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Said antibody according to the invention preferably comprises a first antigen-binding site that binds domain I of ErbB-2 and a second antigen-binding site that binds domain III of ErbB-3. One preferred embodiment provides a method according to the invention for the treatment of a subject having a ErbB-2, ErbB-3 or ErbB-2/ErbB-3 positive tumor wherein the subject has a cardiac function that is lower than 90%, preferably lower than 85%, preferably lower than 80%, preferably lower than 75% or lower than 70%, as compared to a healthy cardiac function, or an antibody according to the invention for use in such treatment, wherein said antibody comprises:

at least the CDR3 sequence, preferably at least the CDR1, CDR2 and CDR3 sequences, or at least the heavy chain variable region sequence, of an ErbB-2 specific heavy chain variable region selected from the group consisting of MF2926, MF2930, MF1849; MF2973, MF3004, MF3958, MF2971, MF3025, MF2916, MF3991, MF3031, MF2889, MF2913, MF1847, MF3001, MF3003 and MF1898 as depicted in FIG. 16A or FIG. 16E, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences; and/or at least the CDR3 sequence, preferably at least the CDR1, CDR2 and CDR3 sequences, or at least the heavy chain variable region sequence, of an ErbB-3 specific heavy chain variable region selected from the group consisting of MF3178; MF3176; MF3163; MF3099; MF3307; MF6055; MF6056; MF6057; MF6058; MF6059; MF6060; MF6061; MF6062; MF6063; MF6064; MF6065; MF6066; MF6067; MF6068; MF6069; MF6070; MF6071; MF6072; MF6073 and MF6074 as depicted in FIG. 16B or FIG. 16E or FIG. 37, or a heavy chain variable region sequence that differs in at most 15 amino acids, preferably in at most 1, 2, 3, 4, 5, 6, 7, 8, 9 or 10 amino acids, more preferably in at most 1, 2, 3, 4 or 5 amino acids, from the recited heavy chain variable region sequences. In one preferred embodiment, said antibody is PB4188.

In one embodiment, said bispecific antibody is for use in the treatment of a subject under heregulin stress conditions, as explained in more detail elsewhere. Further provided is therefore a bispecific antibody according to the invention for use in the treatment of a subject having or at risk of having an ErbB-2, ErbB-3 or ErbB-2/ErbB-3 positive tumor, wherein said subject has a cardiac function that is lower than 90%, preferably lower than 85%, preferably lower than 80%, preferably lower than 75% or lower than 70%, as compared to a healthy cardiac function, and wherein said cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells. Said cardiac function preferably includes the LVEF. Also provided is a method for the treatment of a subject having a ErbB-2, ErbB-3 or ErbB-2/ErbB-3 positive tumor, wherein the subject has a cardiac function that is lower than 90%, preferably lower than 85%, preferably lower than 80%, preferably lower than 75%, preferably lower than 70%, as compared to a healthy cardiac function, and wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells, the method comprising administering to the subject a bispecific antibody or pharmaceutical composition according to the invention. One preferred embodiment provides a use of a bispecific antibody according to the invention for the preparation of a medicament for the treatment of an ErbB-2, ErbB-3 or ErbB-2/ErbB-3 positive tumor in a subject who has a cardiac function, preferably a LVEF, that is lower than 90%, preferably lower than 85%, preferably lower than 80%, preferably lower than 75% or lower than 70%, as compared to a healthy cardiac function, preferably a healthy LVEF, wherein cells of said tumor have a heregulin expression level that is at least 60%, preferably at least 70%, more preferably at least 80%, more preferably at least 85%, more preferably at least 90% or 95% of the heregulin expression level of BXPC3 or MCF7 cells.

Also provided is a bispecific antibody comprising a first antigen-binding site that binds ErbB-2 and a second antigen-binding site that binds ErbB-3 for use in the treatment or prevention of the formation of metastases, wherein said subject has a cardiac function that is lower than 90%, preferably lower than 85%, preferably lower than 80%, preferably lower than 75%, preferably lower than 70% as compared to a healthy cardiac function. Further provided is a use of a bispecific antibody according to the invention for the preparation of a medicament for the treatment or prevention of the formation of metastases, wherein said subject has a cardiac function that is lower than 90%, preferably lower than 85%, preferably lower than 80%, preferably lower than 75%, preferably lower than 70% as compared to a healthy cardiac function. Said ErbB-2, ErbB-3 or ErbB-2/ErbB-3 positive tumor is preferably breast cancer, gastric cancer, colorectal cancer, colon cancer, gastro-esophageal cancer, esophageal cancer, endometrial cancer, ovarian cancer, liver cancer, lung cancer including non-small cell lung cancer, clear cell sarcoma, salivary gland cancer, head and neck cancer, brain cancer, bladder cancer, pancreatic cancer, prostate cancer, kidney cancer, skin cancer, or melanoma. Most preferably, said tumor is breast cancer. Said cardiac function preferably includes the LVEF. In one preferred embodiment, said antibody is antibody PB4188.

In another embodiment, use is made of antibodies according to the invention for counteracting phosphorylation of various factors of the prosurvival pathway Akt (also referred to as the PI3 kinase pathway) and the MAP kinase pathway. These are downstream pro-proliferative signaling pathways of HER3. Surprisingly, the inventors have succeeded in significantly inhibiting phosphorylation of Akt, ERK1/2 and S6 ribosomal protein (S6-RP) with an antibody according to the present invention, whereas trastuzumab and pertuzumab do not have these strong anti-phosphorylation effects. Counteracting phosphorylation of factors of the pro-proliferative PI3 kinase and MAP kinase pathways is advantageous, since this counteracts growth of an ErbB-3 positive tumor cell. Further provided is therefore a use of an antibody according to the invention for counteracting, preferably inhibiting, phosphorylation of Akt, ERK1/2 and/or S6-RP. Importantly, phosphorylation of Akt can be significantly reduced or even completely blocked with an antibody of the invention, both in viro and in vivo, as shown in the Examples. A preferred embodiment therefore provides a use of an antibody according to the invention for counteracting, preferably inhibiting, phosphorylation of Akt. Also provided is a use of an antibody according to the invention for counteracting the formation of a HER3-p85 complex. Since the formation of a HER3-p85 complex is the first phase in Akt activation, it is advantageous to counteracting the formation of said HER3-p85 complex. Said antibody according to the invention is preferably a bispecific antibody comprising a first antigen-binding site that binds domain I ErbB-2 and a second antigen-binding site that binds domain III of ErbB-3. Said antibody preferably comprises an antigen-binding site that binds at least one amino acid of domain I of ErbB-2 selected from the group consisting of T144, T164, R1166, P172, G179, S180 and R181, and surface-exposed amino acid residues that are located within about 5 amino acid positions from T144, T164, R166, P172, G179, S180 or R181. Additionally, or alternatively, said antibody preferably comprises an antigen-binding site that binds at least one amino acid of domain III of ErbB-3 selected from the group consisting of F409 and R426 and surface-exposed amino acid residues that are located within 11.2 Å from R426 in the native ErbB-3 protein. In one embodiment, said antibody comprises at least one CDR1, CDR2 and CDR3 sequence, or at least one VH sequence, as depicted in FIG. 16 or FIG. 37. In one embodiment, said antibody is PB4188.

For the purpose of clarity and a concise description features are described herein as part of the same or separate embodiments, however, it will be appreciated that the scope of the invention may include embodiments having combinations of all or some of the features described.

BRIEF DESCRIPTION OF THE DRAWINGS

FIG. 16A-16E: Nucleic acid and amino acid sequences of VH-chains, common light chain and heavy chains of antibodies of the invention. Where in this figure a leader sequence is indicated this is not part of the VH chain or antibody, but is typically cleaved of during processing of the protein in the cell that produces the protein.

FIGS. 28A and 28B: Inhibition of cell proliferation under HRG stress conditions by HER2xHER3 bispecific antibodies composed of the same HER3 Fab arm and different HER2 arms that are directed against the four HER2 domains.

FIG. 37A-37G: Amino acid and nucleotide alignments of the F3178 variants. CDR regions are indicated.

EXAMPLES

Figure 1:
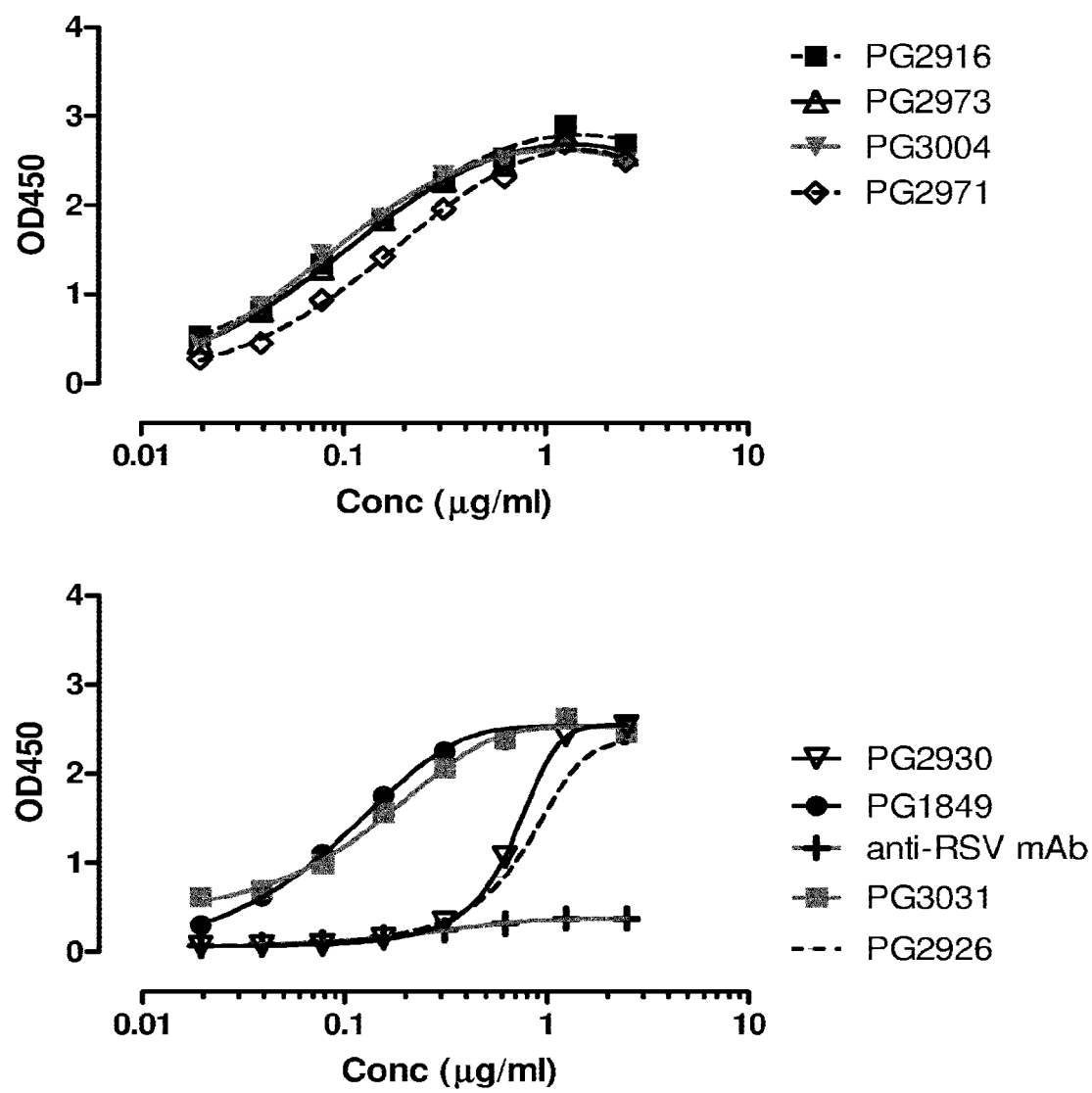
FIG. 1: Antigen titration on monomeric HER2 of a panel of HER2 arms that are also present in active HER2xHER3 bispecific antibodies in combination with one arm of PG3178. All HER2 monoclonals of the HER2xHER3 panel except for PG3025 were tested on an HER2 antigen titration ELISA.

Methods, Materials and Screening for Antibodies
Cell Lines:

BxPC-3-luc2 (Perkin Elmer 125058), N87 (ATCC® CRL-5822™), SK-BR-3 (ATCC® HTB30™), BT-474 (ATCC® HTB-20™), JIMT-1 (DSMZ ACC 589), L929 (Sigma Aldrich 85011425), K562 (DSMZ ACC10), HEK293T (ATCC®-CRL-11268$^T$m), CHO-K1(DSMZ ACC110), MCF-7 (DSMZ ACC 115), MDA-MB-468 (#300279-513. Cell line services) SK-OV-3 (ATCC® HTB-77™), MDA-MB-175 (ATCC-HTB-25), MDA-MB-453 (ATCC-HTB-131), MDA-MB-361(ATCC-H-TB-27), ZR-75-1 (ATCC-CRL-1500) and MKN-45 (DSMZ ACC409) cell lines were purchased from ATCC. DSMZ or Sigma Aldrich and routinely maintained in growth media supplemented with 10% heat inactivated fetal bovine serum (FBS). HEK293F Freestyle cells were obtained from INVITROGEN® and routinely maintained in 293 FreeStyle medium.

Generation of Recombinant Human, Chicken, Rat and Swapped Domain Vectors (Cloning of HER)

Human HER2. Full length Human HER2 was amplified by PCR from cDNA derived from RNA isolated from the breast cancer cell line JIMT-1. The primers used for the amplification of human HER2 were as follows. Forward primer: AAGCTGGCTAGCACCATGGAGCTGGCCTTGTGC (SEQ ID NO: 1). Reversed primer: AATAATTCTAGACTGGCACGTCCAGACCCAGG (SEQ ID NO:2). The full-length amplified product was digested with NheI and XbaI and subsequently cloned in the corresponding sites of pcDNA3.1 (INVITROGEN®). The sequence was verified by comparison with the NCBI Reference Sequence NM_004448.2. To generate constructs solely expressing the human HER2 extracellular domain (ECD) for transfection and immunization purposes the HER2 transmembrane domain and ECD were PCR amplified and recloned in pVax1. For transfection purposes another construct was generated in pDisplay by amplifying the HER2 ECD domain, in this construct the HER2 ECD domain is fused to the PDGFR transmembrane domain.

Human HER3. The full length human cDNA clone of HER3 was obtained from Origene. To generate constructs solely expressing the human HER3 ECD for transfection and immunization purposes the HER3 transmembrane domain and ECD were PCR amplified and recloned in pVax1. In addition another construct was generated in pVax1 whereby the HER3 ECD domain was fused to the PDGFR transmembrane domain. All sequences were verified by comparison with the NCBI Reference NM_001982.3

Cynomolgus HER2 extracellular domain was PCR amplified from cynomolgus cDNA—Monkey) Normal Colon Tissue (Biochain). The primers used for the amplification of cynomolgus HER2 were as follows: Forward primer: AAGCTGGCTAGCACCATGGAGCTGGCGGCCTGGTAC (SEQ ID NO: 3).

Reversed primer: AATAATTCTAGACTGGCACGTCCAGACCCAGG (SEQ ID NO: 4). The full-length amplified product was digested with NheI-XbaI and subsequently cloned in the corresponding sites of pcDNA3.1. The clone was sequenced and aligned with sequences available of rhesus monkeys (XM_002800451) to check correctness of the ErbB-2 clone.

Cynomolgus HER3 extracellular domain was PCR amplified from cynomolgus cDNA—Monkey) Normal Colon Tissue (Biochain). The primers used for the amplification of cynomolgus HER3 were as follows: Forward primer: AAGCTGGCTAGCACCATGAGGGCGAACGGCGCTCTG (SEQ ID NO: 5), Reversed primer: AATAATTCTAGATTACGTTCTCTGGGCATTAGC (SEQ ID NO: 6). The full-length amplified product was digested with NheI-XbaI and subsequently cloned in the corresponding sites of pcDNA3.1. The clone was sequenced and aligned with sequences available of rhesus monkeys (ENSMMUP00000027321) to check correctness of the HER3 clone.

The chicken HER2 sequence was based on the reference sequence NM_001044661.1. Chimeric swapped domain constructs were generated by swapping domains I until IV of the chicken HER2 sequence for the human I domains I until IV. Sequences containing a myc tag were optimized for expression in mammalian cells and synthesized at Geneart.

The rat HER3 sequence was based on the reference sequence NM_001044661.1. Chimeric swapped domain constructs were generated by swapping domains I until IV of the rat HER3 sequence for the human I domains I until IV. Sequences containing a myc tag were optimized for expression in mammalian cells and synthesized at Geneart.

Generation of HER2 and HER3 Over-Expressing Cell Lines

To generate cell lines that express high levels of HER3 on the cell surface a mammalian expression vector was generated by excising the full length HER3 by a NotI and KpnI digestion. Subsequently the fragment was cloned in the corresponding sites of the pcDNA3.1(-)/hygro vector. A full length HER2 and HER3 expression vector encoding a neomycin resistance gene was used to generate cell lines that express high levels of HER2 on the cell surface. Prior to transfection the plasmids were linearized by a SspI and FspI digestion. Both vectors were transfected separately into K562 cells and stable pools were generated following antibiotic selection. The resultant cell lines (K562-HER2 and K562-HER3) expressed high levels of HER2 and HER3 on their cell surface.

Immunizations

HER2 immunizations. Four different immunization strategies were applied. For cohort #A, six C57Bl/6 mice were immunized with $2\times10^6$ L929 cells transiently transfected with HER2 in 200 µl via intraperitoneal injection. Subsequently, mice were boosted with 20 µg Erbb-2-Fc (RND systems) protein dissolved in 125 µl Titermax Gold via intraperitoneal injection on day 14, followed by boosts with $2\times10^6$ L929 cells transiently transfected with HER2 in 200 µl on days 28 and 42. For cohort #C, six C57B116 mice were immunized with $2\times10^6$ L929 cells transiently transfected with HER2 via intraperitoneal injection. Subsequently, mice were boosted with $2\times10^6$ L929 cells transiently transfected with HER2 in 200 µl via intraperitoneal injection on day 14, followed by a protein boosts with 20 µg Erbb-2-Fe protein dissolved in 125 µl Titermax Gold via intraperitoneal injection on day 35 and a final boost with 20 µg Erbb-2-Fc protein dissolved in 200 µl PBS via intraperitoneal injection on day 49. For cohort #E, six C57B/6 mice were immunized with 20 µg Erbb-2-Fe protein dissolved in 125 µl Titermax Gold via intraperitoneal injection. Subsequently, protein boosts with 20 µg Erbb-2-Fc protein dissolved in 125 µl Titermax Gold via intraperitoneal injection were made at day 14 and 28 and a final boost with 20 µg Erbb-2-Fc protein dissolved in 200 µl PBS via intraperitoneal injection on day 42. For cohort #G, six C57Bl/6 mice were immunized by DNA vaccination at Genovac (Freiburg, Germany) according to their protocols. The endotoxin-free provided vectors used for the DNA vaccination encoded the transmembrane and extracellular part of HER2 cloned in pVax1. Subsequently, DNA boosts were given at day 14, 28 and 66.

HER3 immunizations. Four different immunization strategies were applied. For cohort #B, six (C57Bl/6) mice were immunized with $2\times10^6$ L929 cells transiently transfected with HER3 in 200 µl via intraperitoneal injection. Subsequently, mice were boosted with $2\times10^6$ L929 cells transiently transfected with HHER3 in 200 µl on days 14, 28, 49 and 63. For cohort #D, six C57Bl/6 mice were immunized with $2\times10^6$ L929 cells transiently transfected with HER3 via intraperitoneal injection on day 0, 14 and 28. Subsequently, mice were boosted with 20 µg Erbb-3-Fc protein dissolved in 125 µl Titermax Gold via intraperitoneal injection on day 49 and a final boost with 20 µg Erbb-3-Fc protein dissolved in 200 µl PBS via intraperitoneal injection on day 66. For cohort #F, six C57Bl/6 mice were immunized with 20 µg Erbb-3-Fe protein dissolved in 125 µl Titermax Gold via intraperitoneal injection. Subsequently, mice were boosted with 20 µg Erbb-3-Fc protein dissolved in 125 µl Titermax Gold via intraperitoneal injection at day 14 and 28 and a final boost was given with 20 µg Erbb-3-Fc protein dissolved in 200 µl PBS via intraperitoneal injection on day 42. For cohort #H, six C57Bl/6 mice were immunized by DNA vaccination at Genovac (Freiburg, Germany) according to their protocols. The endotoxin-free provided vectors used for the DNA vaccination encoded the transmembrane of PDGFR and extracellular part of HER3 cloned in pVax1. Subsequently, DNA boosts were given at day 14, 28 and 66.

Determination of Antibody Titers.

Anti-HER2 titers in the serum from immunized C57Bl/6 mice were determined by ELISA against ECD-Erbb-2 protein (Bendermedsystems) and FACS analysis on the HER2 negative K562, the HER2 low expressing cell line MCF-7 and HER2 amplified SKBR-3 and BT-474 cells. Anti-HER3 titers in the serum from immunized C57Bl/6 mice were determined by ELISA against Erbb-3-Fe protein and FACS analysis on the HER3 negative K562, the HER2 low expressing cell line MCF-7 and HER2 amplified SKBR-3 and BT-474 cells.

Serum titers against HER2 and HER3 before sacrificing the animals are described in Table 1 and Table 2 respectively. Animals in all cohorts developed antibody responses against HER2 or HER3.

Recovery of Lymphoid Tissue.

Spleen and draining lymph nodes were removed from all mice vaccinated with DNA (cohorts #G and #H). Single cell suspensions were generated from all tissues and subsequently tissues were lysed in Trizol reagent. From cohorts #A until #F spleens were removed from all mice except for one mouse of cohort #C that died after the first boost. Single cell suspensions were generated from all spleens and the total B cell fraction was isolated using the MACS separation procedure either by CD19 enrichment (cohorts #A, E, F) or depletion of non-B cells (cohorts #B, C, D).

Generation of Phage Display Libraries from Immunized Mice

One phage library was built for each mouse. To this end the material from all mice per group (5 or 6 mice per group) was used to prepare phage libraries using the following approach. From each individual mouse RNA was isolated and cDNA was synthesized and VH-family specific PCRs were performed. Subsequently all VH-family PCR products per mouse were purified and the DNA concentration was determined and digested and ligated in a phage-display vector containing the common-light chain to generate a mouse-human chimeric phage library. All phage libraries contained >$10^6$ clones with an insert frequency of >85%.

Selection of Phages Carrying Fab Fragments Specifically Binding to HER2 and HER3

Antibody fragments were selected using antibody phage display libraries. Immunized libraries and synthetic libraries (as described in de Kruif et al. Mol. Biol. (1995), 248, 97-105) were used for selections.

HER2 Phage Selection and Screening

Phage libraries were rescued with VCS-M13 helper phage (Stratagene) and selected for two rounds in immunotubes (Nunc) coated recombinant protein. In the first round ECD-Erbb-2 protein (Bendermedsystems) was coated onto immunotubes whereas in the second round Erbb-2-Fc (RND systems) was coated onto immunotubes. The immunotubes were blocked with 4% non fat dry milk (ELK). Phage antibody libraries were also blocked with 4% ELK prior to the addition of the phage library to the immunotubes. Incubation with the phage library with the coated protein in the immune tubes was performed for 2 H at room temperature under rotating conditions. Immunotubes were then washed five to ten times with 0.05% Tween-20 in PBS followed by 5 to 10 times in PBS. Bound phages were eluted using 50 mM glycine (pH 2.2) and added to *E. coli* XL-1 Blue and incubated at 37° C. for phage infection. Subsequently infected bacteria were plated on agar plates containing Ampicillin, tetracyclin and glucose and incubated at 37° C. overnight. After the first round, colonies were scraped off the plates and combined and thereafter rescued and amplified to prepare an enriched first round library. The enriched library was then selected on Erbb-2-Fe (RND systems) using the protxcol described above. After the second round selection individual clones were picked and rescued to prepare a phage monoclonal miniprep. Positive phage clones binding Erbb2 were then identified in FACS for binding to the breast cancer cell line BT-474. The VH genes of all Erbb2 specific clones were sequenced. VH gene rearrangements were established with VBASE2 software to identify unique clones. All unique clones were then tested in phage format for binding in FACS to HEK293T cells (negative control), HEK293T cells transiently transfected with ErbB-2 and BT-474 cells.

HER3 Phage Selection and Screening

Phage libraries were rescued with VCS-M13 helper phage (Stratagene) and selected for two rounds in immunotubes (Nunc) coated with recombinant protein. In both selection rounds round Erbb-3-Fc (RND systems) was coated onto immunotubes. To overcome a selection bias towards the Fc part of the fusion protein, both selection rounds on Erbb-3-Fc were performed in the presence of 150 µg/ml human IgG. The immunotubes were blocked with 4% ELK. Phage antibody libraries were blocked with 4% ELK prior to the addition of the phage library to the immunotubes. Incubation with the phage library was performed for 2 H under rotating conditions. Immunotubes were then washed five to ten times with 0.05% Tween-20 in PBS followed by 5 to 10 times in PBS. Bound phages were eluted using 50 mM glycine (pH 2.2) and added to E. coli XL-1 Blue and incubated for phage infection. Subsequently infected bacteria were plated on agar plates containing Ampicillin, tetracyclin and glucose and incubated at 37° C. overnight. After the first round, colonies were scraped off the plates and combined and phages were rescued and amplified to prepare an enriched first round library. The enriched library was then selected on Erbb-3-Fc (RND systems) using the protocol described above. After the second round selection individual clones were picked and rescued to prepare a phage monoclonal miniprep. Positive phage clones were identified in FACS for binding to the breast cancer cell line BT-474. The VH genes of all positive clones were sequenced. VH gene rearrangements were established with VBASE2 software to identify unique clones. All unique clones were tested in phage format for binding in FACS to K562 cells (negative control), stable K562-HER3 cells and BT-474 cells.

In total 36 selections were performed on Erbb2 and Erbb3 antigen formats. All selection screening procedures resulted in 89 unique Fab clones directed against HER2 and 137 unique Fab clones directed against HER3. A Fab was considered unique based on its unique H(CDR3 sequence, an indication of a unique VDJ recombination event. In some cases clonal variants were obtained, with an identical HCDR3 but differences in the CDR1 and/or CDR2. From the immunized mice libraries clusters of clonal variants containing substitutions in the VH gene reflecting affinity variants were selected.

Antibody Selection/Characterization
Generation of Monoclonal Antibodies

VH genes of unique antibodies, as judged by VH gene sequence and some sequence variants thereof, derived from the immunized mouse phage libraries were cloned in the backbone IgG1 vector. Two different production cell lines were used during the process: HEK293T and 293F Freestyle cells. Adherent HEK293T cells were cultivated in 6-well plates to a confluency of 80%. The cells were transiently transfected with the individual DNA-FUGENE mixture and further cultivated. Seven days after transfection, supernatant was harvested and medium was refreshed. Fourteen days after transfection supernatants were combined and filtrated through 0.22 µM (Sartorius). The sterile supernatant was stored at 4° C. Suspension adapted 293F Freestyle cells were cultivated in T125 flasks at a shaker plateau until a density of $3.0\times10^6$ cells/ml. Cells were seeded at a density of $0.3-0.5\times10^6$ viable cells/ml in each well of a 24-deep well plate. The cells were transiently transfected with the individual sterile DNA:PE1 mixture and further cultivated. Seven days after transfection, supernatant was harvested and filtrated through 0.22 µM (Sartorius). The sterile supernatant was stored at 4° C.

Generation of Bispecific Antibodies

Bispecific antibodies were generated using the proprietary CH3 technology to ensure efficient hetero-dimerisation and formation of a bispecific antibody. The CH3 technology uses charge-based point mutations in the CH3 region to allow efficient pairing of two different heavy chain molecules as previously described (PCT/NL2013/050294; published as WO 2013/157954 A1).

IgG Purification for Functional Screening

The purification of IgG was performed at small scale (<500 µg), medium scale (<10 mg) and large scale (>10 mg) using affinity chromatography. Small scale purifications were performed under sterile conditions in 24 well filter plates using vacuum filtration. First the pH of the medium was adjusted to pH 8.0 and subsequently the small scale productions were incubated with protein A SEPIAROSE™ CL-4B beads (50% v/v) (Pierce) for 2 I at 25° C. on a shaking platform at 600 rpm (Heidolph plate shaker). Next the beads were harvested by vacuum filtration. Beads were washed twice with PBS pH 7.4. IgG was eluted at pH 3.0 with 0.1 M citrate buffer and the IgG fraction was immediately neutralized by Tris pH 8.0. Buffer exchange was performed by centrifugation using multiscreen ULTRACEIL@ 10 multiplates (MILLIPORES). The samples ended up in a final buffer of PBS pH 7.4

Validation of HER2/HER3 Specific IgGs

Antibodies were tested for binding in FACS to BT-474, HEK293T and HEK29:3T overexpressing HER2 or HER3. Therefore cells were harvested using trypsin and diluted to $10^6$ cells/ml in FACS buffer (PBS/0.5% BSA/0.5 mM EDTA), $1-2\times10^5$ cells were added to each well in a U-bottom 96 well plate. Cells were centrifuged for 2 minutes at 300 g at 4° C. Supernatant was discarded by inverting plate(s), 50 µl of each IgG sample was added at a concentration of 10 µg/ml and incubated for 1H on ice. Cells were centrifuged once, supernatant was removed and cells were washed twice with FACS buffer, 50 µl diluted 1:100 mouse anti human IgG PE (INVITROGEN®) was added and incubated for 30-60 minutes on ice in the dark. After adding FACS buffer, cells were centrifuged once, supernatant was removed and cells were washed twice with FACS buffer. Cells were analysed on a FACSCanto Flow cytometer in a HTS setting. Binding of the antibodies to cells was assessed by mean fluorescence intensity (MFI).

To test for non-specific binding reactivity ELISA assays were used. HER2 and HER3 antibodies were tested for reactivity against the antigens fibrinogen, hemoglobulin and tetanus toxin. To test specific binding to HER2 and HER3, the antibodies were tested for binding to purified recombinant extracellular domains of EGFR. HER2, HER3 and HER4. Antigens were coated overnight to MAXISORP™

ELISA plates. Wells of the ELISA plates were blocked with PBS (pH 7.2) containing 5% BSA for 1 hour at 37° C. Selected antibodies were tested in duplo at a concentration of 10 µg/ml diluted in PBS-2% BSA and allowed to bind for 2 hours at 25° C. As a control the procedure was performed simultaneously with an antibody specific for the coated antigens and a negative control antibody. The ELISA plates were washed 5 times with PBS-T (PBS-0.05% v/v Tween 20). Bound IgG was detected with 1:2000 diluted HRP-conjugate (Goat anti-mouse BD) and was allowed to bind for 2 hours at 25° C. The ELISA plates were washed 5 times with PBS-T (PBS-0.05% Tween 20) and bound IgG was detected by means of OD492 nm measurement.

Epitope Grouping of HER2/HER3 Specific IgGs

The panel of anti-HER2 antibxies was binned based on their reactivity to the HER2 ECD derived from other species (mouse, chicken) and on their binding to specific domains in the HER2 molecule i.e. domains 1. TI. III and IV using chimeric constructs.

The panel of anti-HER3 antibodies was binned based on their reactivity to the HER3 ECD derived from other species (cyno, rat) and on their binding to specific domains in the HER3 molecule i.e. domains I, II, III and IV using chimeric constructs.

For this purpose CHO-K1 cells were transiently transfected with the relevant constructs using lipofectamin/DNA mixes. In the chimeric swapped domain construct, domains of chicken HER2 or rat HER3 are replaced by the human counterpart. Binding of the specific antibodies was measured by FACS. Expression of the constructs was confirmed using an anti-myc antibody. FACS staining with trastuzumab was included as a control for specific binding to domain IV. Antibodies in each group could be ranked based on the intensity of staining (MFI). The HER2 panel of 65 antibodies could be mapped into seven bins (Table 3).

1. Domain I specific (25)
2. Domain II specific (2)
3. Domain III specific (23)
4. Domain IV specific (7)
5. Domain IV specific and cross reactive to mouse (2)
6. Reactive to all constructs (2)
7. Only reactive to human HER2 (4)

Competition with Trastuzumab

Two antibodies mapped to HER2 domain IV inhibited proliferation of SKBR-3 cells. Both antibodies shared a similar CDR3 except for one amino acid difference. One antibody. PG1849 was investigated for its capacity to compete with trastuzumab in a competition ELISA. In this ELISA Fc-HER2 was coated and incubated with a concentration of 15 sg/ml IgG antibody. After an incubation of 15 minutes phages were allowed to incubate for another hour. Thereafter, phages were detected. Table 4 demonstrates that PG1849 and trastuzumab could bind simultaneously to HER2 since no loss of signal appeared during the ELISA. True competition only was observed when the same phage and antibody were combined in the assay.

The HFER3 panel of 124 antibodies could be mapped into five bins (Table 5):

1. High Domain III reactivity, rat and mouse reactive and minor reactivity to domain IV (8)
2. High Domain ITT reactivity, rat, human and cyno reactive, minor reactivity to domain IV (8)
3. Only reactivity to rat, cyno and human HER3 (43)
4. Only reactive to human HER3 (32)
5. Reactive to all constructs (33)

Cell Line Proliferation Assays

SK-BR-3 cells were cultured in DMEM-F/12 supplemented with L-glutamine and 10% heat inactivated FBS. BxPC-3-luc2 cells were cultured in RPMI1640 supplemented with 10% heat inactivated FBS. MCF-7 cells were cultured in RPM 1640 supplemented with 100 µM. NEAA1 mM sodium pyruvate, 4 µg/ml insulin and 10% heat inactivated FBS.

For the proliferation assay of SK-BR-3 cells, subconfluent cell cultures were washed with PBS, trypsinized and trypsin was inactivated by adding culture medium. Cells were diluted to $6 \times 10^4$ cells/ml in culture medium. Antibodies were diluted to concentrations of 10 and 1 µg/ml and added in a volume of 100 µl in 96-well black bottom plates (ABgene AB-0932). Cells were added at density of 6000 cells/well. The cells were cultivated for 3 days at 37° C., 5% CO, in 95% relative humidity. ALAMAR BLUET™ (INVITROGEN®) was added according to the manufacturer's instructions and incubated for 6 hours at 37° C., 5% CO, in 95% relative humidity in the dark. Fluorescence was measured at 550 nm excitation and 590 nm emission wavelength. The extent of growth inhibition was compared to that of the same concentration of trastuzumab (Table 6).

For the proliferation assay of MCF-7 and BxPC-3-luc2 cells, subconfluent cell cultures were washed with PBS, trypsinized and trypsin was inactivated by adding culture medium. Cells were washed twice in large volumes of assay medium (RPMI 1640 medium containing 0.05% BSA and 10 µg/ml Holo Transferrin). MCF-7 cells were diluted to $5 \times 10^4$ cells/ml in culture medium. Antibodies were diluted to concentrations of 10 and I µg/ml and added in a volume of 100 µl in 96-well black bottom plates (ABgene AB-0932). Cells were added at a density of 5000 cells/well in the presence of 1 ng/ml final concentration human Recombinant Human NRG1-beta 1/HRG1-beta 1 EGF Domain: (396-HB-050 RND). Human NRG1-beta 1/HRGI-beta 1 EGF Domain will hereinafter be referred to as HRG. The cells were cultivated for 5 days at 37° C., 5% CO, in 95% relative humidity. ALAMAR BLUE™ (INVITROGEN®) was added according to the manufacturer's instructions and incubated for 24 hours at 37° C., 5% CO2, in 95% relative humidity in the dark. Fluorescence was measured at 550 nm excitation with 590 nm emission wave length. The extent of growth inhibition was compared to that of the same concentration of #Ab6 (Table 7).

BxPC-3-luc-2 proliferation assays were used to screen the bispecific antibodies. BxPC-3-luc-2 cells were diluted to $8 \times 10^4$ cells/ml in culture medium. Antibodies were diluted to concentrations of 10 and 1 µg/ml and added in a volume of 100 µl in 96-well black bottom plates (ABgene AB-0932). Cells were added at density of 8000 cells/well in the absence or presence of 10 ng/ml final concentration human HRG. The cells were cultivated for 4 days at 37° C. 5% CO, in 95% relative humidity. ALAMAR BLUE™ (INVITROGEN®) was added according to the manufacturer's instructions and incubated for 4 hours at 37° C. 5% CO, in 95% relative humidity in the dark. Fluorescence was measured at 550 nm excitation with 590 nm emission wave length.

To minimalize edge effects, the outer wells of the 96 well plates were fully filled with PBS.

Affinity Ranking of HER2 Specific IgGs

We used the method described by Devash (PNAS, 1990) to rank the antibodies in a limited antigen-ELISA. The use of decreased antigen coating concentrations eliminates observed cross-reactivity reactions and can be used to detect high-affinity/avidity antibodies. Therefore the antigen concentration on the solid support was gradually decreased to investigate the weak immunoreactivities. A serial titration of ECD-Erbb-2 protein starting from 2.5 µg/ml until 0.019 µg/ml was coated overnight to MAXISORP™ ELISA plates. Wells of the ELISA plates were blocked with PBS (pH 7.2) containing 5% BSA for 1 hour at 37° C. Selected antibodies were tested in duplo at a concentration of 10 µg/ml diluted in PBS-2% BSA and allowed to bind for 2 hours at 25° C. As a control the procedure was performed simultaneously with an antibody specific for the coated antigens and a negative control antibody. The ELISA plates were washed 5 times with PBS-T (PBS-0.05% v/v Tween 20). Bound IgG was detected with 1:2000 diluted IIRP-conjugate (Goat anti-mouse IgG, BD Biosciences) and was allowed to bind for 2 hours at 25° C. The ELISA plates were washed 5 times with PBS-T (PBS-0.05% Tween 20) and bound IgG was detected by means of OD492 nm measurement. PG1849, PG2916, PG2926, PG2930, PG2971, PG2973, PG3004 and PG3031 were tested in an HER2 antigen titration ELISA (FIG. 1).

Binding of HER2 VH Genes with Various Kappa Light Chains

To investigate the binding of HER2 V, Hs derived from different phage display libraries a panel of HER2 antibodies was cloned and expressed in the context of another VK kappa chain, i.e, the V1, of MEHD7945A. Produced IgGs were subjected to FACS analysis on K562 cells and stable K562-HER2 cells. VH genes derived from the combinatorial libraries and non-combinatorial libraries are listed in Table 8. The VH chains MF2971, MF3958, MF2916, MF2973, MF3004, MF3025, MF3031 all could be combined with the MEHID7945A light chain without loosing significant antigen specificity and binding as observed when combined with the common light chain IGKV1-39, VH chain MF1849 was not able to combine with the variant kappa light chain and retain antigen specificity and binding.

Other HER2 and HER3 Antibodies

Antibodies that inhibit the function of HER2 or HER3 are known in the art. Further antibodies were constructed according to published information and expressed in 293F Freestyle cells. The anti-HER2 antibodies pertuzumab and trastuzumab were generated based on the information disclosed in US2006/0212956 A1 (Genentech). The anti-HER3 antibody #Ab6, was based on the information disclosed in WO 2008/100624 (Merrimack Pharmaceuticals. Inc.) and recloned in a IgG1 back bone vector. The information of the 1-53 and U1-59 anti-HER3 antibodies was obtained from U.S. Pat. No. 7,705,103 B2 (U3 Pharma AG). The information of the anti-HER3 LJM716 antibody was obtained from US 2012/0107306. The information for the construction of the two-in-one anti-EGFR anti-HER3 antibody MEHD7945A was obtained from WO2010/108127.

Screening of HER2xHER3 Bispecific Antibodies

VH from the HER2 and HER3 antibody panel were recloned into the charged engineered vectors such that upon expression of the antibody heavy chains heterodimerization of heavy chains is forced resulting in the generation of bispecific antibodies after transfection. Three different strategies were used in combining HER2 and HER3 arms in bispecific IgG format:
1. HER2 (blocking ligand independent growth) xHER3 (blocking ligand independent growth)
2. HER2 (blocking ligand independent growth) xHER3 (blocking ligand dependent growth)
3. HER2 from different epitope bins x HFER3 (blocking ligand dependent growth)

In some bispecific combinations, antibodies generated in group 2 and 3 overlapped with group 1.

Figure 2:
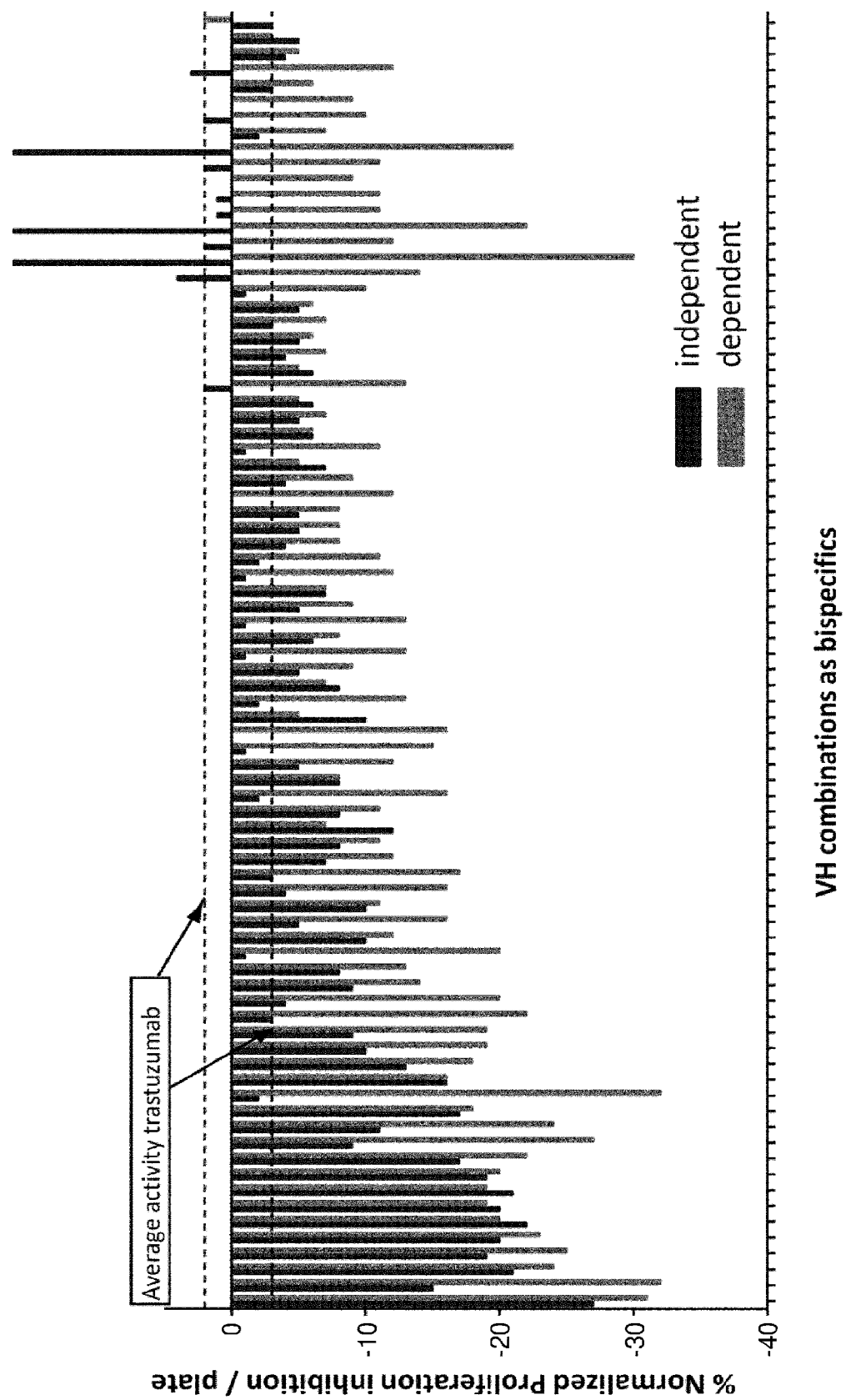
FIG. 2: Functional activity of HER2xHER3 bispecific antibodies on BxPC3 cells with or without ligand stimulation. Dotted lines represent activity of trastuzumab, the reference antibody in this assay, with or without ligand stimulation.

A total of 495 bispecific antibodies was produced in 24-well format and purified. All antibodies were tested for their capacity to inhibit the proliferation of the I HER2- and HER3-expressing pancreatic BxPC-3-luc-2 cell line (Caliper). The potency of the antibodies was determined in a HRG-dependent and HRG-independent setting in a black and white screening with antibodies being present at a concentration of 10 and 1 µg/ml. Trastuzumab was included as a reference antibody as well as a negative control antibody at the same concentrations. The functional activity of the top 80 HER2xHER3 bispecifics (based on combined inhibition) at 1 µg/ml is shown in FIG. 2.

Figure 3:
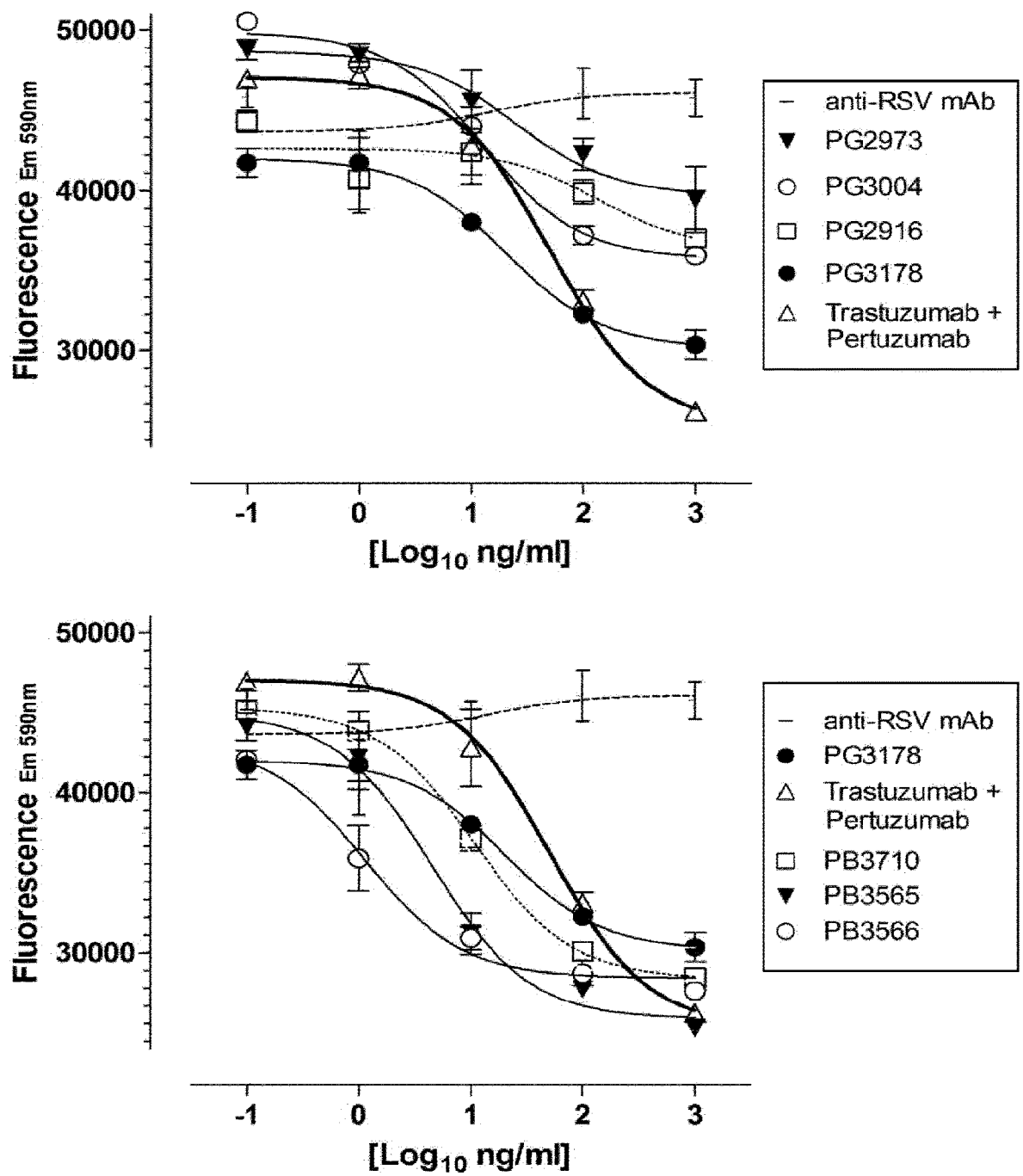
FIG. 3: Titration curves of HER2 and HER3 monoclonal antibodies (Upper panel) and HER2xHER3 bispecific antibodies thereof (Lower panel) in the MCF-7 assay

Antibodies (40 in total) that showed a higher inhibitory activity compared to the positive control antibody were selected, reproduced and purified in a 24-well format and tested again in the black-and-white BxPC-3-luc-2 screen at 10 and 1 µg/ml concentrations. These antibodies were further titrated in HRG-dependent MCF-7 assay and compared against the combination of trastuzumab and pertuzumab (1:1) and a negative control antibody. FIG. 3 shows an example of titration curves of three bispecific antibodies in comparison to the parental HER3 antibody and the combination of trastuzumab+pertuzumab. The parental monoclonal antibodies are shown in the top panel and the bispecific antibodies are shown in the lower panel. (FIG. 3).

The $IC_{50}$ for the bispecific antibodies, monoclonals and comparator antibodies was calculated using non-linear regression analysis with Prism software. Graph pad software lists the $IC_{50}$ values of the bispecific antibodies in the MCF-7 assay and their inhibitory activity in the BxPC3 assay for comparison. A panel of 12 HER2xHER3 bispecific antibodies had more potent inhibiting activity compared to trastuzumab+pertuzumab. In addition the bispecific antibodies were equally or more potent than the parental monoclonal PG3178 (Table 9).

The bispecific antibodies that inhibited ligand dependent cell growth were composed of HER2 arms in combination with the HER3 arms 3178, 3163, 3099 and 3176. Both the HER2 and HER3 arms of the most potent bispecifics were as a bivalent monoclonal also capable of inhibiting ligand-independent SK3R-3 proliferation (both the HER2 and HER3 arms) (Table 6) or ligand dependent MCF-7 proliferation (HER3 arms) (Table 7). The majority of the potent antibodies was composed of a HER2 arm recognizing domain I in combination with anti-HER3 antibody 3178.

Inhibition of BxPC-3-luc2 Tumor Growth

The antilxxlies described in Table 9 were tested in a BxPC-3-luc2 pancreatic xenograft model. The BxPC-3-luc2 cell line expresses both HER2 and HER3 and is considered a HER2 low expressing cell line. C1317 SCID female mice, 8-10 weeks old at the beginning of the study were engrafted orthotopically in the pancreas with $1\times10^6$ tumor cells in 20 µl. To this aim mice were anesthetized and laid on the right side to expose the left side and a 0.5 cm incision was made on the left flank region. The pancreas and spleen were exteriorized and $1\times10^6$ tumor cells in 20 µl was injected into the sub-capsulary space of the pancreas tail. One week after implantation, bioluminescence (BLI) data were generated, 15 minutes prior to the imaging, all of the mice received i.p. injections of 150 mg/kg Luciferin (D-Luciferin-EF Potassium Salt. Cat. #E6552, Promega). BLI imaging was performed once or twice weekly using the left side view. Outlier animals—based on BLI/tumor volume—were removed and the mice were randomly distributed into groups of 7 mice each. On experimental day 8, the treatment was started. The animals in the antibody treatment group were dosed weekly for 3 consecutive weeks (days 0, 7, 14 and 21) with 30 mg/kg of antibody. At day 0 of the treatment the animals received twice the loading dose, i.e. 60 mg/kg of antibody. The final imaging was carried out at day 31.

Two BxPC-3-luc2 xenograft models were run with a different panel of bispecific antibodies and parental antibodies In the first BxPC-3-luc2 xenograft model (FIG. 4), one group received the negative control anti-RSV antibody (Ctrl IgG), one group received the control antibody trastuzumab and one group received the positive control antibody trastuzumab+pertuzumab (1:1 v/v). The seven remaining groups received one of the monoclonal (PG) or bispecific (PB) antibodies PG3004, PG3178, PB3566, PB3710, PB3443, PB3448 and PB33441. Details of the composition of the bispecific antibodies are depicted in Table 9.

Figure 4:
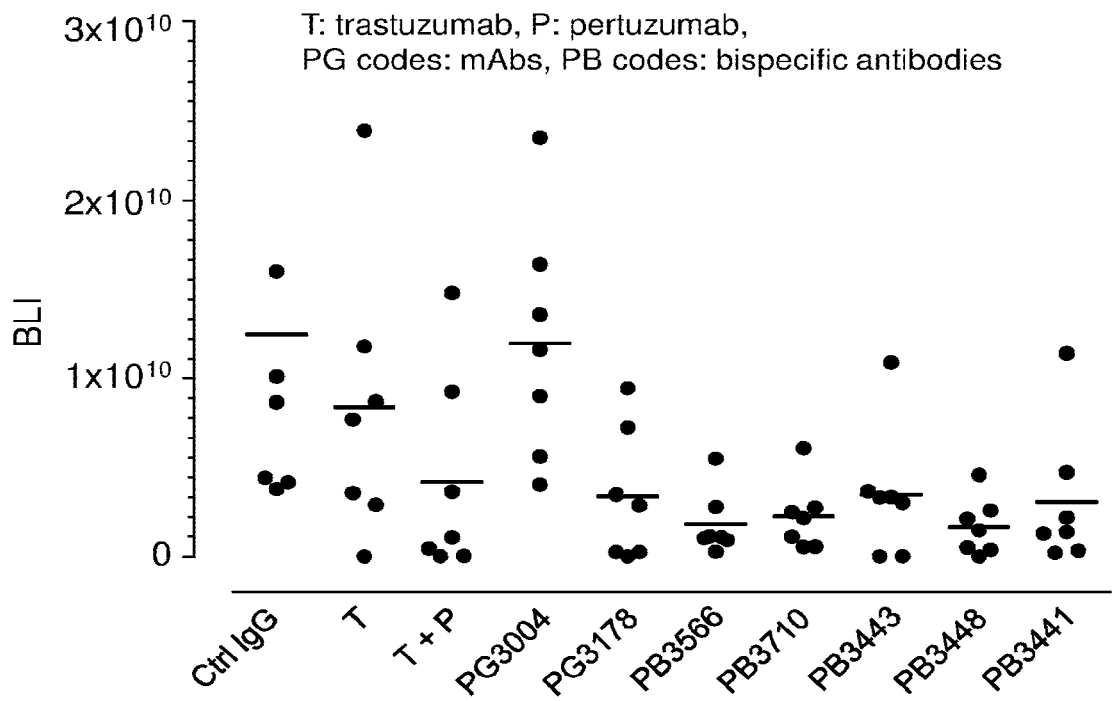
FIG. 4: Antibody treatment effect on BxPC3-luc2 tumor size at day 31 in an orthotopic murine model, BLI, tumor growth as measured by bioluminescence.

All five bispecific antibodies tested were able to inhibit tumor growth. The mean tumor mass (BLI) of bispecific HER2xHER3 antibody treated animals was similar to that in the animals treated with the combination of trastuzumab+pertuzumab. (FIG. 4)

Figure 5:
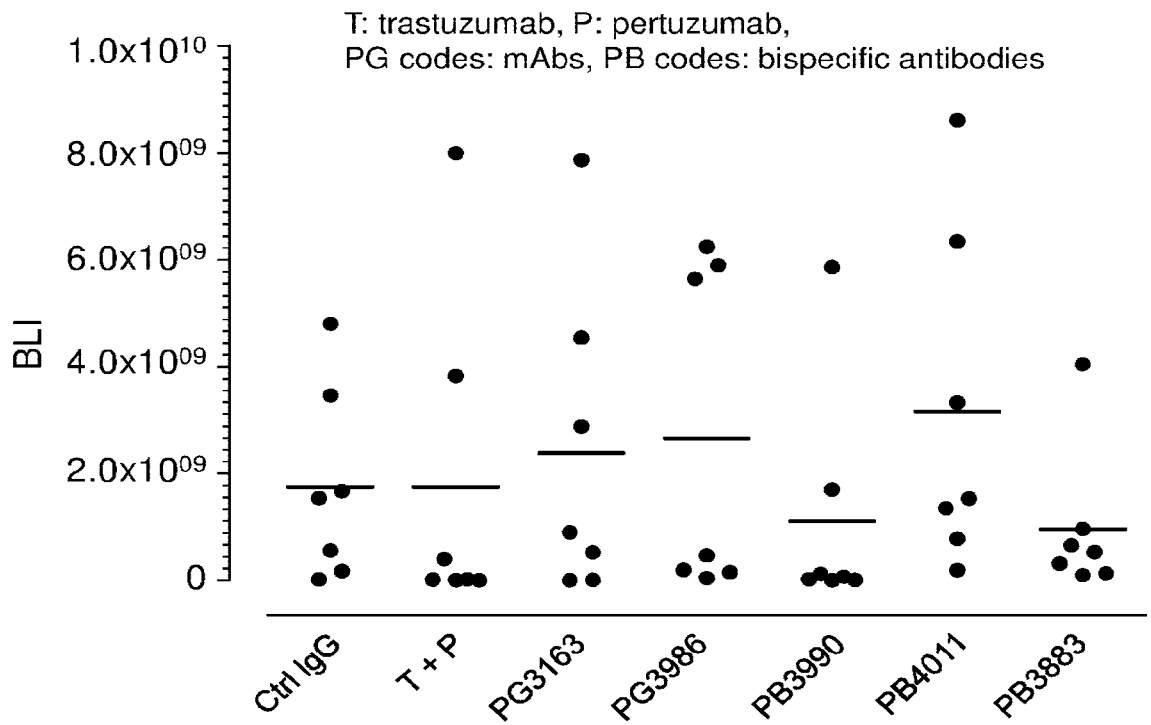
FIG. 5: Antibody treatment effect on BxPC3-luc2 tumor size at day 31 in an orthotopic murine model, BLI, tumor growth as measured by bioluminescence.

In the second BxPC-3-luc2 xenograft model (FIG. 5), one group received the negative control anti-RSV antilxxly (Ctrl IgG) and one group received the positive control antibody combination trastuzumab+pertuzumab (1:1 v/v). The five remaining groups received one of the antibodies P03163. PB3986, PB3990. PB4011 and PB3883. For details about the bispecific PB antibodies: Table 9. These bispecific antibodies contained three different HER3 binding arms combined with the same HER2 arm MF2971 and an additional HER2 arm combined with the HER3 binding arm MF3163. In this experiment the tumors in the control group did not show the same level of accelerated growth as in the first experiment complicating interpretation of the results. Nevertheless, in comparison to trastuzumab+pertuzumab the PB3883 and PB3990 HER2xHER3 bispecifics had similar inhibitory activities (FIG. 5).

Based on the in vivo and in vitro data a bispecific panel of antibodies was selected of which the HER2 arms were composed of MF2971, MF3004, MF1849 and the HER3 arm was composed of MF3178. The MF2971 and MF3004 arm were of mouse origin and were humanized.

Figure 6:
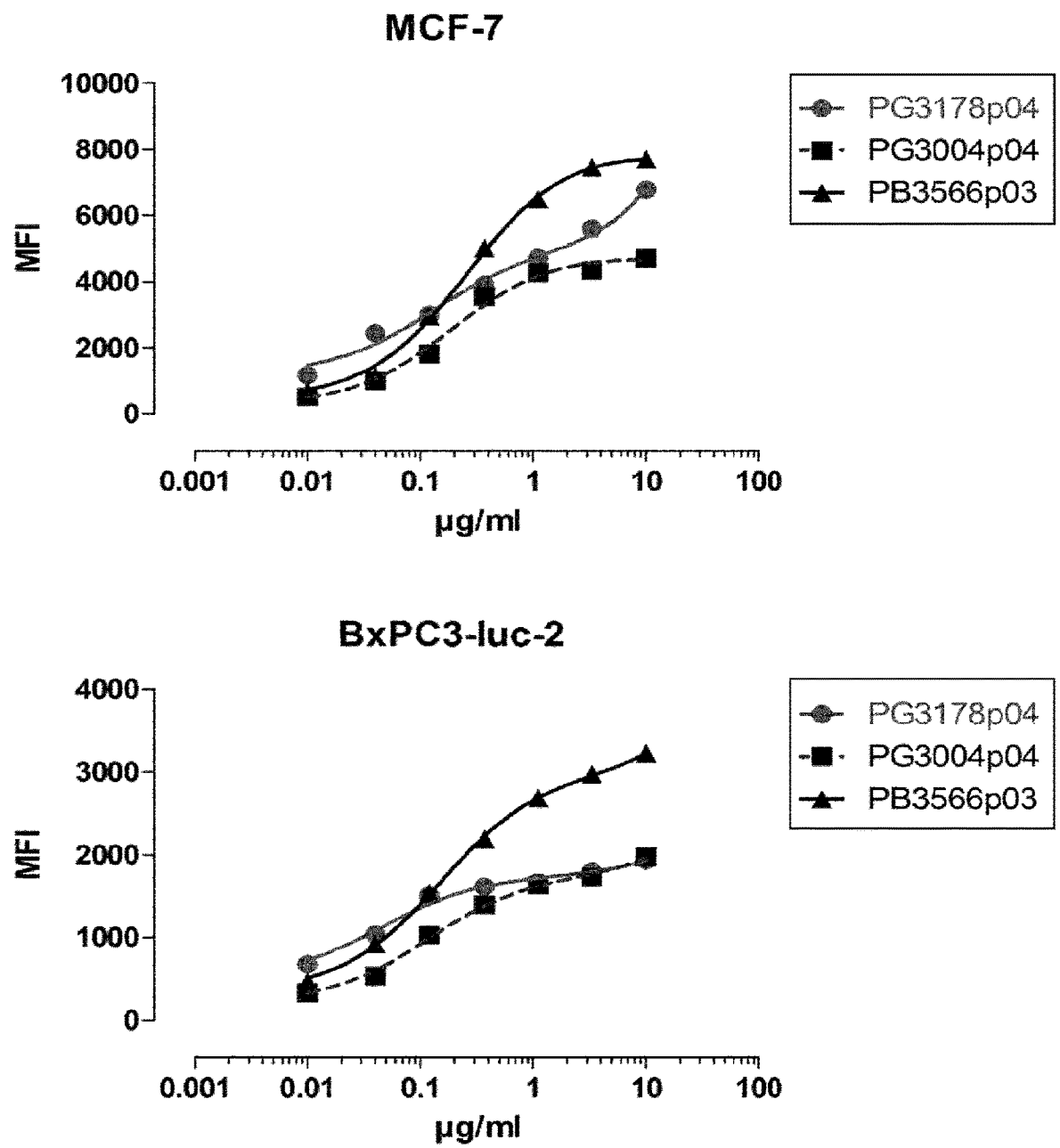
FIG. 6: FACS analysis of a bispecific HER2xHER3 antibody and its parental monoclonal antibodies on MCF-7 and BxPC3-luc2 HER2 expressing cells. MFI, mean fluorescence intensity.
Figure 7A:
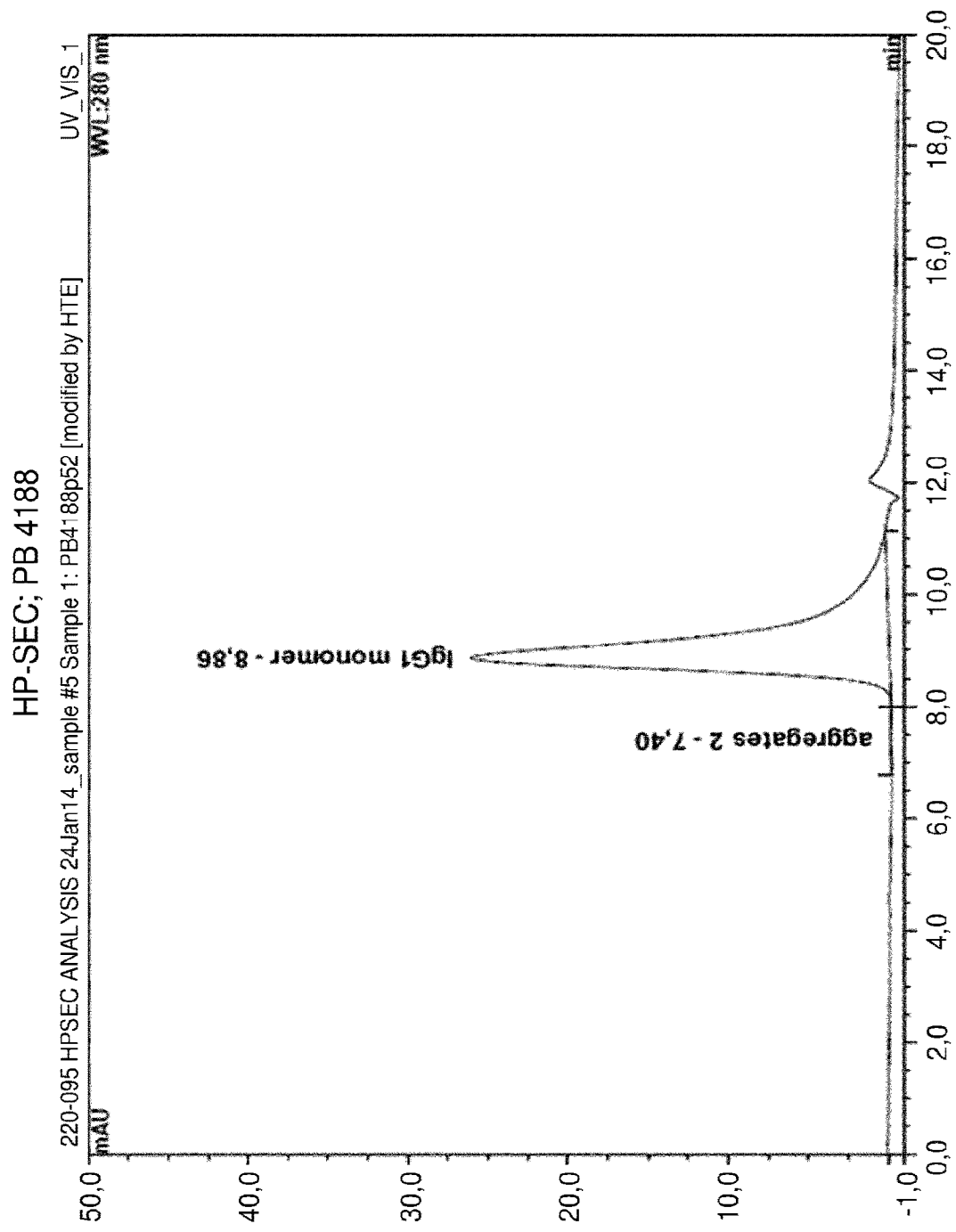
FIG. 7A-7E: Analytical characterization by IP-SEC and CIEX-IPLC. PB4188 (7A and 7B), anti-HER2 parental monoclonal antibody (7C and 7D), anti-RSV monoclonal reference IgG (7E and 7F).
Figure 7B:
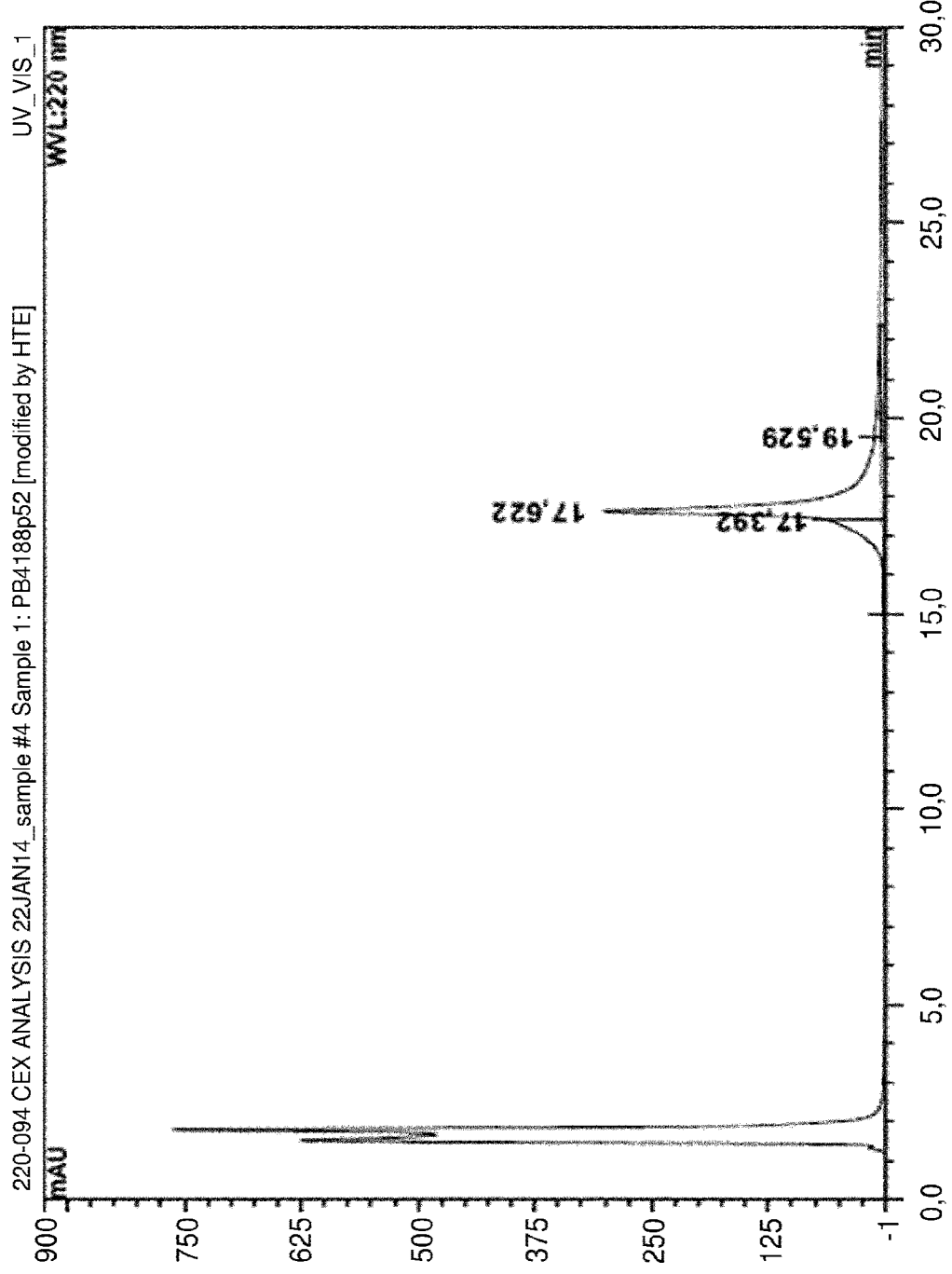
Figure 7C:
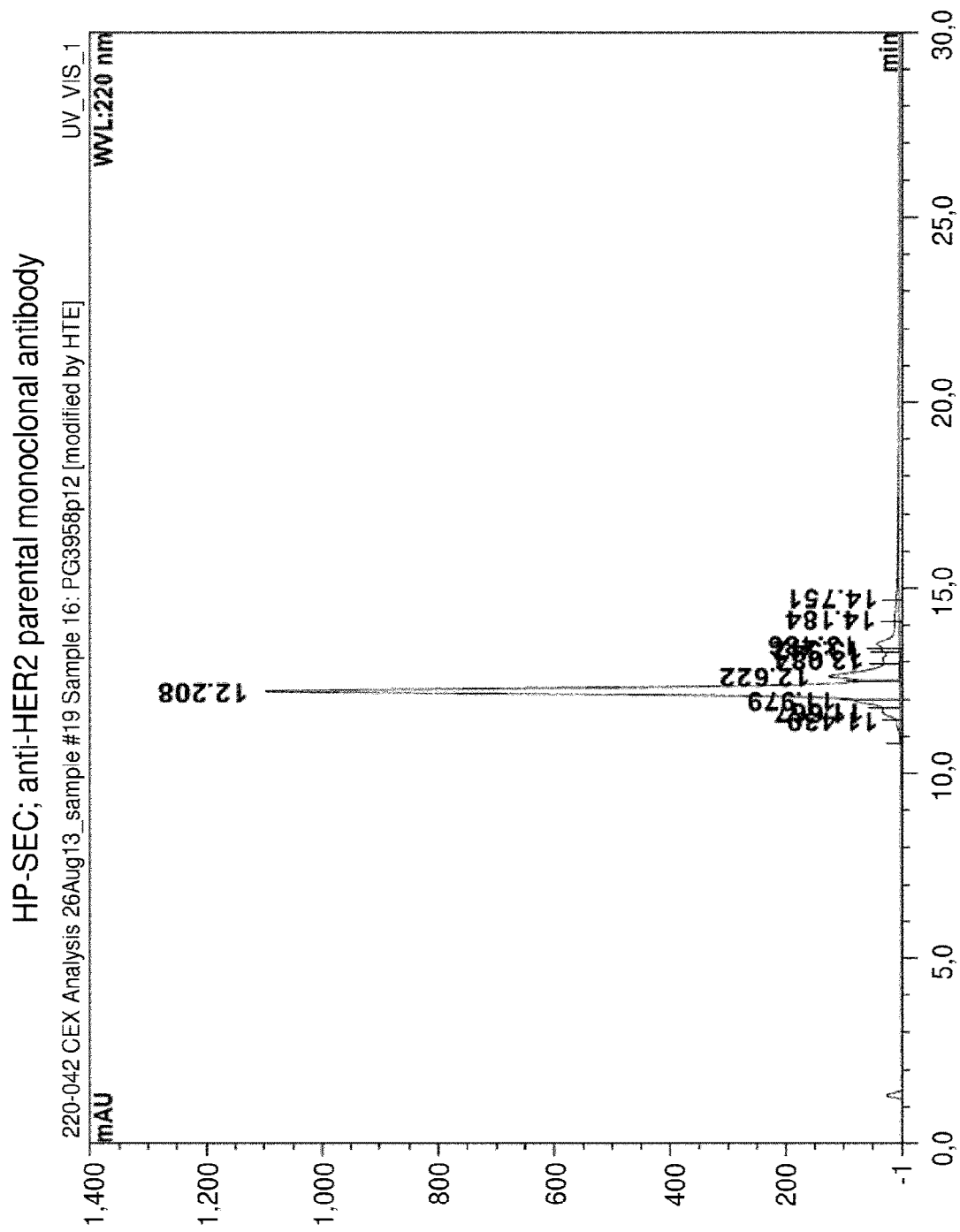
Figure 7D:
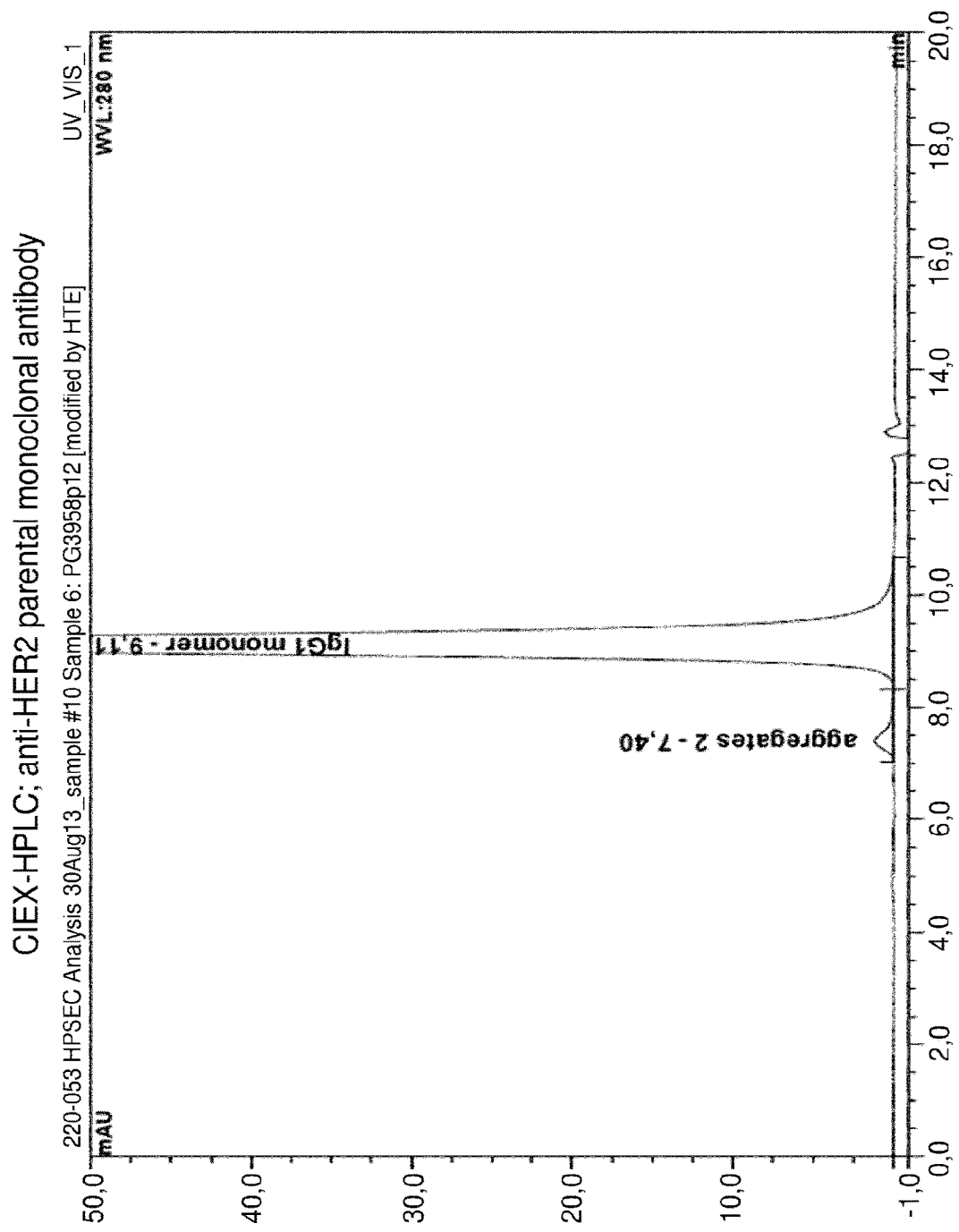
Figure 7E:
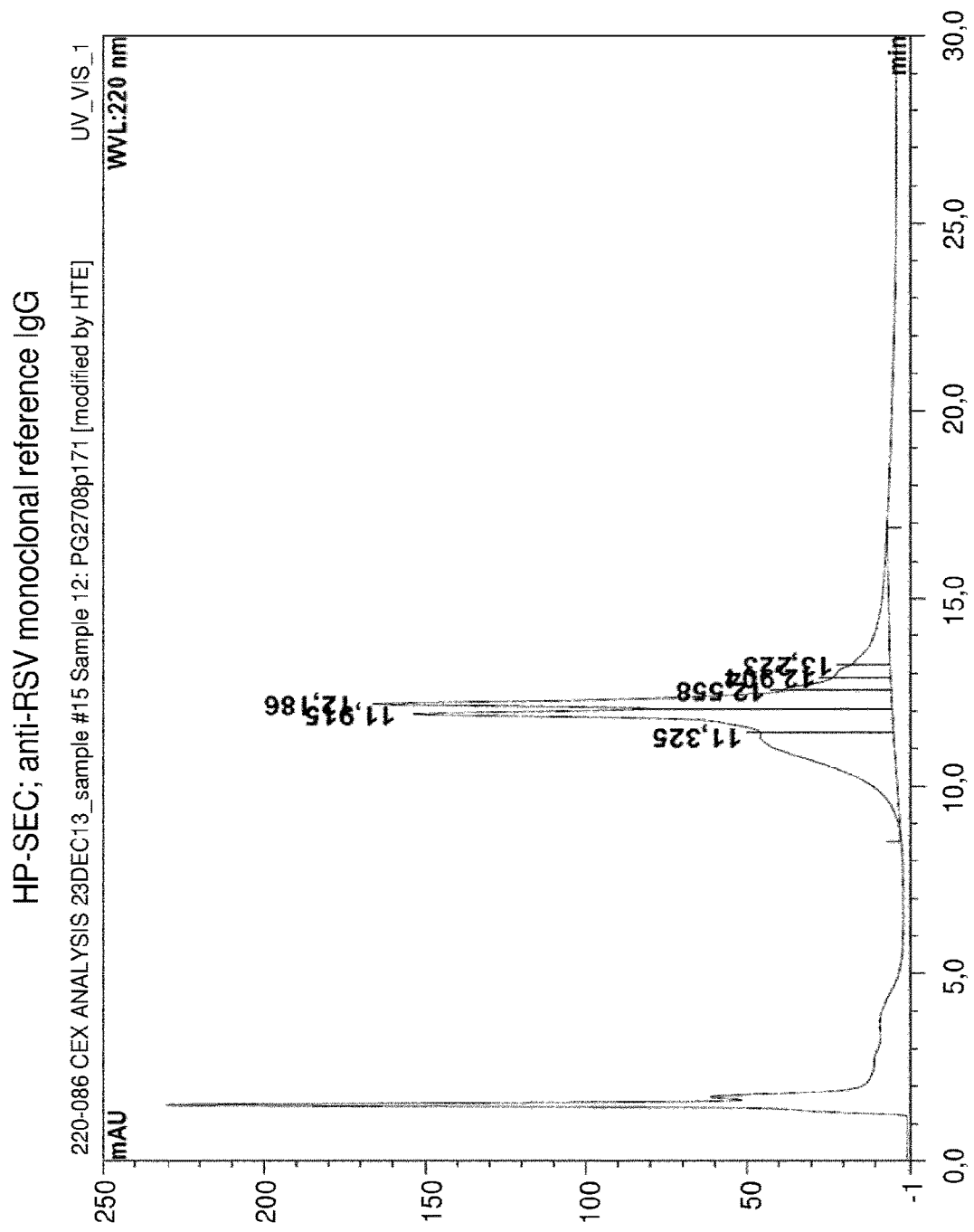
Figure 7F:
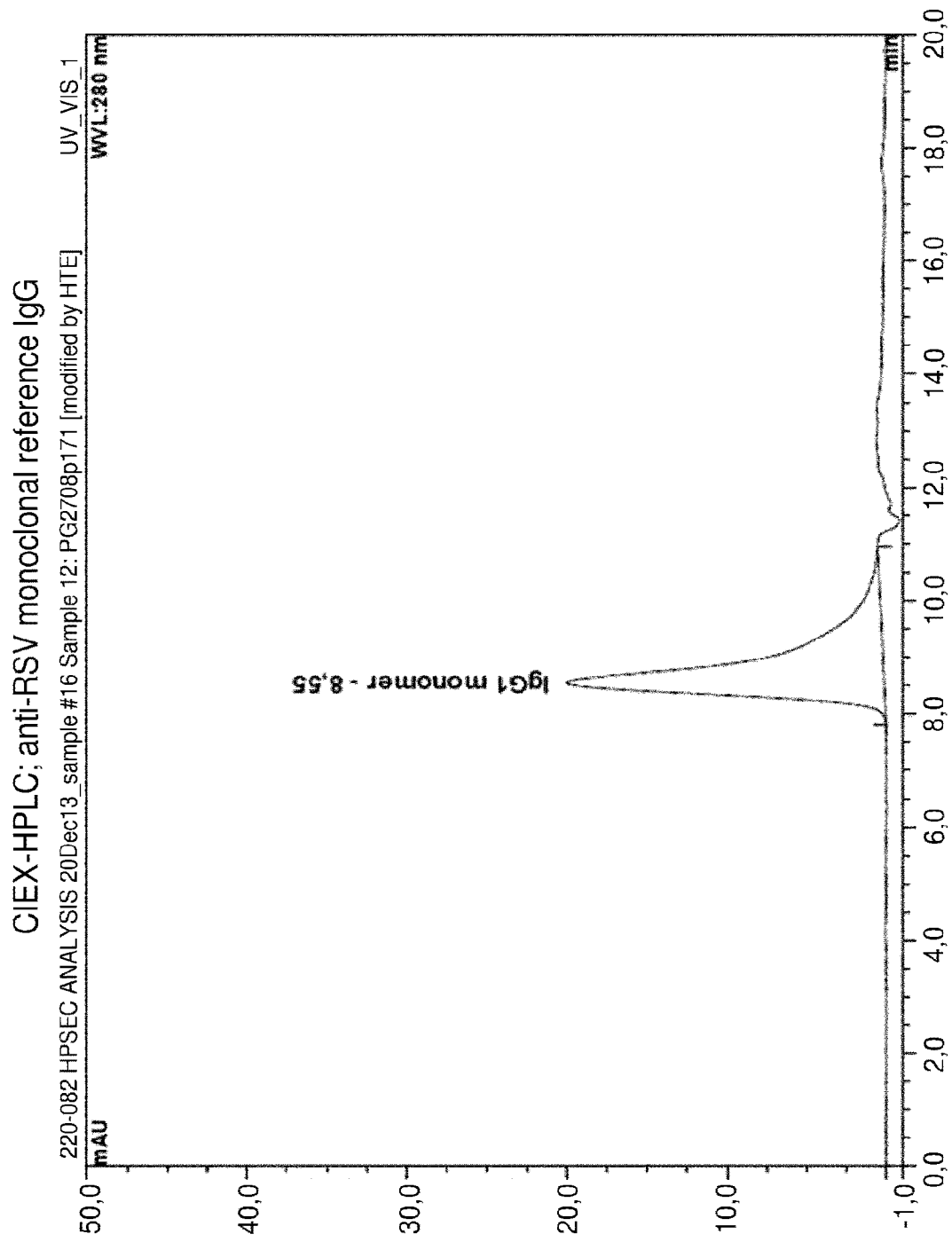

Binding of Bispecific HER2xHER3 Antibody Compared to Parental Monoclonal Antibodies Binding of HER2xHER3 bispecific antibodies as compared to their parental counterparts was determined by FACS analysis. A FACS was performed on BxPC-3-luc2 cells and MCF-7 cells with a serial titration of antibodies ranging from 2.5 sg g/ml-0, 01 μg g/ml. The tested antibody panel was composed of the bispecific antibody PB3566 and its parental antibodies the anti-HER3 antibody PG3178 and the anti-HER2 antibody PG3004. The MFI data were plotted and the graphs on both cell lines show that the bispecific PB3566 binds more effectively to both tumor cell lines compared to the anti-HER3 antibody PG3178 and the anti-HER2 antibody PG3004. (FIG. 6)

Humanization of MF2971 and MF3004

MF2971 and MF3004 were humanized according to technology known in the art. A total of seven humanised/deimmunised variant sequences of MF2971 were expressed, validated and characterised in vitro as monoclonal and in bispecific format combination with the HER3-specific antibody MF3178. The same was done for seven variant sequences of MF3004, which were created by replacing the HCDR3 of MF2971 in the seven MF2971 variants with the HCDR3 of MF3004. The expression, integrity, thermal stability and functional activity of all humanized variants was analysed. Based on production, integrity, stability and functionality integrity, a variant of MF2971 (2971-var2) was chosen as the optimal humanized variant of the VH to be used in a bispecific format with MF3178. This 2971-var2 was renamed MF3958. The bispecific HHER2xHER3 combination MF3958xMF3178 resulted in PB4188.

Large Scale Production, Purification and Analytical Studies of PB4188

Suspension adapted 293F Freestyle cells were cultivated in Erlenmeyer flasks at a shaker plateau until a density of $3.0 \times 10^6$ cells/ml. Cells were seeded in a 4 L erlen flasks at a density of $0.3-0.5 \times 10^1$ viable cells/ml. The cells were transiently transfected with the individual sterile DNA:PEI mixture and further cultivated. Seven days after transfection, conditioned medium containing bispecific antibody was harvested by low-speed centrifugation, 5 minutes 1000 g, followed by high speed centrifugation, 5 minutes at 4000 g. Collected conditioned medium was concentrated over a 5 kDa Satorius hydrosart cassette to about 600 ml and subsequently diafiltrated against 4 L PBS. Antibodies were bound on column to ~35 ml MabSelectSure XL (11° C.). A-specifically bound proteins were removed by washing the column in reversed flow mode with 150 ml PBS, 150 ml PBS containing 1 M NaCl, 100 ml PBS. The bound antibodies were eluted using 100 mM citrate pH 3.0 in reversed flow mode and 5 ml fractions were collected in 10 ml tubes containing 4 ml 1Tris pH 8.0 for neutralization. The eluted antibodies were further purified by gel-filtration using superdex 200 50/1000. The purified antibody was filter-sterilized using a 0.22 μm syringe filter. IgG concentration was determined by OD280 measurement and the protein concentration was calculated based on the amino acid sequence. Protein was tested for aggregation (HPSEC), purity (SDS-PAGE, nMS, IEX and IEF). Protein samples were stored at −80° C.

IgG Purification for Analytical and Xenograft Studies.

Medium scale purifications were performed on an AKTA 100 Explorer using HiTrap MabSelect Sure columns and HiTrap desalting columns. Samples were loaded at 5 ml/min. The column was washed with 2 column volumes of PBS. IgG was eluted at pH 3.0 with 0.1 M citrate buffer. Next the sample was desalted and ended up in a final buffer of PBS pH 7.4. IgGs were filtered through a 0.45 μM filter (Sartorius). The IgG concentration was measured using Octet with protein A sensors. Protein was tested for aggregation (HPSEC), purity (SDS-PAGE, nMS, IEX and IEF). Protein samples were stored at −80° C.

Analytical Characteristics of PB4188

The PB4188 (MF3958xMF3178) was subjected to analysis by HP-SEC and CIEX-HPLC (TSK gel-STAT 7 μm column, 4.6 mm ID×10 cm U. The analytical profile of PB4188 was in general consistent with the behavior of normal monospecific IgG1, such as the parental HER2 arm PG3958 and the anti-RSV monoclonal control antibody (FIG. 7).

Affinity Determination

The monovalent binding affinity of PB4188 and PB3448 for recombinant HER2 and HER3 was determined by SPR (BIACORE™ T100). BIACORE™ T100 (GE Healthcare, Uppsala. Sweden) was used to conduct all experiments described. Sensor surface preparation and interaction analyses were performed at 25° C. Buffer and BIACORE™ reagents were purchased from GE Healthcare. ErbB2-Fc and ERbB3-Fc(RND) was coated to the surface of a CM5 sensor chip in potassium acetate buffer (pH5.5) at the target immobilization level of 500 RU. Running buffer was HBS (hepes-buffered saline): 10 mM HEPES pH 7.4, 150 mM NaCl, 0.005% Tween-20; 0.2 μm) filter-sterilized. The bispecific antibodies were diluted to 100, 50, 20, 10, 1 and 0.1 nM in HBIS and run at high (30 µl/min) flow rate over the antigen-coupled surface of the CM5 sensor chip. With the BIA evaluation software, a curve fitting model for 1:1 monovalent interaction allowed for determination of the HER2 arms affinities (mono-valent interaction), the affinities of the HER2 arms, could be determined. Due to the low-off rate of the HER3 arm the affinity could not be determined. To determine the affinity of the HER3 arm PB4188 was coated to a CM5 sensor chip at the target immobilization level of 500 RU. Her2-Fc and Her3-Fe antigens were diluted to 100, 50, 20, 10, 1 and 0.1 nM in HBS and run at high flow rate (40 µl/min) over the PB4188 surface. To determine the $k_{on}$ and $k_{off}$ values, the BIA evaluation software was used in conjunction with a model that takes into account that a monovalent molecule was coated to the sensor chip surface and that the ErbB3-Fc antigen was a bivalent molecule. The affinities of PB4188 and PB3448 are shown in Table 10.

PB4188 Affinity Determination on Cells

Figure 20A:
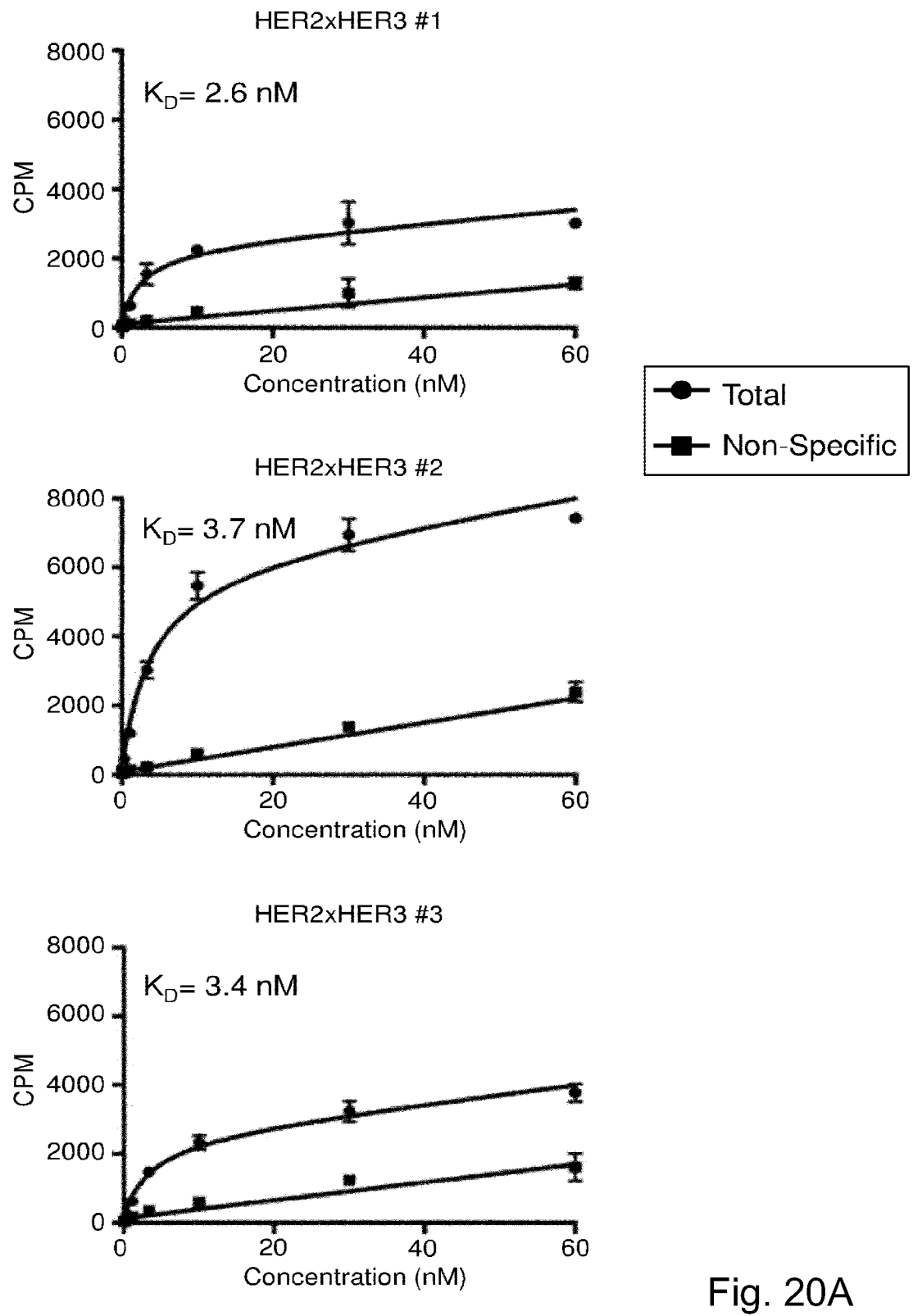
FIGS. 20A and 20B: Steady state cell affinity measurements of $^{125}$I-labeled IgG HER2xHER3 (PB4188) towards BT-474 cells (20A; three independent assays) and SK-BR-3 cells (20B; three independent assays). Non-specific binding was determined using a 100-fold excess of unlabeled HER2xHER3.
Figure 20B:
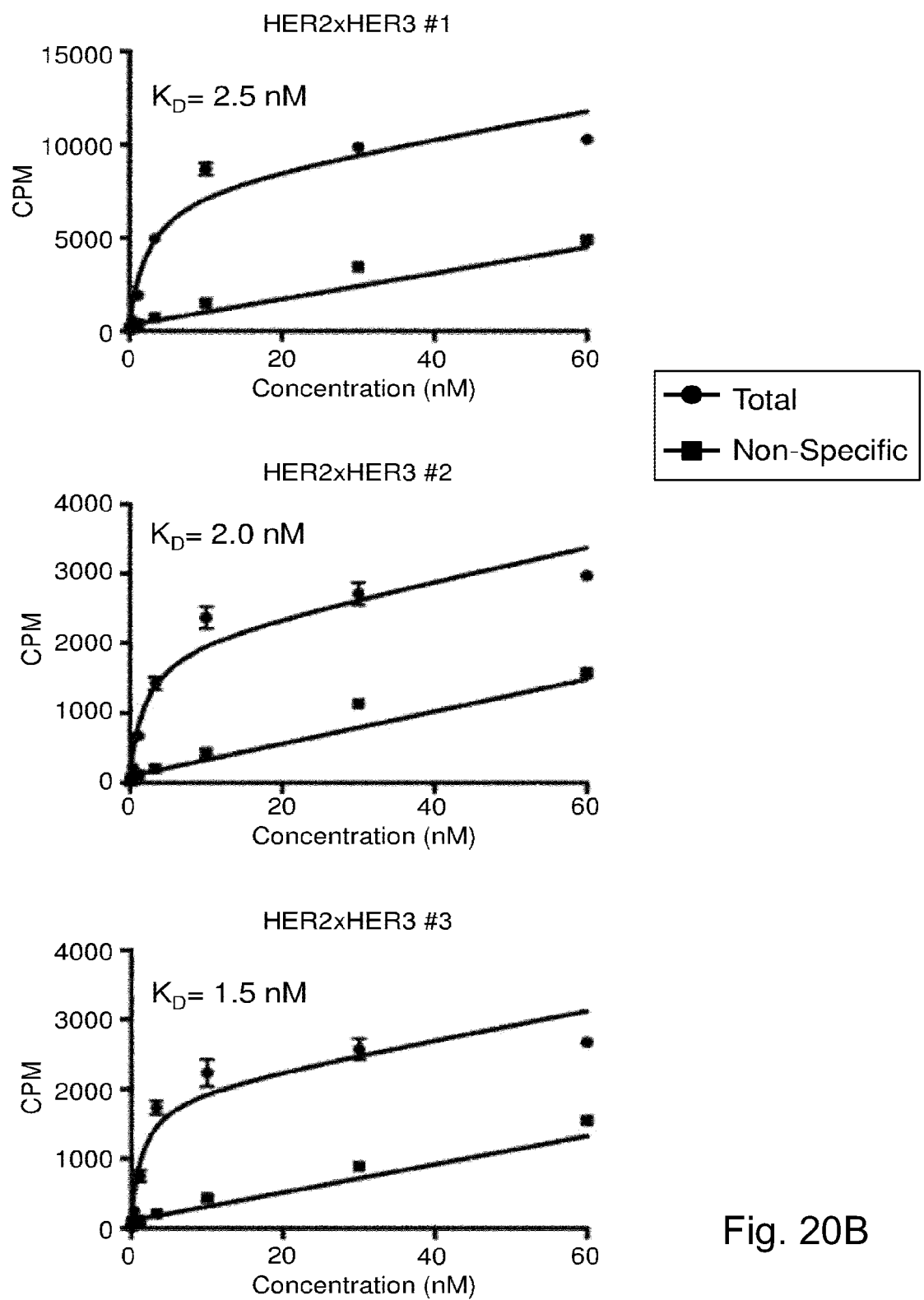

Binding affinities were also determined via steady state cell affinity measurements using BT-474 and SK-BR-3 cells. Four IgG were analyzed: 1) PB4188 (bispecific HER2xHER3), containing anti-HER2 antibody 3958 and anti-HER3 antibody 3178; 2) PB9215 (bispecific HER3xTT), containing anti-HER3 antibody 3178 and anti-TT (tetanus toxoid) antibody 1337; 3) PB9216 (bispecific HER2xTT), containing anti-HER2 antibody 3958 and anti-TT antibody 1337; 4) HERCEPTIN® (monospecific HER2). The IgG were radioactively labeled with $^{125}$I using IODO-GEN® Precoated Iodonation Tubes (Pierce) and associated instructions. The labeled IgG were diluted to an activity of ~1-2×10$^8$ cpm/ml in 25 mM Tris-HCl, 0.4 M NaCl, 0.25% BSA, 5 mM EDTA, 0.05% NaN$_3$. Protein concentrations were determined with the BCA Protein Assay Kit (Pierce). Flow cytometry analysis of the labeled and non-labeled IgG using BT-474 and SK-BR-3 cells showed no or only minor signs of reduction in binding after labeling. Steady state cell affinity measurements were performed as follows. Cells were seeded in 96-well plates and incubated at 4° C. with various concentrations of labeled IgG. Unbound radioactivity was removed after 4 hours and the cell-bound radioactivity was measured using a gamma well counter. Non-specific binding was measured by adding a receptor-blocking concentration (100-fold excess) of unlabeled antibody. Each condition was tested in triplicate and three independent experiments were performed per antibody. $K_D$ values were calculated based on a non-linear regression model that compensates for non-specific binding, using Prism 6.0d (GraphPad Software). Graphs including fitted curves are given in FIG. 20 for binding of the HER2xHER3 IgG (PB4188) to both cell lines. K D data for all 24 assays, including mean values, are given in Table 12. In summary, the mean KD values as determined using BT-474 and SK-BR-3 cells were 3.2 and 2.0 nM for HER2xHER3, 3.7 and 1.3 nM for HERCEPTIN®, 3.9 and 2.3 nM for HER2xTT, and 0.23 and 0.99 nM for HER3xTT, respectively. Thus PB4188 shows a higher affinity for HER3 compared to HHER2 which is in contrast to the HER2xHER3 bispecific molecule MI-111 that targets HER2 with a higher affinity compared to HER3.

Anti-Proliferative Activity on HER2 Amplified Breast Cancer Cells

JIAIT-1 in Soft Agar

Figure 8:
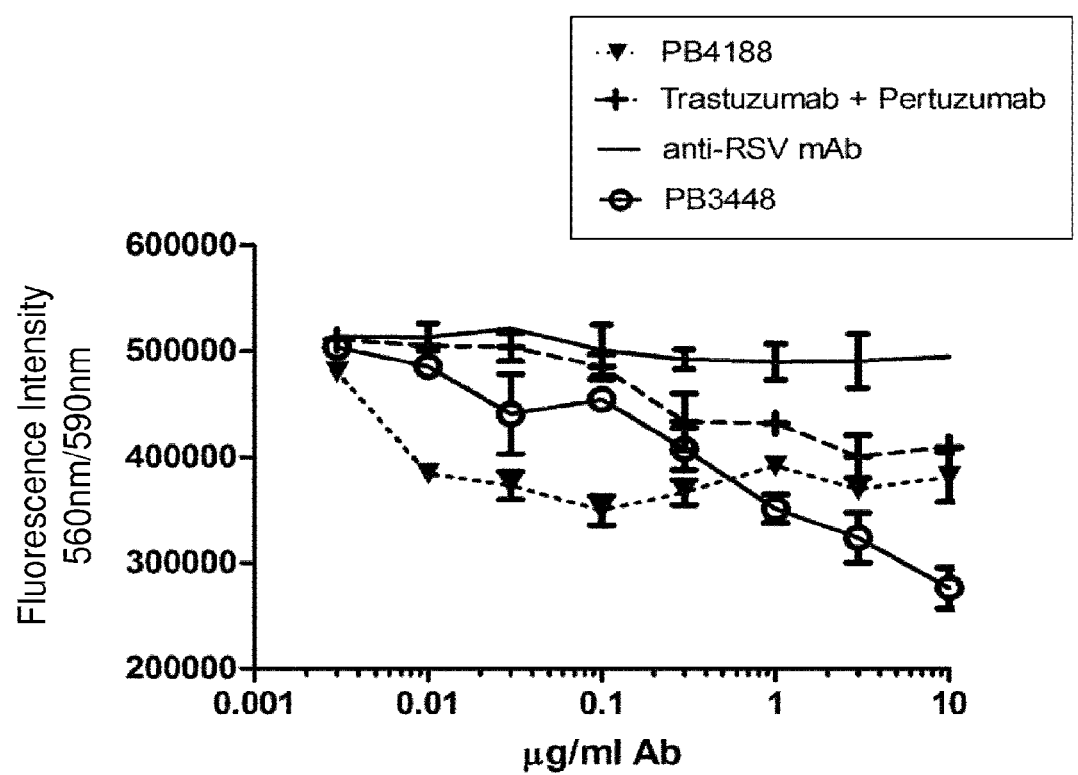
FIG. 8: Inhibition of JIMT-1 cell proliferation in soft agar by a serial titration of antibody.

PB3448 and PB4188 were tested for their potency to inhibit the growth of the trastuzumab resistant JIMT-1 cells in soft agar. To this aim 96 well suspension cell culture plates were prepared, 100 µL of the soft agar bottom layer (0.6% final concentration in complete medium) was poured and left to solidify, 50 µL of the soft agar top layer (0,4% final concentration) containing 10.000 JIMT-1 cells/well were then added on top, solidified and such 96 well plates incubated overnight at 37° C., 10% CO2. Next day, a negative control antibody, pertuzumab+trastuzumab (1:1 v/v), PB3448 and PB4188 were added in DMEM medium in a semi-log titration ranging from 10-0.003 g/ml. Subsequently, the assay was incubated in cell culture incubators for 8 days. Finally, the cells were incubated with Alamar Blue for 3-5 h at 37° C., and fluorescence intensity was determined (excitation: 560 nm: emission: 590 nm). An example of dose dependent inhibition of JIMT-1 proliferation by PB3448 and PB4188 is shown. (FIG. 8).

BT-474 and SKBR-3 in MATRIGEL®

Figure 9A:
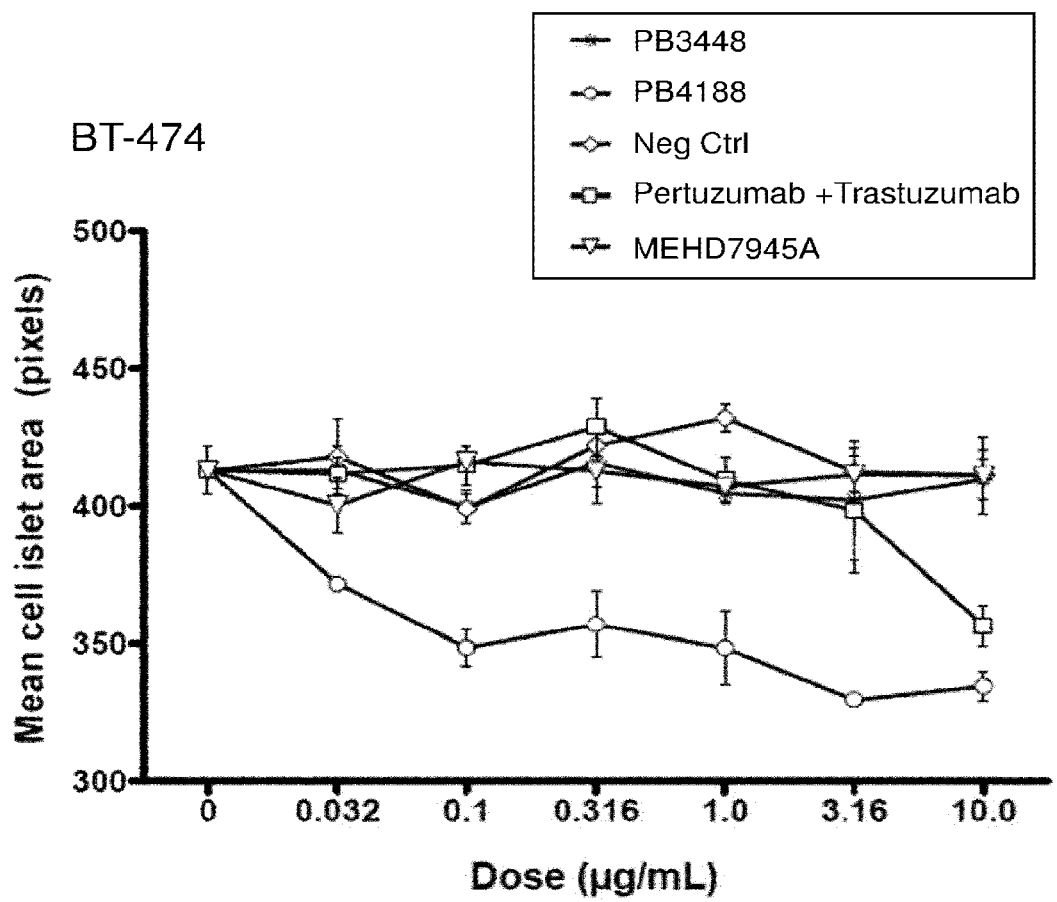
FIGS. 9A and 9B: Inhibition of BT-474 (9A) and SKBR3 (98) cell proliferation in MATRIGEL by a serial titration of antibody.
Figure 9B:
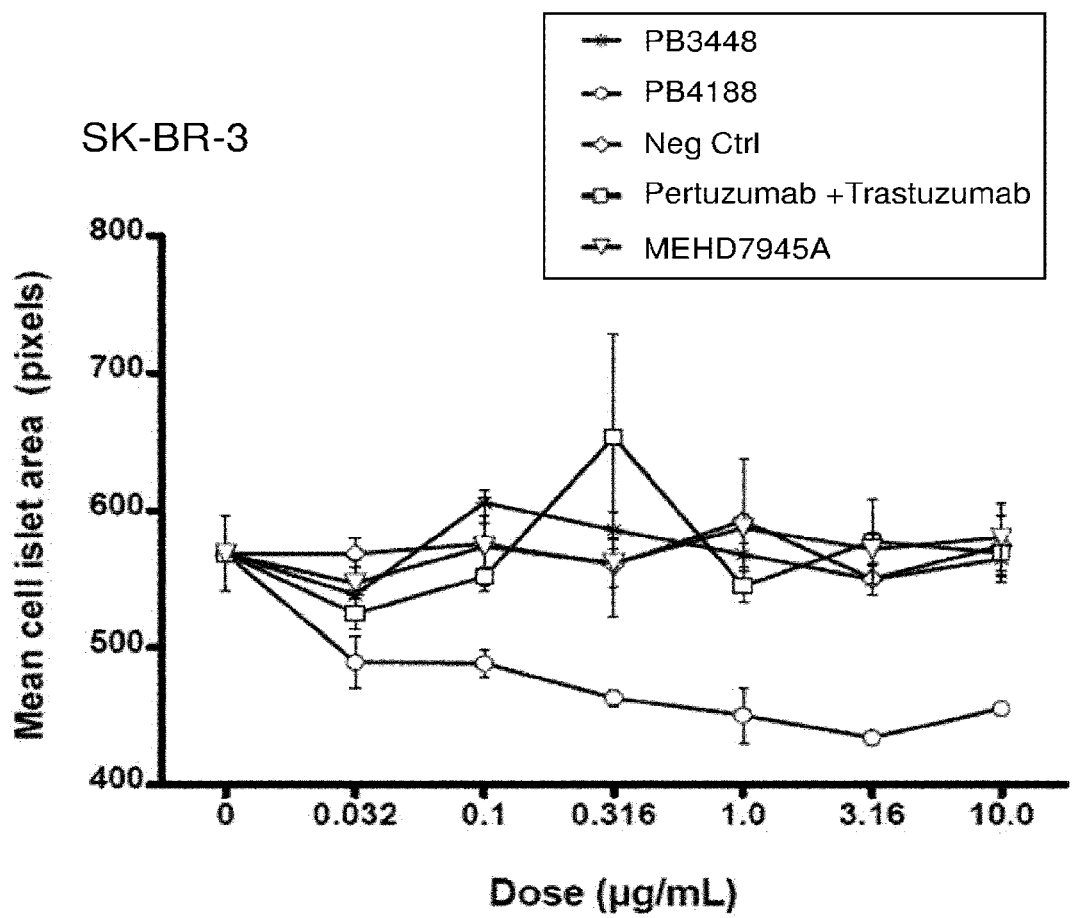

PB3448 and PB4188 were tested for their potency to inhibit the growth of BT-474 and SKBR-3 cells. The cells were tested at the company Ocello based in Leiden, the Netherlands that grows cells in three dimensional MATRIGEL® and uses principle component analysis to distinguish non-treated cells from treated cells, 2000 SK-BR-3 or 2250 BT474 cells were seeded in 15 µl MATRIGEL® per well of a 384 well plate (Greiner 781091). The next day a semi-log titration ranging from 10 to 0.003 µg/ml of antibodies were added in culture medium in the absence or presence of 5 ng/ml HRG. The test antibodies included a negative control antibody, pertuzumab+trastuzumab (1:1 v/v), PB3448, PB4188 and the bispecific anti-EGFRxHER3 two-in-one antibody MEHD7945A. In addition a dose-dependent titration of HRG was included as a positive control. Each dose was tested in quadruplicate. Cells were incubated for 7 days in a cell culture incubator at 37° C., 5% CO2. Next, the cells were fixed and actin cytoskeleton of the cells was stained with phalloidin and the nuclei are stained with Hoechst. Next, fluorescent images were taken at different levels through the gel (Z-stack) and the images were superimposed. A broad range of morphological features were measured (800 in total). Only features that differed between medium and HRG treatments were selected for analysis. Features that were associated with growth, mean spheroid area and nuclei per spheroid were most significantly different between medium and HRG treatments. Both multiparameter and single parameter analyses were made. For single parameter measurements, t-tests were performed to compare treatments (HRG or antibody) to medium. P-values for each point were determined. Principal component analysis (PCA), a method for finding low-dimensional combinations of high-dimensional data that capture most of the variability was used in relation to antibody concentration, to plot the data. FIG. 9 demonstrates the effect of pertuzumab+trastuzumab (1:1 v/v). PB3448 and PB4188 in the presence of HRG. In both HER2 amplified breast cancer cell lines PB4188 showed superior activity compared to pertuzumab+trastuzumab. PB$^1$3448 and the two-in-one antibody MEH1D7945A in the presence of HRG.

Figure 10A:
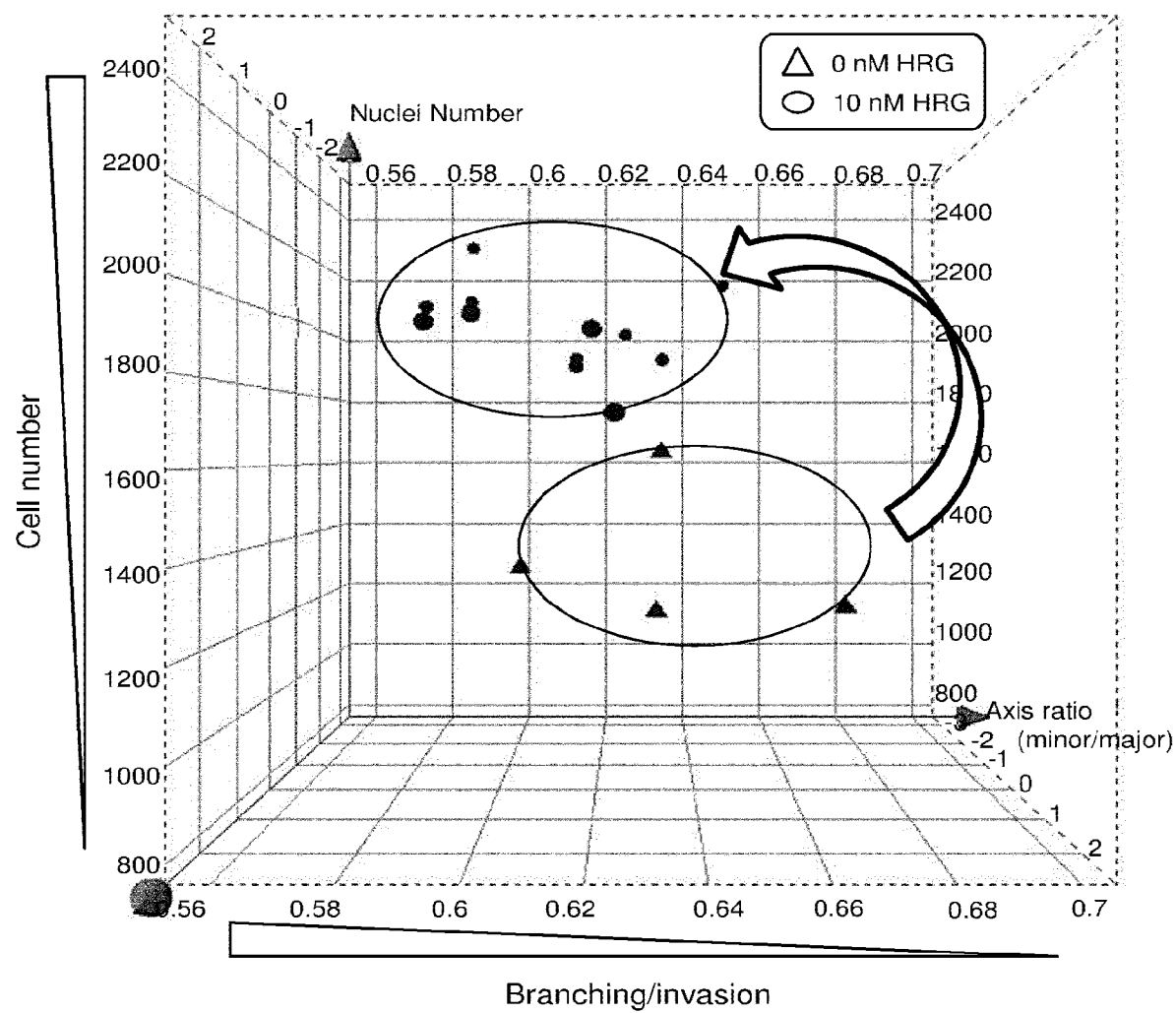
FIG. 10a: HRG induced proliferation and branching/invasion of SKBR-3 cells in MATRIGEL®.
Figure 10B:
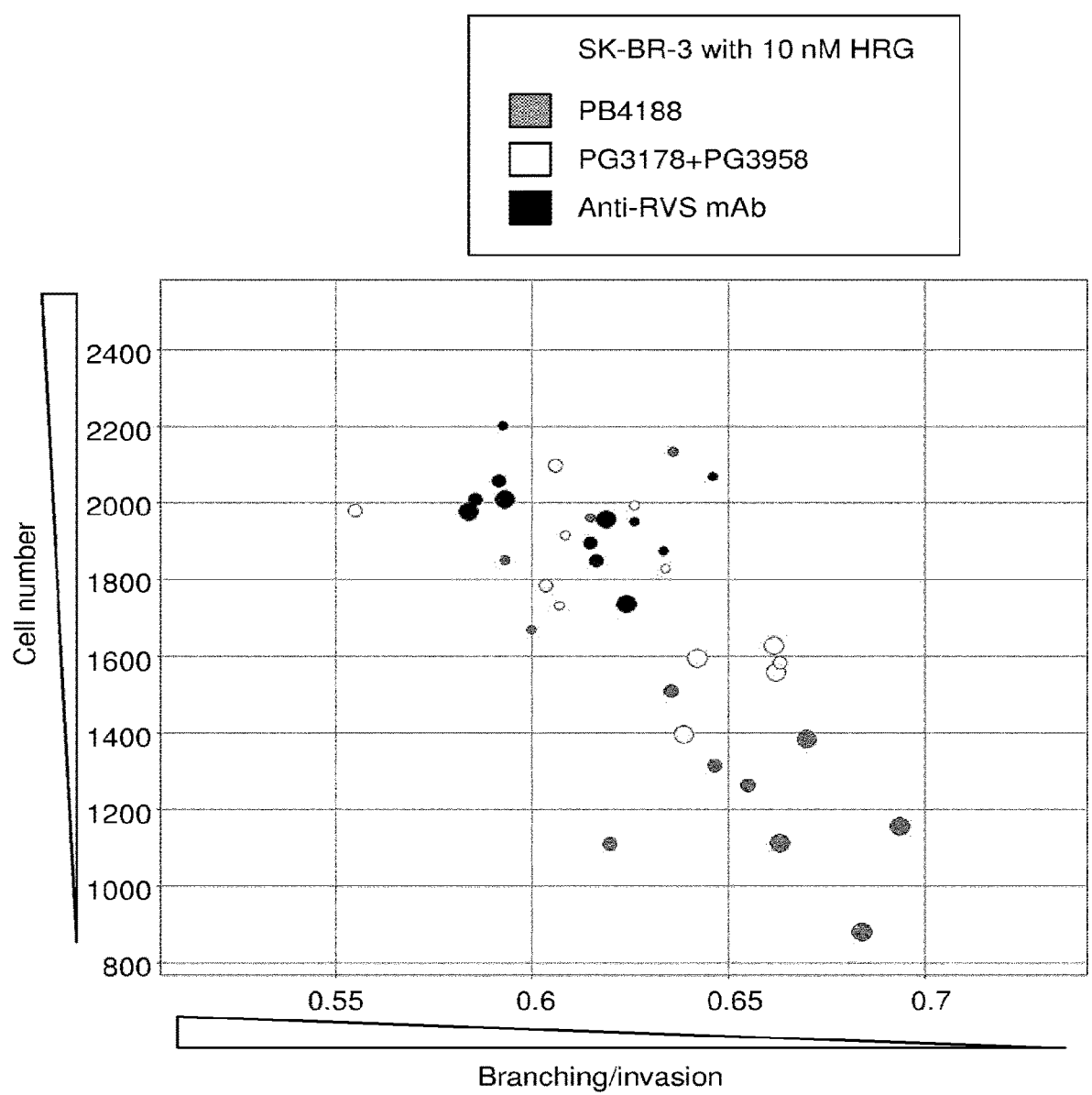
FIG. 10b: Inhibition of HRG induced proliferation and branching/invasion of SKBR-3 cells in MATRIGEL® by PB4188 in contrast to the parental monoclonal antibodies.
Figure 10C:
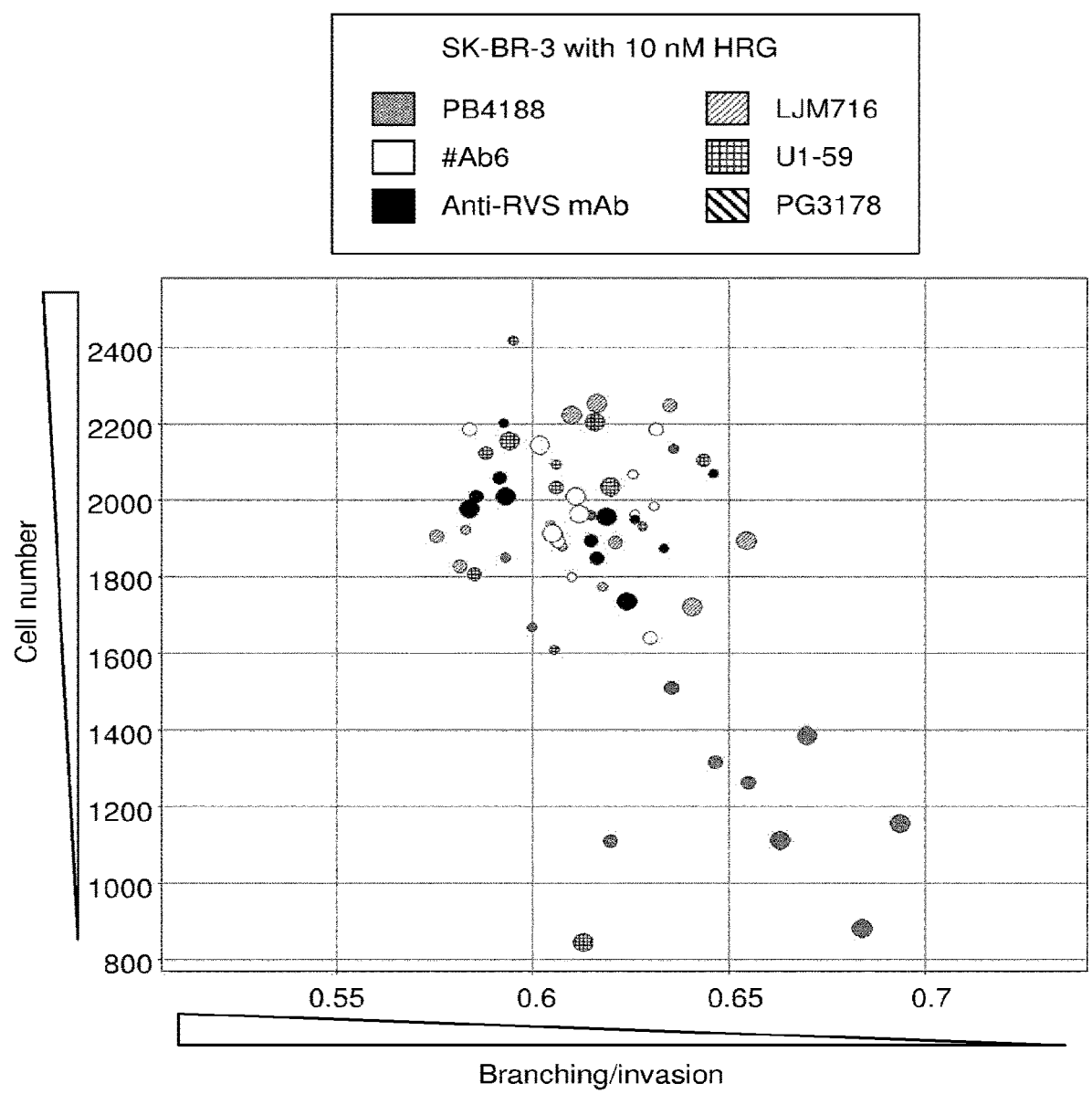
FIG. 10c: Inhibition of HRG induced proliferation and branching/invasion of SKBR-3 cells in MATRIGEL® by PB34188 in contrast to anti-HER3 monoclonal antibodies.
Figure 10D:
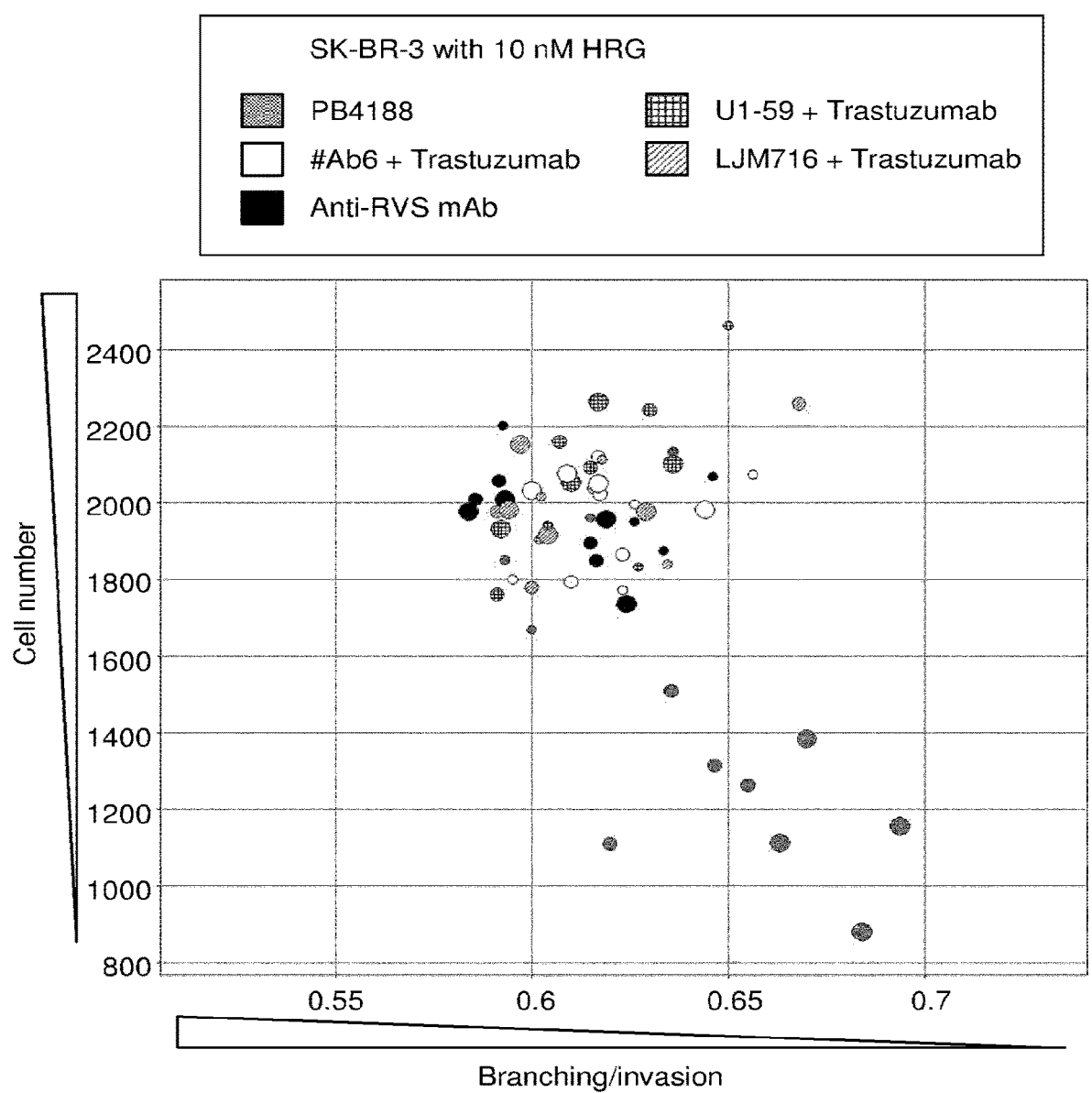
FIG. 10d: Inhibition of HRG induced proliferation and branching/invasion of SKBR-3 cells in MATRIGEL® by PB4188 in contrast to combinations of anti-HER3 monoclonal antibodies with trastuzumab.
Figure 10E:
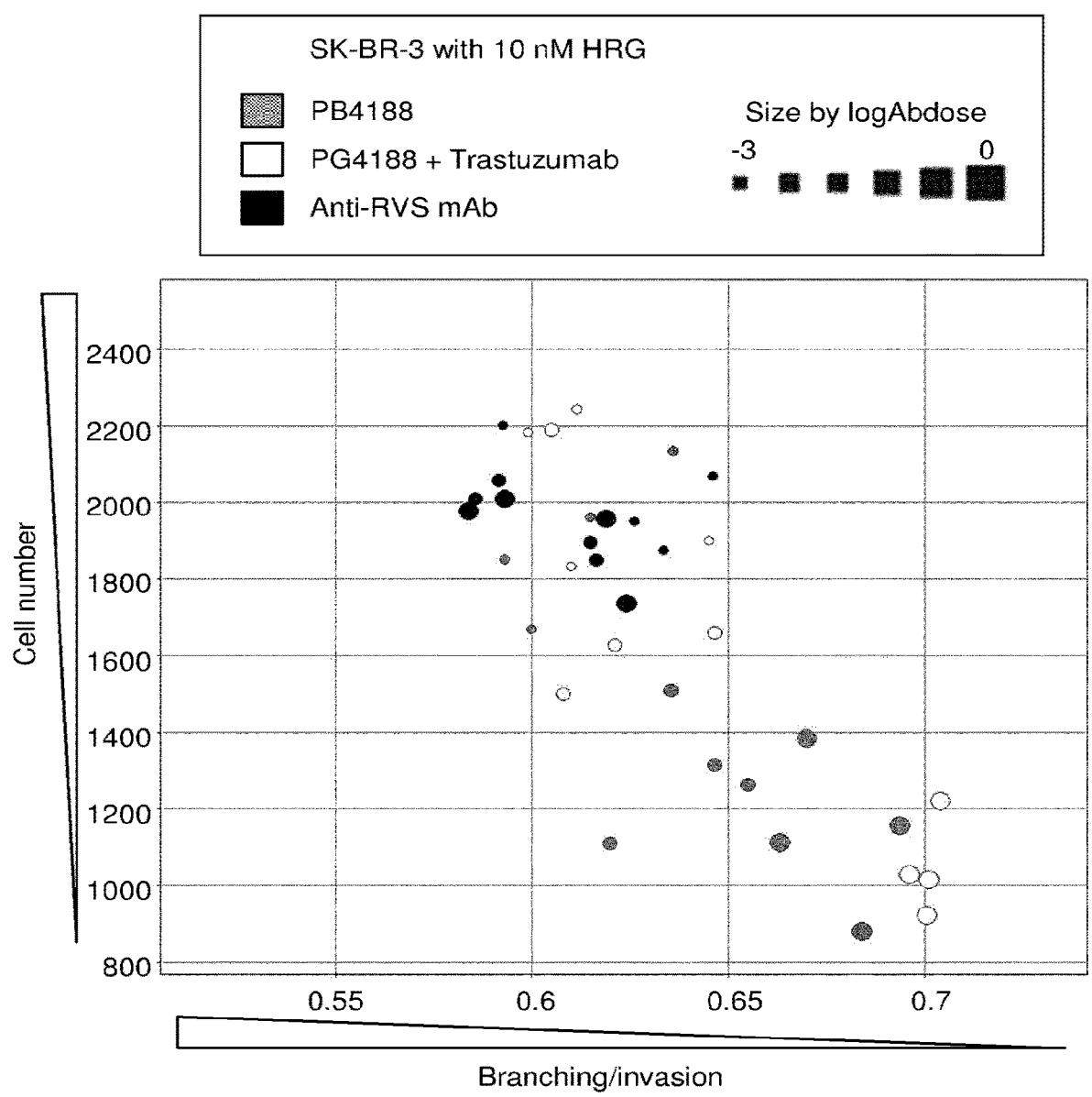
FIG. 10e: Inhibition of HRG induced proliferation and branching/invasion of SKBR-3 cells in MATRIGEL® by PB4188 and the combination PB4188 plus trastuzumab

Superior Anti-Proliferative Activity of PB4188 in the Presence of HRG on HER2 Amplified Breast Cancer Cells The activity of PB4188 in the presence of 10 ng/ml HRG on SKBR-3 and BT-474 was compared to a panel of HER2. HER3 antibodies and combinations thereof. The assay was performed in MATRIGEL® as described above, and morphological features were analyzed. PCA data plotted in FIG. 10a show the HRG-induced proliferation and branching/invasion of SKBR-3 cells in MATRIGEL®. FIG. 10b shows that antibody PB4188 can completely revert the HRG induced phenotype, whereas the combination of the parental monoclonal antibodies (PG3958+PG3178) has no effect. Moreover, PB4188 was far more effective compared to all anti-HER3 antibodies tested (FIG. 10c). In addition, combinations of the individual anti-HER3 antibodies with trastuzumab (the current standard of care in metastatic breast cancer (mBC)) were not able to revert the HRG induced phenotype (FIG. 10d). Adding trastuzumab to PB4188 in the presence of HRG reduced the proliferation and branching/invasion of SK-13R-3 cells compared to PB4188 alone (FIG. 10e).

Superior Anti-Proliferative Activity of PB4188 on HER2 Amplified Gastric Cancer Cells Compared to HER2 and HER3 Monoclonal Antibodies.

Figure 11A:
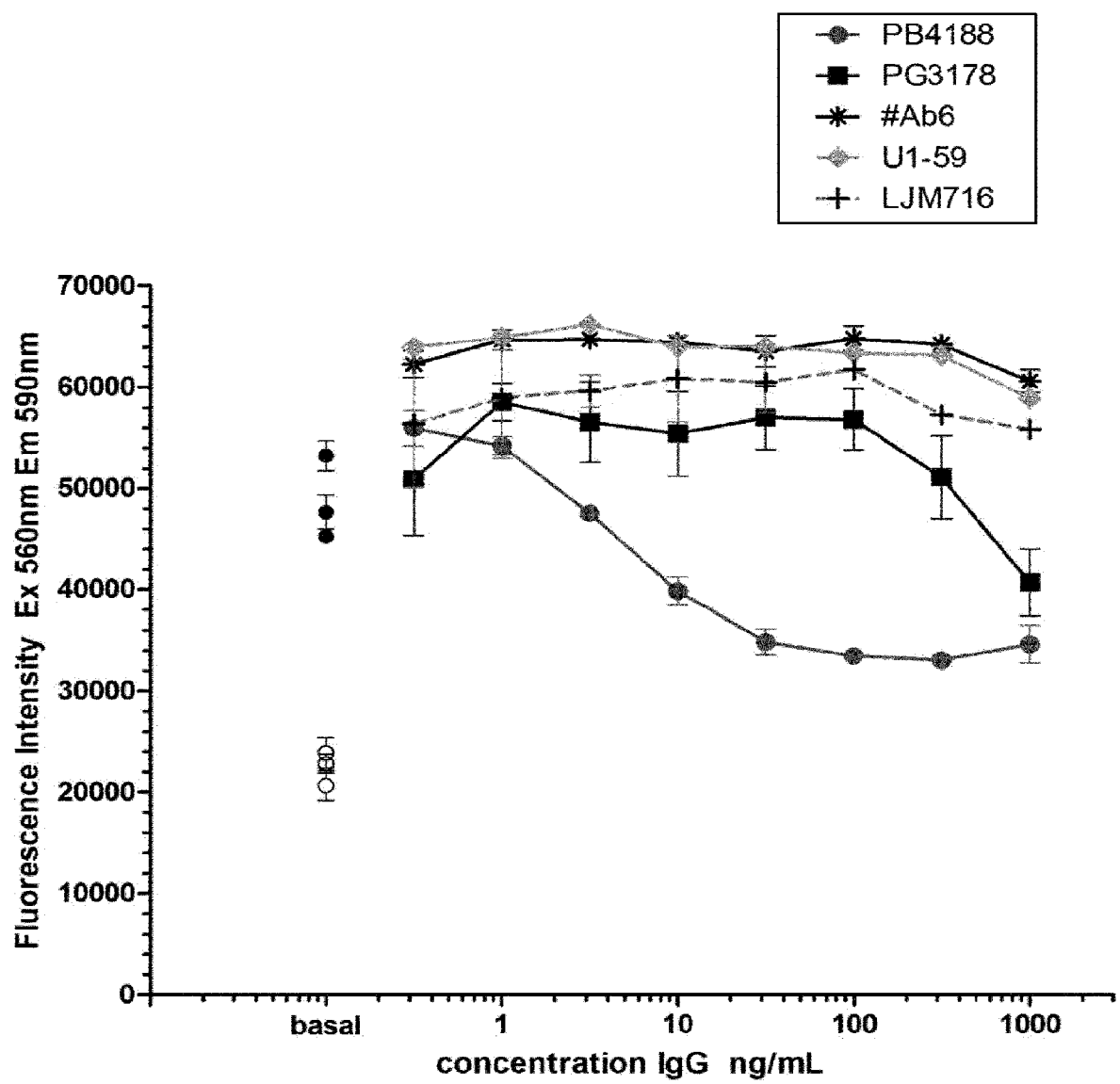
FIGS. 11A and 11B: Superior inhibitory activity of PB4188 in HER2'" N87 cells in the presence of 100 ng/ml HRG.
Figure 11B:
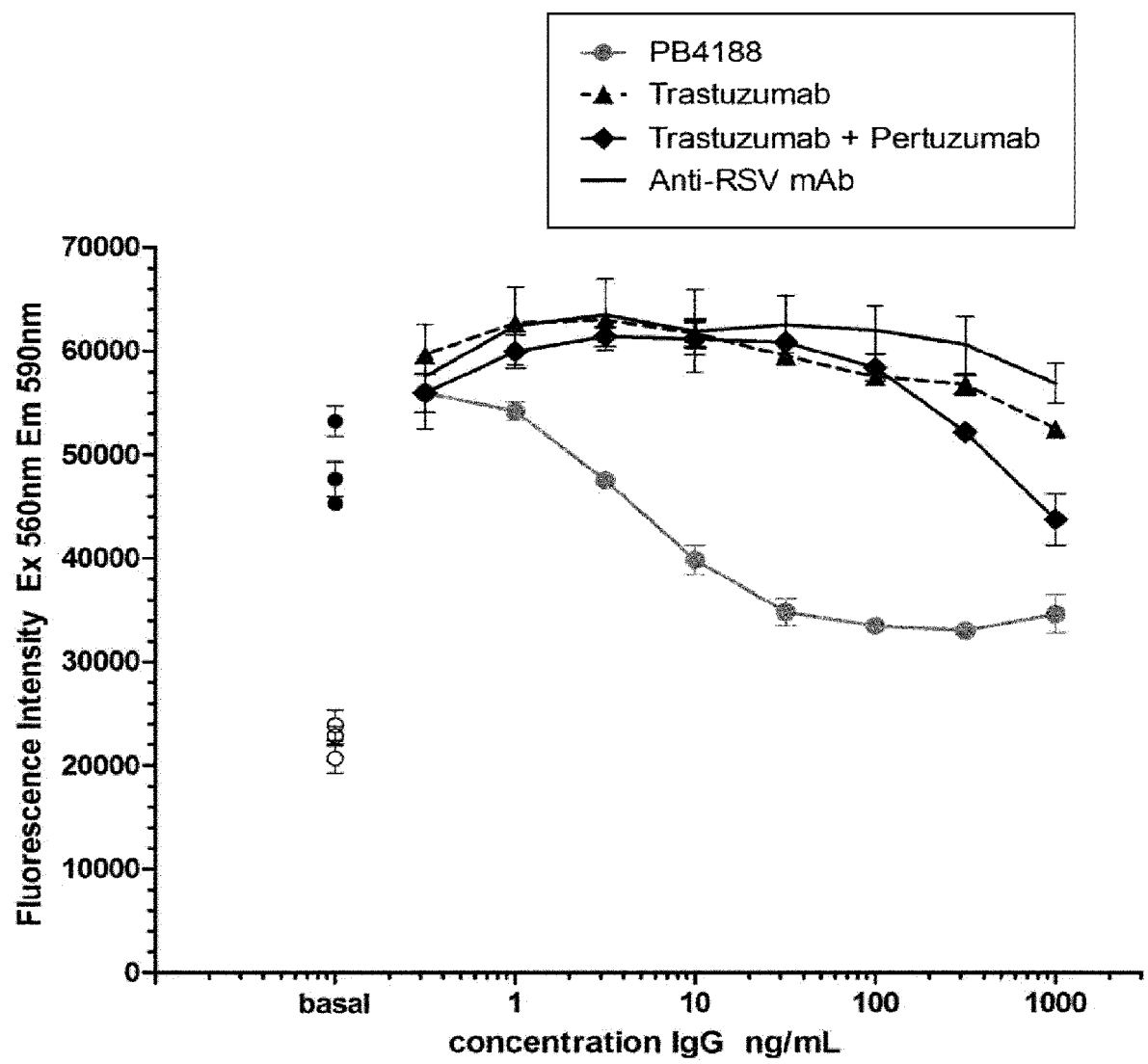

Upregulation of NRG1-β1 is a key resistance mechanism against HER2 targeted therapies (Wilson, 2012). To evaluate whether upregulation of NRG1-β1 would interfere with the anti-proliferative potency of PB4188 a panel of antibodies was tested at 100 ng/ml HHRG on the N87 (HER2 amplified) gastric cancer cell line. N87 cells were cultured in RPMI 1640 supplemented with 10% heat inactivated FBS. For the proliferation assay subxonfluent cell cultures of N87 cells were washed with PBS trypsinized and trypsin was inactivated by adding culture medium. Cells were washed twice in large volumes of assay medium (RPMI 1640 medium containing 0.05% BSA and 10 µg/ml Holo Transferrin). Antibodies were diluted in a semi-log titration that varied from 1-0.0001 µg/ml. Cells were added at a density of 10000 cells/well in the presence of 100 ng/ml final concentration of HRG. The cells were cultivated for 3 days at 37° C. 5% C02, in 95% relative humidity. ALAMAR BLUE™ (INVITROGEN®) was added according to the manufacturer's instructions and incubated for 6 hours at 37° C. 5% CO2, in 95% relative humidity in the dark. Fluorescence was measured at 550 nm excitation with 590 nm emission wavelength. PB4188 showed superior activity over anti-HER2 or anti-HER3 monoclonal antibodies (FIG. 11).

HER2XHER3 Bispecific Antibodies Induce ADCC

Figure 12:
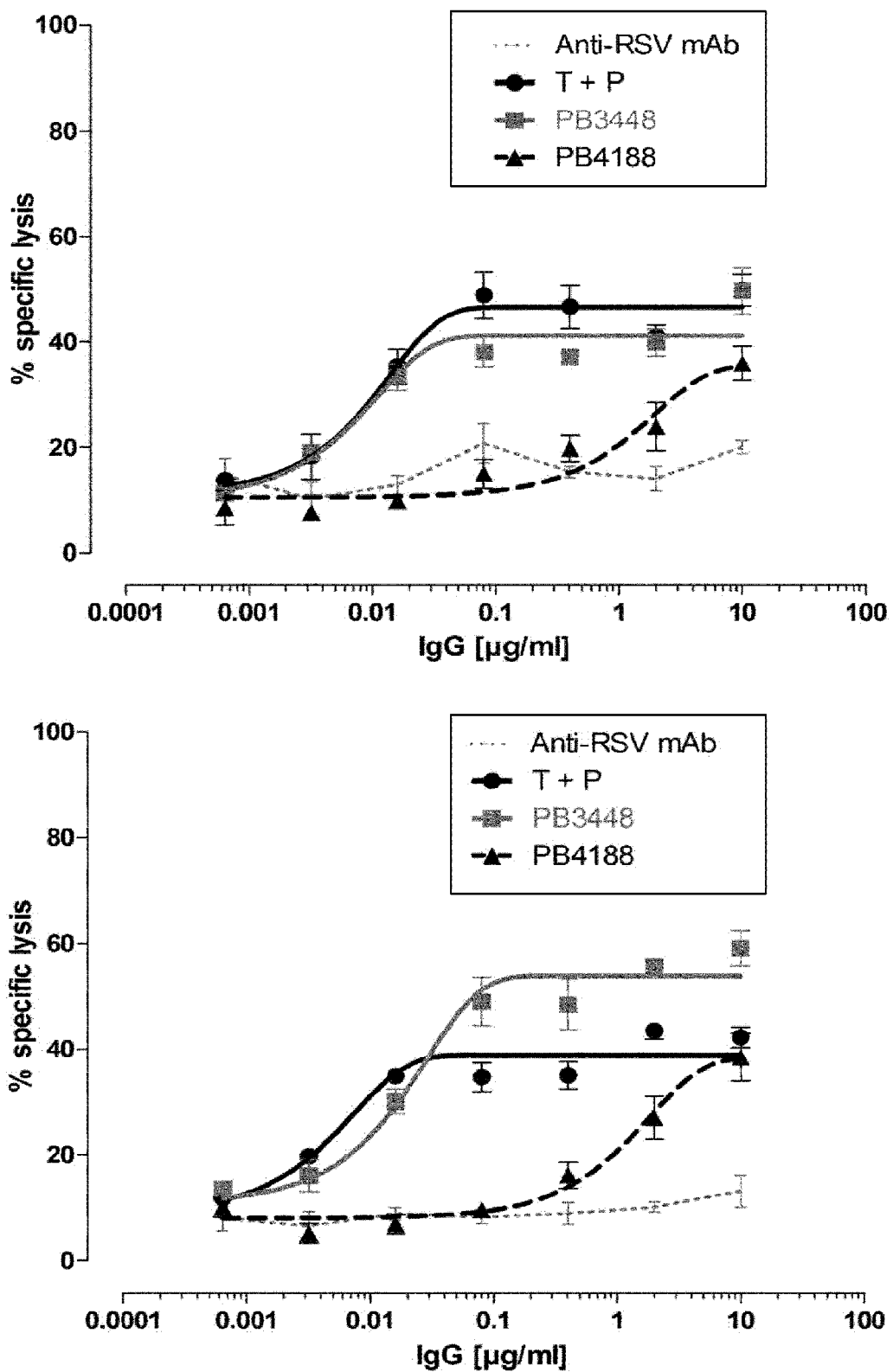
FIG. 12: ADCC activity of PB4188 and PB3448 in a dose titration

ADCC activity is an important anti-tumour mechanism of action for therapeutic antibodies in cancer. Human monoclonal antibodies directed to the HER family of receptors like cetuximab and trastuzumab induce ADCC. The baseline and enhanced ADCC activity of PB4188 and PB3448 were determined in validated in vitro ADCC assays. Trastuzumab and a negative control antibody were included as control antibodies in the experiment. Whole blood and PBMC fractions were obtained from healthy donors. Each antibody was tested against the HER2 high (SK-BR-3) and HER2 low (MCF-7) expressing target cells. Target cells were loaded with $^{51}$Cr (Amersham) and opsonized with the indicated concentrations of antibody. Whole-blood or PBMC fraction were used as effector cells in a 200 µl, reaction in RPMI 1640+10% heat inactivated FCS. Cells were incubated together for 4 h, and lysis was estimated by measuring radioactivity in the supernatant using a γ-scintillator. Percentage of specific lysis was calculated as follows: (experimental cpm−basal cpm)/(maximal cpm−basal cpm)×100, with maximal lysis determined in the presence of 5% Triton X-100 and basal lysis in the absence of antibody and effectors. As shown in FIG. 12 bispecific antibody PB3448 showed similar ADCC activity compared to the combination pertuzumab+trastuzumab. Bispecific antibody PB4188 was effective at high antibody concentrations (10 µg/ml).

Figure 13:
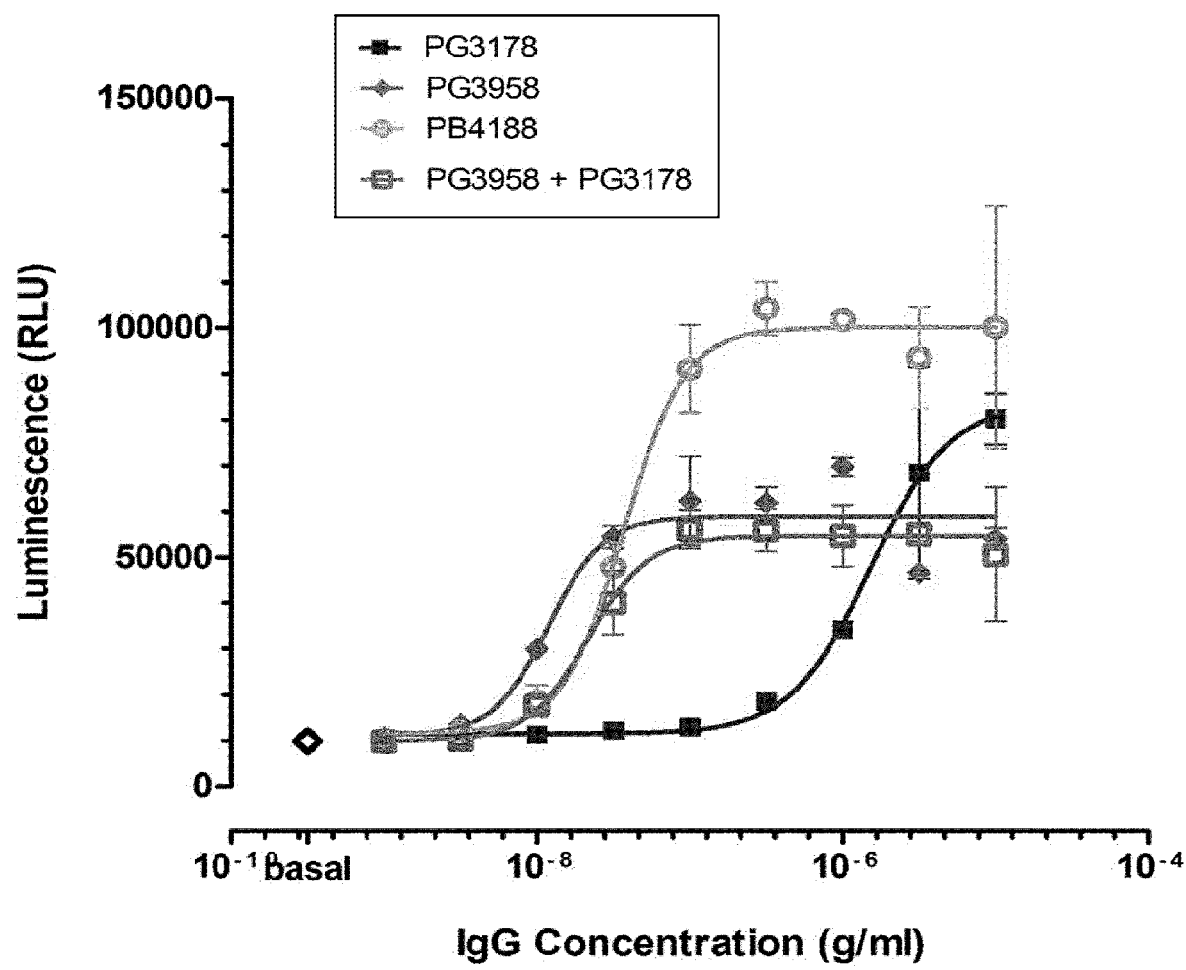
FIG. 13: Increased ADCC activity of bispecific antibody compared to monoclonal parental antibodies or a combination thereof

HER2XHER3 Bispecific Antibodies Show Higher ADCC Compared to the Combination of Parental Antibodies In a different ADCC setup, the ADCC Reporter Bioassay (Promega) was used. The bioassay uses engineered Jurkat cells stably expressing the FcγRIIIa receptor, V158 (high affinity) or F158 (low affinity) variant, and an NFAT response element driving expression of firefly luciferase. The assay was validated by comparing data obtained with the ADCC Reporter Bioassay to the classical $^{51}$Cr release assay. The ADCC assays were performed using the Promega ADCC Bioassay kit using 384 white well plates. In this experimental setup SKBR-3 cells were plated at a density of 1000 cells/well in 30 µl assay medium (RPMI with 4% low IgG serum) 20-24H before the bioassay. The next day, the culture medium was removed. Next, a serial dilution of antibodies, PB4188 and its parental anti-HER2 PG3958 and anti-HER3 PG3178 as well as the combination thereof was generated in duplo, 10 µl antibody dilutions were added to the wells. The starting concentration of the antibody was 10 µg/ml and a 10 points semi-log fold serial dilution was generated to provide a full dose-response curve. Finally, 5 µl of ADCC Bioassay effector cells (15000 cells/well. V158) were added. The cells were incubated for 6H at 37° C. Next, 15 µl B10-Glo luciferase substrate was added and 5 minutes later luminescence was detected in a plate reader. The obtained data are shown in FIG. 13. The PB4188 bispecific anti-HER2xHER3 antibodies showed a higher ADCC potentency compared to the parental HER2 and HER3 monoclonals or a combination thereof.

ADCC Enhancement of PB4188

Figure 14:
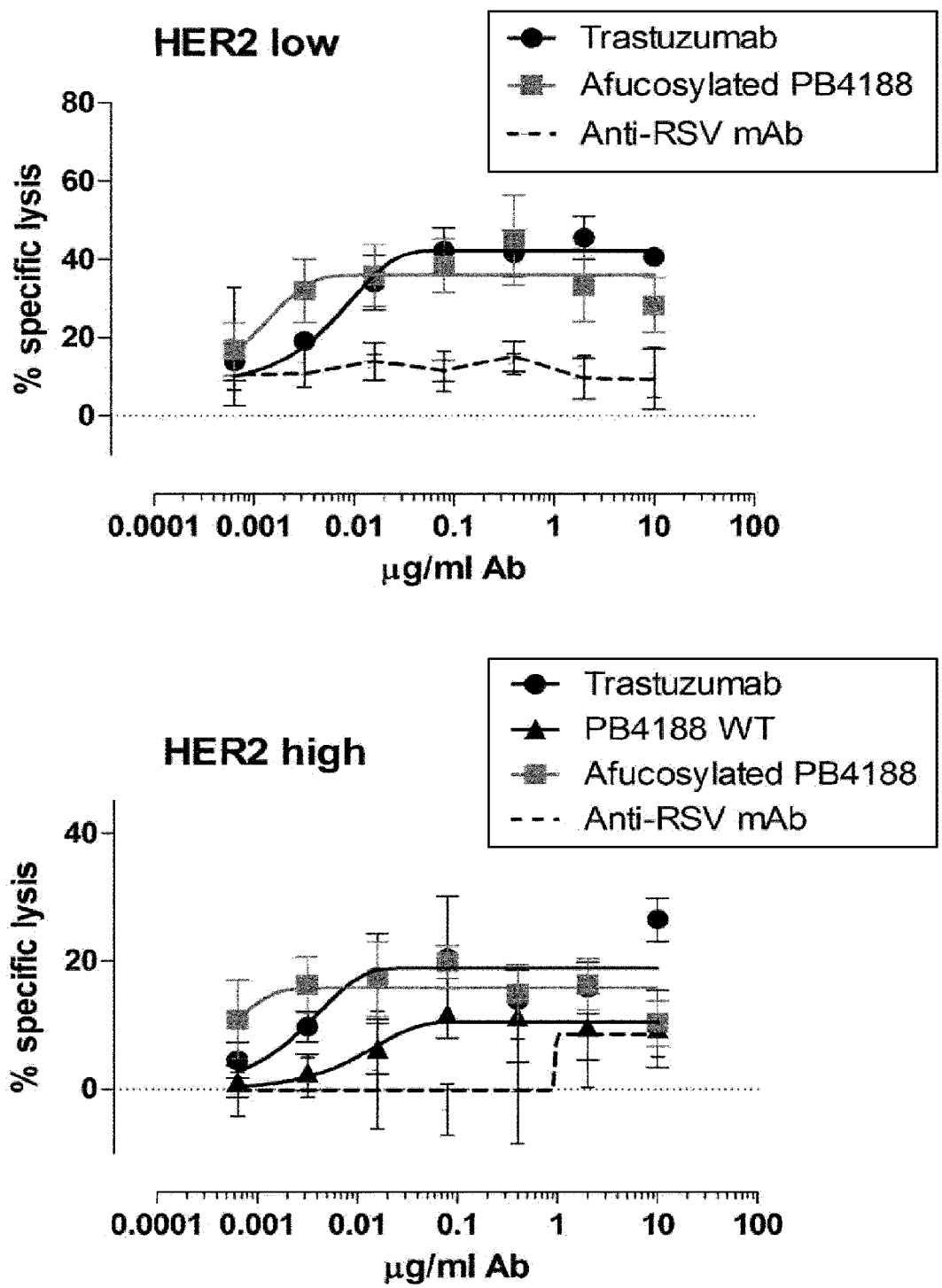
FIG. 14: ADCC activity of afucosylated PB4188 compared to trastuzumab on low (upper panel) and high (lower panel) HER2 expressing cells

ADCC activity can be enhanced by different techniques, one of them being the removal of fucose. Removal of fucose has resulted in increased anti-tumour activity in several in vivo models [Junttila, 2010]. To maximize PB4188 activity, afucosylation technology was applied (Cheng Liu and Andreia Lee. ADCC Enhancement Technologies for Next Generation Therapeutic Antibody. Antibody therapeutics-Trends in Bio/Pharmaceutical Industry 2009 [13-17]), thereby preventing fucosylation of the N-linked carbohydrate structure in the Fc region. The ADCC potency of afucosylated PB4188 compared to the wildtype PB4188 was determined in an ADCC $^{51}$Cr release assay using HER2 low expressing cells (MCF-7) and HER2 amplified cells (SK-BR-3). Both antibodies were applied in a serial dilution and a negative control antibody and trastuzumab were included in the assay. FIG. 14 shows the increase in ADCC potency of afucosylated PB4188 compared to the wild type version and/or trastuzumab in both high and low HER2 expressing cells.

Figure 15A:
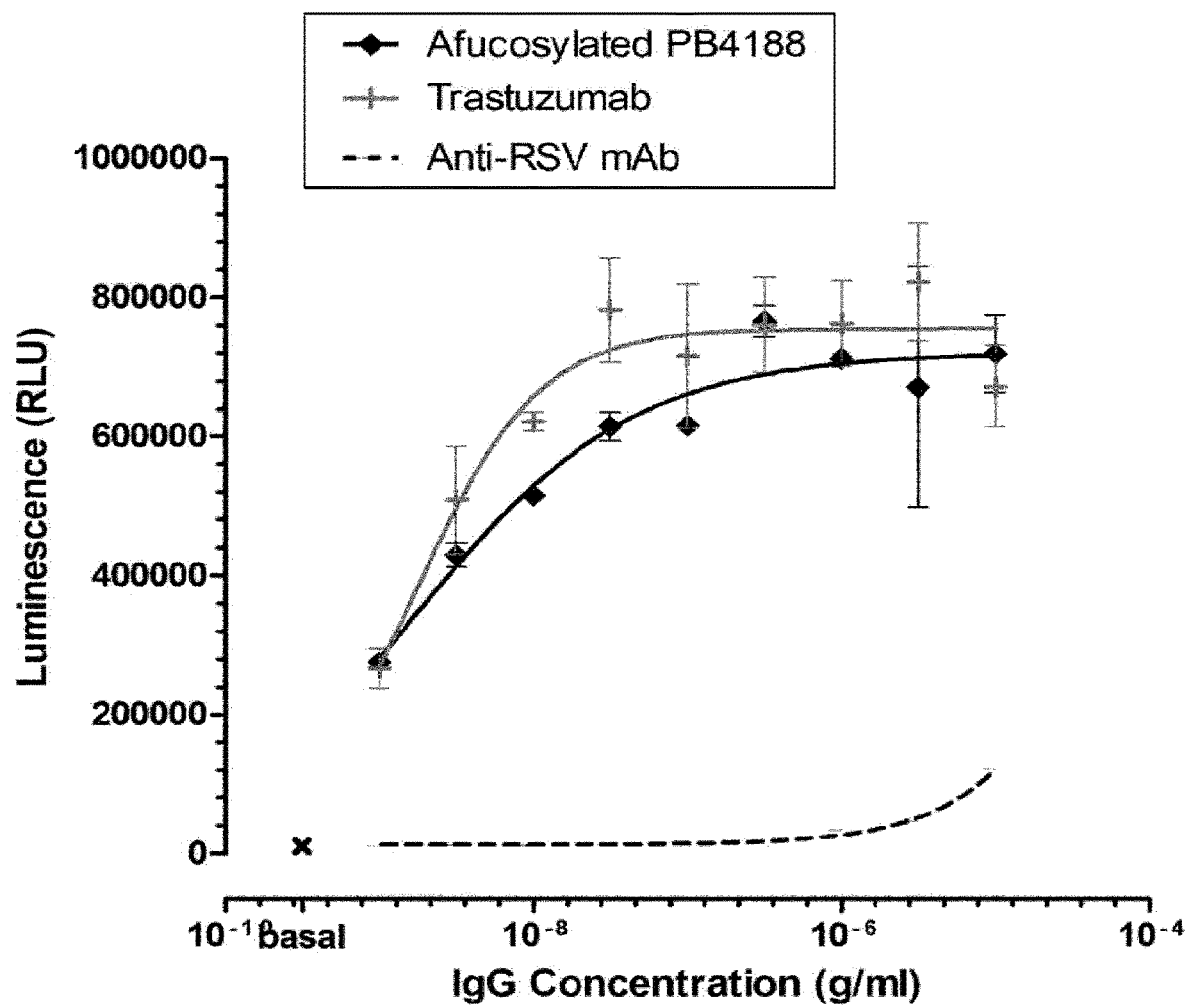
FIGS. 15A and 15B: ADCC activity of afucosylated PB4188 on SKBR-3 HER2$^{+++}$ cells in the presence of reporter cells expressing a high or low FcγR variant
Figure 15B:
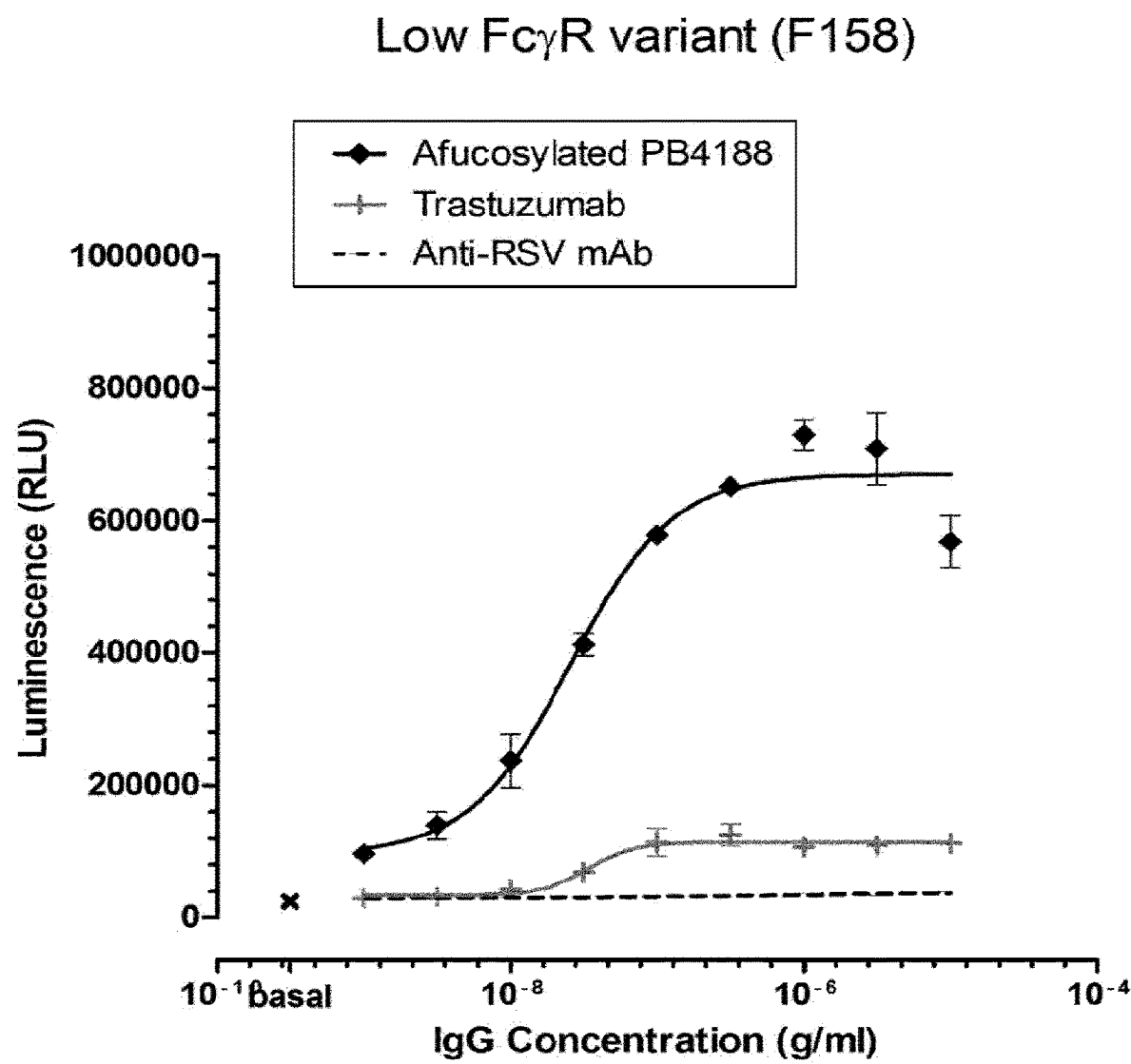

Afucosylated PB4188 Shows Superior ADCC Activity with Low Affinity FcγRIII Receptors Afucosylated PB4188 activity was tested on ADCC reporter cells containing either the V158 (high affinity) FcγRIIIa receptor variant or the F158 (low affinity) FcγRIIa receptor variant. A serial titration of antibody. i.e. control antibody, trastuzumab and afucosylated PB4188, was added in combination with ADCC reporter cells harbouring the different FeγRIHla variants to adherent SK-BR-3 cells. ADCC activity was measured by measuring luciferase activity. Mucosylated PB4188 showed equal activity compared to trastuzumab in combination with the high affinity V158 FcγRIIIa receptor variant. In contrast afucosylated PB4188 displayed superior ADCC activity compared to trastuzumab in combination with the low affinity F158 FcγRIIIa receptor variant. (FIG. 15)

JIMT-1 Zenograft Study

JIMT-1 human breast carcinoma cells were grown in DMEM containing 10% fetal bovine serum, 100 units/mL penicillin G sodium, 100 µg/mL streptomycin sulfate, 25 µg/mL gentamicin, and 2 mM glutamine until the time of implantation. At the day of implantation JIMT-1 breast cells were harvested during log phase growth and resuspended in cold PBS. Female CB.17 SCID mice (Charles River) were 8 weeks old on Day 1 of the study and had a body weight range of 16.5 to 20.7 g. Each mouse was injected subcutaneously in the right flank with 5×10⁶ tumor cells (0.2 mL cell suspension). The tumors were measured with a caliper in two dimensions to monitor size as the mean volume twice per week. Once tumors had reached approximately 100-150 mm³ in size animals were enrolled in the efficacy study. Outlier animals-tumor volume—were removed and the mice were randomly distributed into groups of 10 mice each. Mice were injected once weekly (antibody) or daily (lapatinib) for a period of four weeks. Details of the treatment groups are depicted in Table 11.

Figure 17A:
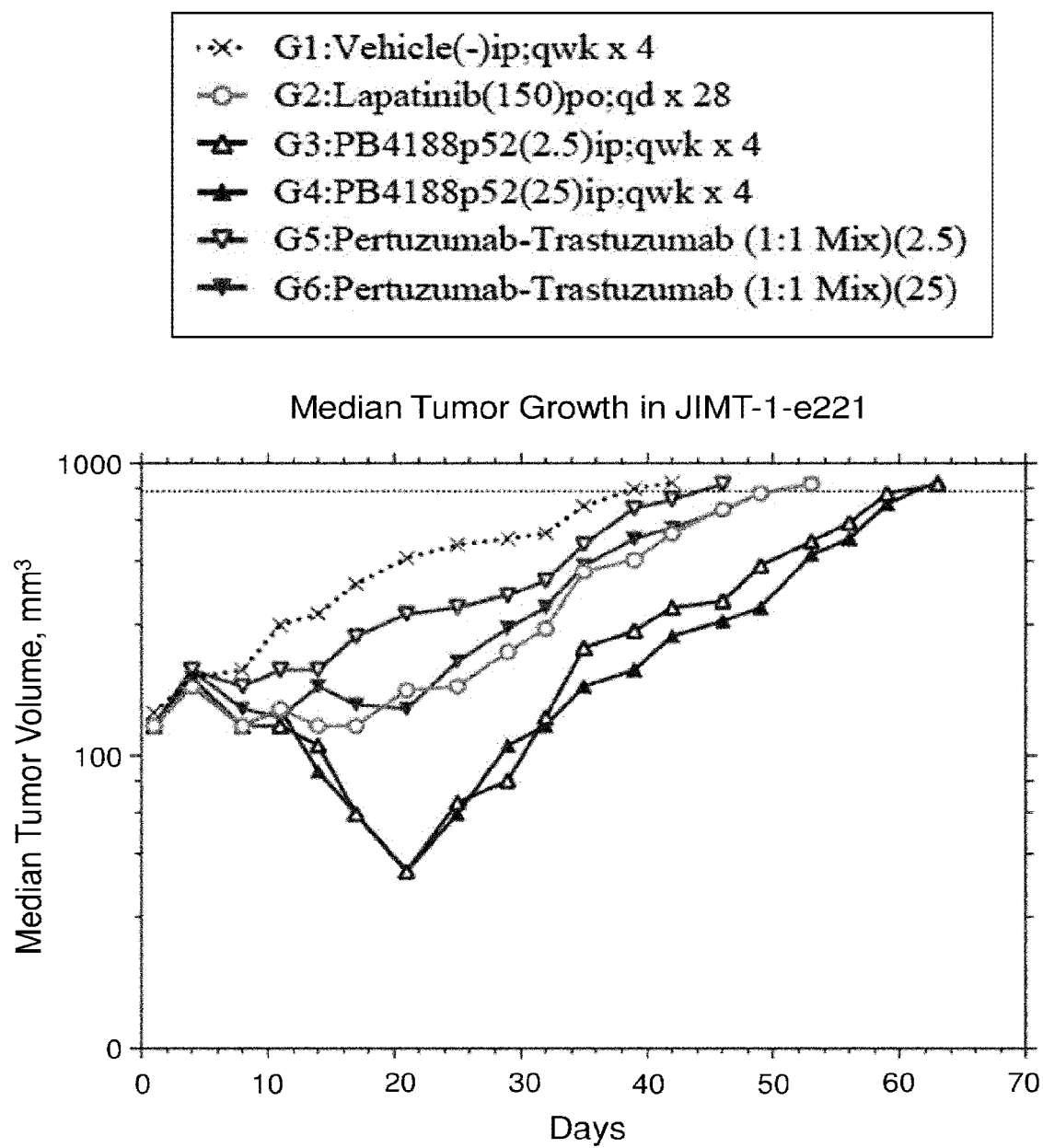
FIGS. 17A and 17B: Antibody treatment effect on tumor size in a JIMT-1 murine xenograft model. Tumor growth measured by tumor volume caliper measurement of the different treatment groups, 17A: tumor growth during 60 days; 17B: tumor growth inhibition (TGI) at the end of treatment period (29 days).
Figure 17B:
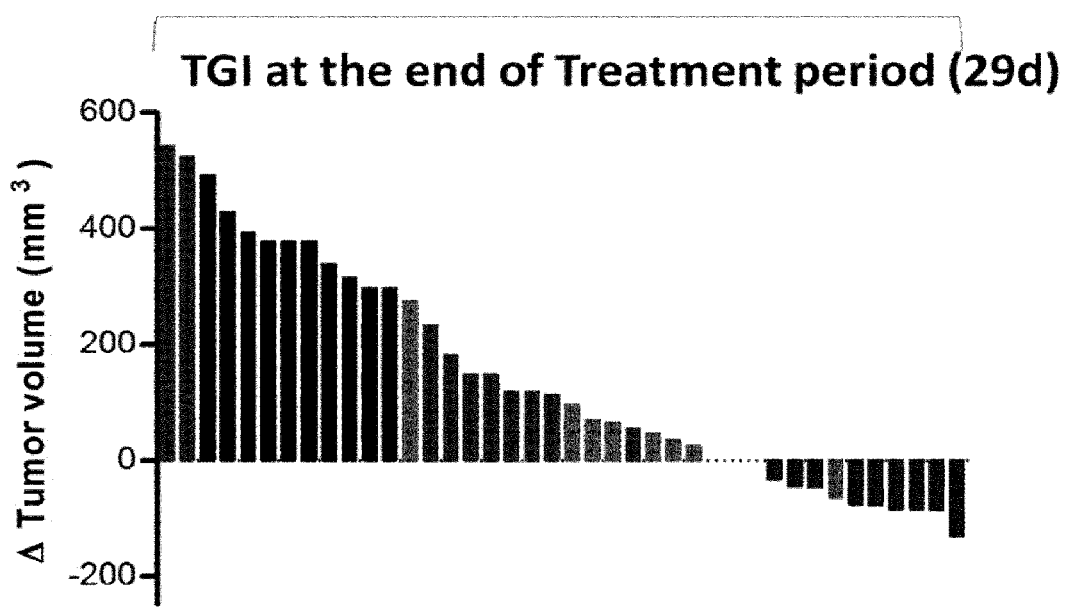
Figure 18:
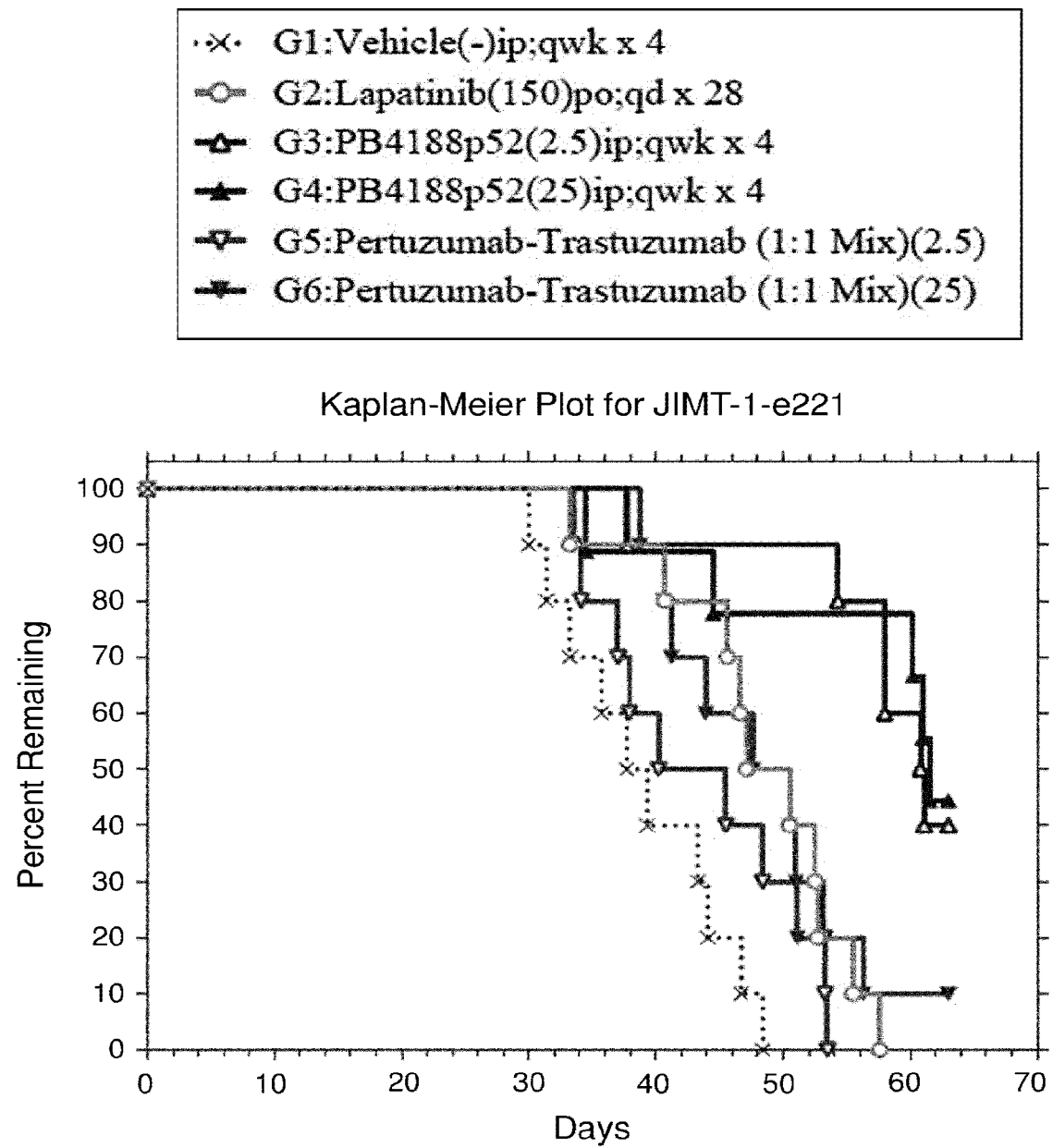
FIG. 18: Kaplan-Meier survival curves of the different treatment groups in the JIMT-1 murine xenograft model.

Tumor sizes were measured weekly by caliper measurement. The efficacy study revealed that PB4188 at both dosing schedules was equal effective and more potent than lapatinib or the combination pertuzumab and trastuzumab. The data are shown in FIGS. 17 and 18.

PB4188 can Overcome HRG Mediated Resistance

Figure 19:
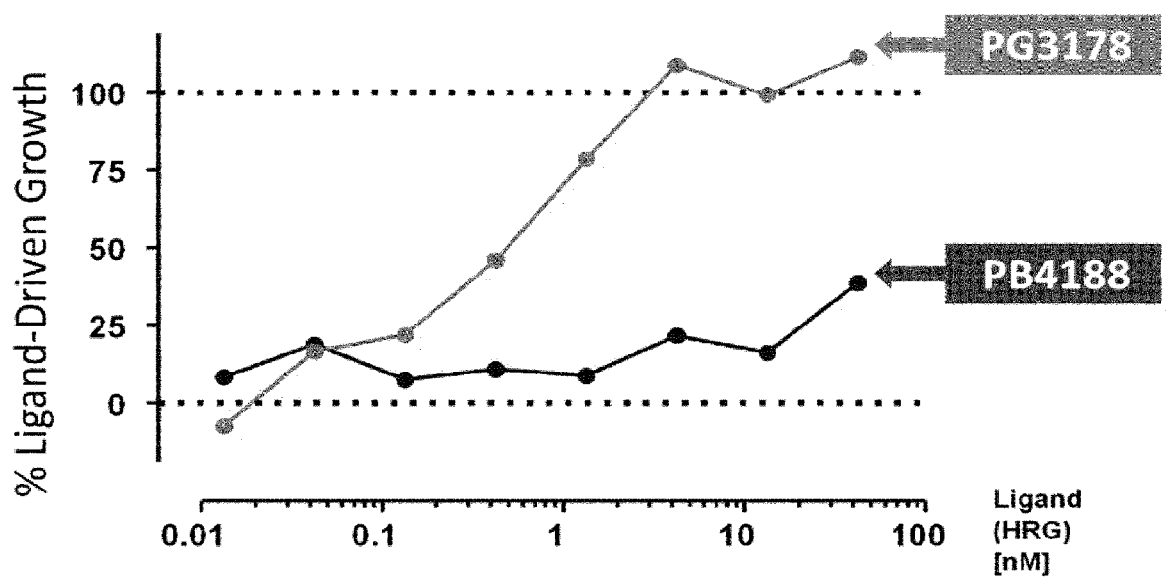
FIG. 19: Inhibition of N87 ligand driven growth. HRG driven proliferation of N87 can be overcome over a wide range of HRG by PB4188 in contrast to the parental anti-HER3 antibody. Data shown at antibody concentration of 40 ng/ml.

Upregulation of NRG1-P1 is a key resistance mechanism against HER2 targeted therapies (Wilson, 2012). PB4188 was tested in comparison to its parental anti-HER3 monoclonal antibody PG3178 in a serial titration in the presence of an increasing concentration of HRG (NRG1-P1 EGF). To this aim N87 cells were cultured in RPMI 1640 supplemented with 10% heat inactivated FBS. For the proliferation assay subconfluent cell cultures of N87 cells were washed with PBS trypsinized and trypsin was inactivated by adding culture medium. Cells were washed twice in large volumes of assay medium (RPMI 1640 medium containing 0.05% BSA and 10 µg/ml Holo Transferrin). Antibodies were diluted in a semi-log titration ranging from 1 to 0.0001 µg/ml. Cells were added at a density of 10000 cells/well in the presence an increasing concentration of HRG (0.04-39.5 nM). The cells were cultivated for 3 days at 37° C., 5% CO2, in 95% relative humidity. ALAMAR BLUE™ (INVITROGEN®) was added according to the manufacturer's instructions and incubated for 6 hours at 37° C., 5% CO2, in 95% relative humidity in the dark. Fluorescence was measured at 550 nm excitation with 590 nm emission wavelength. PB4188 showed superior activity compared to the parental anti-HER3 monoclonal antibody (FIG. 19).

Hence, in case of an escape mechanism, such as for instance upregulation of NRG-β1, a bispecific antibody according to the invention is preferred.

Epitope Mapping of HER2/HER3 Specific IgGs

Shotgun Mutagenesis Experiments

Alanine scanning mutagenesis was used to map the epitopes of PG3958 and PG3178 for HER2 and respectively HER3. In the shotgun mutagenesis assay, clones are generated whereby each amino acid residue of the HER2/HFER3 extracellular domain (ECD) is substituted for alanine. Next, a cell array was prepared by reverse transfection (patent US2011/0077163A1). Therefore, DNA of each clone was mixed with lipofectamin and the mixture was placed in a dedicated well of a 384 well plate. HEK293T cells were added to each well and expression of protein was measured 24H later. Subsequently, the reactivity of antibodies was measured by immunofluorescent staining leading to binding maps and identification of critical residues for antibody binding. Expression levels of the HER2 and HER3 ECD constructs were verified by FACS analysis using commercially available monoclonal antibodies (R&D mAb 1129 (HER2) and R&D mAb 66223 (HER3)).

HER2

Figure 21A:
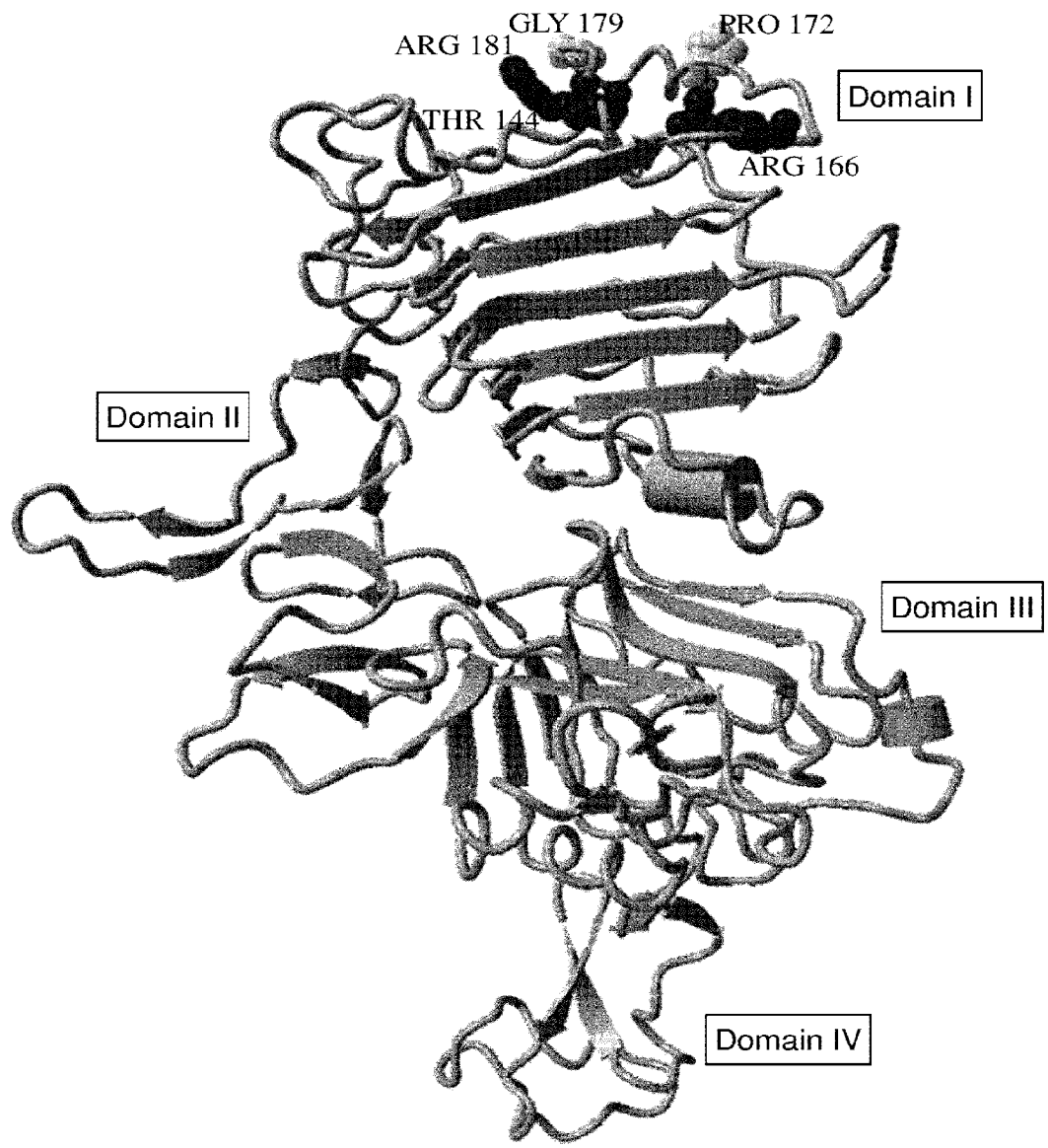
FIG. 21A: Epitope mapping HER2. Critical residues identified are represented as black spheres on the HER2 crystal structure, secondary critical residues identified are represented as gray spheres (PDB ID #1S78).
Figure 21B:
FIG. 21B
a) HER2 crystal structure (PDB #1S78) showing verified PG3958 epitope residues as light gray spheres and surrounding residues (+/−five amino acid residues) as dark gray spheres. b) Solvent exposed surface of epitope region showing verified epitope residues in gray and surrounding residues (+/−five residues) in black. c) Detailed view of epitope region with verified epitope residues in light gray and surrounding residues (+/−five residues) in dark gray. d) Primary amino acid sequence of HER2 PC3958 epitope region indicating verified epitope residues (gray underlined), surrounding residues (black) and distant residues (gray italic, not shown in a, b and c). Figures and analyses were made with Yasara (www.yasara.org).
Figure 21B:
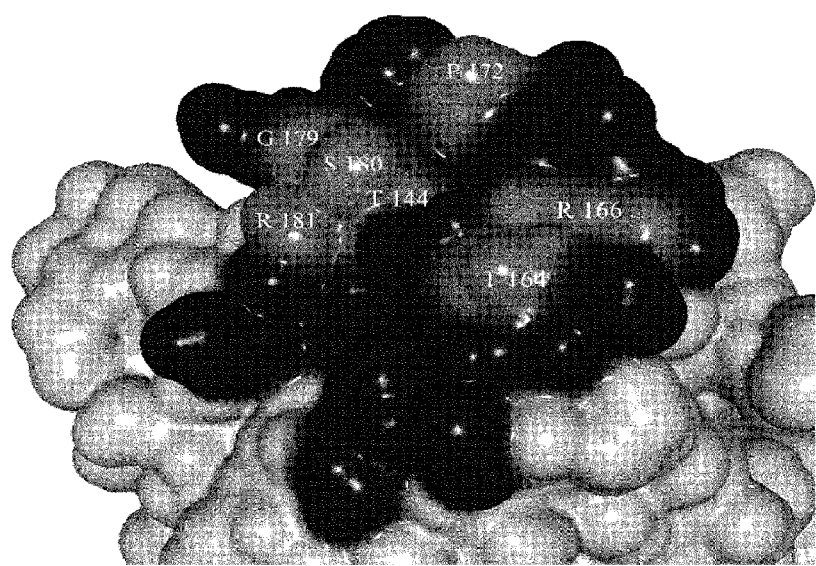
Figure 21B:
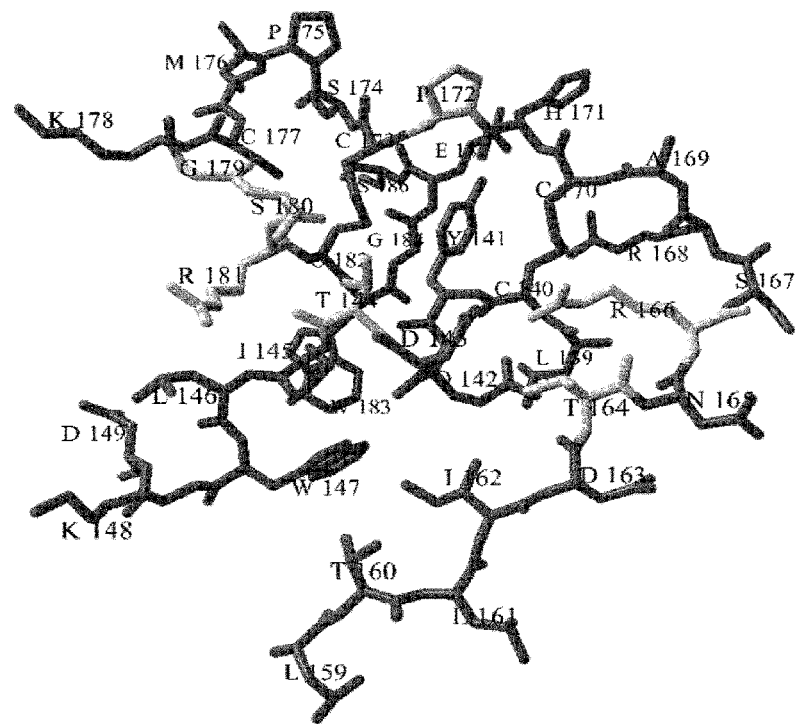
Figure 21C:
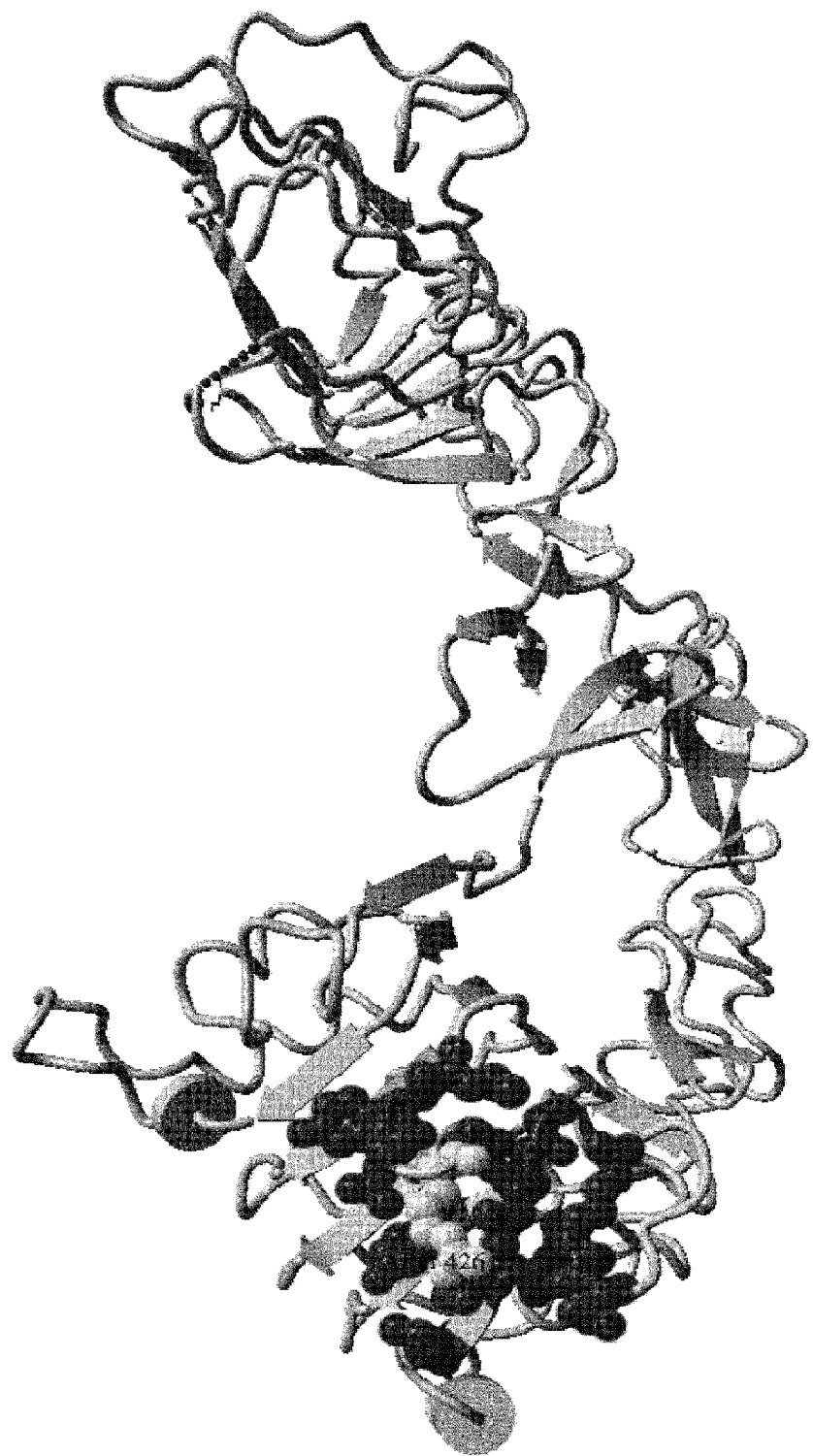
FIG. 21C:
a) HER3 crystal structure (PDB #4P59) showing epitope residue Arg 426 in gray spheres and all surface exposed residues within an 11.2 Å radius from Arg 426 in black spheres. b) Solvent exposed surface of epitope region with Arg 426 and distant residues shown in gray and all surface exposed residues within a 11.2 Å radius from Arg 426 shown in black. c) Residues in the epitope region Arg 426 in light gray and surrounding residues (all labeled) in dark gray. Figures and analyses were made with Yasara (www.yasara.org).
Figure 21C:
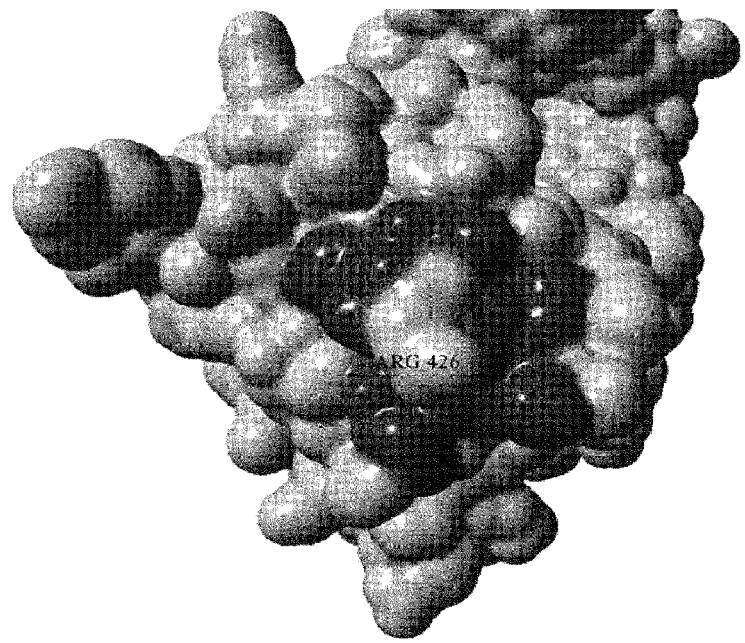
Figure 21C:
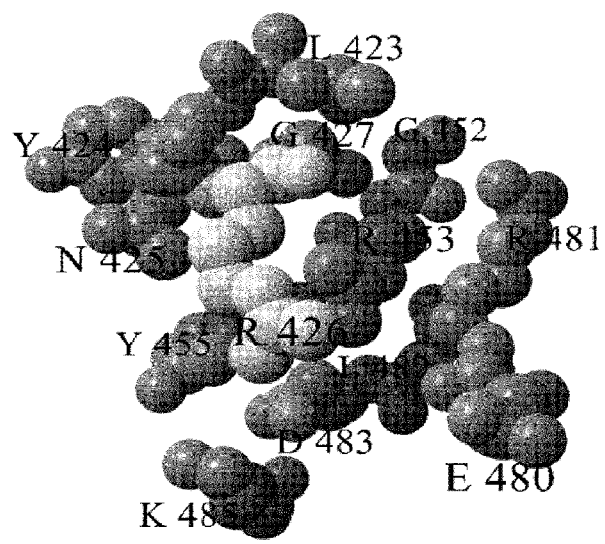

Binding of monovalent PG3958 Fab to HER2 ECD mutants was tested at a concentration of 0.25 µg/ml in the assay and stringent washing conditions were used (pH 9.0, 350 mM NaCl). This resulted in the identification of three 'critical' residues (T144, R166, R181) in HER2 that showed less than 35% residual binding of the PG3958 Fab compared to WT HER2 while retaining control mAb binding. Two residues (P172, G179) that are positioned near the critical residues in the HER2 structure showed significant, but less severe loss of binding and were designated 'secondary critical' residues (Table 13 and FIG. 21A). All these surface-exposed residues are located in Domain I of HER2 and together they form a discontinuous patch on the surface of the HER2 molecule.

Confirmation Experiments HER2 Epitope

Constructs encoding Wildtype (WT) HER2 ECD and the HER2 ECD variants listed in Table 13 were expressed in CHO-K1 cells. Three Domain I residues that are surface exposed and structurally near the determined critical residues were selected for further analysis. T164, S180 and D143 point mutations to tyrosine were generated in the HER2 ECD construct and the resulting constructs were also expressed in CHO-K1. The L159A HER2 ECD variant was expressed in CHO-K1 cells as control sample.

Figure 22:
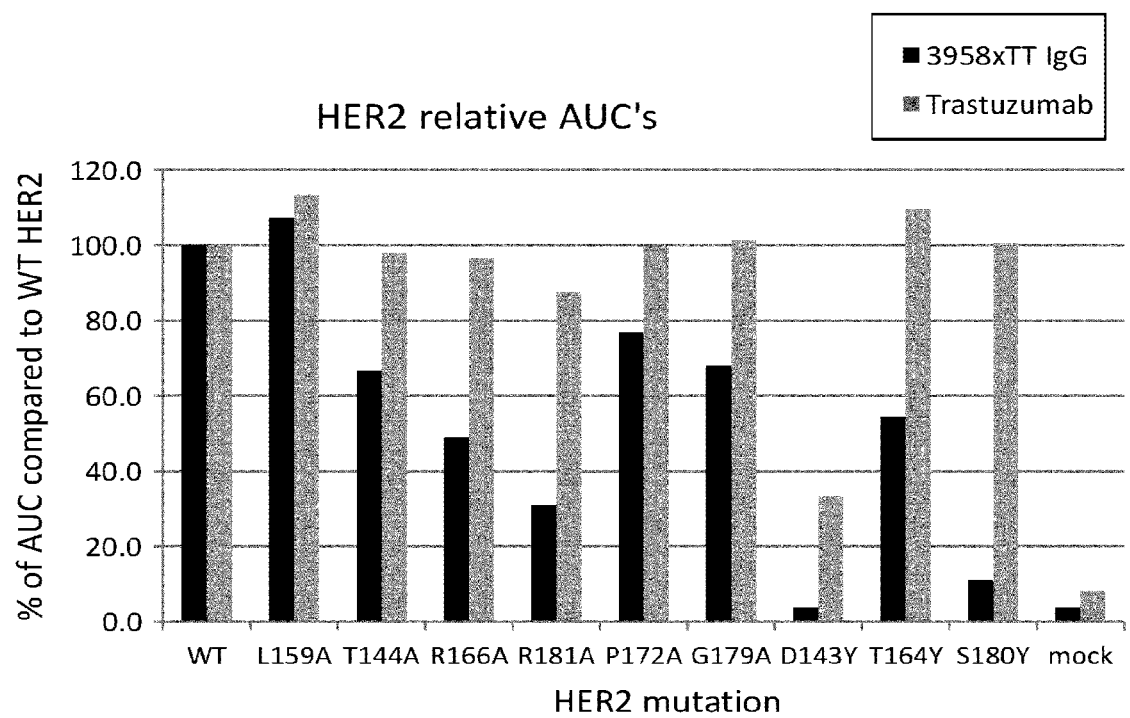
FIG. 22: Confirmation of critical binding residues for Fab arm 3958 to HER2. Trastuzumab was included as a control antibody. Binding was determined in a FACS titration and binding is expressed as AUC in comparison to trastuzumab binding. D143Y is not considered to be part of the 3958 epitope as binding of Trastuzumab to this mutant is also blocked.

The bispecific PG3958xTT antibody tested for binding to the ECD variants in a FACS titration experiment. The anti-HER2 antibody trastuzumab which binds domain IV of HER2 was used to verify HER2 ECD expression at the cell surface. Mean MFI values were plotted and for each curve the AUC was calculated using GraphPad Prism 5 software. WT HER2 binding was used to normalize the data. The FACS data showed that in addition to T144A, R166A, R181A, P172A, G179A the mutations T164Y and S180Y resulted in significant reduction in binding of the PG3958xTT antibody (FIG. 22). The D143Y mutation resulted in severe loss of expression as demonstrated by the decreased binding of the control mAb, so its potential role in the PG3958 epitope could not be determined.

HER3

Figure 23:
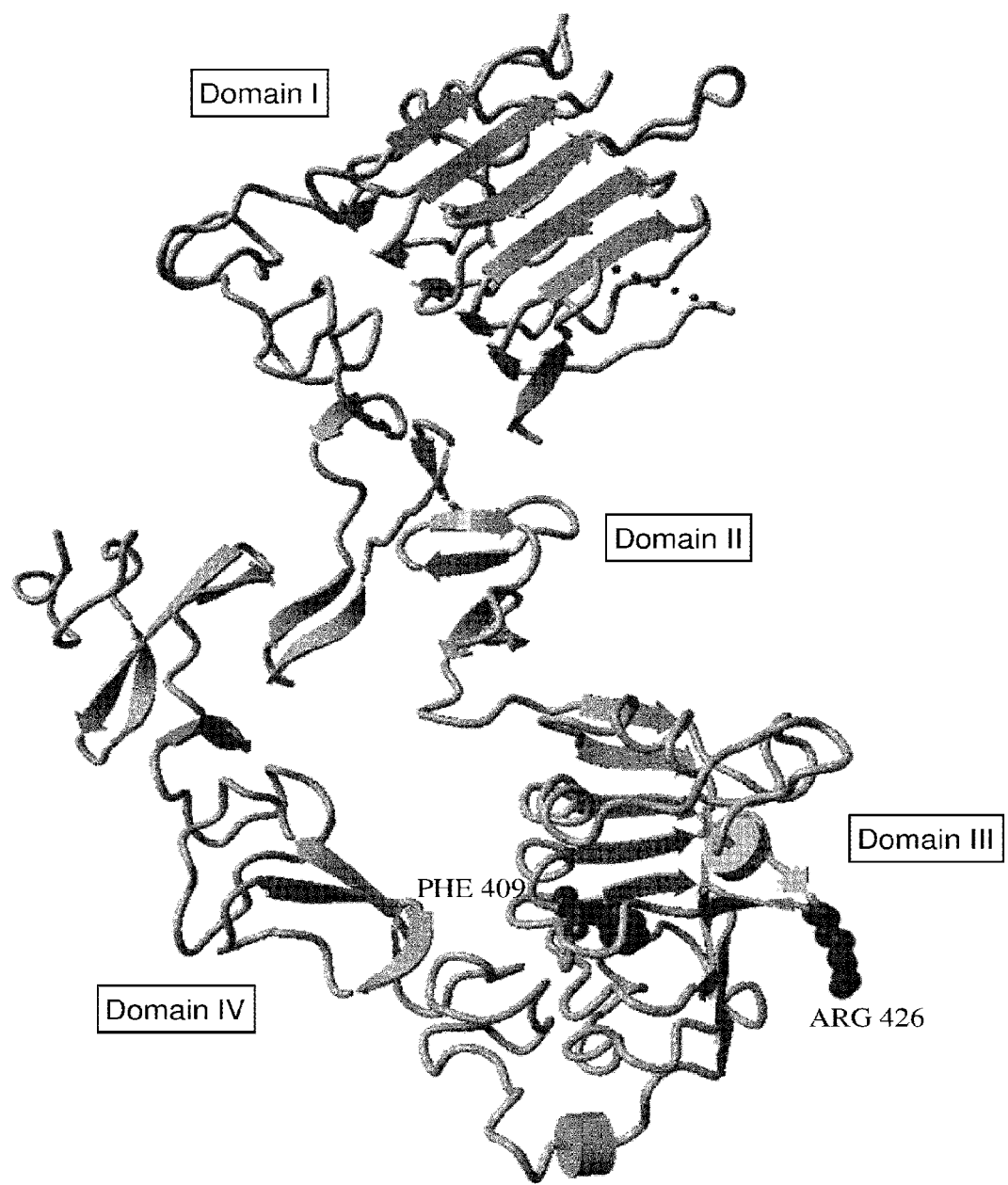
FIG. 23: Critical residues for PG3178 binding represented in the HER3 crystal structure. Critical residues identified for PG3178 binding are represented as black spheres on the HER3 crystal structure (PDB ID #4P59).

Binding analysis of PG3178 IgG at 0.25 µg/ml to HER3 ECD mutants in FACS resulted in the identification of two so-called 'critical' residues (F409, R426) for which mutation to alanine caused substantial loss of binding compared to WT HER3, while binding of the control mAb was retained (Table 14 and FIG. 23). Both residues are located in Domain III of HER3 and spatially distant. Moreover. F409 is buried in the HER3 hydrophobic core, which makes it unlikely to be part of the P03178 epitope.

Confirmation Experiments HER3 Epitope

Figure 24:
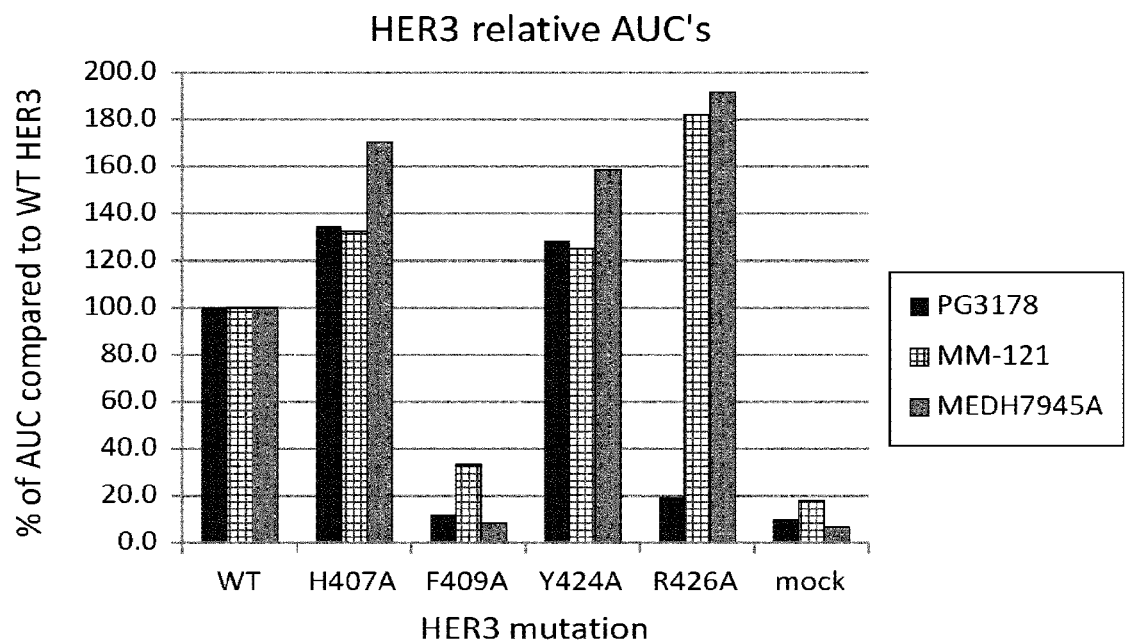
FIG. 24: Confirmation of R426 as a critical binding residue for PG3175 to HER3. Two anti-HER3 antibodies were included as control antibodies. Binding was determined in a FACS titration and binding is expressed as AUC in comparison to binding to WT HER3.

CHO-K1 cells were transfected with HER3 ECD mutation constructs (listed in Table 14), WT HFER3 ECD and two control constructs (H407A and Y424A). P03178 binding to the HER3 ECD variants was tested in a FACS titration experiment. Two control antibodies, binding Domain I (MM-121) and Domain III (MEHD7945A) of HER3 were included to verify HER3 ECD expression on the cell surface. Mean MFI values were plotted and for each curve the AUC was calculated using GraphPad Prism 5 software. WT HER3 binding was used to normalize the data. The R426A mutation was shown to be critical for PG3178 binding whereas the binding to F409A could not be confirmed due to loss of cell surface expression (FIG. 24).

PB4188 Activity on Cardiomyocytes In Vitro

Figure 25:
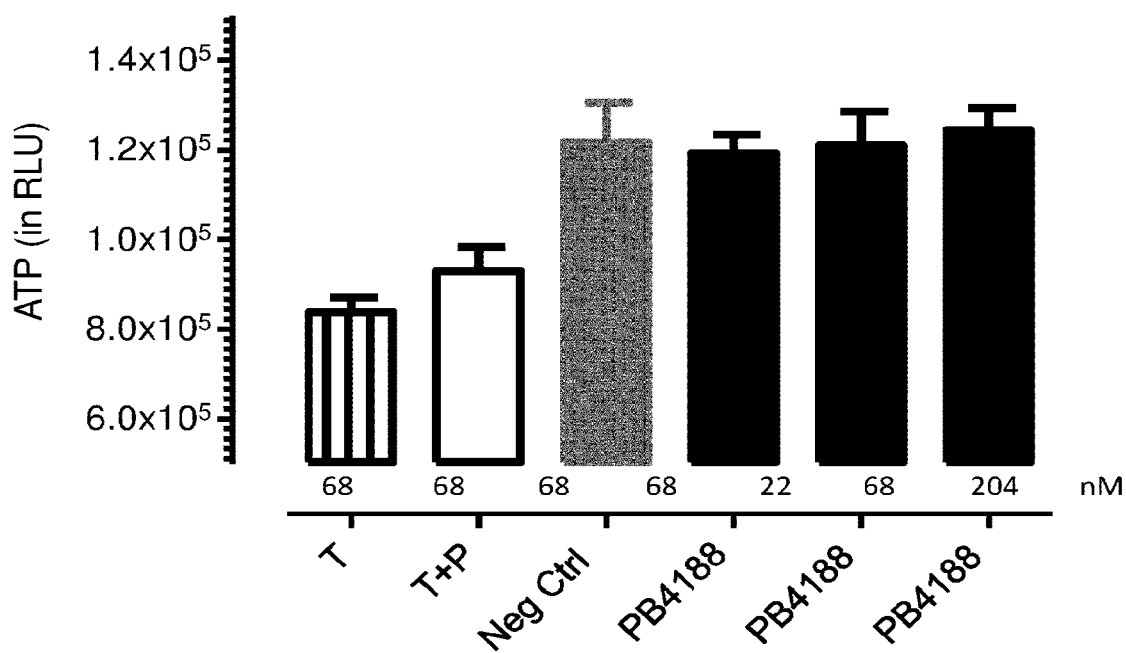
FIG. 25: Absence of PB4188 toxicity under cardiac stress in vitro. Incubation of cardiomyocytes with PB4188 or monospecific benchmark antibodies in the presence 3 μM of the anthracyclin doxorubicin. Viability of the cardiomyocytes was determined by quantification of ATP and expressed in relative light units (RLU). T, trastuzumab: P, pertuzumab.

HER2 is involved in growth, repair, and survival of adult cardiomyocytes as part of a signalling network that involves the heregulin receptor complex HER2:HER4. Cardiotoxicity is a known risk factor in HER2 targeting and the frequency of complications is increased when trastuzumab is used in conjunction with anthracyclines thereby inducing cardiac stress. A model system based on human stem cell derived cardiomyocytes was used to test the potential toxicity of PB4188 and benchmark it against trastuzumab and the combination of trastuzumab and pertuzumab in the presence of the anthracyclin doxorubicin. Human stem cell derived cardiomyocytes (Pluriomics BX) were seeded at a concentration of 20.000 well in white flat-bottom assay plates (corning 655098). On day 5 of culture the medium was replaced for glucose and galactose free culture medium supplemented with 10 ng/ml HRG. On day 7 test antibodies were added in combination with doxorubicin (3 μM). Cell viability was assayed on day 9 using the Promega Cell titer Glo assay. The monospecific antibodies were tested at single concentrations of 68 nM whereas PB4188 was tested at three concentrations in the presence of 3 μM doxorubicin. FIG. 25 shows that the viability of the cardiomyocyte was unaffected by all PB4188 concentrations tested. In contrast, trastuzumab and the combination of trastuzumab and pertuzumab both reduced cardiomyocyte cell viability.

PB4188 Binding to Cells with Different HER2 Levels

Figure 26:
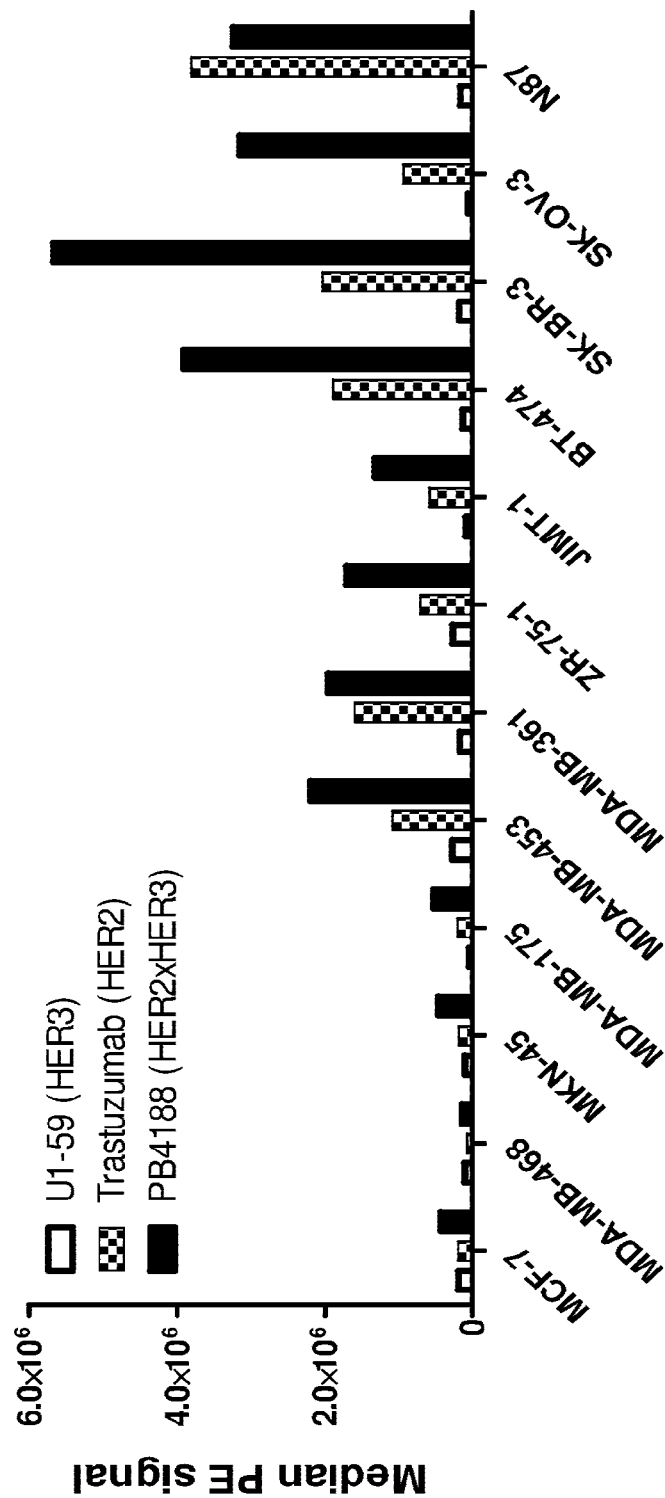
FIG. 26: Binding of PB4188 in comparison to trastuzumab and a HER3 antibody to HER2 amplified cells. FACS titrations were performed on the indicated cell lines expressing different HER2 levels. Area under the curve of Median PE signal values were plotted per cell line.

The binding of PB4188 in comparison to trastuzumab and the HER3 antibody U1-59 was analyzed by FACS on breast and gastric cancer cell lines expressing different levels of HER2. Cells were considered HER2+++ if they express millions of HER2 copies and/or are HER2 gene amplified. The following cell lines were used: MCF-7 (HER 2+): MDA-MB-468 (HER2+, MKN-45 (HER2) MDA-MB-175 (HER2+), MDA-MB-453 (HER2++), MDA-MB-361 (HER2++), ZR-75-1(HER2++). JIMT-1 (HER2+++), BT-474 (HER2+++), SKBR-3 (HER2+++). SK-OV-3 (HER2+++), N87 (HER2+++). Cells of an exponentially grown culture were harvested by trypsin and diluted to $10^6$ cells/ml in FACS buffer (PBS/0.5% BSA/0.5 mM EDTA), 1-2 $10^5$ cells were added to each well in a U-bottom 96 well plate. Cells were centrifuged for 2 minutes at 300 g at 4° C. Supernatant was discarded by inverting plate(s) above, followed by flicking once, 50 μl of each IgG sample was added in a serial dilution from 3.16 ng-10 μg/ml and incubated for 1H on ice. Cells were centrifuged once, supernatant was removed and cells were washed twice with FACS buffer, 50 μl diluted 1:100 mouse anti human IgG gamma PE (INVITROGEN®) was added and incubated for 30-60 minutes on ice in the dark. Cells were centrifuged once, supernatant was removed and cells were washed twice with FACS buffer. Cells were analysed on a FACSCanto Flow cytometer in a HTS setting. The quantity of antibody bound was was assessed by median fluorescence. Data were plotted and the area under the curve (AUC, a cumulative measurement of the median fluorescence intensity) was determined for each antibody per cell line tested (FIG. 26).

From this experiment it is concluded that PB4188 has a higher binding affinity for HER2+++ cells. HER++ cells and HER+ cells as compared to trastuzumab.

Simultaneous Binding with Trastuzumab

PB4188 and Trastuzumab do not Compete for Binding to HER2

Figure 27:
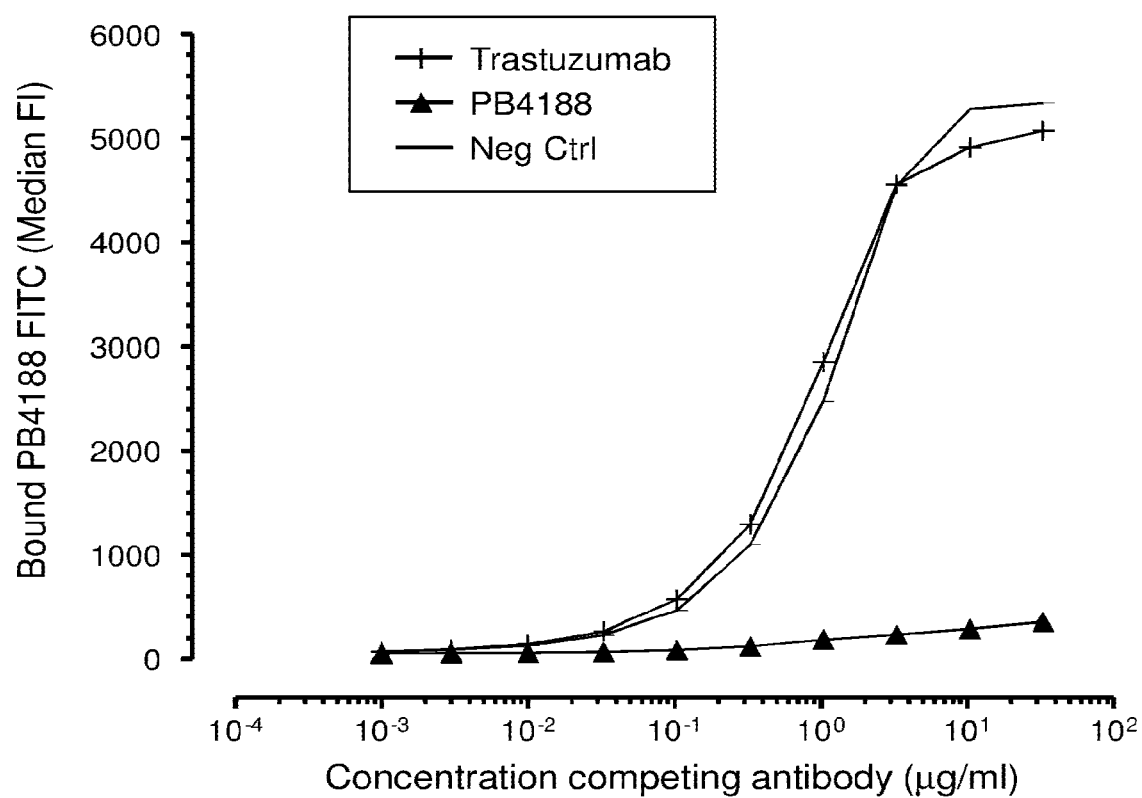
FIG. 27: Binding of a serial titration of PB4188$^{FITC}$ to SKBR-3 cells pre-incubated with a saturated concentration of PB4188, trastuzumab or a negative control antibody. PB4188$^{FITC}$ binds as effectively to SKBR-3 in the presence of trastuzumab or control antibody.

PB4188 binds domain I of the HER2 protein whereas the binding epitope of trastuzumab is localized in domain IV. To demonstrate that both antibodies do not compete for HER2 binding, a binding assay with HER2 amplified SKBR-3 breast cells was performed. First unlabeled antibody was allowed to bind SKBR-3 at saturating concentrations. Next FITC-labeled PB34188 was added in a titration range and fluorescence was measured by FACS. FIG. 27 demonstrates that $PB4188^{FITC}$ bound as effectively to cells in the presence of trastuzumab or the negative control. Pre-incubation of SKBR-3 cells with PB4188 prevented $PB4188^{FITC}$ from binding. Thus, trastuzumab and PB4188 do not compete for binding to HER2

Targeting Domain I of HER2 by a HER2xHER3 Bispecific Molecule can Overcome Heregulin Resistance To test whether the orientation of PB4188 on the HER2xHER3 dimer was preferred for inhibiting cell proliferation under HRG stress conditions, bispecific antibodies were generated composed of the 3178 HER3 arm and HER2 arms targeting either domain I, II, III or IV. Two HER2xHER3 bispecific antibodies were generated for each of the HER2 domains I-IV. The HER2 arms included; MF3958 and MF3003 targeting domain I; MF2889 and MF2913 targeting domain II; MF1847 and MF3001 targeting domain III and MF1849 and MF1898 targeting domain IV. Each HER2 Fab arm was combined with the 3178 HER3 Fab arm and tested for their potency to inhibit cell proliferation in the presence of high concentrations of heregulin. Antibody titrations were performed on HER2 low expressing MCF-7 cells and the HER2 overexpresssing N87 and SK-BR-3 cells. Subconfluent cell cultures of N87, SK-BR-3, and MCF-7 cells were washed with PBS trypsinized and trypsin was inactivated by adding culture medium. Cells were washed twice in large volumes of assay medium (RPMI 1640 medium containing 0.05% BSA and 10 μg/ml Holo Transferrin). Antibodies were diluted in a semi-log titration. Cells were added at a density of 10000 cells/well (N87, SKB-BR-3) and 5000 cells/well MCF-7 in the presence the experimentally defined stress concentration of HRG (10 nM SK-BR-3, 100 nM N87 and MCF-7). The cells were cultivated for 3-4 days at 37° C. 5% CO2, in 95% relative humidity. ALAAR BLUE™ (INVITROGEN®) was added to assess the proliferation. Absorbance was measured at 550 nm excitation with 590 nm emission wave length. In all assays tested, only the bispecific antibodies targeting domain I of HER2 were able to inhibit proliferation in the presence of a high heregulin concentration (FIG. 28).

Drug Combinations with PB4188 In Vitro

Figure 29:
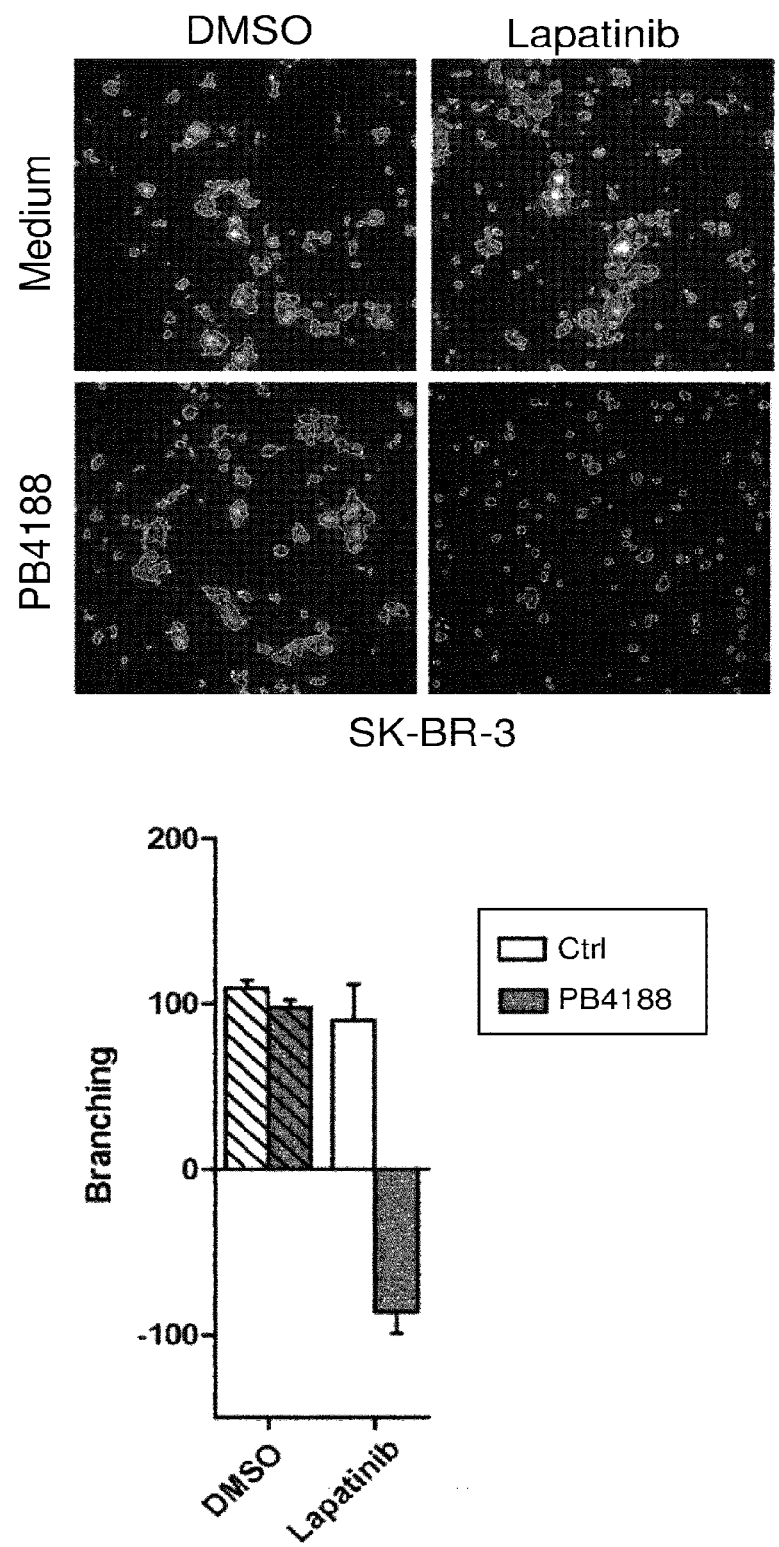
FIG. 29: Synergistic combination of PB4188 with lapatinib on the growth and morphology of SKBR-3 cells. Left, microscopical views of cells treated under different conditions; right morphological changes plotted graphically in relation to the treatment conditions
Figure 30A:
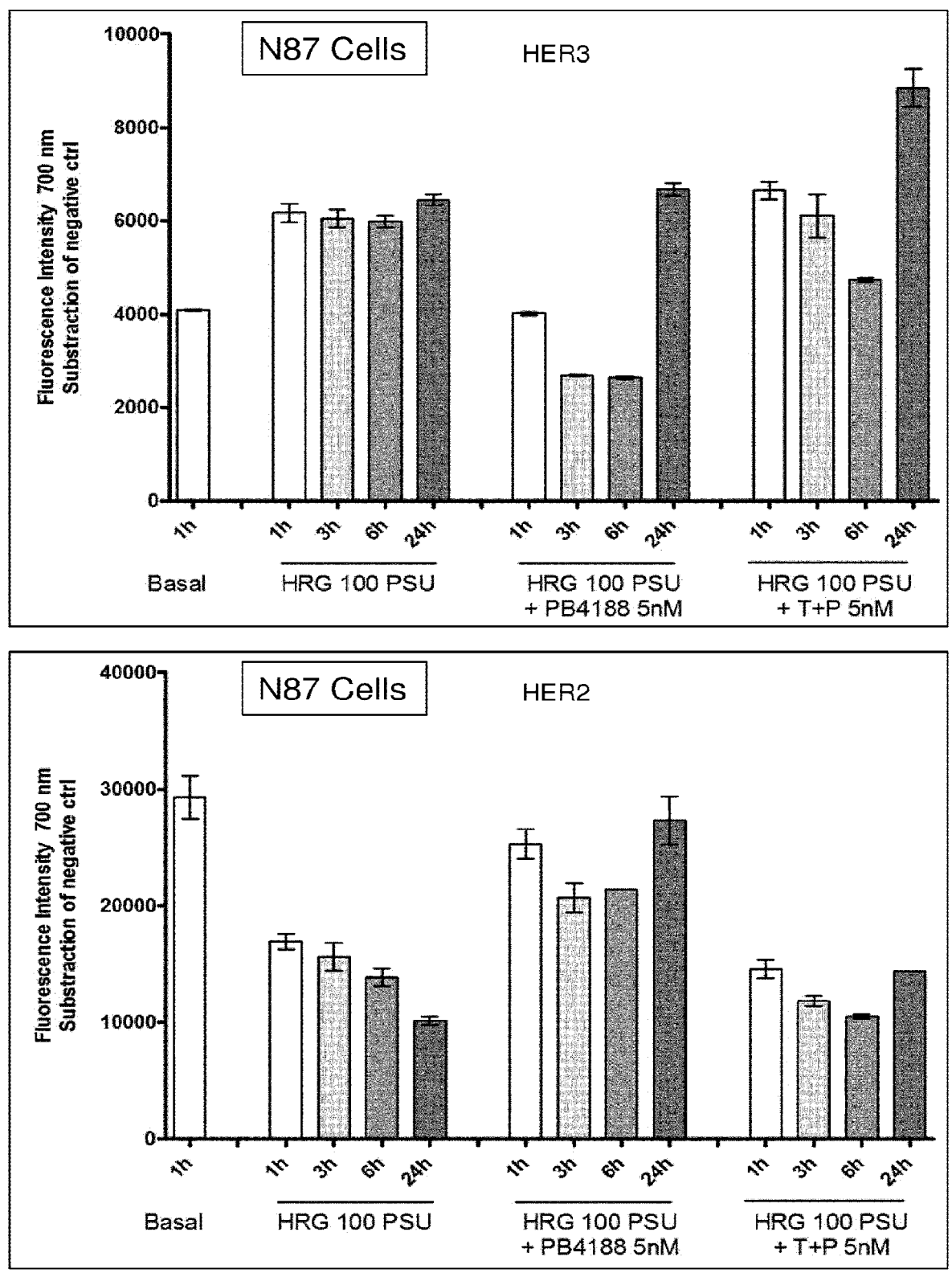
FIGS. 30A and 30B: Inhibition of HRG mediated phosphorylation of N87 and SKBR-3 cells by PB4188 in a time course experiment. Trastuzumab+Pertuzumab and HRG alone were included as controls.
Figure 30A:
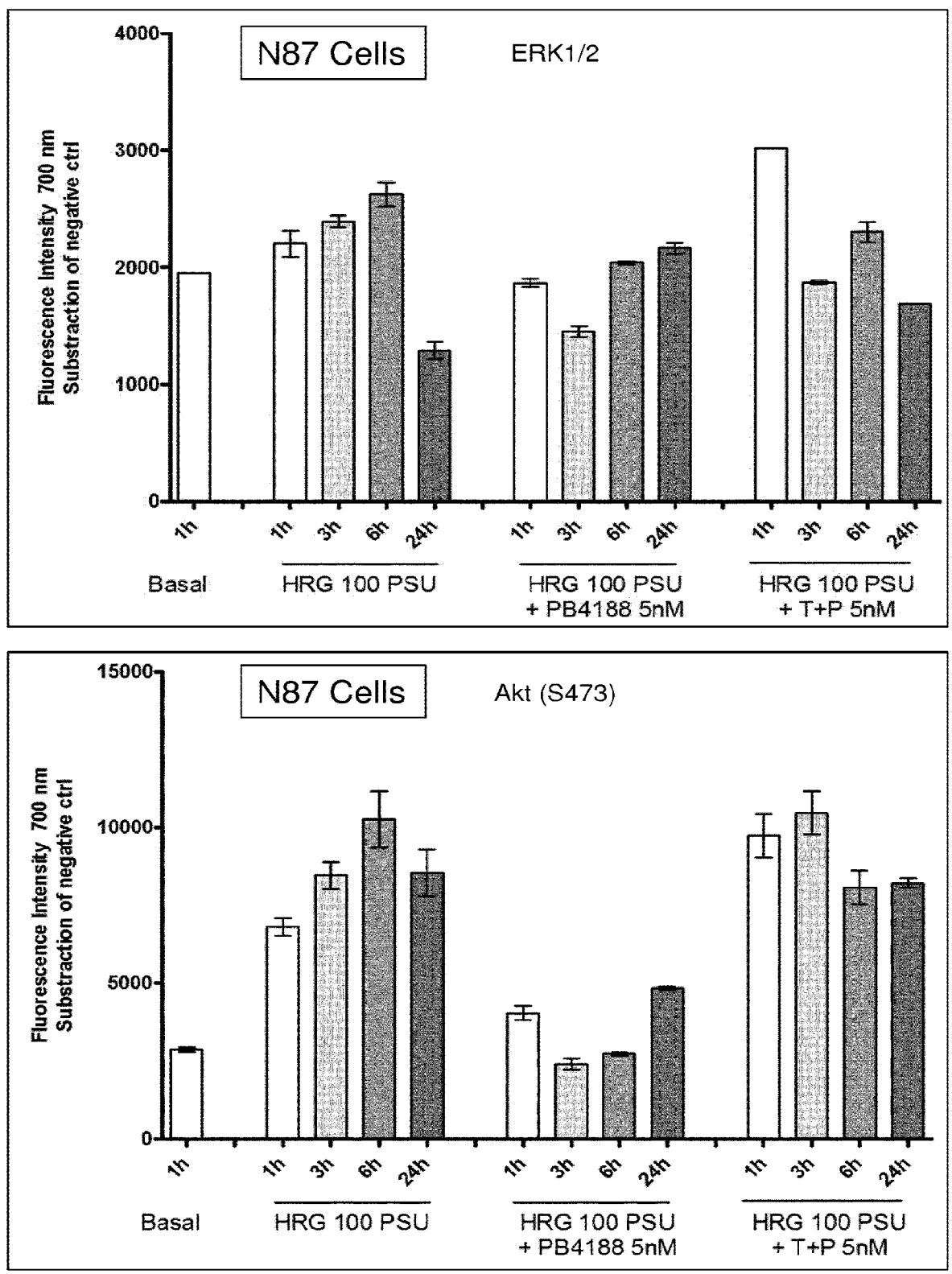
Figure 30A:
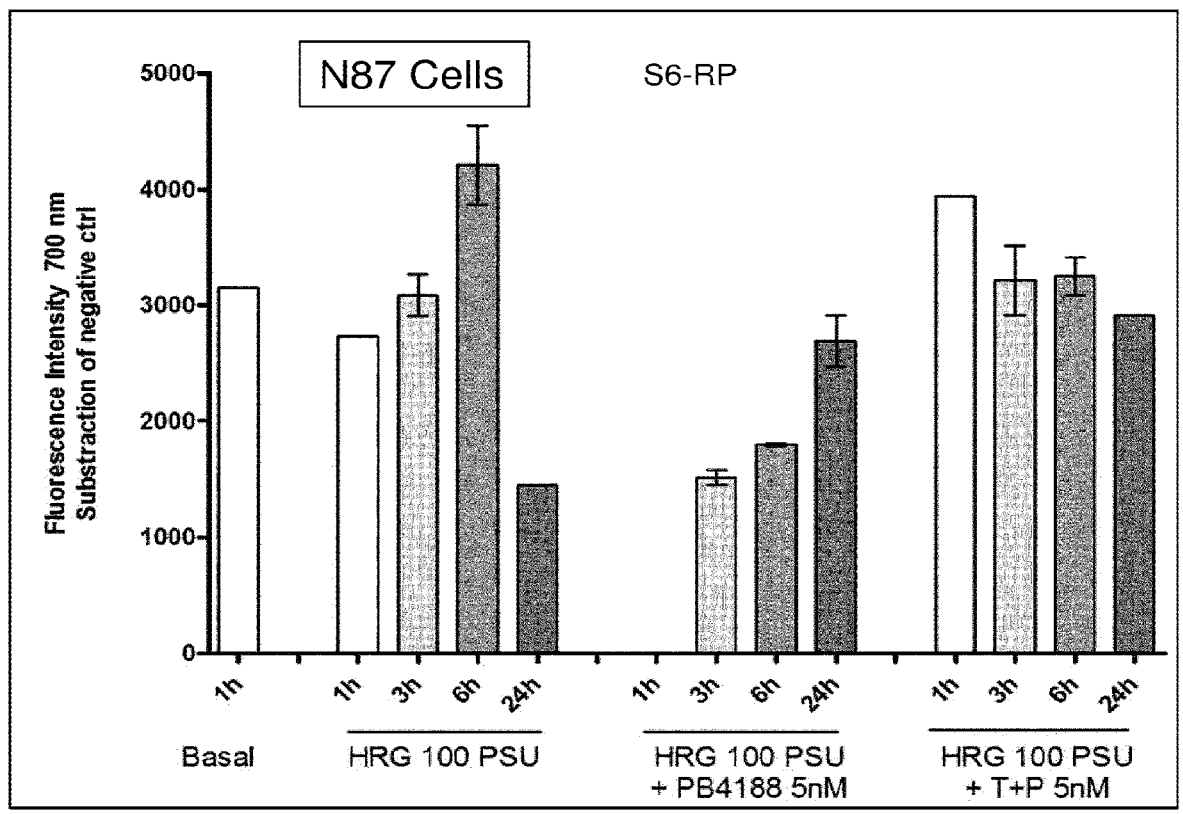
Figure 30B:
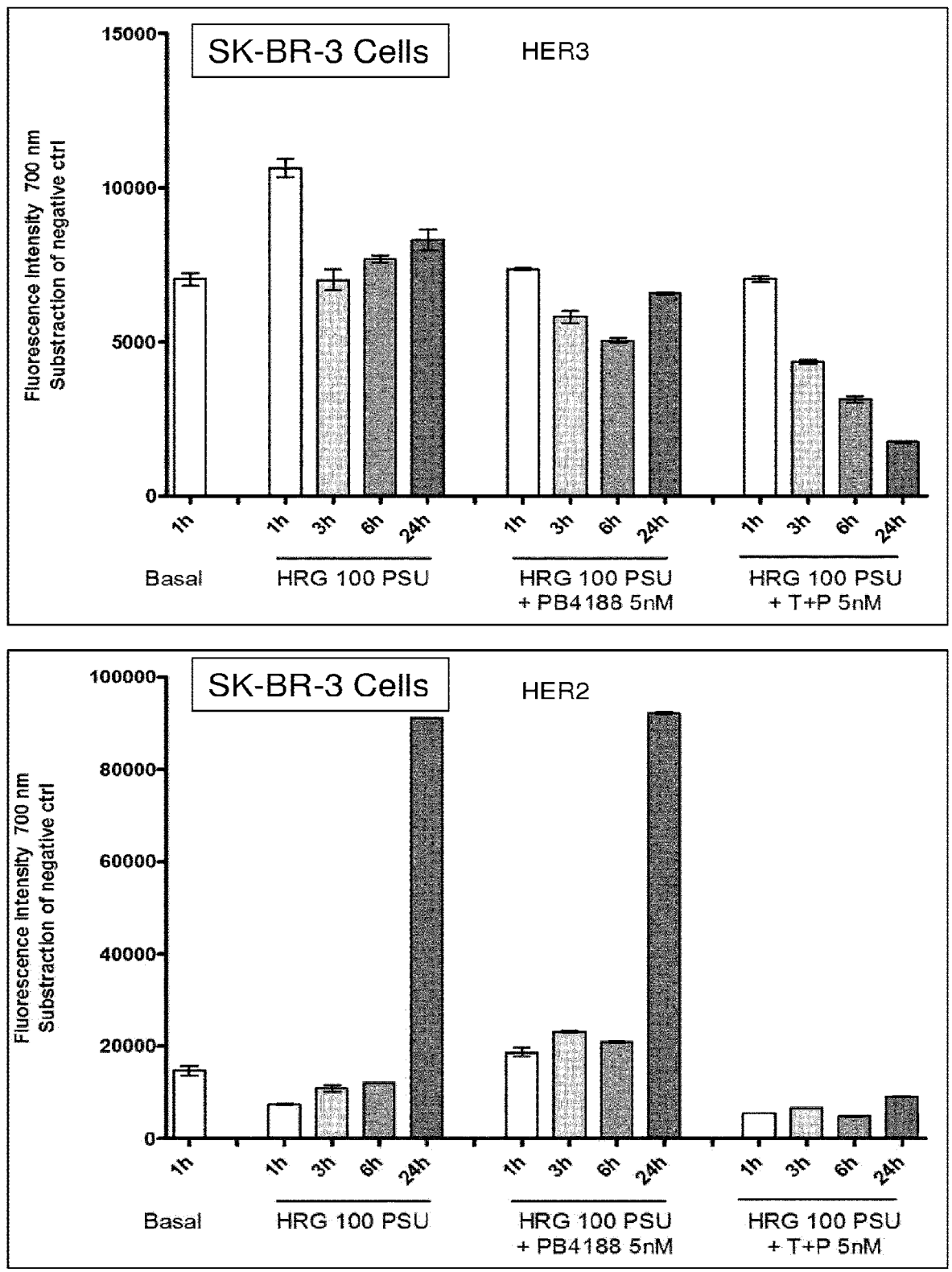
Figure 30B:
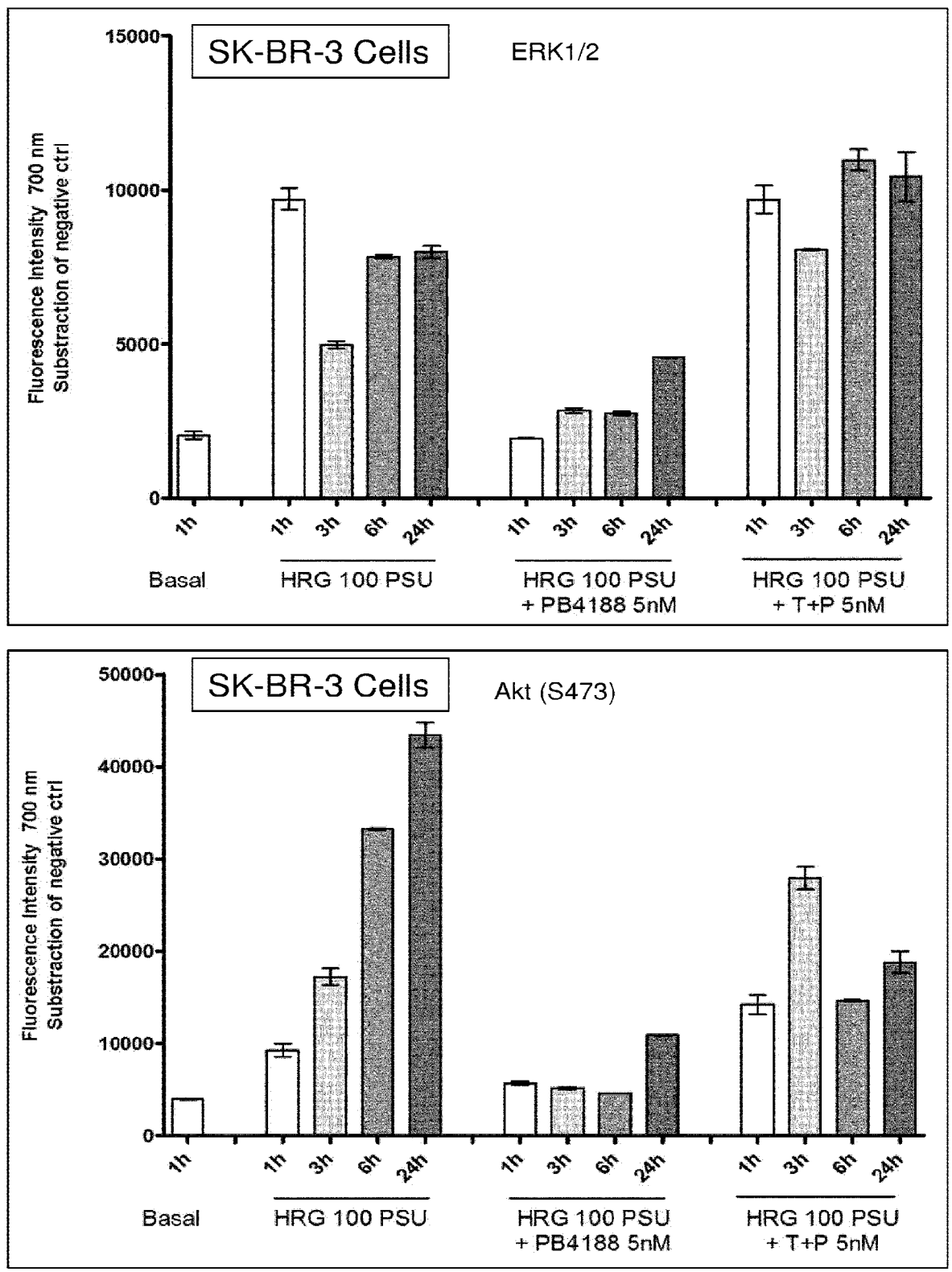
Figure 30B:
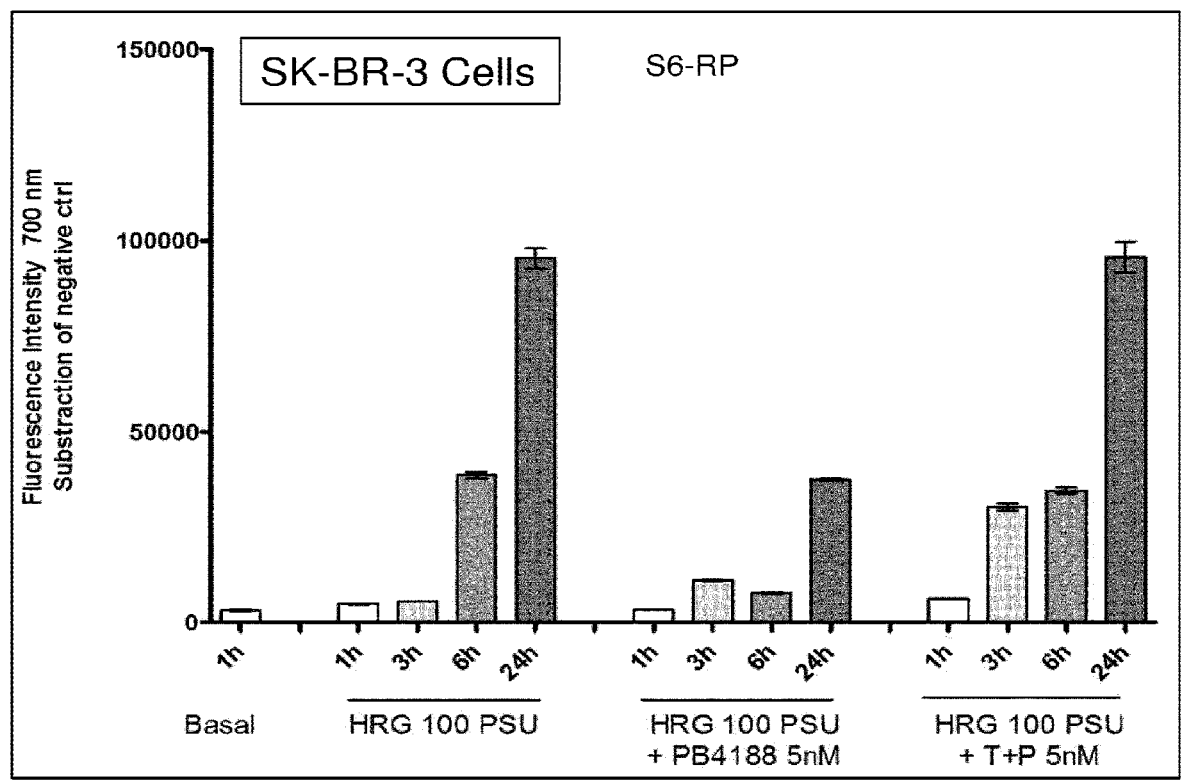

To investigate the possibility to combine PB4188 with small molecule drugs PB4188 was combined with drugs interfering at different levels of the PI3K or MAPK pathway. Moreover, combination with chemotherapeutic drugs and cyclin inhibitors were tested. Combinations were tested on HER2 overexpressing cells growing in the presence of HRG in MATRIGEL® (SK-BR-3 and BT-474) or in the presence of HRG stress concentrations (N87 and SK-BR-3 as described in proliferation assays). The inhibitory effect of drug combinations was tested by imaging or by measuring proliferation using Alamar Blue as described herein before. First, the EC20 P84188 and drugs tested was determined. Next, checkerboard titrations were performed with PB4188 and the drugs. Synergies were observed in all cell lines tested with tyrosine kinase inhibitors (afatinib, lapatinib, neratinib), the PI3Ka inhibitor BYL719, the Akt inhibitor MK-2206, the mTOR inhibitor everolimus, the Src inhibitor saracatinib, the microtubuli disrupting drug paclitaxel, and the HDAC inhibitor vorinostat (which is misspelled in FIG. 40 as "voronistat"). FIG. 29 shows an example of the synergistic combination of PB4188 with lapatinib on SKBR-3 cells grown in MATRIGEL® resulting in morphological changes and reduction of cell growth. The extent of growth inhibition obtained with each combination was calculated. Potency shifting can be shown using isobolograms (Greco et al 1995) which shows how much less drug is required in a combination to achieve a desired level when compared to the single agent required to reach that effect. The inhibition values of the combination experiments were used by CHALICE™ Analyzer software to generate the isobolograms. Isobolograms of the different drug combinations on HER2 amplified cells are shown in FIG. 40.

Isobologram analysis indicated that PB4188 displayed synergistic drug combinations with afatinib, lapatinib, neratinib. BYL719, MK-2206, everolimus, saracatinib, vorinostat and paclitaxel.

These data demonstrate that drugs acting on the PI3K pathway are particular effective in combination with PB4188. In addition, combinations with Tyrosine Kinase Inhibitors are effective. Moreover, a combination with the growth and migration/invasion drug saracatinib can be favourable in the metastatic setting.

PB4188 In Vitro Inhibition of Phosphorylation

Cells of an exponentially grown culture were harvested and seeded in 6 well plates ($3.75 \times 10^6$ cells for N87 and $1.5 \times 10^6$ cells for SKBR-3) in starvation medium (N87 cells: RPMI-1640, 0.05% BSA, 10 µg/ml Holo-transferrin: SKBR-3 cells: DMEM/F-12, 2 mM L-glutamine, 0.05% BSA, 10 µg/ml Holo-transferrin) and incubated incubated overnight at 37° C., 5% CO2, in 95% relative humidity. The next day, antibodies were added to a final concentration of 5 nM and cells were incubated for one hour at 37° C. 5% (C02, in 95% relative humidity. HRG was then added to a final concentration of 100 ng/ml. After 1, 3, 6 or 24 hours at 37° C., 5% CO2, in 95% relative humidity, plates were placed on ice, cells were washed twice with cold PBS. Subsequently 0.3 ml ice-cold lysis buffer was added (Cell signaling RTK #9803 or IC #7018) and cells were lysed for a minimum of 30 minutes on ice. Next, protein concentrations were measured using BCA (Pierce #23235). Protein concentrations were adjusted to 2 mg/ml with lysis buffer. Next, lysates were applied to PathScan RTK Signaling Antibody Arrays (Cell signaling #7949) or PathScan Intracellular Signaling Antibody Arrays. All incubations were performed with sealed wells on an orbital shaker at room temperature. Lysates (75 µl were diluted 2 times to 0.8 mg/ml concentration with 75 µl Array Diluent Buffer supplemented with protease inhibitor cocktail and kept on ice. Array wells were blocked with 100 µl Array block buffer for 15 minutes. Block buffer was removed and Lysates were applied to the wells and allowed to incubate for 2 hours. Lysate was aspirated and wells were washed 4 times with 100 µl Wash buffer. Next, 100 µl detection antibody cocktail was added per well and incubated for 1 hour. Antibody cocktail was aspirated and wells were washed 4 times with 100 µl Wash buffer, 75 µl DYLIGHT80™ Streptavidin was added to each well. DYLIGHIT80™ Streptavidin was aspirated and wells were washed 4 times with 100 µl Wash buffer. The multi-gasket was removed and slides were washed for 10 seconds in 10 ml in deionized water. Slides were allowed to dry and processed for imaging on an ODYSEE®Clx. Spot fluorescence intensity was calculated using Image Studio software.

In N87 and SKBR-3, PB34188 completely blocks AKT phosphorylation during the first 6H of incubation, in contrast to the combination of trastuzumab+pertuzumab. In addition a strong inhibition is observed in ERK and SG phosphorylation in contrast to the combination of trastuzumab+pertuzumab. PB34188 does not inhibit phosphorylation of HER2 (FIG. 30)

Western Blot Analyses

To verify the phosphorylation inhibition observed in the RTK and intracellular Pathscan arrays Western blots were performed of cells treated with PB4188, the combination pertuzumab and trastuzumab and a control antibody in the presence of HRG stress concentrations. Cells of an exponentially grown culture were harvested and seeded in 10 cm dishes ($20 \times 10c$ cells for N87 and $7 \times 10^6$ cells for SKBR-3) in starvation medium (N87 cells: RPMI-1640, 0.05% BSA, 10 µg/ml Holo-transferrin: SKBR-3 cells: DMEM/F-12, 2 mM L-glutamine, 0.05% BSA, 10 µg/ml Holo-transferrin). The next day, antibodies were added to a final concentration of 5 nM and cells were incubated for one hour. HRG was then added to a final concentration of 100 ng/ml. After 1, 3, 6 or 24 hours, dishes were placed on ice, cells were washed twice with cold PBS, transferred to Eppendorf tubes and lysed with 250 µl of RIPA lysis buffer (20 mM Tris-HCl pH 7.5, 150 mM NaCl, 1 mM Na2EDTA, 1 mM EGTA, 1% NP-40, 1% sodium deoxycholate, 0.1% SDS, 2.5 mM sodium pyrophosphate, 1 mM beta-glycerophosphate, 1 mM Na3VO4, 1 µg/ml leupeptin). Lysis was allowed to proceed for 30 minutes on ice. Cell lysates were centrifuged and supernatants were collected in new Eppendorf tubes. Protein concentration was determined using the BCA method (Pierce), 30 µg of the lysate was separated on a 4-12% Bis-Tris NuPage gel (INVITROGEN®) and proteins on the gel were transferred to a nitrocellulose membrane. Membranes were blocked for one hour with TBS-T containing 5% BSA and stained with the indicated antibodies according to the manufacturer's instructions (Cell Signaling Technology). Membranes were then incubated with a HIRP-conjugated secondary antibody, incubated with ECL substrate and subjected to autoradiography using X-ray films (Amersham). All detection antibodies were from Cell Signaling Technology: Phospho-Akt (ser 473) #4060. Total Akt #4691, Phospho-HER2 (Tyr 1221/1222) #2243, Total HER2 #2242. Phospho-HER3 (Tyr 1289) #4791, Total HER3 #4754, Phospho-ERK1/2 (Thr 202/fyr 204) #4377. Total ERK1/2 #4695, Phospho-S6 RP (Ser 235/236) #2211, Total SG RP #2217, Goat anti-rabbit HRP-linked #7074.

Figure 31:
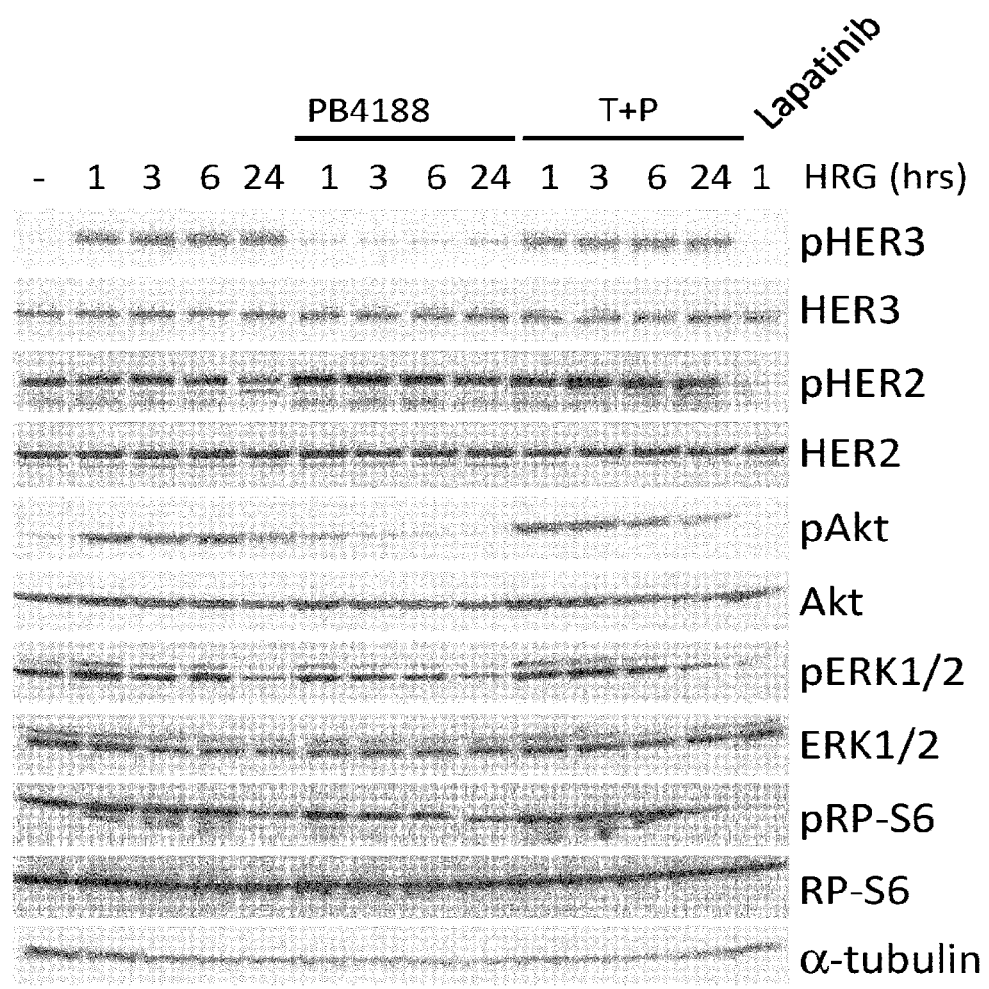
FIG. 31: Inhibition of HRG mediated phosphorylation of N87 cells by PB4188 in a time course experiment. Trastuzumab+Pertuzumab and lapatinib were included as controls.

The results show that PB4188 shows a prolonged inhibition of HER3 phosphorylation resulting in the inhibition of both the MAPK and PI3 kinase pathway with a profound effect on AKT phosphorylation inhibition (FIG. 31).

PB4188 In Vivo Pharmacodynamics

Phosphoprotein Analysis by Luminex

Tumors (100 mm3) of JIMT-1 transplanted mice treated with 2 doses of PB4188 and 4 doses of PB4188 were removed 24H after dosing. Tumors were flash-frozen and processed to powder. Tumor lysates were prepared to a concentration of 50 mg tumor/mL using cold BioRad Lysis Buffer (supplemented with 0.4% BioRad Factor 1, 0.2% BioRad Factor 2, and 2 mM PMSF) to the frozen powder samples, incubated at 4° C. on a rocker for 60 minutes to ensure complete lysis. The samples were centrifuged at 4° C. for 10 minutes at 16000×g, and aliquoted. Total protein was determined using the Biorad DC Protein Assay reagents according to manufacturer's instructions. Luminex Assay: The JIMT-1 tumor lysate samples were processed and analyzed for: Total AKT AKT(Ser473) and AKT(Thr308 using commercially available Luminex kits from Millipore (Cat #48-618MAG (Lot No. 2532050), 46-645MAG (Lot No. 46645M-1K). Each sample was tested in duplicate. Dilutions were prepared in sample diluent to load a target of approximately 25 µg protein per well for all total and phosphorylated analyte determinations. The Millipore kits were used according to the manufacturer's specifications.

Figure 32:
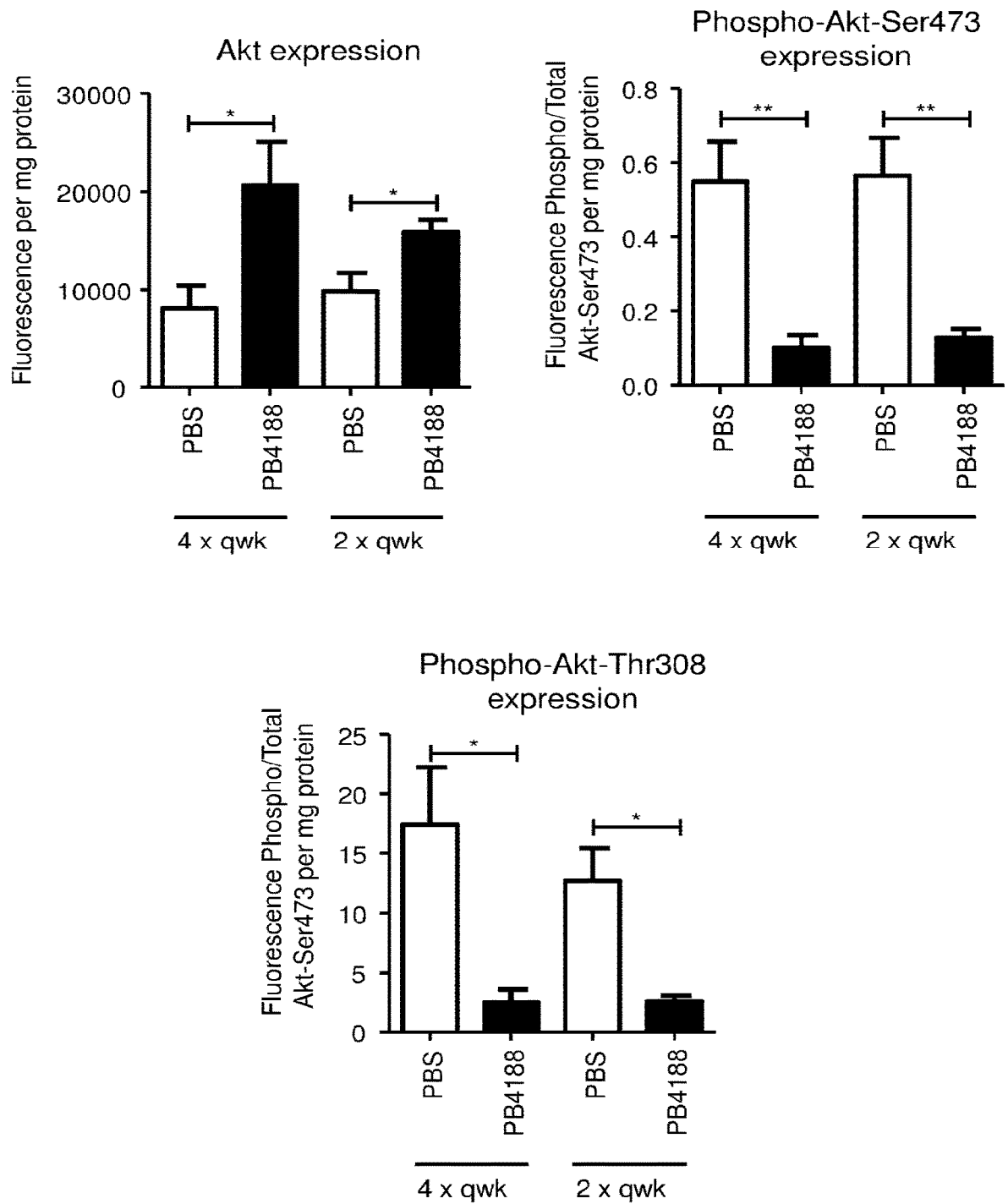
FIG. 32: Changes in Akt levels and Akt phosphorylation were assessed 4 H after a two weekly of four weekly dose of PB4188. Phosphorylation levels in tumor lysates were assessed by Luminex assays. Analysis were performed in duplicate and five tumors were analyzed per group.
Figure 33:
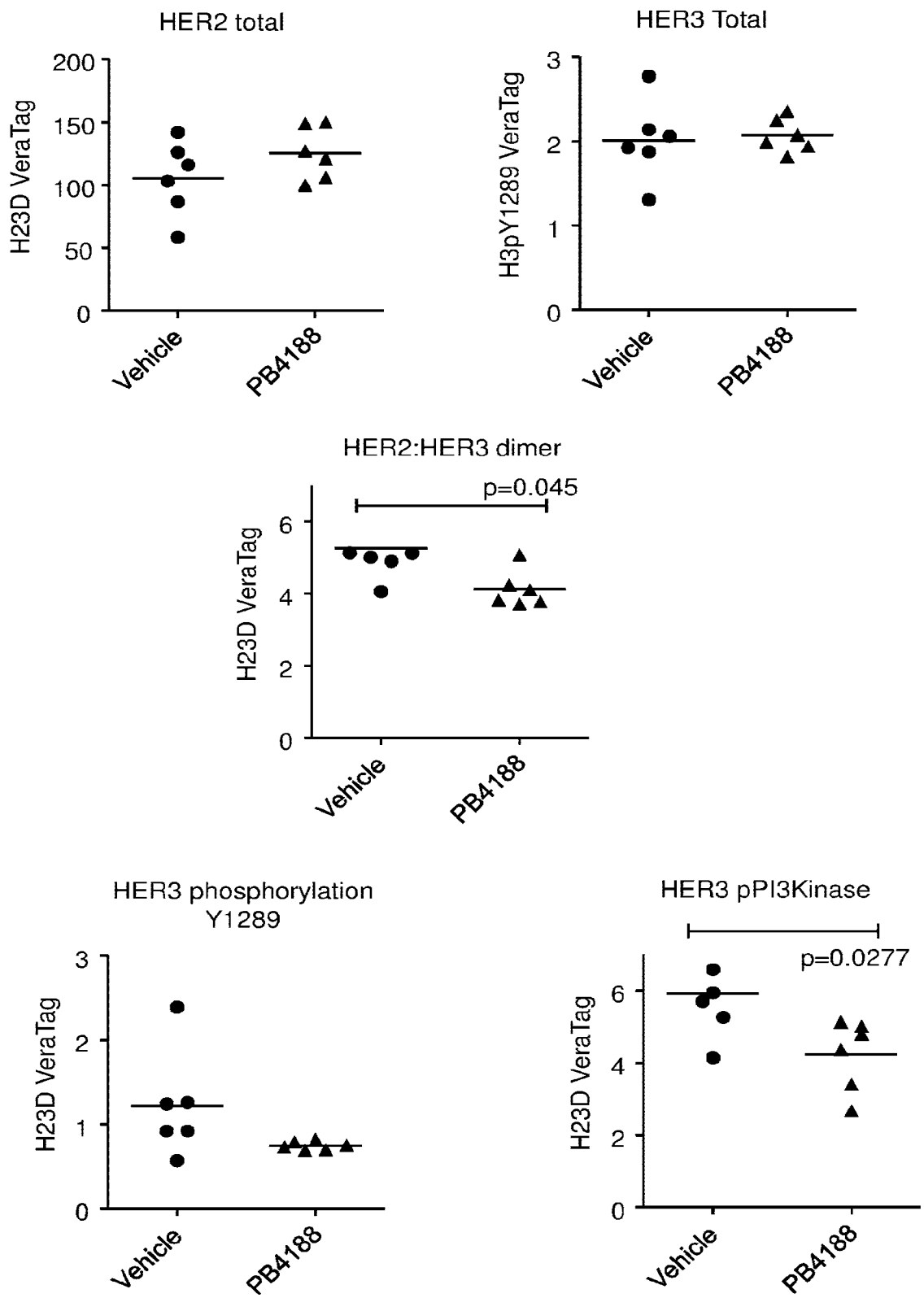
FIG. 33: In vivo mediated effect of PB4188 on HER2: HER3 mediated signaling as analyzed by Vera Tag analysis on JIMT-1 tumor material. Tumors were analyzed 4 H after dosing, tumors derived from PBS treated animals were included as controls.

Tumors treated with PB4188 showed an increase in Akt expression in comparison to untreated tumors. Phosphorylation of AKT was completely inhibited by PB4188 both after a two-weekly dose as after a four-weekly dose (FIG. 32).

Phosphoprotein Analysis by VeraTag Assay

Tumors (100 $mm^3$ or 400 $mm^3$) of JIMT-1 transplanted mice treated with 1 or 2 doses doses of PB4188 were removed and fixed in 10% neutral buffered formalin. Mice bearing 100 mm³ tumors were sacrificed 24H after a single PB4188 dose (25 mg/kg) whereas mice bearing 400 mm³ tumors received 2 weekly dosis of 25 mg/kg and were sacrificed 4H after dosing. Next, samples were paraffin-embedded. Sections of 7 um in thickness were sliced with a microtome (LEICA) and placed on positively charged glass slides (VWR) with serial number labeled. Slides were air-dried for 30 min and then baked in a heated oven set at 60° C. Next samples were processed for different VeraTag analysis. Total HER2 analysis (HT2) according to U.S. patent application Ser. No. 12/340,436, total HER3 analysis (H3T) according to U.S. Pat. No. 8,349,574; U.S. Patent Appl. No. 2013/0071859 and finally HHER2-HER3 heterodimer (H23D), HER3pY1289 (H3pY1289) and HER3-PI3 kinase (H3PI3K) according to Int'l Patent Appl. No. PCT/US2014/033208. In both dosing regimens a significant PB4188 mediated reduction in HER2:HER3 dimers became apparent in comparison to untreated controls. There was no difference observed in total HER2, HER3 or phosphorylated HER3 between PB4188 treated tumors and controls. Tumors that were analyzed 4H after PB34188 dosing showed a significant reduction in HER3-p85 (PI3K) compared with untreated controls.

PB4188 Reduces Cell Cycle Progression in HRG-Stimulated Cancer Cells

The ability of PB4188 to influence cell cycle progression was investigated in cancer cell lines expressing various protein levels of HER2. HER2+(MCF-7). HER2+++ (JIMT-1, SK-BR-3 and N87 cells) cells were seeded in assay medium (MCF-7 cells: RPMI-1640, 0.05% BSA, 10 µg/ml Holo-transferrin, 1 mM sodium pyruvate, MEM NEAA; JIMT-1: DMEM, 0.05% BSA, 10 µg/ml Holo-transferrin: SK-BR-3 cells: DMEM/F-12, 2 mM L-glutamine, 0.05% BSA, 10 µg/ml Holo-transferrin: N87 cells: RPMI-1640, 0.05% BSA, 10 µg/ml Holo-transferrin). Per well of 24-well plate, 300.000 MCF-7, or 400.000 N87 or 150.000 SK-BR-3 or 150.000 JIMT-1 or cells seeded in 1 ml assay medium and incubated overnight at 37° C. 5% CO2, in 95% relative humidity. The next day. PB4188 or pertuzumab+trastuzumab or P03178 or PG1337 were added to the cells in the presence of a final concentration of HRG of 1 or 100 ng/ml. After 24 hrs (for JIMT-1, N87 or SK-BR-3 cells) or 48 hrs (for MCF-7 cells) incubation at 37° C. 5% CO2, in 95% relative humidity, cells were supplemented with EdU (10 µM final concentration) for 2 hrs before being harvested and stained for EdU incorporation using the Chick-iT EdU AlexaFluor488 kit according to the manufacturer instructions (LifeTechnologies, cat. no. C10425). At least 30 min before analyzing the cells by flow cytometry on FACSCanto, cells were incubated with 200 nM FxCycle far red dye (LifeTechnologies, cat. no. F10348) and 100 µg/ml RNAse A (LifeTechnologies, cat. no. 12091-039). Events were acquired in the AlexFluor488 channel (for EdU detection) and in the APC channel (for total DNA stain with the FxCycle dye). Data were analyzed by gating single cells on a FSC-width vs FSC-height scatter plot, and subgating the G0/01. S and (2M phases of the cell cycle on an APC vs AlexaFluor488 scatter plot, as $EdU^{neg}APC^{low}$, $EdU^{pos}$ and $EdU^{neg}APC^{high}$ populations, respectively.

Figure 34A:
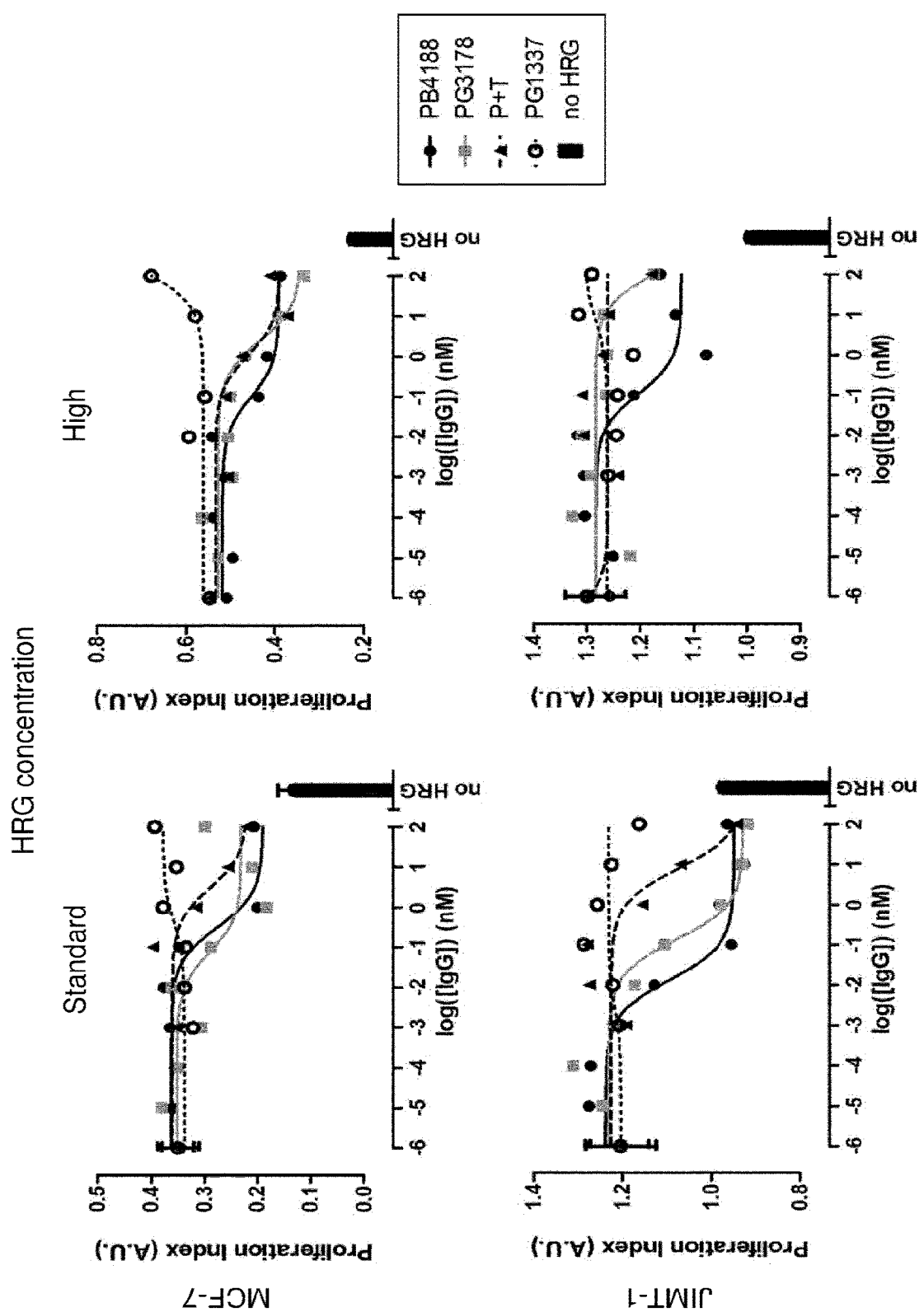
FIGS. 34A and 34B: PB4188 reduces cell cycle progression. Cell seeded in assay medium were incubated with titration of antibodies in the presence of a standard (1 ng/ml) or high (100 ng/ml) concentration of HRG, 24 hrs later (or 48 hrs for MCF-7 cells), cells were analyzed for their distribution in the different phases of the cell cycle (G0/G1, S or G2/M phases). Proliferation index was calculated as the ratio between the percentage of cells in the S and G2/M phases and the percentage of cells in the G0/G1 phase, P+T, pertuzumab+trastruzumab.
Figure 34B:
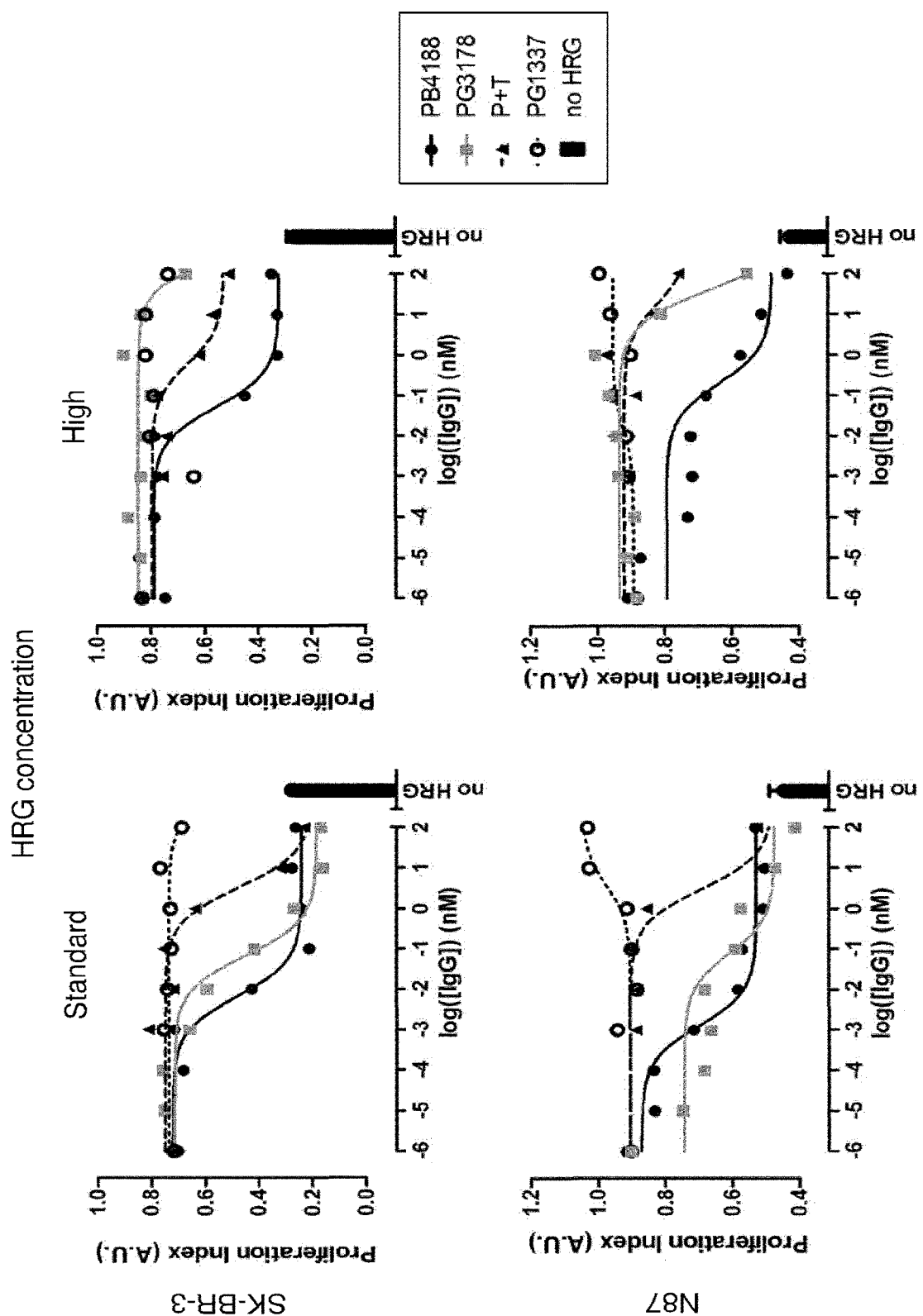
Figure 35A:
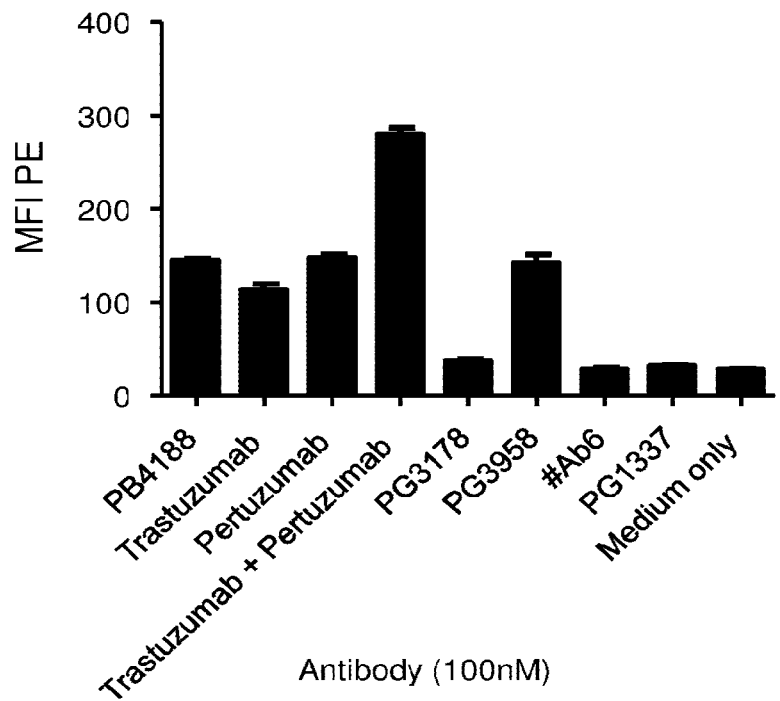
FIG. 35A-35D: Internalization of antibodies labelled with pH-sensitive dye in HER2-overexpressing cancer cells, N87 (35A, 35B) and SKBR-3 (35C, 35D) seeded in assay medium supplemented with I ng/ml HRG were incubated for 24 hrs with 100 nM pH-sensitive dye-labelled antibodies. After harvesting, cells were stained with APC-labelled anti-human IgG secondary antibody to detect cell surface-bound antibodies. Cells were analyzed by FACS for fluorescence in the PE (35A, 35C) to determine internalization and APC (35B, 35D) channels to determine surface binding of the antibodies.
Figure 35B:
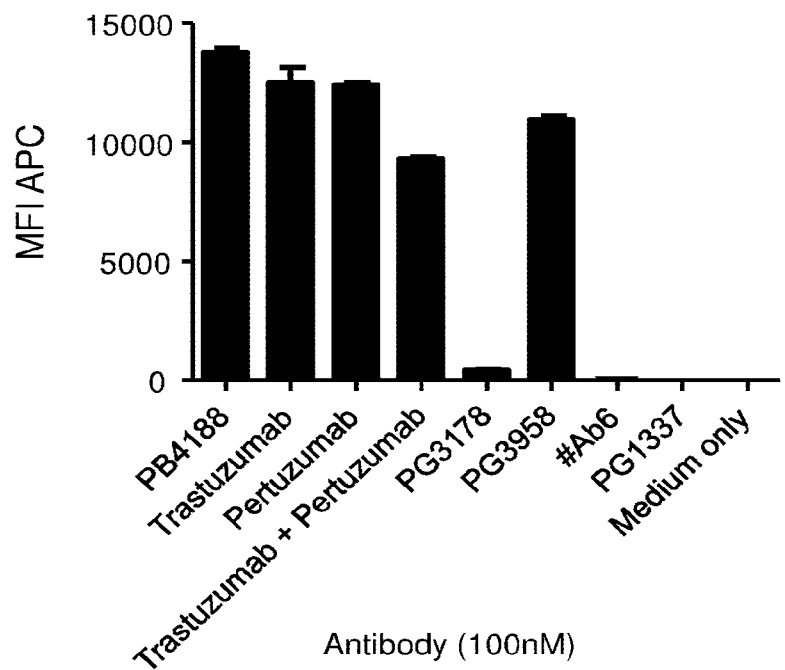
Figure 35C:
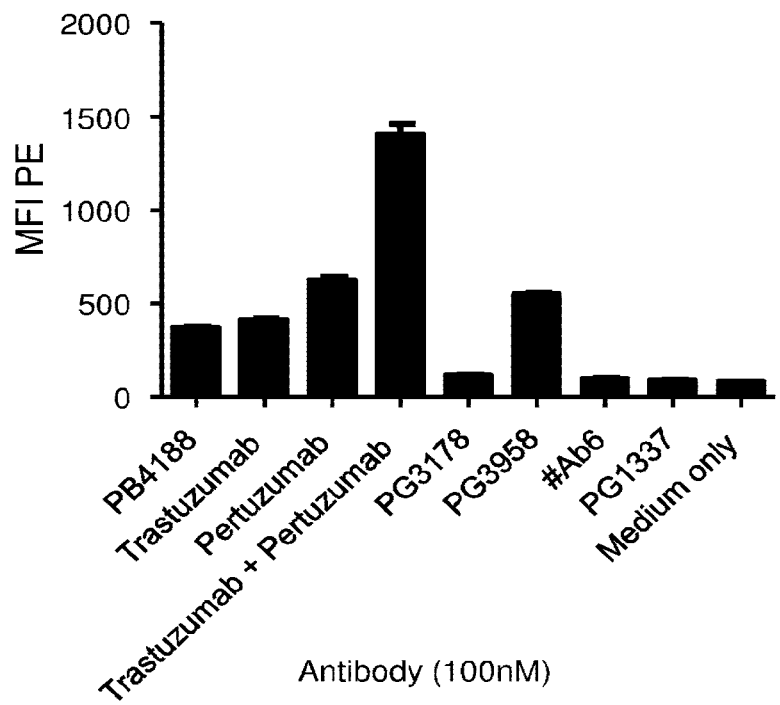
Figure 35D:
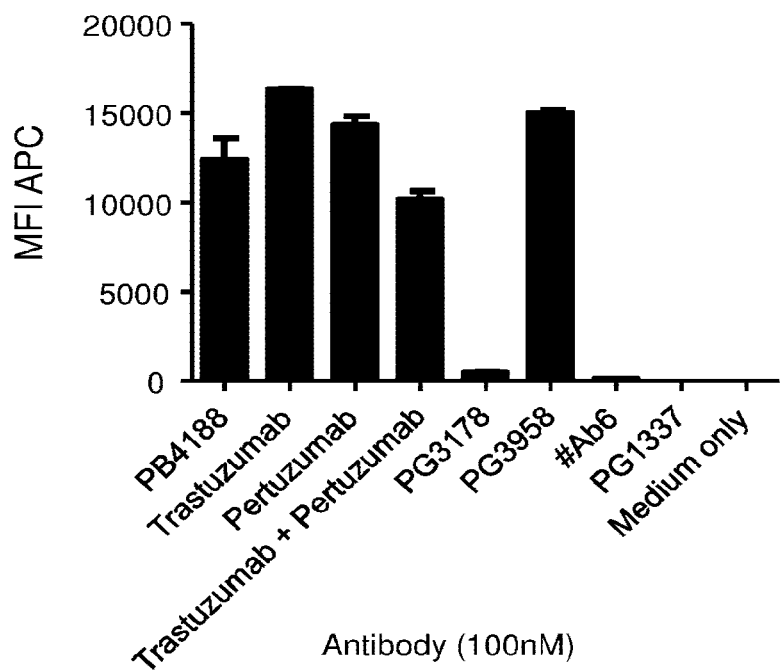

Data are represented as the proliferation index calculated by dividing the percentage of cells in the S and G2/M phases by the percentage of cells in the G0/G1 phase. FIG. 34 shows that PB4188 is consistently more potent than PG3178 or pertuzumab+trastuzumab in inhibiting proliferation induced by a standard (1 ng/ml) or a high (100 ng/ml) concentration of HRG. At high concentrations of HRG PB4188 still inhibits the cell cycle progression.

PB4188 Induces Receptor Internalization

Figure 36:
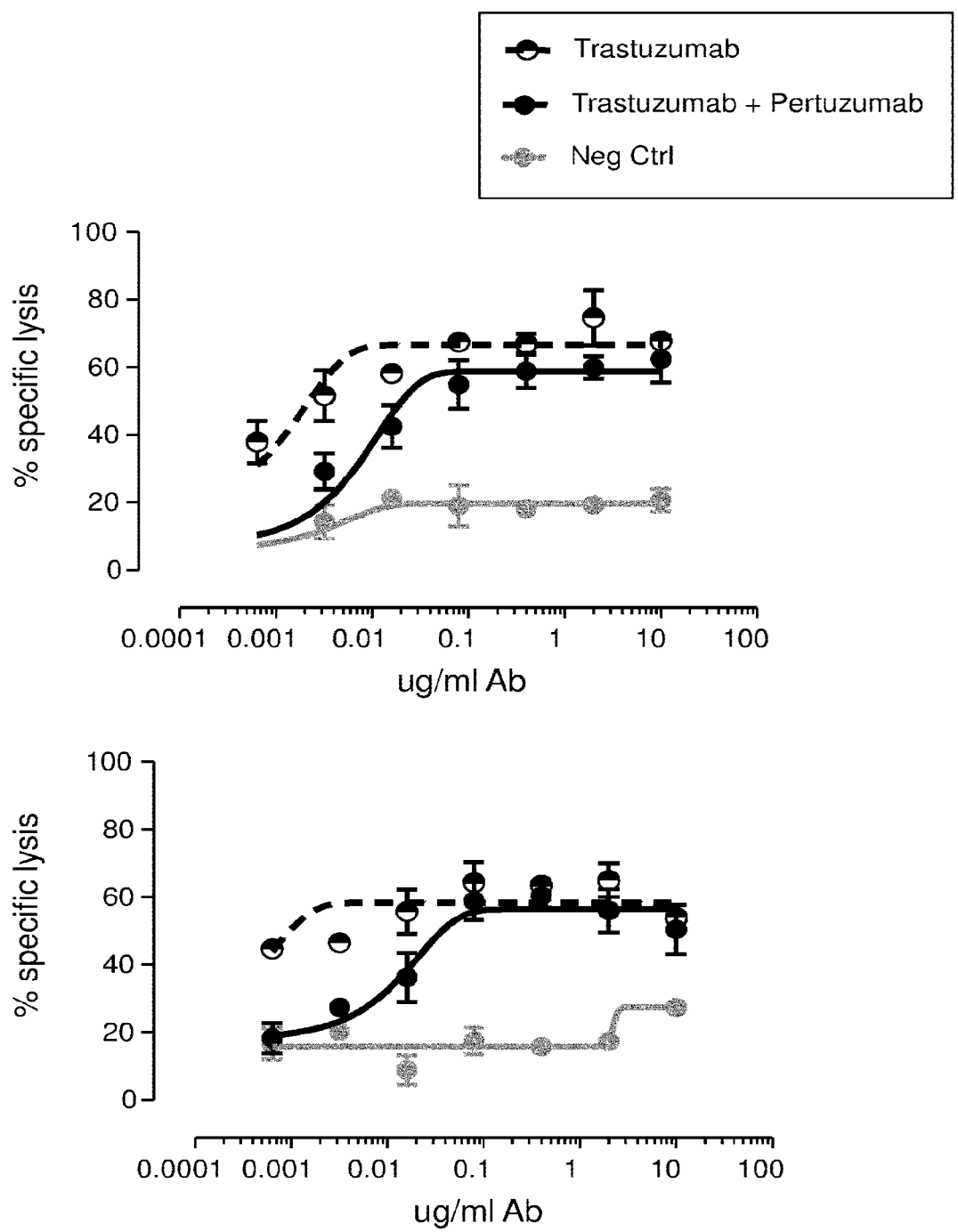
FIG. 36: ADCC activity of Trastuzumab versus Trastuzumab+Pertuzumab with cells derived from two different donors.

Internalization pattern of antibodies was measured using pH-sensitive dyes. This has been described in the art in WO2013134686 A1 where such dyes, when coupled to an antibody, display an increased fluorescence signal when exposed to lower pH. This occurs when the dye-coupled antibodies internalize from the surface of target cells into mildly acidic endosomes (pH 6-6.5) to acidic lysosomes (pH lower than 5.5). To investigate whether PB4188 internalizes in cancer cells, the antibody was coupled to the pH sensor dye with succinimidyl ester reactive group (Promega, cat. no. CS1783A01) according to the manufacturer's instructions. As comparators, anti-HER2 (trastuzumab, pertuzumab, PG3958), anti-HER3 (PG3178, #Ab6) and negative control (anti-tetanus toxin, PG1337) dye labeled antibodies were included. HER2-overexpressing SKBR-3 and N87 cancer cells of an exponentially grown culture were harvested and seeded on 96 well plates (15×10³ cells per well) in 100 µl assay medium (N87 cells: RPMI-1640, 0.05% BSA, 10 µg/ml Holo-transferrin: SKBR-3 cells: DMEM/F-12, 2 mM L-glutamine, 0.05% BSA, 10 µg/ml Holo-transferrin) containing 1 ng/ml HRG and incubated overnight at 37° C., 5% CO2, in 95% relative humidity. The next day, 20 µl pH-sensitive dye-labelled antibodies were added to reach a final concentration of 100 nM and cells were incubated overnight at 37° C., 5% CO2, in 95% relative humidity. The next day, cells were harvested by collecting non-adherent cells and trypsinizing adherent cells. After washing cells with FACS buffer (PBS 0.5% BSA 0.1% sodium azide), cells were stained with APC-labelled anti-human IgG (Jackson Immunoresearch, cat. no. 109-136-098, 1:100 dilution). Cells were analyzed by flow cytometry on FACSCanto (BD Biosciences) measuring median fluorescence intensities (MFI) of the PE and APC channels to determine internalization and residual surface binding of antibodies, respectively. Data shown in FIG. 35 show that PB4188 internalizes to the same extend as trastuzumab whereas the combination trastuzumab+pertuzumab leads to enhanced internalization. The combination of trastuzumab+pertuzumab reduces the ADCC in comparison to trastuzumab alone (FIG. 36). It is therefore anticipated that the level of PB4188 internalization leaves the ADCC potency unaffected.

Generation and Characterization of Anti-HER3 Antibody 3178 Variants

Figure 38:
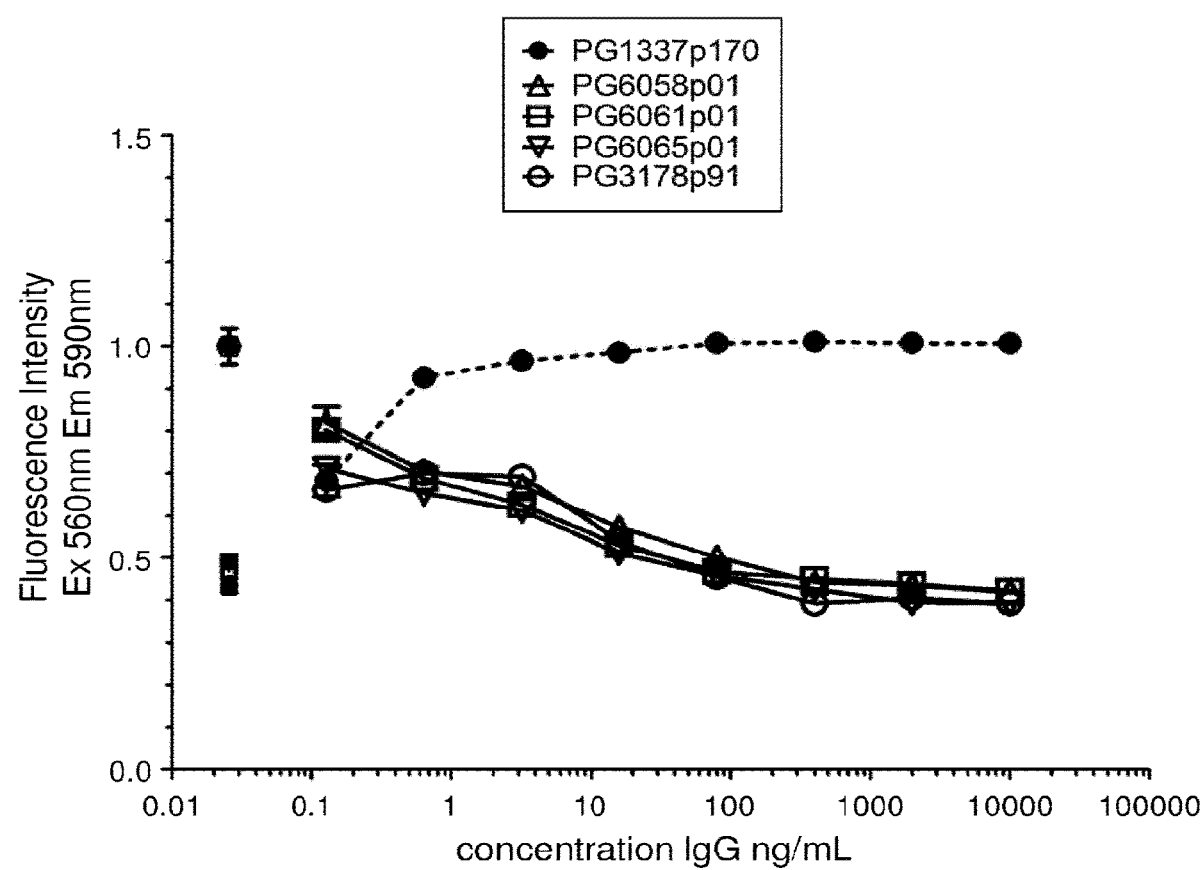
FIG. 38: Titration curves of HER3 monoclonal antibodies in the HRG dependent N87 assay, P06058, PG6061 and P06065 are variants of PG3178, PG1337 is a negative control specific for tetanus toxoid. Data were normalized to basal proliferation with ligand present on each plate.
Figure 39A:
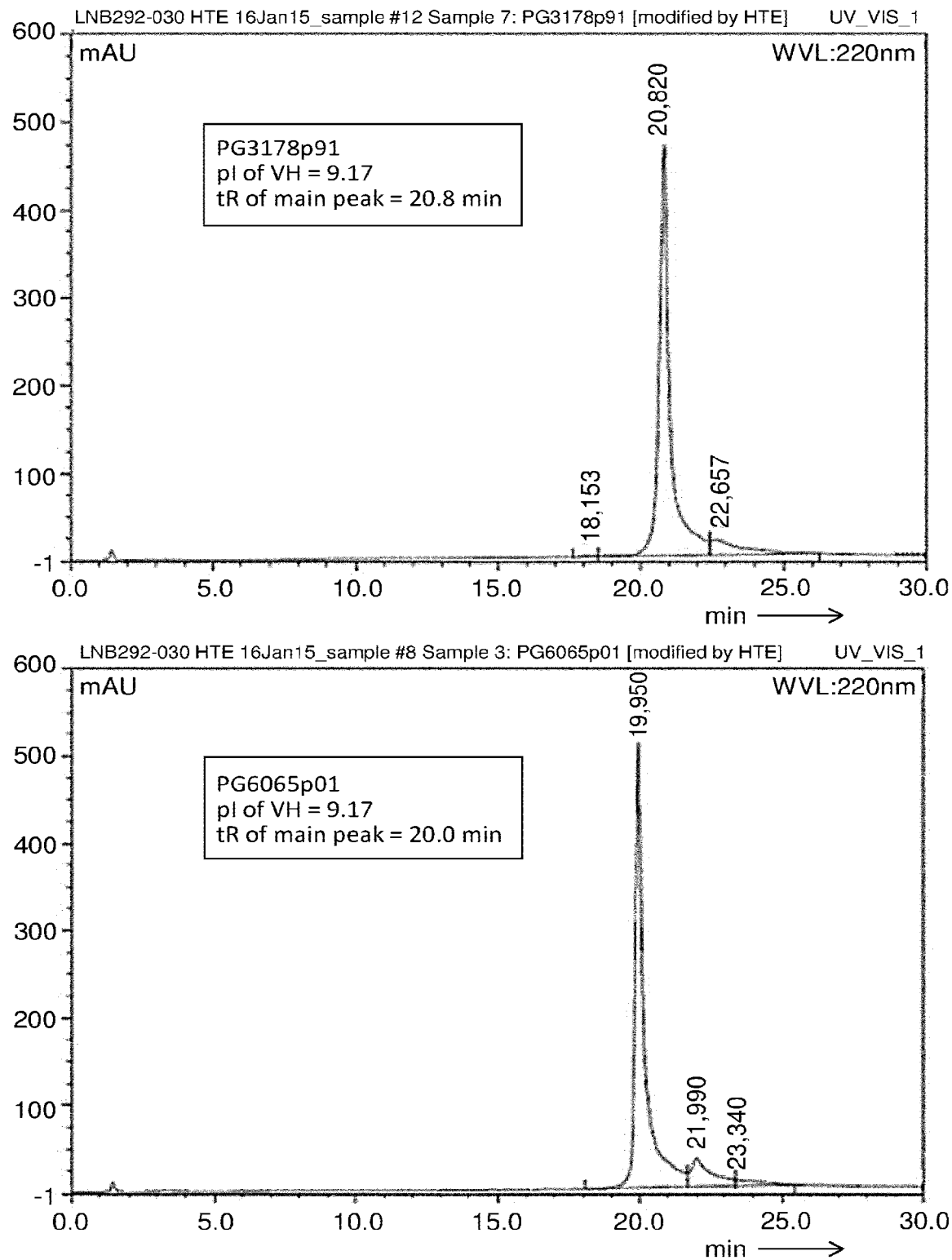
FIGS. 39A and 39B: CTEX-HPLC profiles of HER3 monoclonal antibodies. PG6058, PG6061 and PG6065 are variants of P03178. The calculated iso-electric point (pI) of the VH region and the retention time (t R) of the main peak are given for each antibody.
Figure 39B:
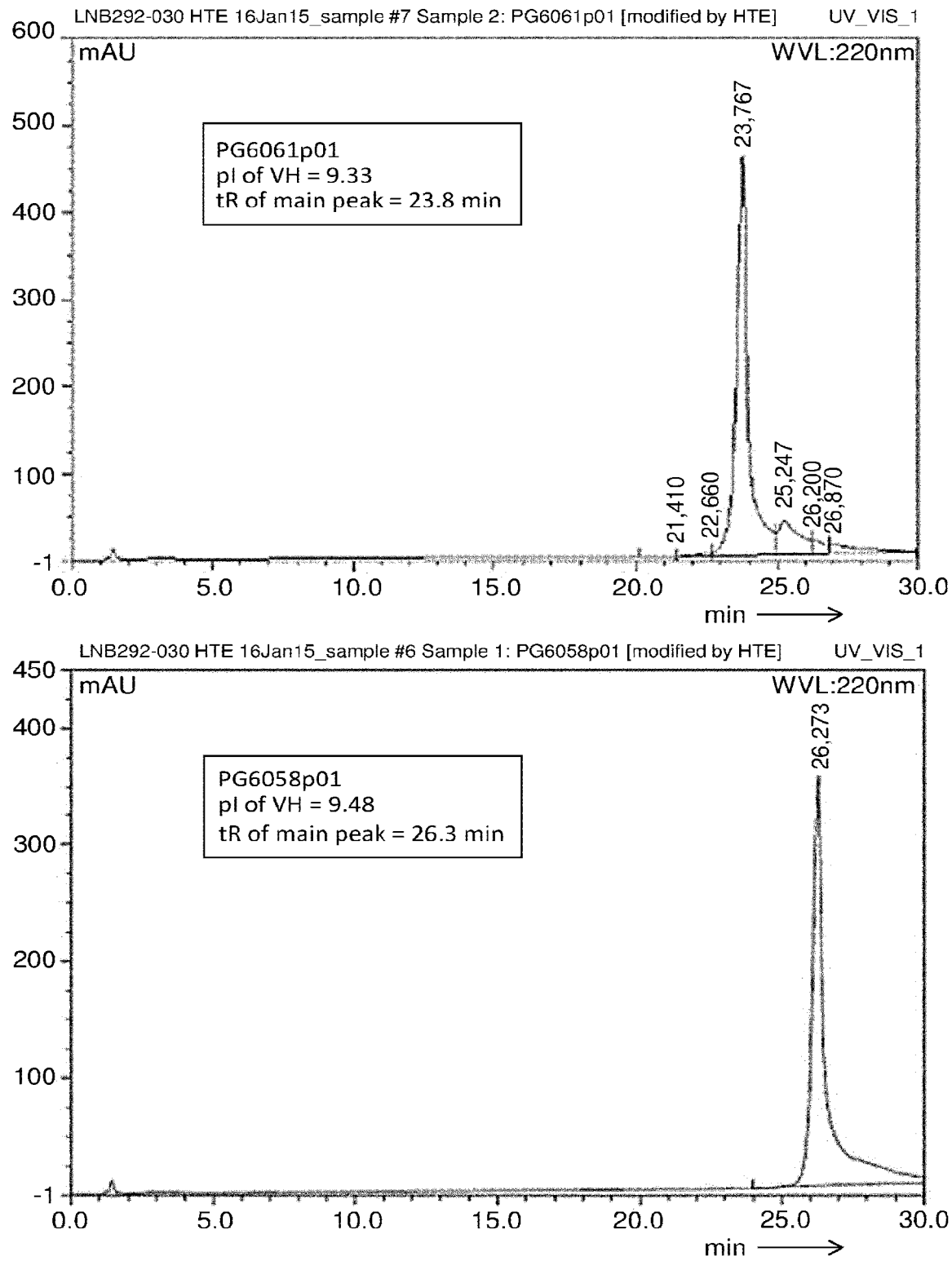
Figure 40A:
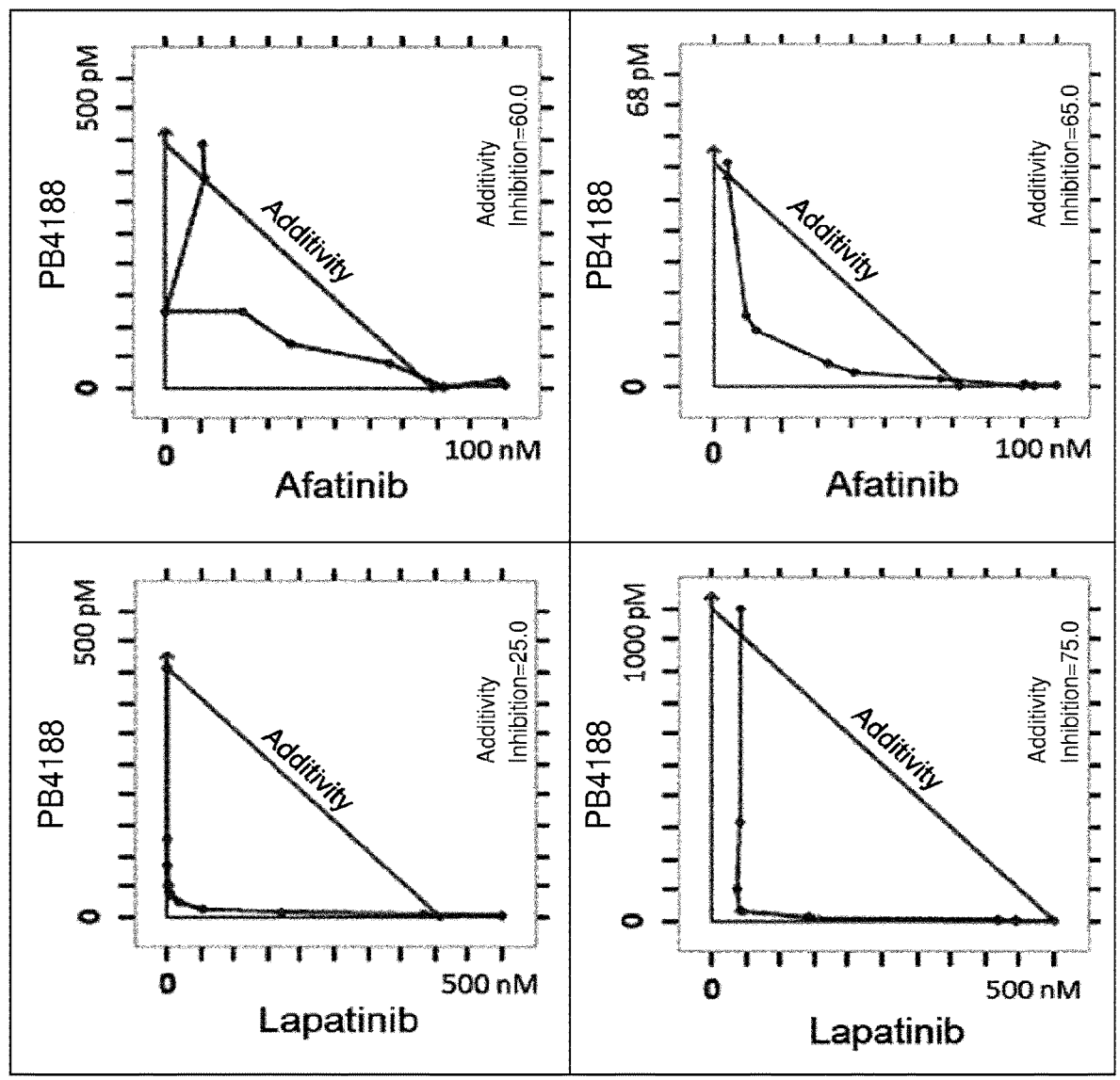
FIGS. 40A and 40B: In vitro drug combination isobolograms with PB4188 on HER2 amplified cell lines at HRG stress concentrations (40A) or grown in MATRIGEL® (40B).
Figure 40A:
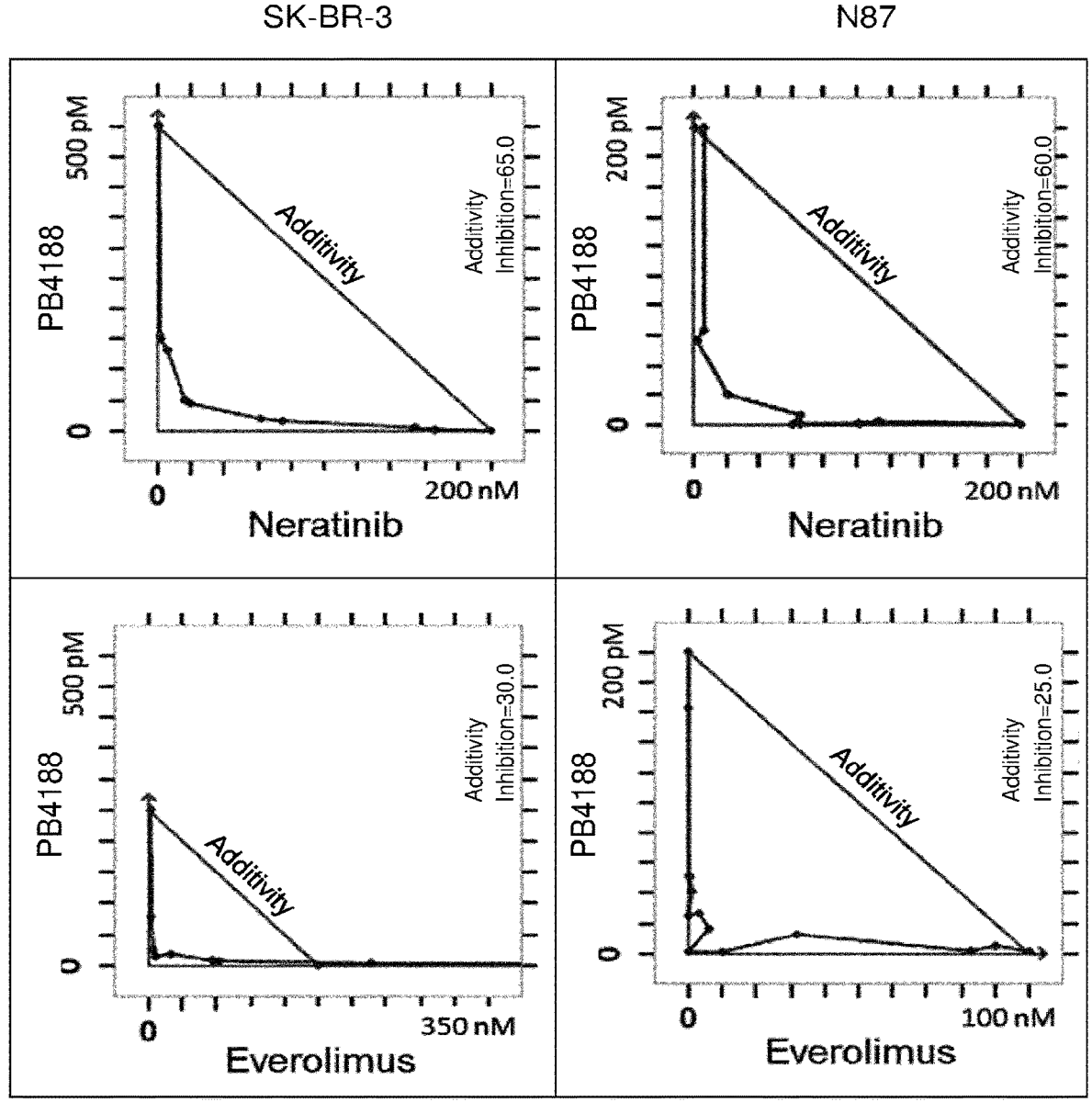
Figure 40A:
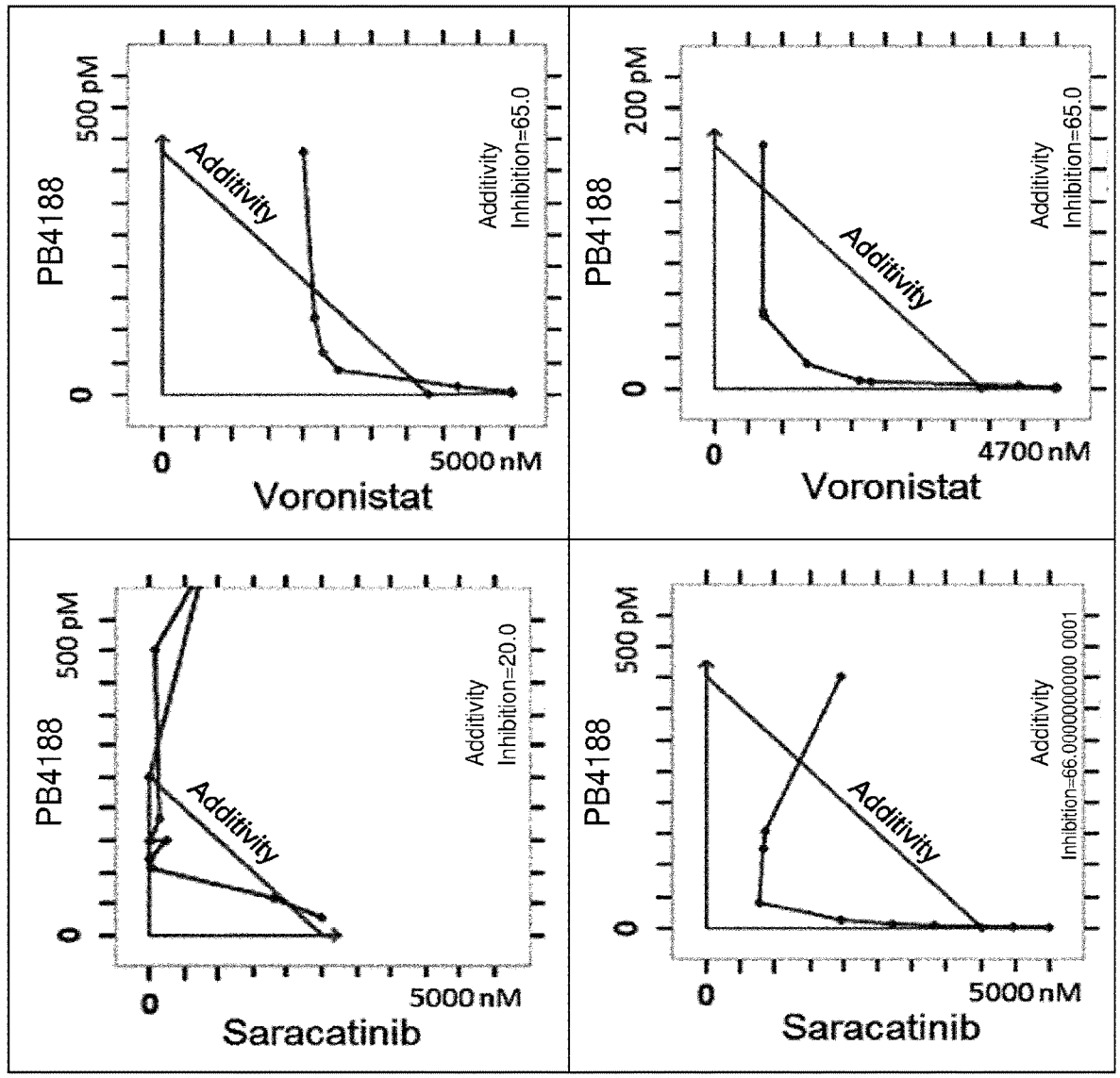
Figure 40A:
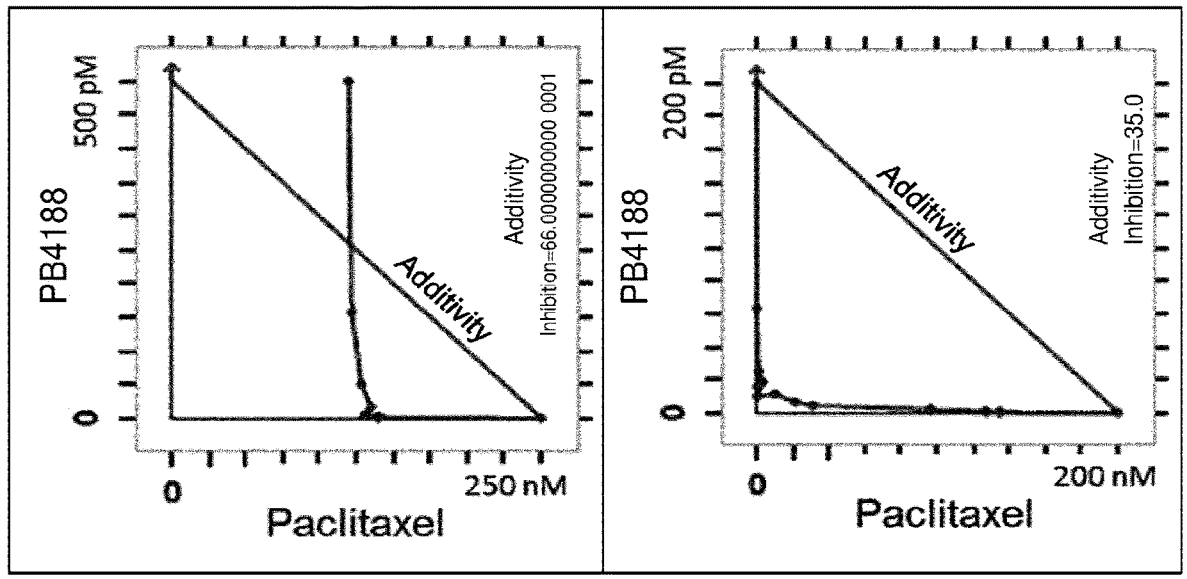
Figure 40B:
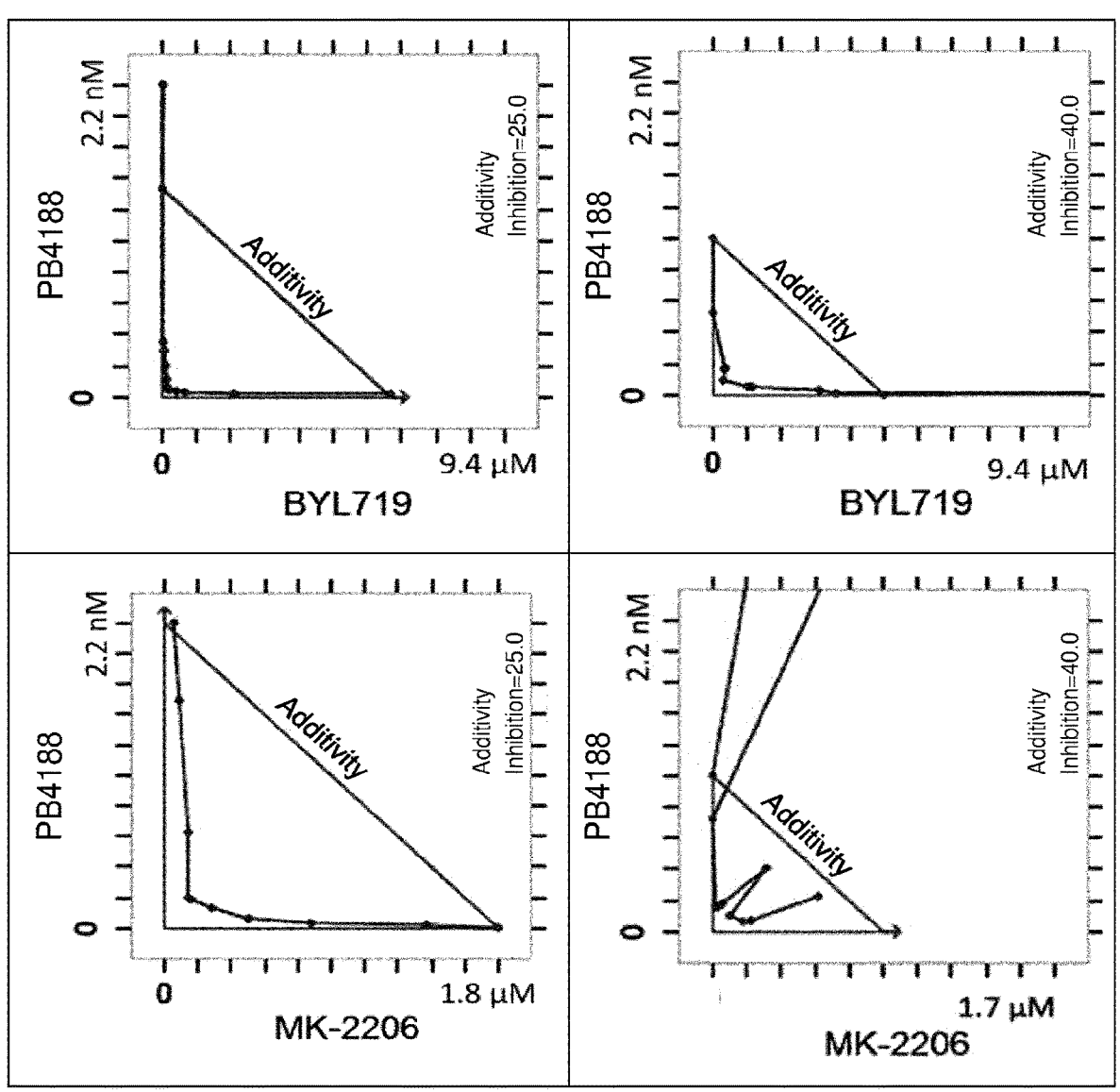

Variants of anti-HER3 antibody MF3178 were designed with the aim to improve antibody properties. Mutations were introduced in the VH gene framework region 1 (FR1), complementarity determining region 1 (CDR1), FR2. CDR2 and/or FR3, while CDR3 and FR4 were not modified. The design included, but was not limited to, mutations that were introduced to remove post-translational modification (PTM) motifs (e.g. by changing the deamidation motif NS to NQ), to reduce surface hydrophobicity (e.g. by changing I to T) or to increase the iso-electric point (pI; e.g. by changing Q to K). All 20 variants (See FIG. 37) were expressed as bispecific antibody combined with a Tetanus Toxoid (TT) arm and tested in the MCF-7 functional assay and all 20 variants had a similar potency as the MF3178 antibody in this format. All 20 variants were also tested in this format in FACS in a titration for binding to MCF-7 and all variants had very similar binding profiles suggesting that the affinities of all variants are similar. Three lead variants MF6058, MF6061 and MF6065 were selected for further experiments that contain ten, three and seven amino acid mutations, respectively (see sequences in FIG. 16E and FIG. 37). The corresponding monospecific IgG1 PG6058, PG6061 and PC6065 were produced and purified at large scale. As shown in FIG. 38, the inhibitory activity of the three variants in the HRG-dependent N87 cell line proliferation assay is similar to that of PG3178. The CIEX-HPLC profile of the three variants was similar to that of PG3178 with respect to charge heterogeneity as well as peak width and symmetry, as shown in FIG. 39. The retention time (tR) of the main peak correlated roughly with the pI of the antibodies, i.e. higher pI resulted in longer retention time. In the design of bispecific antibodies or mixtures of antibodies, selecting antibody variants with optimal tR is valuable since purification of the desired antibody components using CIEX can be facilitated.

Serum titers of the differenc cohorts of immunized mice as determined by FACS. D=day of antibody titer determination. Table 1: response against HER2. Table 2: response against HER3. Cell lines used are indicated (MCF7, SKBR3, BT474). The different mice are in the columns

TABLE 1 anti-HER2 response

| ErbB2 | K562 | | | | | | MCF7 | | | | | |
|---|---|---|---|---|---|---|---|---|---|---|---|---|
| A,D35 | 236 | 168 | 315 | 148 | 116 | 145 | 5909 | 5728 | 6147 | 5491 | 4838 | 4930 |
| C,D42 | 163 | 144 | 154 | 152 | 166 | | 2574 | 3212 | 2140 | 2346 | 2172 | |
| E,D35 | 129 | 134 | 152 | 132 | 147 | 157 | 6214 | 5542 | 5625 | 5634 | 1812 | 3905 |
| G,U52 | 145 | 129 | 126 | 133 | 163 | | 5752 | 5088 | 4268 | 4899 | 5240 | |
| Average | 130,8 | | | | | | Average | 194,4 | | | | |
| D0 | | | | | | | D0 | | | | | |
| 5x | 654 | | | | | | 5x | 972,2 | | | | |
| 10x | 1308 | | | | | | 10x | 1944 | | | | |
| 20x | 2616 | | | | | | 20x | 3889 | | | | |
| 30x | 3924 | | | | | | 30x | 5833 | | | | |

| ErbB2 | SKBR3 | | | | | | BT474 | | | | | |
|---|---|---|---|---|---|---|---|---|---|---|---|---|
| A,D35 | 67748 | 29537 | 45315 | 44737 | 33508 | 38355 | 38707 | 18928 | 27240 | 24784 | 17659 | 18713 |
| C,D42 | 15448 | 17188 | 12627 | 12432 | 12067 | | 10259 | 9669 | 7789 | 6618 | 6030 | |
| E,D35 | 27730 | 19765 | 26863 | 26232 | 19478 | 13968 | 22716 | 17413 | 19139 | 18317 | 16397 | 12787 |
| G,U52 | 22769 | 26157 | 16726 | 14633 | 15783 | | 19413 | 16640 | 16424 | 16959 | 18633 | |
| Average | 300,2 | | | | | | Average | 241 | | | | |
| D0 | | | | | | | D0 | | | | | |
| 5x | 1501 | | | | | | 5x | 1205 | | | | |
| 10x | 3002 | | | | | | 10x | 2410 | | | | |
| 20x | 6004 | | | | | | 20x | 4819 | | | | |
| 30x | 9005 | | | | | | 30x | 7229 | | | | |

TABLE 2 anti-HER3 response

| ErbB3 | K562 | | | | | | MCF7 | | | | | |
|---|---|---|---|---|---|---|---|---|---|---|---|---|
| B,D56 | 332 | 356 | 453 | 535 | 417 | 645 | 1630 | 1236 | 3251 | 1401 | 1297 | 1814 |
| D,D56 | 336 | 445 | 277 | 185 | 319 | | 1159 | 3260 | 959 | 643 | 2362 | |
| F,D35 | 265 | 245 | 249 | 285 | 291 | 262 | 4370 | 3985 | 3445 | 3428 | 3579 | 2718 |
| H,D52 | 263 | 289 | 233 | 271 | 242 | | 4083 | 4239 | 2970 | 4167 | 4584 | |
| Average | 130 | | | | | | Average | 172 | | | | |
| D0 | | | | | | | D0 | | | | | |
| 5x | 326 | | | | | | 5x | 430 | | | | |
| 10x | 651 | | | | | | 10x | 859 | | | | |
| 20x | 1303 | | | | | | 20x | 1718 | | | | |
| 30x | 2605 | | | | | | 30x | 3437 | | | | |

| ErbB3 | SKBR3 | | | | | | BT474 | | | | | |
|---|---|---|---|---|---|---|---|---|---|---|---|---|
| B,D56 | 1666 | 1100 | 3072 | 1199 | 1268 | 1503 | 1675 | 1204 | 3393 | 1380 | 1295 | 1725 |
| D,D56 | 964 | 2180 | 721 | 510 | 1577 | | 1030 | 3754 | 945 | 584 | 2042 | |
| F,D35 | 4139 | 3378 | 2676 | 2659 | 2674 | 2414 | 4618 | 3690 | 3522 | 3144 | 3208 | 2776 |
| H,D52 | 5183 | 4319 | 3256 | 5408 | 5474 | | 6326 | 4920 | 4542 | 6653 | 6938 | |
| Average | 200 | | | | | | Average | 222 | | | | |
| D0 | | | | | | | D0 | | | | | |
| 5x | 501 | | | | | | 5x | 556 | | | | |
| 10x | 1002 | | | | | | 10x | 1112 | | | | |
| 20x | 2004 | | | | | | 20x | 2223 | | | | |
| 30x | 4008 | | | | | | 30x | 4446 | | | | |

TABLE 3

Binning of HER2 antibodies depending on their reactivity with chicken-human-HER2 chimera's and reactivity to mouse HER2. 'Number' indicates the number of unique antibodies in each group

| Group | Domain reactivity | Number |
|---|---|---|
| 1 | Domain I specific | 25 |
| 2 | Domain II specific | 2 |
| 3 | Domain III specific | 23 |
| 4 | Domain IV specific | 7 |
| 5 | Domain IV specific + murine cross-reactive | 2 |
| 6 | Reactive to all constructs | 2 |
| 7 | Human WT reactive only | 4 |

TABLE 4

Competition ELISA using IgGs and phage antibodies. Four IgG antibodies are used in the competition assay: two HER2 antibodies recognizing domain IV (trastuzumab and PG1849); one antibody recognizing domain II (PG2971) and one negative control anti-RSV antibody. Loss of signal is observed when the phage and antibody encoded by the same variable region genes are competing; i.e. MF1849 and PG1849 and MF2971 and PG2971.

|  | — | MF1849 | MF2971 | MF2708 |
|---|---|---|---|---|
| Trastuzumab | 0.046 | 1.02 | 1.115 | 0.044 |
| PG1849 | 0.043 | 0.384 | 1.139 | 0.041 |
| PG2971 | 0.042 | 1.202 | 0.091 | 0.042 |
| Anti-RSV mAb | 0.044 | 0.94 | 1.003 | 0.047 |
| — | 0.045 | 1.432 | 1.481 | 0.038 |

TABLE 5

Binning of HER3 antibodies depending on their reactivity with rat-human-HER2 chimera's and reactivity to HER3 and HER3 of other species. 'Number' indicates the number of unique antibodies in each group

| Group | Reactivity | Number |
|---|---|---|
| 1 | High Domain III reactivity, rat and mouse reactive and minor reactivity to domain IV | 8 |
| 2 | High Domain III reactivity, rat, human and cyno reactive, minor reactivity to domain IV | 8 |
| 3 | Reactivity to rat, cyno and human HER3 | 43 |
| 4 | Reactive to human HER3 | 32 |
| 5 | Reactive to all constructs | 33 |

TABLE 6

Functional activity of the most potent HER2 monoclonals at 1 μg/ml IgG. Percentage activity compared to reference antibodies, i.e. trastuzumab in SKBR-3 and #Ab6 in MCF-7. For HER2 antibodies the domains of all antibodies except PG2926 were mapped to domains I, III or IV

| PG ID nr | Target | Epitope Bin | HER2 domain | SKBR-3 | MCF-7 |
|---|---|---|---|---|---|
| PG2916 | HER2 | 1 | I | 58% | 30% |
| PG2973 | HER2 | 1 | I | 49% | 58% |
| PG3004 | HER2 | 1 | I | 49% | 56% |
| PG1849 | HER2 | 5 | IV | 42% | 22% |
| PG3025 | HER2 | 1 | I | 38% | 28% |
| PG2971 | HER2 | 1 | I | 25% | 51% |
| PG3031 | HER2 | 1 | I | 33% | 38% |
| PG2926 | HER2 | 7 | NA | 0% | 35% |
| PG2930 | HER2 | 3 | III | 0% | 7% |

TABLE 7

Functional activity of the most potent HER3 monoclonals at 1 μg/ml IgG in a HRG dependent MCF-7 assay. Percentage activity compared to reference antibody #Ab6.

| PG ID nr | Target | Epitope group | MCF-7 |
|---|---|---|---|
| PG3178 | HER3 | 5 | 162% |
| PG3163 | HER3 | 5 | 119% |
| PG3176 | HER3 | 5 | 68% |
| PG3099 | HER3 | 3 | ND |

TABLE 8

FACS stainings of HER2 antibodies whereby the HER2 VH is combined with a different light chain than the common light chain indicated in FIG. 16. MFI, indicates Mean Fluorescence Intensity in FACS. The HER2 MF number is indicated in between brackets, HER2 binding clones in the context of the different light chain are indicated in bold.

| PGnumber | MFI K562 cells (neg control) | MFI K562 HER2 |
|---|---|---|
| PG4462 (MF2971) | 267 | 14900 |
| PG4463 (MF3958) | 248 | 15600 |
| PG4474 (MF2916) | 254 | 14700 |
| PG4478 (MF2973) | 254 | 18000 |
| PG4481 (MF3004) | 267 | 16200 |
| PG4482 (MF3025) | 299 | 12000 |
| PG4483 (MF3031) | 260 | 14900 |
| PG4465 (MF1849) | 270 | 249 |
| Anti-HER2 mAb | 309 | 7618 |
| Anti-RSV mAb | 263 | 276 |

TABLE 9

Functional activity of lead HER2 x HER3 bispecific antibodies (indicated using the PB prefix; each PB comprises an HER2 arm and an HER3 arm as indicated in the table) compared to comparator antibodies in the HRG dependent MCF-7 and BxPC3 assays. Based on binding profiles using chimeric constructs HER2 and HER3 antibodies could be separated over different bins. For HER2 antibodies the domains all antibodies except PG2926 could be mapped to domains I, III or IV.

| Name | Her2 arm | Her2 domain | Her3 arm | Her3 bin | MCF-7 IC50 (pM) | BxPC3 % Inhibition |
|---|---|---|---|---|---|---|
| PB3441 | 2926 | NA | 3178 | 5 | 51.7 | −24% |
| PB3443 | 2930 | III | 3178 | 5 | 136 | −31% |
| PB3448 | 1849 | IV | 3178 | 5 | 371 | −22% |
| PB3565 | 2973 | I | 3178 | 5 | 30.9 | −19% |
| PB3566 | 3004 | I | 3178 | 5 | 7.9 | −20% |
| PB3567 | 2971 | I | 3178 | 5 | 46.5 | −17% |
| PB3709 | 3025 | I | 3178 | 5 | 34.5 | −19% |
| PB3710 | 2916 | I | 3178 | 5 | 74.2 | −19% |
| PB3883 | 2971 | I | 3176 | 5 | 113 | −19% |
| PB3986 | 3025 | I | 3163 | 5 | 30.7 | −21% |
| PB3990 | 2971 | I | 3163 | 5 | 13 | −18% |
| PB4011 | 2971 | I | 3099 | 3 | 40.2 | ND |
| PB3437 | 3031 | I | 3178 | 5 | 14 | −10% |
| PG3178 | NA | NA | 3178 | 5 | 139 | −17% |
| #Ab6 |  |  |  |  | 504 | −7% |
| trastuz. + pertuz. |  |  |  |  | 352 | ND |
| trastuzumab |  |  |  |  | 500 | −3% |

TABLE 10

Monovalent binding affinities of PB4188 and PB3448 for HER2 and HER3 as measured in BIACORE ™. Both bispecific antibodies share the same HER3 arm. ND, not done.

| PB | KD on Her2 (nM) | KD on Her3 (nM) |
|---|---|---|
| PB3448 | 5.4* | ND |
| PB4188 | 0.16* | 3.9 |

TABLE 11

JIMT-1 xenograft study treatment groups

| Gr. | N | Agent | Vehicle | mg/kg | Route | Schedule |
|---|---|---|---|---|---|---|
| 1# | 10 | PBS | X | — | ip | qwk x 4 (start on day 1) |
| 2 | 10 | lapatinib | — | 150 | po | qd x 28 (start on day 1) |
| 3 | 10 | PB4188 | — | 2.5 | ip | qwk x 4 (start on day 1) |
| 4 | 10 | PB4188 | — | 25 | ip | qwk x 4 (start on day 1) |
| 5 | 10 | Pertuzumab + Trastuzumab | — | 2.5 | ip | qwk x 4 (start on day 1) |
| 6 | 10 | Pertuzumab + Trastuzumab | — | 25 | ip | qwk x 4 (start on day 1) |

TABLE 12

Affinities of $^{125}$I-labeled IgG HER2xHER3 IgG (PB4188), HER3xTT (PB9215), HER2xTT (PB9216) and HERCEPTIN ® (monospecific for HER2), as determined using steady state cell affinity measurements with BT-474 cells and SK-BR-3 cells. Data were obtained from three independent experiments.

| | BT-474 | SK-BR-3 |
|---|---|---|
| HERCEPTIN ® | 3.7 ± 0.5 nM | 1.3 ± 0.1 nM |
| PB4188 | 3.2 ± 0.5 nM | 2.0 ± 0.4 nM |
| HER2xTT | 3.9 ± 0.6 nM | 2.3 ± 0.7 nM |
| HER3xTT | 0.23 ± 0.08 nM | 0.99 ± 0.4 nM |

TABLE 13

The mean binding protein reactivities (and ranges) listed for all critical residues identified. Critical residues involved in PG3958Fab binding were identified as those mutated in clones that were negative for PG3958Fab binding (<35% WT) but positive for the control mAb 1129 binding (>80% WT). Two additional critical residues were identified which did not meet the threshold guidelines, but whose mutation reduced antibody binding by a lesser extent. Residue numbering is that of PDB ID #1S78.

| HER2 Residue | Mutation | PG3958 Fab binding % of wt binding (range) | Control mAb binding % of wt binding (range) | Designation |
|---|---|---|---|---|
| 144 | T144A | 31.9 (11) | 82.1 (13) | Critical |
| 166 | R166A | 32.2 (5) | 93.7 (17) | Critical |
| 181 | R181A | 10.1 (5) | 98.6 (34) | Critical |
| 172 | P172A | 52.5 (2) | 94.9 (24) | Secondary |
| 179 | G179A | 41.7 (18) | 87.9 (25) | Secondary |

TABLE 14

The mean binding protein reactivities (and ranges) are listed for both critical residues. Critical residues involved in PG3178 binding were identified as those mutated in clones that were negative for PG317 mAb binding (<20% WT) but positive for the control mAb 66223 binding (>70% WT). Residue numbering is that of PDB ID #4P59.

| HER3 Residue | Mutation | PG3178 binding % of wt binding (range) | Control mAb binding % of wt binding (range) | Designation |
|---|---|---|---|---|
| 409 | F409A | 16.74 (8) | 79.63 (0) | Critical |
| 426 | R426A | 3.17 (5) | 93.08 (36) | Critical |

TABLE 15

List of exposed residues within 11.2 Å radius of Arg 426 in HER3:

| | |
|---|---|
| Leu 423 | L423 |
| Tyr 424 | Y424 |
| Asn 425 | N425 |
| Gly 427 | G427 |
| Gly 452 | G452 |
| Arg 453 | R453 |
| Tyr 455 | Y455 |
| Glu 480 | E480 |
| Arg 481 | R481 |
| Leu 482 | L482 |
| Asp 483 | D483 |
| Lys 485 | K485 |

REFERENCES

Arteaga C L, Sliwkowski M X, Osborne C K, Perez E A, Puglisi F, Gianni L, 2011. Treatment of HER2-positive breast cancer: current status and future perspectives. Nat Rev Clin Oncol, 2011 Nov. 29:9(1):16-32.

Balko J M, Miller T W, Morrison M M, Hutchinson K, Young C, Rinehart C, Sdnchez V, Jee D, Polyak K, Prat A, Perou C M, Arteaga C L, Cook R S, 2012. The receptor tyrosine kinase ErbB3 maintains the balance between luminal and basal breast epithelium. Proc Natl Acad Sci USA. January 3:109(1):221-6.

Baselga J, Corths J, Kim S B, Im S A, Hegg R, Im Y H, Roman L, Pedrini J L, Pienkowski T, Knott A, Clark E, Benyunes M C, Ross G, Swain S M, 2012. Pertuzumab plus trastuzumab plus docetaxel for metastatic breast cancer. N Engl J Med. January 12; 366(2):109-19.

de Kruif et al. Mol. Biol. (1995), 248, 97-105

Ewer M S, Ewer S M. Cardiotoxicity of anticancer treatments: What the cardiologist needs to know. Nat Rev Cardiol 2010; 7:564-75

Guarneri Jain K K, Casper E S, Geller N L, et al. A prospective randomized comparison of epirubicin and doxorubicin in patients with advanced breast cancer; J Clin Oncol 1985; 3:818-26

Junttila T T, Akita R W, Parsons K, Fields C, Lewis Phillips G D, Friedman L S, Sampath D, Sliwkowski M X, 2009. Ligand-independent HER2/HER3/PI3K complex is disrupted by trastuzumab and is effectively inhibited by the PI3K inhibitor GDC-0941. Cancer Cell. May 5; 15(5): 429-40.

Junttila, T. T., K. Parsons, et al. (2010). "Superior In vivo Efficacy of Afucosylated Trastuzumab in the Treatment of HER2-Amplified Breast Cancer." Cancer Research 70(11): 4481-4489

Merchant et al. Nature Biotechnology. Vol. 16 Jul. 1998 pp 677-681

Nissim A, Hoogenboom H R, Tomlinson I M, Flynn G, Midgley C, Lane D, Winter G, 1994. Antibody fragments from a 'single pot' phage display library as immunochemical reagents. EMBO J. 1994 Feb. 1:13(3):692-8.

Ocana A, Vera-Badillo F. Seruga B. Templeton A. Pandiella A. Amir E. 2013. HER3 overexpression and survival in solid tumors: a meta-analysis. J Natl Cancer Inst. February 20; 105(4):266-73.

Sergina N V, Rausch M, Wang D, Blair J, Hann B, Shokat K M, Moasser M M, 2007. Escape from HER-family tyrosine kinase inhibitor therapy by the kinase-inactive HER3. Nature. January 25; 445(712):437-41.

Schaefer et al. Cancer Cell 20, 472-486. October 2011

Schoeberl B, Faber A C, Li D, Liang M C, Crosby K, Onsum M, Burenkova O, Pace E, Walton Z, Nie L, Fulgham A, Song Y, Nielsen U B, Engelman J A, Wong K K, 2010. An ErbB3 antibody. MM-121, is active in cancers with ligand-dependent activation. Cancer Res. March 15; 70(6):2485-94.

Shames et al. PLOS ONE. February 2013, Vol. 8. Issue 2, pp 1-10

Tanner M, Kapanen A I, Junttila T, Raheem O, Grenman S, Elo J, Elenius K, Isola J. 2004. Characterization of a novel cell line established from a patient with Herceptin-resistant breast cancer. Mol Cancer Ther. 2004 December; 3(12):1585-92. Yarden Y. Pines G.2012. The ERBB network: at last, cancer therapy meets systems biology. Nat Rev Cancer July 12; 12(8):553-63.

Thery J.-C. et al., Resistance to human epidermal growth factor receptor type 2-targeted therapies. Eur J Cancer (2014), Vol. 50. Issue 5, pages 892-901

Wadhwa D. Fallah-Rad N. Grenier D. et al. Trastuzumab mediated cardiotoxicity in the setting of the adjuvant chemotherapy for breast cancer: A retrospective study. Breast Cancer Res Treat 2009; 117:357-64.

Wehrman T S, Raab W J, Casipit C L, Doyonnas R, Pomerantz J H, Blau H M. 2006. A system for quantifying dynamic protein interactions defines a role for flerceptin in modulating ErbB2 interactions. Proc Natl Acad Sci USA. December 12; 103(50):19063-8.

Wilson T R, Fridlyand J, Yan Y, Penuel E, Burton L, Chan E, Peng J, Lin E, Wang Y, Sosman J, Ribas A, Li J, Moffat J, Sutherlin D P, Koeppen H, Merchant M, Neve R, Settleman J, 2012. Widespread potential for growth-factor-driven resistance to anticancer kinase inhibitors. Nature. July 26; 487(7408):505-9.

Yonesaka et al., Sci, transl. Med., Vol. 3, Issue 99 (2011): pp 1-11

Zhang H, Berezov A, Wang Q, Zhang G, Drebin J, Murali R, Greene M I, 2007. ErbB receptors: from oncogenes to targeted cancer therapies. J Clin Invest. August; 117(8): 2051-8.

Greco, Bravo, Parsons (1995) The search for synergy: a critical review from a response surface perspective. Pharmacol. Rev 47 (2): 331-8

---

The invention claimed is:

1. A bispecific antibody comprising a first binding arm that specifically binds to the extracellular domain of a human ErbB2 polypeptide and comprises a heavy chain variable region comprising the CDR1, CDR2, and CDR3 sequences of AYYIN (SEQ ID NO:49), RIYPGSGYT-SYAQKFQG (SEQ ID NO:50), and PPVYYDSAWFAY (SEQ ID NO:51) and a light chain variable region comprising the CDR1, CDR2, and CDR3 sequences of a light chain comprising SEQ ID NO: 87; and a second binding arm that specifically binds to the extracellular domain of a human ErbB3 polypeptide and comprises a heavy chain variable region comprising the CDR1, CDR2, and CDR3 sequences GYYMH (SEQ ID NO:64), WINPNSGGTNYAQKFQG (SEQ ID NO:65), and DHGSRHFWSYWGEFDY (SEQ ID NO:66) and a light chain variable region comprising the CDR1, CDR2, and CDR3 sequences of a light chain comprising SEQ ID NO: 87.

2. The bispecific antibody of claim 1, which is afucosylated in order to enhance antibody dependent cellular cytotoxicity (ADCC).

3. The bispecific antibody of claim 1, wherein the bispecific antibody comprises two different immunoglobulin heavy chains with compatible heterodimerization domains.

4. The bispecific antibody of claim 3, wherein the compatible heterodimerization domains are compatible immunoglobulin heavy chain CH3 heterodimerization domains.

5. A pharmaceutical composition comprising the bispecific antibody of claim 1.

6. A method for the treatment of a subject having a ErbB-2, ErbB-3 or ErbB-2/ErbB-3 positive tumor the method comprising: administering to the subject the antibody of claim 1 or the pharmaceutical composition of claim 5.

7. A method for the treatment of a subject having a ErbB-2, ErbB-3 or ErbB-2/ErbB-3 positive tumor, the method comprising:

administering to the subject:
the bispecific antibody of claim 1, and
at least one additional therapeutic agent.

8. The bispecific antibody of claim 1, wherein the antibody comprises the light chain variable region comprising the amino acid sequence DIQMTQSPSSLSASVGDRVTIT-CRASQSISSYLNWYQQKPGKAPKLLIYAASSLOSGVP SRFSGSGSGTDFTLTISSLQPEDFATYYCQQSYS-TPPTFGQGTKVEIKRTVAAPSVFIF PPSDEQLKSG-TASVVCLLNNEYPREAKVQWKVD-NALQSGNSQESVTEQDSKDSTYSL SSTLTLSKADYEKHKVYACE-VTHQGLSSPVTKSFNRGEC (SEQ ID NO: 87).

9. The method of claim 7, wherein said at least one additional therapeutic agent is selected from afatinib, lapatinib, neratinib, BYL719, MK-2206, everolimus, saracatinib, paclitaxel, vorinostat.

10. The bispecific antibody of claim 1, wherein the first binding arm comprises a heavy chain variable region comprising SEQ ID NO: 48, the second binding arm comprises a heavy chain variable region comprising SEQ ID NO: 63, and both the first and second binding arms comprise a light chain variable region comprising SEQ ID NO: 87.

11. The bispecific antibody of claim 1, wherein the first binding arm comprises a heavy chain comprising SEQ ID NO: 88, the second binding arm comprises a heavy chain comprising SEQ ID NO: 89, and both the first and second binding arms comprise a light chain comprising SEQ ID NO: 87.

12. The method of claim 6, wherein the tumor is a ErbB-2/ErbB-3 positive tumor.

13. The method of claim 6, wherein the tumor is a ErbB-2 positive tumor.

14. The method of claim 6, wherein the tumor is a ErbB-3 positive tumor.

15. The method of claim 7, wherein the tumor is a ErbB-2/ErbB-3 positive tumor.

16. The method of claim 7, wherein the tumor is a ErbB-2 positive tumor.

17. The method of claim 7, wherein the tumor is a ErbB-3 positive tumor.

* * * * *

UNITED STATES PATENT AND TRADEMARK OFFICE
CERTIFICATE OF CORRECTION

PATENT NO. : 11,279,770 B2
APPLICATION NO. : 15/121623
DATED : March 22, 2022
INVENTOR(S) : Geuijen et al.

It is certified that error appears in the above-identified patent and that said Letters Patent is hereby corrected as shown below:

In the Specification

In Column 1, Line 60, delete "(HERH2+)" and insert -- (HER2+) --, therefor.

In Column 2, Line 5, delete "(HERCEPTINS)" and insert -- (HERCEPTIN®) --, therefor.

In Column 5, Line 14, delete "Fe" and insert -- Fc --, therefor.

In Column 10, Line 18, delete "Fe" and insert -- Fc --, therefor.

In Column 10, Line 41, delete "Fe" and insert -- Fc --, therefor.

In Column 10, Line 50, delete "Fe" and insert -- Fc --, therefor.

In Column 15, Line 8, delete "vitm," and insert -- vitro, --, therefor.

In Column 16, Line 18, delete "pert uzumab" and insert -- pertuzumab --, therefor.

In Column 17, Line 22, delete "Fe" and insert -- Fc --, therefor.

In Column 19, Line 5, delete "N3307;" and insert -- MF3307; --, therefor.

In Column 19, Line 6, delete "N6057;" and insert -- MF6057; --, therefor.

In Column 19, Line 8, delete "MHF6066;" and insert -- MF6066; --, therefor.

In Column 19, Line 15, delete "MvNF3099;" and insert -- MF3099; --, therefor.

In Column 19, Line 15, delete "MHF6056;" and insert -- MF6056; --, therefor.

Signed and Sealed this
Thirtieth Day of August, 2022

Katherine Kelly Vidal
*Director of the United States Patent and Trademark Office*

CERTIFICATE OF CORRECTION (continued)
U.S. Pat. No. 11,279,770 B2

In Column 19, Line 16, delete "MHF6059;" and insert -- MF6059; --, therefor.

In Column 19, Line 30, delete "N6068;" and insert -- MF6068; --, therefor.

In Column 19, Line 30, delete "N6071;" and insert -- MF6071; --, therefor.

In Column 19, Line 52, delete "MHF3001," and insert -- MF3001, --, therefor.

In Column 20, Line 35, delete "MIF6062;" and insert -- MF6062; --, therefor.

In Column 22, Line 36, delete "N6072;" and insert -- MF6072; --, therefor.

In Column 23, Line 8, delete "MIF6059;" and insert -- MF6059; --, therefor.

In Column 23, Line 9, delete "MIF6062;" and insert -- MF6062; --, therefor.

In Column 23, Line 12, delete "MF607; 3" and insert -- MF6073 --, therefor.

In Column 23, Line 18, delete "MIF6073" and insert -- MF6073 --, therefor.

In Column 23, Line 46, delete "MIF2971" and insert -- MF2971 --, therefor.

In Column 25, Line 47, delete "VHI" and insert -- VH --, therefor.

In Column 26, Line 1, delete "(I)" and insert -- (KD) --, therefor.

In Column 26, Line 30, delete "VI chain MIF3178;" and insert -- VH chain MF3178; --, therefor.

In Column 26, Line 33, delete "N6067;" and insert -- MF6067; --, therefor.

In Column 27, Line 17, delete "MF3958:" and insert -- MF3958; --, therefor.

In Column 27, Line 61, delete "VI" and insert -- VH --, therefor.

In Column 28, Line 6, delete "VIH" and insert -- VH --, therefor.

In Column 28, Line 38, delete "XII" and insert -- VH --, therefor.

In Column 28, Line 46, delete "XII" and insert -- VH --, therefor.

In Column 28, Line 55, delete "XII" and insert -- VH --, therefor.

In Column 29, Line 4, delete "VI" and insert -- VH --, therefor.

In Column 30, Line 39, delete "(113" and insert -- CH3 --, therefor.

CERTIFICATE OF CORRECTION (continued)
U.S. Pat. No. 11,279,770 B2

In Column 31, Line 33, delete "(113" and insert -- CH3 --, therefor.

In Column 33, Line 20, delete "1+1" and insert -- [+] --, therefor.

In Column 33, Line 49, delete "(I)" and insert -- (KD) --, therefor.

In Column 38, Line 17, delete "MF300," and insert -- MF3001, --, therefor.

In Column 38, Line 45, delete "N3991," and insert -- MF3991, --, therefor.

In Column 38, Line 53, delete "MF2930." and insert -- MF2930, --, therefor.

In Column 47, Line 3, delete "PB34188" and insert -- PB4188 --, therefor.

In Column 47, Line 12, delete "HER2""" and insert -- HER2+++ --, therefor.

In Column 47, Line 63, delete "PC3958" and insert -- PG3958 --, therefor.

In Column 49, Line 6, delete "348:" and insert -- 34B: --, therefor.

In Column 49, Line 34, delete "assay, P06058," and insert -- assay. PG6058, --, therefor.

In Column 49, Line 35, delete "P06065" and insert -- PG6065 --, therefor.

In Column 49, Line 35, delete "PG3178," and insert -- PG3178. --, therefor.

In Column 49, Line 40, delete "P03178." and insert -- PG3178. --, therefor.

In Column 51, Line 61, delete "Fe" and insert -- Fc --, therefor.

In Column 52, Line 13, delete "Fe" and insert -- Fc --, therefor.

In Column 59, Line 24, delete "P03163." and insert -- PG3163, --, therefor.

In Column 59, Line 47, delete "sg g/ml-0," and insert -- µg g/ml-0, --, therefor.

In Column 68, Line 29, delete "P84188" and insert -- PB4188 --, therefor.

In Column 69, Line 2, delete "neratinib." and insert -- neratinib, --, therefor.

In Column 80, Line 10, delete "flerceptin" and insert -- Herceptin --, therefor.

In the Claims

In Column 205, Claim 1, Line 43, delete "DHGSRHFWSYWGEFDY" and insert

-- DHGSRHFWSYWGFDY --, therefor.

In Column 206, Claim 9, Lines 43-44, delete "laptinib," and insert -- lapatinib, --, therefor.

SEQUENCE LISTING

```
<160> NUMBER OF SEQ ID NOS: 175

<210> SEQ ID NO 1
<211> LENGTH: 36
<212> TYPE: DNA
<213> ORGANISM: Artificial Sequence
<220> FEATURE:
<223> OTHER INFORMATION: primer

<400> SEQUENCE: 1
aagctggcta gcaccatgga gctggcggcc ttgtgc                     36

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
aataattcta gactggcacg tccagaccca gg                         32

<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3
aagctggcta gcaccatgga gctggcggcc tggtac                     36

<210> SEQ ID NO 4
<211> LENGTH: 32
<212> TYPE: DNA
<213> ORGANISM: Artificial Sequence
```

<220> FEATURE:
<223> OTHER INFORMATION: primer

<400> SEQUENCE: 4
aataattcta gactggcacg tccagaccca gg        32

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
aagctggcta gcaccatgag ggcgaacggc gctctg        36

<210> SEQ ID NO 6
<211> LENGTH: 33
<212> TYPE: DNA
<213> ORGANISM: Artificial Sequence
<220> FEATURE:
<223> OTHER INFORMATION: primer

<400> SEQUENCE: 6
aataattcta gattacgttc tctgggcatt agc        33

<210> SEQ ID NO 7
<211> LENGTH: 370
<212> TYPE: DNA
<213> ORGANISM: Artificial Sequence
<220> FEATURE:
<223> OTHER INFORMATION: MF2926: heavy chain variable region sequence of
      an erbB-2 binding antibody
<220> FEATURE:
<221> NAME/KEY: CDS
<222> LOCATION: (20)..(370)

<400> SEQUENCE: 7
ggcccagccg gccatggcc cag gtc cag ctg cag cag tct gga cct gag ctg        52
                     Gln Val Gln Leu Gln Gln Ser Gly Pro Glu Leu
                      1               5                  10 gtg aaa cct ggg gct tca gtg atg att tcc tgc aag gct tct ggt tac        100
Val Lys Pro Gly Ala Ser Val Met Ile Ser Cys Lys Ala Ser Gly Tyr
         15                  20                  25 tca ttc act ggc tac cac atg aac tgg gtg aag caa agt cct gaa aag        148
Ser Phe Thr Gly Tyr His Met Asn Trp Val Lys Gln Ser Pro Glu Lys
                 30                  35                  40 agc ctt gag tgg att gga gac ata aat cct agc att ggt acg act gcc        196
Ser Leu Glu Trp Ile Gly Asp Ile Asn Pro Ser Ile Gly Thr Thr Ala
 45                  50                  55 cac aac cag att ttc agg gcc aag gcc aca atg act gtt gac aaa tcc        244
His Asn Gln Ile Phe Arg Ala Lys Ala Thr Met Thr Val Asp Lys Ser
 60                  65                  70                  75 tcc aac aca gcc tac atg cag ctc aag agc ctg aca tct gaa gac tct        292
Ser Asn Thr Ala Tyr Met Gln Leu Lys Ser Leu Thr Ser Glu Asp Ser
                 80                  85                  90 gga gtc ttt tac tgt gtt aga aga ggg gac tgg tcc ttc gat gtc tgg        340
Gly Val Phe Tyr Cys Val Arg Arg Gly Asp Trp Ser Phe Asp Val Trp
             95                 100                 105 ggc aca ggg acc acg gtc acc gtc tcc agt        370
Gly Thr Gly Thr Thr Val Thr Val Ser Ser
        110                 115

<210> SEQ ID NO 8

```
<211> LENGTH: 117
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Gln Gln Ser Gly Pro Glu Leu Val Lys Pro Gly Ala
1               5                   10                  15

Ser Val Met Ile Ser Cys Lys Ala Ser Gly Tyr Ser Phe Thr Gly Tyr
            20                  25                  30

His Met Asn Trp Val Lys Gln Ser Pro Glu Lys Ser Leu Glu Trp Ile
        35                  40                  45

Gly Asp Ile Asn Pro Ser Ile Gly Thr Thr Ala His Asn Gln Ile Phe
    50                  55                  60

Arg Ala Lys Ala Thr Met Thr Val Asp Lys Ser Ser Asn Thr Ala Tyr
65                  70                  75                  80

Met Gln Leu Lys Ser Leu Thr Ser Glu Asp Ser Gly Val Phe Tyr Cys
                85                  90                  95

Val Arg Arg Gly Asp Trp Ser Phe Asp Val Trp Gly Thr Gly Thr Thr
            100                 105                 110

Val Thr Val Ser Ser
        115

<210> SEQ ID NO 9
<211> LENGTH: 16
<212> TYPE: PRT
<213> ORGANISM: Artificial Sequence
<220> FEATURE:
<223> OTHER INFORMATION: MF2926 CDR1

<400> SEQUENCE: 9

Gly Tyr His Met Asn Trp Val Lys Gln Ser Pro Glu Lys Ser Leu Glu
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: MF2926 CDR2

<400> SEQUENCE: 10

Asn Gln Ile Phe Arg Ala
1               5

<210> SEQ ID NO 11
<211> LENGTH: 8
<212> TYPE: PRT
<213> ORGANISM: Artificial Sequence
<220> FEATURE:
<223> OTHER INFORMATION: MF2926 CDR3

<400> SEQUENCE: 11

Arg Gly Asp Trp Ser Phe Asp Val
1               5

<210> SEQ ID NO 12
<211> LENGTH: 379
<212> TYPE: DNA
<213> ORGANISM: Artificial Sequence
<220> FEATURE:
<223> OTHER INFORMATION: MF2930: heavy chain variable region sequence of
      an erbB-2 binding antibody
```

```
<220> FEATURE:
<221> NAME/KEY: CDS
<222> LOCATION: (20)..(379)

<400> SEQUENCE: 12
ggcccagccg gccatggcc gag gtc cag ctg cag cag tct ggg gct gaa ctg      52
                     Glu Val Gln Leu Gln Gln Ser Gly Ala Glu Leu
                      1               5                  10 gtg aag cct gga gcc tca gtg atg atg tcc tgt aag gtt tct ggc tac     100
Val Lys Pro Gly Ala Ser Val Met Met Ser Cys Lys Val Ser Gly Tyr
         15                  20                  25 acc ttc act tcc tat cct ata gcg tgg atg aag cag gtt cat gga aag     148
Thr Phe Thr Ser Tyr Pro Ile Ala Trp Met Lys Gln Val His Gly Lys
         30                  35                  40 agc cta gag tgg att gga aat ttt cat cct tac agt gat gat act aag     196
Ser Leu Glu Trp Ile Gly Asn Phe His Pro Tyr Ser Asp Asp Thr Lys
     45                  50                  55 tac aat gaa aac ttc aag ggc aag gcc aca ttg act gta gaa aaa tcc     244
Tyr Asn Glu Asn Phe Lys Gly Lys Ala Thr Leu Thr Val Glu Lys Ser
 60                  65                  70                  75 tct agc aca gtc tac ttg gag ctc agc cga tta aca tct gat gac tct     292
Ser Ser Thr Val Tyr Leu Glu Leu Ser Arg Leu Thr Ser Asp Asp Ser
                 80                  85                  90 gct gtt tat tac tgt gca aga agt aac cca tta tat tac ttt gct atg     340
Ala Val Tyr Tyr Cys Ala Arg Ser Asn Pro Leu Tyr Tyr Phe Ala Met
             95                 100                 105 gac tac tgg ggt caa gga acc tcg gtc acc gtc tcc agt                 379
Asp Tyr Trp Gly Gln Gly Thr Ser Val Thr Val Ser Ser
        110                 115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Gln Gln Ser Gly Ala Glu Leu Val Lys Pro Gly Ala
 1               5                  10                  15

Ser Val Met Met Ser Cys Lys Val Ser Gly Tyr Thr Phe Thr Ser Tyr
             20                  25                  30

Pro Ile Ala Trp Met Lys Gln Val His Gly Lys Ser Leu Glu Trp Ile
         35                  40                  45

Gly Asn Phe His Pro Tyr Ser Asp Asp Thr Lys Tyr Asn Glu Asn Phe
     50                  55                  60

Lys Gly Lys Ala Thr Leu Thr Val Glu Lys Ser Ser Ser Thr Val Tyr
 65                  70                  75                  80

Leu Glu Leu Ser Arg Leu Thr Ser Asp Asp Ser Ala Val Tyr Tyr Cys
                 85                  90                  95

Ala Arg Ser Asn Pro Leu Tyr Tyr Phe Ala Met Asp Tyr Trp Gly Gln
            100                 105                 110

Gly Thr Ser Val Thr Val Ser Ser
        115                 120

<210> SEQ ID NO 14
<211> LENGTH: 16
<212> TYPE: PRT
<213> ORGANISM: Artificial Sequence
<220> FEATURE:
<223> OTHER INFORMATION: MF2930 CDR1
```

<400> SEQUENCE: 14

Ser Tyr Pro Ile Ala Trp Met Lys Gln Val His Gly Lys Ser Leu Glu
1               5                   10                  15

<210> SEQ ID NO 15
<211> LENGTH: 6
<212> TYPE: PRT
<213> ORGANISM: Artificial Sequence
<220> FEATURE:
<223> OTHER INFORMATION: MF2930 CDR2

<400> SEQUENCE: 15

Asn Glu Asn Phe Lys Gly
1               5

<210> SEQ ID NO 16
<211> LENGTH: 11
<212> TYPE: PRT
<213> ORGANISM: Artificial Sequence
<220> FEATURE:
<223> OTHER INFORMATION: MF2930 CDR3

<400> SEQUENCE: 16

Ser Asn Pro Leu Tyr Tyr Phe Ala Met Asp Tyr
1               5                   10

<210> SEQ ID NO 17
<211> LENGTH: 385
<212> TYPE: DNA
<213> ORGANISM: Artificial Sequence
<220> FEATURE:
<223> OTHER INFORMATION: MF1849: heavy chain variable region sequence of
      an erbB-2 binding antibody
<220> FEATURE:
<221> NAME/KEY: CDS
<222> LOCATION: (20)..(385)

<400> SEQUENCE: 17

```
ggcccagccg gccatggcc cag gtg cag ctg gtg gag tct ggg gga ggc gtg      52
                     Gln Val Gln Leu Val Glu Ser Gly Gly Gly Val
                      1               5                  10 gtc cag cct ggg agg tcc ctg aga ctc tcc tgt gca gcc tct gga ttc      100
Val Gln Pro Gly Arg Ser Leu Arg Leu Ser Cys Ala Ala Ser Gly Phe
            15                  20                  25 acc ttc agt agc tat ggc atg cac tgg gtc cgc cag gct cca ggc aag      148
Thr Phe Ser Ser Tyr Gly Met His Trp Val Arg Gln Ala Pro Gly Lys
        30                  35                  40 ggg ctg gag tgg gtg gca gtt ata tca tat gat gga agt aat aaa tac      196
Gly Leu Glu Trp Val Ala Val Ile Ser Tyr Asp Gly Ser Asn Lys Tyr
    45                  50                  55 tat gca gac tcc gtg aag ggc cga ttc acc atc tcc aga gac aat tcc      244
Tyr Ala Asp Ser Val Lys Gly Arg Phe Thr Ile Ser Arg Asp Asn Ser
60                  65                  70                  75 aag aac acg ctg tat ctg caa atg aac agc ctg aga gct gag gac acg      292
Lys Asn Thr Leu Tyr Leu Gln Met Asn Ser Leu Arg Ala Glu Asp Thr
                80                  85                  90 gcc gtg tat tac tgt gca aaa ggt gac tac ggt tct tac tct tct tac      340
Ala Val Tyr Tyr Cys Ala Lys Gly Asp Tyr Gly Ser Tyr Ser Ser Tyr
            95                  100                 105 gcc ttt gat tat tgg ggc caa ggt acc ctg gtc acc gtc tcc agt          385
Ala Phe Asp Tyr Trp Gly Gln Gly Thr Leu Val Thr Val Ser Ser
        110                 115                 120
```

```
<210> SEQ ID NO 18
<211> LENGTH: 122
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Asp Tyr Gly Ser Tyr Ser Ser Tyr Ala Phe Asp Tyr Trp
            100                 105                 110

Gly Gln Gly Thr Leu Val Thr Val Ser Ser
        115                 120

<210> SEQ ID NO 19
<211> LENGTH: 5
<212> TYPE: PRT
<213> ORGANISM: Artificial Sequence
<220> FEATURE:
<223> OTHER INFORMATION: MF1849 CDR1

<400> SEQUENCE: 19

Ser Tyr Gly Met His
1               5

<210> SEQ ID NO 20
<211> LENGTH: 17
<212> TYPE: PRT
<213> ORGANISM: Artificial Sequence
<220> FEATURE:
<223> OTHER INFORMATION: MF1849 CDR2

<400> SEQUENCE: 20

Val Ile Ser Tyr Asp Gly Ser Asn Lys Tyr Tyr Ala Asp Ser Val Lys
1               5                   10                  15

Gly

<210> SEQ ID NO 21
<211> LENGTH: 13
<212> TYPE: PRT
<213> ORGANISM: Artificial Sequence
<220> FEATURE:
<223> OTHER INFORMATION: MF1849 CDR3

<400> SEQUENCE: 21

Gly Asp Tyr Gly Ser Tyr Ser Ser Tyr Ala Phe Asp Tyr
1               5                   10

<210> SEQ ID NO 22
<211> LENGTH: 385
<212> TYPE: DNA
<213> ORGANISM: Artificial Sequence
```

```
<220> FEATURE:
<223> OTHER INFORMATION: MF2973: heavy chain variable region sequence of
      an erbB-2 binding antibody
<220> FEATURE:
<221> NAME/KEY: CDS
<222> LOCATION: (20)..(385)

<400> SEQUENCE: 22
ggcccagccg gccatggcc cag gtg cag ctg aag cag tct ggg gct gag ctg        52
                     Gln Val Gln Leu Lys Gln Ser Gly Ala Glu Leu
                      1               5                  10 gtg agg cct ggg gct tca gtg aag ttg tcc tgc aag gct tct ggc tac       100
Val Arg Pro Gly Ala Ser Val Lys Leu Ser Cys Lys Ala Ser Gly Tyr
         15                  20                  25 att ttc act ggc tac tat ata aac tgg ttg agg cag agg cct gga cag       148
Ile Phe Thr Gly Tyr Tyr Ile Asn Trp Leu Arg Gln Arg Pro Gly Gln
             30                  35                  40 gga ctt gaa tgg att gca aaa att tat cct gga agt ggt aat act tac       196
Gly Leu Glu Trp Ile Ala Lys Ile Tyr Pro Gly Ser Gly Asn Thr Tyr
    45                  50                  55 tac aat gag aag ttc agg ggc aag gcc aca ctg act gca gaa gaa tcc       244
Tyr Asn Glu Lys Phe Arg Gly Lys Ala Thr Leu Thr Ala Glu Glu Ser
60                  65                  70                  75 tcc agc act gcc tac atg cag ctc agc agc ctg aca tct gag gac tct       292
Ser Ser Thr Ala Tyr Met Gln Leu Ser Ser Leu Thr Ser Glu Asp Ser
                80                  85                  90 gct gtc tat ttc tgt gca aga ggg ccc cac tat gat tac gac ggc ccc       340
Ala Val Tyr Phe Cys Ala Arg Gly Pro His Tyr Asp Tyr Asp Gly Pro
            95                 100                 105 tgg ttt gtt tac tgg ggc caa ggg act ctg gtc acc gtc tcc agt           385
Trp Phe Val Tyr Trp Gly Gln Gly Thr Leu Val Thr Val Ser Ser
        110                 115                 120

<210> SEQ ID NO 23
<211> LENGTH: 122
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Lys Gln Ser Gly Ala Glu Leu Val Arg Pro Gly Ala
 1               5                  10                  15

Ser Val Lys Leu Ser Cys Lys Ala Ser Gly Tyr Ile Phe Thr Gly Tyr
             20                  25                  30

Tyr Ile Asn Trp Leu Arg Gln Arg Pro Gly Gln Gly Leu Glu Trp Ile
         35                  40                  45

Ala Lys Ile Tyr Pro Gly Ser Gly Asn Thr Tyr Tyr Asn Glu Lys Phe
     50                  55                  60

Arg Gly Lys Ala Thr Leu Thr Ala Glu Glu Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Gly Pro His Tyr Asp Tyr Asp Gly Pro Trp Phe Val Tyr Trp
            100                 105                 110

Gly Gln Gly Thr Leu Val Thr Val Ser Ser
        115                 120

<210> SEQ ID NO 24
<211> LENGTH: 16
<212> TYPE: PRT
```

<213> ORGANISM: Artificial Sequence
<220> FEATURE:
<223> OTHER INFORMATION: MF2973 CDR1

<400> SEQUENCE: 24

Gly Tyr Tyr Ile Asn Trp Leu Arg Gln Arg Pro Gly Gln Gly Leu Glu
1               5                   10                  15

<210> SEQ ID NO 25
<211> LENGTH: 6
<212> TYPE: PRT
<213> ORGANISM: Artificial Sequence
<220> FEATURE:
<223> OTHER INFORMATION: MF2973 CDR2

<400> SEQUENCE: 25

Asn Glu Lys Phe Arg Gly
1               5

<210> SEQ ID NO 26
<211> LENGTH: 13
<212> TYPE: PRT
<213> ORGANISM: Artificial Sequence
<220> FEATURE:
<223> OTHER INFORMATION: MF1973 CDR3

<400> SEQUENCE: 26

Gly Pro His Tyr Asp Tyr Asp Gly Pro Trp Phe Val Tyr
1               5                   10

<210> SEQ ID NO 27
<211> LENGTH: 382
<212> TYPE: DNA
<213> ORGANISM: Artificial Sequence
<220> FEATURE:
<223> OTHER INFORMATION: MF3004: heavy chain variable region sequence of
    an erbB-2 binding antibody
<220> FEATURE:
<221> NAME/KEY: CDS
<222> LOCATION: (20)..(382)

<400> SEQUENCE: 27
ggcccagccg gccatggcc cag gtg cag ctg aag cag tct ggg gct gag ctg        52
                     Gln Val Gln Leu Lys Gln Ser Gly Ala Glu Leu
                       1               5                  10 gtg agg cct ggg gct tca gtg aag ctg tcc tgc aag gct tct ggc tac       100
Val Arg Pro Gly Ala Ser Val Lys Leu Ser Cys Lys Ala Ser Gly Tyr
             15                  20                  25 act ttc act ggc tac tat ata aac tgg gtg aag cag agg cct gga cag       148
Thr Phe Thr Gly Tyr Tyr Ile Asn Trp Val Lys Gln Arg Pro Gly Gln
         30                  35                  40 gga ctt gag tgg att gca agg att tat cct gga agt ggt tat act tac       196
Gly Leu Glu Trp Ile Ala Arg Ile Tyr Pro Gly Ser Gly Tyr Thr Tyr
     45                  50                  55 tac aat gag aag ttc aag ggc aag gcc aca ctg act gca gaa gaa tcc       244
Tyr Asn Glu Lys Phe Lys Gly Lys Ala Thr Leu Thr Ala Glu Glu Ser
 60                  65                  70                  75 tcc agc act gcc tac atg cac ctc agc agc ctg aca tct gag gac tct       292
Ser Ser Thr Ala Tyr Met His Leu Ser Ser Leu Thr Ser Glu Asp Ser
                 80                  85                  90 gct gtc tat ttc tgt gca aga ccc cac tat ggt tac gac gac tgg tac       340
Ala Val Tyr Phe Cys Ala Arg Pro His Tyr Gly Tyr Asp Asp Trp Tyr
             95                 100                 105

```
ttc ggt gtc tgg ggc aca ggc acc acg gtc acc gtc tcc agt         382
Phe Gly Val Trp Gly Thr Gly Thr Thr Val Thr Val Ser Ser
        110                 115                 120
```

<210> SEQ ID NO 28
<211> LENGTH: 121
<212> TYPE: PRT
<213> ORGANISM: Artificial Sequence
<220> FEATURE:
<223> OTHER INFORMATION: Synthetic Construct

<400> SEQUENCE: 28

```
Gln Val Gln Leu Lys Gln Ser Gly Ala Glu Leu Val Arg Pro Gly Ala
1               5                   10                  15

Ser Val Lys Leu Ser Cys Lys Ala Ser Gly Tyr Thr Phe Thr Gly Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Tyr Thr Tyr Tyr Asn Glu Lys Phe
    50                  55                  60

Lys Gly Lys Ala Thr Leu Thr Ala Glu Glu Ser Ser Ser Thr Ala Tyr
65                  70                  75                  80

Met His Leu Ser Ser Leu Thr Ser Glu Asp Ser Ala Val Tyr Phe Cys
                85                  90                  95

Ala Arg Pro His Tyr Gly Tyr Asp Asp Trp Tyr Phe Gly Val Trp Gly
            100                 105                 110

Thr Gly Thr Thr Val Thr Val Ser Ser
        115                 120
```

<210> SEQ ID NO 29
<211> LENGTH: 16
<212> TYPE: PRT
<213> ORGANISM: Artificial Sequence
<220> FEATURE:
<223> OTHER INFORMATION: MF3004 CDR1

<400> SEQUENCE: 29

```
Gly Tyr Tyr Ile Asn Trp Val Lys Gln Arg Pro Gly Gln Gly Leu Glu
1               5                   10                  15
```

<210> SEQ ID NO 30
<211> LENGTH: 6
<212> TYPE: PRT
<213> ORGANISM: Artificial Sequence
<220> FEATURE:
<223> OTHER INFORMATION: MF3004 CDR2

<400> SEQUENCE: 30

```
Asn Glu Lys Phe Lys Gly
1               5
```

<210> SEQ ID NO 31
<211> LENGTH: 12
<212> TYPE: PRT
<213> ORGANISM: Artificial Sequence
<220> FEATURE:
<223> OTHER INFORMATION: MF3004 CDR3

<400> SEQUENCE: 31

```
Pro His Tyr Gly Tyr Asp Asp Trp Tyr Phe Gly Val
1               5                   10
```

-continued

```
<210> SEQ ID NO 32
<211> LENGTH: 382
<212> TYPE: DNA
<213> ORGANISM: Artificial Sequence
<220> FEATURE:
<223> OTHER INFORMATION: MF2971: heavy chain variable region sequence of
      an erbB-2 binding antibody
<220> FEATURE:
<221> NAME/KEY: CDS
<222> LOCATION: (20)..(382)

<400> SEQUENCE: 32
ggcccagccg gccatggcc cag gtg cag ctg aag cag tct ggg gct gag ctg        52
                     Gln Val Gln Leu Lys Gln Ser Gly Ala Glu Leu
                       1               5                  10 gtg agg cct ggg gct tca gtg aaa ctg tcc tgc aag gct tct ggc tac        100
Val Arg Pro Gly Ala Ser Val Lys Leu Ser Cys Lys Ala Ser Gly Tyr
         15                  20                  25 act ttc act gcc tac tat ata aac tgg gtg aag cag agg cct gga cag        148
Thr Phe Thr Ala Tyr Tyr Ile Asn Trp Val Lys Gln Arg Pro Gly Gln
             30                  35                  40 gga ctt gag tgg att gca agg att tat cct gga agt ggt tat act tac        196
Gly Leu Glu Trp Ile Ala Arg Ile Tyr Pro Gly Ser Gly Tyr Thr Tyr
         45                  50                  55 tac aat gag att ttc aag ggc agg gcc aca ctg act gca gac gaa tcc        244
Tyr Asn Glu Ile Phe Lys Gly Arg Ala Thr Leu Thr Ala Asp Glu Ser
 60                  65                  70                  75 tcc agc act gcc tac atg caa ctc agc agc ctg aca tct gag gac tct        292
Ser Ser Thr Ala Tyr Met Gln Leu Ser Ser Leu Thr Ser Glu Asp Ser
                 80                  85                  90 gct gtc tat ttc tgt gca aga cct ccg gtc tac tat gac tcg gcc tgg        340
Ala Val Tyr Phe Cys Ala Arg Pro Pro Val Tyr Tyr Asp Ser Ala Trp
             95                 100                 105 ttt gct tac tgg ggc caa ggg act ctg gtc acc gtc tcc agt              382
Phe Ala Tyr Trp Gly Gln Gly Thr Leu Val Thr Val Ser Ser
        110                 115                 120

<210> SEQ ID NO 33
<211> LENGTH: 121
<212> TYPE: PRT
<213> ORGANISM: Artificial Sequence
<220> FEATURE:
<223> OTHER INFORMATION: Synthetic Construct

<400> SEQUENCE: 33

Gln Val Gln Leu Lys Gln Ser Gly Ala Glu Leu Val Arg Pro Gly Ala
  1               5                  10                  15

Ser Val Lys Leu Ser Cys Lys Ala Ser Gly Tyr Thr Phe Thr Ala Tyr
             20                  25                  30

Tyr Ile Asn Trp Val Lys Gln Arg Pro Gly Gln Gly Leu Glu Trp Ile
         35                  40                  45

Ala Arg Ile Tyr Pro Gly Ser Gly Tyr Thr Tyr Tyr Asn Glu Ile Phe
     50                  55                  60

Lys Gly Arg Ala Thr Leu Thr Ala Asp Glu Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Pro Pro Val Tyr Tyr Asp Ser Ala Trp Phe Ala Tyr Trp Gly
            100                 105                 110

Gln Gly Thr Leu Val Thr Val Ser Ser
        115                 120
```

<210> SEQ ID NO 34
<211> LENGTH: 16
<212> TYPE: PRT
<213> ORGANISM: Artificial Sequence
<220> FEATURE:
<223> OTHER INFORMATION: MF2971 CDR1

<400> SEQUENCE: 34

```
Ala Tyr Tyr Ile Asn Trp Val Lys Gln Arg Pro Gly Gln Gly Leu Glu
1               5                   10                  15
```

<210> SEQ ID NO 35
<211> LENGTH: 6
<212> TYPE: PRT
<213> ORGANISM: Artificial Sequence
<220> FEATURE:
<223> OTHER INFORMATION: MF2971 CDR2

<400> SEQUENCE: 35

```
Asn Glu Ile Phe Lys Gly
1               5
```

<210> SEQ ID NO 36
<211> LENGTH: 12
<212> TYPE: PRT
<213> ORGANISM: Artificial Sequence
<220> FEATURE:
<223> OTHER INFORMATION: MF2971 CDR3

<400> SEQUENCE: 36

```
Pro Pro Val Tyr Tyr Asp Ser Ala Trp Phe Ala Tyr
1               5                   10
```

<210> SEQ ID NO 37
<211> LENGTH: 382
<212> TYPE: DNA
<213> ORGANISM: Artificial Sequence
<220> FEATURE:
<223> OTHER INFORMATION: MF3025: heavy chain variable region sequence of
    an erbB-2 binding antibody
<220> FEATURE:
<221> NAME/KEY: CDS
<222> LOCATION: (20)..(382)

<400> SEQUENCE: 37

```
ggcccagccg gccatggcc cag gtg cag ctg aag cag tct ggg gct gag ctg      52
                     Gln Val Gln Leu Lys Gln Ser Gly Ala Glu Leu
                         1               5                   10 gtg agg cct ggg act tca gtg aag ctg tcc tgc aag gct tct ggc tac     100
Val Arg Pro Gly Thr Ser Val Lys Leu Ser Cys Lys Ala Ser Gly Tyr
            15                  20                  25 act ttc act ggc tac tat ata aac tgg gtg aag cag agg cct gga cag     148
Thr Phe Thr Gly Tyr Tyr Ile Asn Trp Val Lys Gln Arg Pro Gly Gln
        30                  35                  40 gga ctt gag tgg att gca agg att tat cct gga agt ggt tat act tac     196
Gly Leu Glu Trp Ile Ala Arg Ile Tyr Pro Gly Ser Gly Tyr Thr Tyr
    45                  50                  55 tac aat gag aag ttc aag ggc aag gcc aca ctg act gca gaa gaa tcc     244
Tyr Asn Glu Lys Phe Lys Gly Lys Ala Thr Leu Thr Ala Glu Glu Ser
60                  65                  70                  75 tcc aac act gcc tat atg cac ctc agc agc ctg aca tct gag gac tct     292
Ser Asn Thr Ala Tyr Met His Leu Ser Ser Leu Thr Ser Glu Asp Ser
                80                  85                  90
```

```
gct gtc tat ttc tgt gca agg ccc cac tat ggt tac gac gac tgg tac        340
Ala Val Tyr Phe Cys Ala Arg Pro His Tyr Gly Tyr Asp Asp Trp Tyr
        95                  100                 105 ttc gct gtc tgg ggc aca ggg acc acg gtc acc gtc tcc agt                382
Phe Ala Val Trp Gly Thr Gly Thr Thr Val Thr Val Ser Ser
        110                 115                 120
```

<210> SEQ ID NO 38
<211> LENGTH: 121
<212> TYPE: PRT
<213> ORGANISM: Artificial Sequence
<220> FEATURE:
<223> OTHER INFORMATION: Synthetic Construct

<400> SEQUENCE: 38

```
Gln Val Gln Leu Lys Gln Ser Gly Ala Glu Leu Val Arg Pro Gly Thr
1               5                   10                  15

Ser Val Lys Leu Ser Cys Lys Ala Ser Gly Tyr Thr Phe Thr Gly Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly Tyr Thr Tyr Tyr Asn Glu Lys Phe
    50                  55                  60

Lys Gly Lys Ala Thr Leu Thr Ala Glu Glu Ser Ser Asn Thr Ala Tyr
65                  70                  75                  80

Met His Leu Ser Ser Leu Thr Ser Glu Asp Ser Ala Val Tyr Phe Cys
                85                  90                  95

Ala Arg Pro His Tyr Gly Tyr Asp Asp Trp Tyr Phe Ala Val Trp Gly
            100                 105                 110

Thr Gly Thr Thr Val Thr Val Ser Ser
        115                 120
```

<210> SEQ ID NO 39
<211> LENGTH: 16
<212> TYPE: PRT
<213> ORGANISM: Artificial Sequence
<220> FEATURE:
<223> OTHER INFORMATION: MF3025 CDR1

<400> SEQUENCE: 39

```
Gly Tyr Tyr Ile Asn Trp Val Lys Gln Arg Pro Gly Gln Gly Leu Glu
1               5                   10                  15
```

<210> SEQ ID NO 40
<211> LENGTH: 6
<212> TYPE: PRT
<213> ORGANISM: Artificial Sequence
<220> FEATURE:
<223> OTHER INFORMATION: MF3025 CDR2

<400> SEQUENCE: 40

```
Asn Glu Lys Phe Lys Gly
1               5
```

<210> SEQ ID NO 41
<211> LENGTH: 12
<212> TYPE: PRT
<213> ORGANISM: Artificial Sequence
<220> FEATURE:
<223> OTHER INFORMATION: MF3025 CDR3

<400> SEQUENCE: 41

Pro His Tyr Gly Tyr Asp Asp Trp Tyr Phe Ala Val
1               5                   10

<210> SEQ ID NO 42
<211> LENGTH: 385
<212> TYPE: DNA
<213> ORGANISM: Artificial Sequence
<220> FEATURE:
<223> OTHER INFORMATION: MF2916: heavy chain variable region sequence of
      an erbB-2 binding antibody
<220> FEATURE:
<221> NAME/KEY: CDS
<222> LOCATION: (20)..(385)

<400> SEQUENCE: 42

```
ggcccagccg gccatggcc cag gtc cag ctg cag cag tct ggg gct gag ctg         52
                     Gln Val Gln Leu Gln Gln Ser Gly Ala Glu Leu
                       1               5                  10 gtg agg cct ggg gct tca gtg aag ctg tcc tgc aag gct tct ggc tac        100
Val Arg Pro Gly Ala Ser Val Lys Leu Ser Cys Lys Ala Ser Gly Tyr
             15                  20                  25 act ttc act ggc tac tat ata aac tgg gtg aag cag agg cct gga cag        148
Thr Phe Thr Gly Tyr Tyr Ile Asn Trp Val Lys Gln Arg Pro Gly Gln
         30                  35                  40 gga ctt gag tgg att gca agg att tat cct ggc agt ggt cat act tcc        196
Gly Leu Glu Trp Ile Ala Arg Ile Tyr Pro Gly Ser Gly His Thr Ser
     45                  50                  55 tac aat gag aag ttc aag ggc aag gcc aca ctg act aca gaa aaa tcc        244
Tyr Asn Glu Lys Phe Lys Gly Lys Ala Thr Leu Thr Thr Glu Lys Ser
 60                  65                  70                  75 tcc agc act gcc tac atg cag ctc agc agc ctg aca tct gag gac tct        292
Ser Ser Thr Ala Tyr Met Gln Leu Ser Ser Leu Thr Ser Glu Asp Ser
                 80                  85                  90 gct gtc tat ttc tgt gca aga cct atc tac ttt gat tac gca ggg ggg        340
Ala Val Tyr Phe Cys Ala Arg Pro Ile Tyr Phe Asp Tyr Ala Gly Gly
             95                 100                 105 tac ttc gat gtc tgg ggc aca aga acc tcg gtc acc gtc tcc agt            385
Tyr Phe Asp Val Trp Gly Thr Arg Thr Ser Val Thr Val Ser Ser
        110                 115                 120
```

<210> SEQ ID NO 43
<211> LENGTH: 122
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Gly Tyr
            20                  25                  30

Tyr Ile Asn Trp Val Lys Gln Arg Pro Gly Gln Gly Leu Glu Trp Ile
        35                  40                  45

Ala Arg Ile Tyr Pro Gly Ser Gly His Thr Ser Tyr Asn Glu Lys Phe
    50                  55                  60

Lys Gly Lys Ala Thr Leu Thr Thr Glu Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

```
Ala Arg Pro Ile Tyr Phe Asp Tyr Ala Gly Gly Tyr Phe Asp Val Trp
            100                 105                 110

Gly Thr Arg Thr Ser Val Thr Val Ser Ser
        115                 120

<210> SEQ ID NO 44
<211> LENGTH: 16
<212> TYPE: PRT
<213> ORGANISM: Artificial Sequence
<220> FEATURE:
<223> OTHER INFORMATION: MF2916 CDR1

<400> SEQUENCE: 44

Gly Tyr Tyr Ile Asn Trp Val Lys Gln Arg Pro Gly Gln Gly Leu Glu
1               5                   10                  15

<210> SEQ ID NO 45
<211> LENGTH: 6
<212> TYPE: PRT
<213> ORGANISM: Artificial Sequence
<220> FEATURE:
<223> OTHER INFORMATION: MF2916 CDR2

<400> SEQUENCE: 45

Asn Glu Lys Phe Lys Gly
1               5

<210> SEQ ID NO 46
<211> LENGTH: 13
<212> TYPE: PRT
<213> ORGANISM: Artificial Sequence
<220> FEATURE:
<223> OTHER INFORMATION: MF2916 CDR3

<400> SEQUENCE: 46

Pro Ile Tyr Phe Asp Tyr Ala Gly Gly Tyr Phe Asp Val
1               5                   10

<210> SEQ ID NO 47
<211> LENGTH: 382
<212> TYPE: DNA
<213> ORGANISM: Artificial Sequence
<220> FEATURE:
<223> OTHER INFORMATION: MF3958: heavy chain variable region sequence of
      an erbB-2 binding antibody
<220> FEATURE:
<221> NAME/KEY: CDS
<222> LOCATION: (20)..(382)

<400> SEQUENCE: 47
ggcccagccg gccatggcc cag gtg cag ctg gtg cag tct ggc gcc gaa gtg     52
                     Gln Val Gln Leu Val Gln Ser Gly Ala Glu Val
                     1               5                   10 aag aaa cct ggc gcc agc gtg aag ctg agc tgc aag gcc agc ggc tac    100
Lys Lys Pro Gly Ala Ser Val Lys Leu Ser Cys Lys Ala Ser Gly Tyr
            15                  20                  25 acc ttc acc gcc tac tac atc aac tgg gtc cga cag gcc cca ggc cag    148
Thr Phe Thr Ala Tyr Tyr Ile Asn Trp Val Arg Gln Ala Pro Gly Gln
        30                  35                  40 ggc ctg gaa tgg atc ggc aga atc tac ccc ggc tcc ggc tac acc agc    196
Gly Leu Glu Trp Ile Gly Arg Ile Tyr Pro Gly Ser Gly Tyr Thr Ser
    45                  50                  55 tac gcc cag aag ttc cag ggc aga gcc acc ctg acc gcc gac gag agc    244
Tyr Ala Gln Lys Phe Gln Gly Arg Ala Thr Leu Thr Ala Asp Glu Ser
60                  65                  70                  75
```

```
acc agc acc gcc tac atg gaa ctg agc agc ctg cgg agc gag gat acc      292
Thr Ser Thr Ala Tyr Met Glu Leu Ser Ser Leu Arg Ser Glu Asp Thr
            80                  85                  90 gcc gtg tac ttc tgc gcc aga ccc ccc gtg tac tac gac agc gct tgg      340
Ala Val Tyr Phe Cys Ala Arg Pro Pro Val Tyr Tyr Asp Ser Ala Trp
        95                 100                 105 ttt gcc tac tgg ggc cag ggc acc ctg gtc acc gtc tcc agt              382
Phe Ala Tyr Trp Gly Gln Gly Thr Leu Val Thr Val Ser Ser
        110                 115                 120
```

<210> SEQ ID NO 48
<211> LENGTH: 121
<212> TYPE: PRT
<213> ORGANISM: Artificial Sequence
<220> FEATURE:
<223> OTHER INFORMATION: Synthetic Construct

<400> SEQUENCE: 48

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ala Tyr
            20                  25                  30

Tyr Ile Asn Trp Val Arg Gln Ala Pro Gly Gln Gly Leu Glu Trp Ile
        35                  40                  45

Gly Arg Ile Tyr Pro Gly Ser Gly Tyr Thr Ser Tyr Ala Gln Lys Phe
    50                  55                  60

Gln Gly Arg Ala Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Pro Pro Val Tyr Tyr Asp Ser Ala Trp Phe Ala Tyr Trp Gly
            100                 105                 110

Gln Gly Thr Leu Val Thr Val Ser Ser
        115                 120
```

<210> SEQ ID NO 49
<211> LENGTH: 5
<212> TYPE: PRT
<213> ORGANISM: Artificial Sequence
<220> FEATURE:
<223> OTHER INFORMATION: MF3958 CDR1

<400> SEQUENCE: 49

```
Ala Tyr Tyr Ile Asn
1               5
```

<210> SEQ ID NO 50
<211> LENGTH: 17
<212> TYPE: PRT
<213> ORGANISM: Artificial Sequence
<220> FEATURE:
<223> OTHER INFORMATION: MF3958 CDR2

<400> SEQUENCE: 50

```
Arg Ile Tyr Pro Gly Ser Gly Tyr Thr Ser Tyr Ala Gln Lys Phe Gln
1               5                   10                  15

Gly
```

<210> SEQ ID NO 51
<211> LENGTH: 12
<212> TYPE: PRT

<213> ORGANISM: Artificial Sequence
<220> FEATURE:
<223> OTHER INFORMATION: MF3958 CDR3

<400> SEQUENCE: 51

Pro Pro Val Tyr Tyr Asp Ser Ala Trp Phe Ala Tyr
1               5                   10

<210> SEQ ID NO 52
<211> LENGTH: 382
<212> TYPE: DNA
<213> ORGANISM: Artificial Sequence
<220> FEATURE:
<223> OTHER INFORMATION: MF3031: heavy chain variable region sequence of
      an erbB-2 binding antibody
<220> FEATURE:
<221> NAME/KEY: CDS
<222> LOCATION: (20)..(382)

<400> SEQUENCE: 52

```
ggcccagccg gccatggcc cag gtc cag ctg cag cag tct ggg gct gag ctg        52
                     Gln Val Gln Leu Gln Gln Ser Gly Ala Glu Leu
                       1               5                   10 gtg agg cct ggg gct tca gtg aag ctg tcc tgc aag gct tct ggc tac       100
Val Arg Pro Gly Ala Ser Val Lys Leu Ser Cys Lys Ala Ser Gly Tyr
             15                  20                  25 act ttc act gcc tac tat ata aac tgg gtg aag cag agg cct gga cag       148
Thr Phe Thr Ala Tyr Tyr Ile Asn Trp Val Lys Gln Arg Pro Gly Gln
             30                  35                  40 gga ctt gag tgg att gca aag att tat cct gga agt ggt tat act tac       196
Gly Leu Glu Trp Ile Ala Lys Ile Tyr Pro Gly Ser Gly Tyr Thr Tyr
    45                  50                  55 tac aat gag aat ttc agg ggc aag gcc aca ctg act gca gaa gaa tcc       244
Tyr Asn Glu Asn Phe Arg Gly Lys Ala Thr Leu Thr Ala Glu Glu Ser
60                  65                  70                  75 tcc agt act gcc tac ata caa ctc agc agc ctg aca tct gag gac tct       292
Ser Ser Thr Ala Tyr Ile Gln Leu Ser Ser Leu Thr Ser Glu Asp Ser
                80                  85                  90 gct gtc tat ttc tgt gca aga ggc gtc tat gat tac gac ggg gcc tgg       340
Ala Val Tyr Phe Cys Ala Arg Gly Val Tyr Asp Tyr Asp Gly Ala Trp
                95                 100                 105 ttt gct tac tgg ggc caa ggg act ctg gtc acc gtc tcc agt               382
Phe Ala Tyr Trp Gly Gln Gly Thr Leu Val Thr Val Ser Ser
            110                 115                 120
```

<210> SEQ ID NO 53
<211> LENGTH: 121
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Gln Gln Ser Gly Ala Glu Leu Val Arg Pro Gly Ala
1               5                   10                  15

Ser Val Lys Leu Ser Cys Lys Ala Ser Gly Tyr Thr Phe Thr Ala Tyr
            20                  25                  30

Tyr Ile Asn Trp Val Lys Gln Arg Pro Gly Gln Gly Leu Glu Trp Ile
        35                  40                  45

Ala Lys Ile Tyr Pro Gly Ser Gly Tyr Thr Tyr Tyr Asn Glu Asn Phe
    50                  55                  60

Arg Gly Lys Ala Thr Leu Thr Ala Glu Glu Ser Ser Ser Thr Ala Tyr
65                  70                  75                  80

```
Ile Gln Leu Ser Ser Leu Thr Ser Glu Asp Ser Ala Val Tyr Phe Cys
                85                  90                  95

Ala Arg Gly Val Tyr Asp Tyr Asp Gly Ala Trp Phe Ala Tyr Trp Gly
            100                 105                 110

Gln Gly Thr Leu Val Thr Val Ser Ser
        115                 120

<210> SEQ ID NO 54
<211> LENGTH: 16
<212> TYPE: PRT
<213> ORGANISM: Artificial Sequence
<220> FEATURE:
<223> OTHER INFORMATION: MF3031 CDR1

<400> SEQUENCE: 54

Ala Tyr Tyr Ile Asn Trp Val Lys Gln Arg Pro Gly Gln Gly Leu Glu
1               5                   10                  15

<210> SEQ ID NO 55
<211> LENGTH: 6
<212> TYPE: PRT
<213> ORGANISM: Artificial Sequence
<220> FEATURE:
<223> OTHER INFORMATION: MF3031 CDR2

<400> SEQUENCE: 55

Asn Glu Asn Phe Arg Gly
1               5

<210> SEQ ID NO 56
<211> LENGTH: 12
<212> TYPE: PRT
<213> ORGANISM: Artificial Sequence
<220> FEATURE:
<223> OTHER INFORMATION: MF3031 CDR3

<400> SEQUENCE: 56

Gly Val Tyr Asp Tyr Asp Gly Ala Trp Phe Ala Tyr
1               5                   10

<210> SEQ ID NO 57
<211> LENGTH: 382
<212> TYPE: DNA
<213> ORGANISM: Artificial Sequence
<220> FEATURE:
<223> OTHER INFORMATION: MF3991: heavy chain variable region sequence of
      an erbB-2 binding antibody
<220> FEATURE:
<221> NAME/KEY: CDS
<222> LOCATION: (20)..(382)

<400> SEQUENCE: 57
ggcccagccg gccatggcc cag gtg cag ctg gtg cag tct ggc gcc gaa gtg       52
                     Gln Val Gln Leu Val Gln Ser Gly Ala Glu Val
                      1               5                   10 aag aaa cct ggc gcc agc gtg aag ctg agc tgc aag gcc agc ggc tac      100
Lys Lys Pro Gly Ala Ser Val Lys Leu Ser Cys Lys Ala Ser Gly Tyr
             15                  20                  25 acc ttc acc gcc tac tac atc aac tgg gtc cga cag gcc cca ggc cag      148
Thr Phe Thr Ala Tyr Tyr Ile Asn Trp Val Arg Gln Ala Pro Gly Gln
         30                  35                  40 ggc ctg gaa tgg atc ggc aga atc tac ccc ggc tcc ggc tac acc agc      196
Gly Leu Glu Trp Ile Gly Arg Ile Tyr Pro Gly Ser Gly Tyr Thr Ser
     45                  50                  55
```

```
tac gcc cag aag ttc cag ggc aga gcc acc ctg acc gcc gac gag agc    244
Tyr Ala Gln Lys Phe Gln Gly Arg Ala Thr Leu Thr Ala Asp Glu Ser
60              65                  70                  75 acc agc acc gcc tac atg gaa ctg agc agc ctg cgg agc gag gat acc    292
Thr Ser Thr Ala Tyr Met Glu Leu Ser Ser Leu Arg Ser Glu Asp Thr
            80                  85                  90 gcc gtg tac ttc tgc gcc aga ccc cac tac ggc tac gac gac tgg tac    340
Ala Val Tyr Phe Cys Ala Arg Pro His Tyr Gly Tyr Asp Asp Trp Tyr
        95                  100                 105 ttc ggc gtg tgg ggc cag ggc acc ctg gtc acc gtc tcc agt            382
Phe Gly Val Trp Gly Gln Gly Thr Leu Val Thr Val Ser Ser
        110                 115                 120
```

<210> SEQ ID NO 58
<211> LENGTH: 121
<212> TYPE: PRT
<213> ORGANISM: Artificial Sequence
<220> FEATURE:
<223> OTHER INFORMATION: Synthetic Construct

<400> SEQUENCE: 58

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ala Tyr
            20                  25                  30

Tyr Ile Asn Trp Val Arg Gln Ala Pro Gly Gln Gly Leu Glu Trp Ile
        35                  40                  45

Gly Arg Ile Tyr Pro Gly Ser Gly Tyr Thr Ser Tyr Ala Gln Lys Phe
    50                  55                  60

Gln Gly Arg Ala Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Pro His Tyr Gly Tyr Asp Asp Trp Tyr Phe Gly Val Trp Gly
            100                 105                 110

Gln Gly Thr Leu Val Thr Val Ser Ser
        115                 120

<210> SEQ ID NO 59
<211> LENGTH: 5
<212> TYPE: PRT
<213> ORGANISM: Artificial Sequence
<220> FEATURE:
<223> OTHER INFORMATION: MF3991 CDR1

<400> SEQUENCE: 59

Ala Tyr Tyr Ile Asn
1               5

<210> SEQ ID NO 60
<211> LENGTH: 17
<212> TYPE: PRT
<213> ORGANISM: Artificial Sequence
<220> FEATURE:
<223> OTHER INFORMATION: MF3991 CDR2

<400> SEQUENCE: 60

Arg Ile Tyr Pro Gly Ser Gly Tyr Thr Ser Tyr Ala Gln Lys Phe Gln
1               5                   10                  15

Gly

```
<210> SEQ ID NO 61
<211> LENGTH: 12
<212> TYPE: PRT
<213> ORGANISM: Artificial Sequence
<220> FEATURE:
<223> OTHER INFORMATION: MF3991 CDR3

<400> SEQUENCE: 61

Pro His Tyr Gly Tyr Asp Asp Trp Tyr Phe Gly Val
1               5                   10

<210> SEQ ID NO 62
<211> LENGTH: 391
<212> TYPE: DNA
<213> ORGANISM: Artificial Sequence
<220> FEATURE:
<223> OTHER INFORMATION: MF3178: heavy chain variable region sequence of
      an erbB-3 binding antibody
<220> FEATURE:
<221> NAME/KEY: CDS
<222> LOCATION: (20)..(391)

<400> SEQUENCE: 62
ggcccagccg gccatggcc cag gtg cag ctg gtg cag tct ggg gct gag gtg         52
                     Gln Val Gln Leu Val Gln Ser Gly Ala Glu Val
                      1               5                   10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
         15                  20                  25 acc ttc acc ggc tac tat atg cac tgg gtg cga cag gcc cct gga caa        148
Thr Phe Thr Gly Tyr Tyr Met His Trp Val Arg Gln Ala Pro Gly Gln
         30                  35                  40 ggg ctt gag tgg atg gga tgg atc aac cct aac agt ggt ggc aca aac        196
Gly Leu Glu Trp Met Gly Trp Ile Asn Pro Asn Ser Gly Gly Thr Asn
     45                  50                  55 tat gca cag aag ttt cag ggc agg gtc acg atg acc agg gac acg tcc        244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg        292
Ile Ser Thr Ala Tyr Met Glu Leu Ser Arg Leu Arg Ser Asp Asp Thr
                 80                  85                  90 gct gtg tat tac tgt gca aga gat cat ggt tct cgt cat ttc tgg tct        340
Ala Val Tyr Tyr Cys Ala Arg Asp His Gly Ser Arg His Phe Trp Ser
             95                  100                 105 tac tgg ggc ttt gat tat tgg ggc caa ggt acc ctg gtc acc gtc tcc        388
Tyr Trp Gly Phe Asp Tyr Trp Gly Gln Gly Thr Leu Val Thr Val Ser
         110                 115                 120 agt                                                                    391
Ser

<210> SEQ ID NO 63
<211> LENGTH: 124
<212> TYPE: PRT
<213> ORGANISM: Artificial Sequence
<220> FEATURE:
<223> OTHER INFORMATION: Synthetic Construct

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

```
Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 64
<211> LENGTH: 5
<212> TYPE: PRT
<213> ORGANISM: Artificial Sequence
<220> FEATURE:
<223> OTHER INFORMATION: MF3178 CDR1

<400> SEQUENCE: 64

Gly Tyr Tyr Met His
1               5

<210> SEQ ID NO 65
<211> LENGTH: 17
<212> TYPE: PRT
<213> ORGANISM: Artificial Sequence
<220> FEATURE:
<223> OTHER INFORMATION: MF3178 CDR2

<400> SEQUENCE: 65

Trp Ile Asn Pro Asn Ser Gly Gly Thr Asn Tyr Ala Gln Lys Phe Gln
1               5                   10                  15

Gly

<210> SEQ ID NO 66
<211> LENGTH: 15
<212> TYPE: PRT
<213> ORGANISM: Artificial Sequence
<220> FEATURE:
<223> OTHER INFORMATION: MF3178 CDR3

<400> SEQUENCE: 66

Asp His Gly Ser Arg His Phe Trp Ser Tyr Trp Gly Phe Asp Tyr
1               5                   10                  15

<210> SEQ ID NO 67
<211> LENGTH: 385
<212> TYPE: DNA
<213> ORGANISM: Artificial Sequence
<220> FEATURE:
<223> OTHER INFORMATION: MF3176: heavy chain variable region sequence of
      an erbB-3 binding antibody
<220> FEATURE:
<221> NAME/KEY: CDS
<222> LOCATION: (20)..(385)

<400> SEQUENCE: 67
ggcccagccg gccatggcc gag gtg cag ctg ttg gag tct ggg gga ggc ttg         52
                     Glu Val Gln Leu Leu Glu Ser Gly Gly Gly Leu
                      1               5                   10 gta cag cct ggg ggg tcc ctg aga ctc tcc tgt gca gcc tct gga ttc         100
Val Gln Pro Gly Gly Ser Leu Arg Leu Ser Cys Ala Ala Ser Gly Phe
            15                  20                  25
```

```
acc ttt agc agc tat gcc atg agc tgg gtc cgc cag gct cca ggg aag      148
Thr Phe Ser Ser Tyr Ala Met Ser Trp Val Arg Gln Ala Pro Gly Lys
    30              35                  40 ggg ctg gag tgg gtc tca gct att agt ggt agt ggt ggt agc aca tac      196
Gly Leu Glu Trp Val Ser Ala Ile Ser Gly Ser Gly Gly Ser Thr Tyr
45              50              55 tac gca gac tcc gtg aag ggc cgg ttc acc atc tcc aga gac aat tcc      244
Tyr Ala Asp Ser Val Lys Gly Arg Phe Thr Ile Ser Arg Asp Asn Ser
60              65                  70              75 aag aac acg ctg tat ctg caa atg aac agc ctg aga gcc gag gac acg      292
Lys Asn Thr Leu Tyr Leu Gln Met Asn Ser Leu Arg Ala Glu Asp Thr
                80              85                  90 gct gtg tat tac tgt gca aga gat tgg tgg tac ccg ccg tac tac tgg      340
Ala Val Tyr Tyr Cys Ala Arg Asp Trp Trp Tyr Pro Pro Tyr Tyr Trp
            95                  100             105 ggc ttt gat tat tgg ggc caa ggt acc ctg gtc acc gtc tcc agt          385
Gly Phe Asp Tyr Trp Gly Gln Gly Thr Leu Val Thr Val Ser Ser
        110             115                 120
```

<210> SEQ ID NO 68
<211> LENGTH: 122
<212> TYPE: PRT
<213> ORGANISM: Artificial Sequence
<220> FEATURE:
<223> OTHER INFORMATION: Synthetic Construct

<400> SEQUENCE: 68

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Trp Trp Tyr Pro Pro Tyr Tyr Trp Gly Phe Asp Tyr Trp
            100                 105                 110

Gly Gln Gly Thr Leu Val Thr Val Ser Ser
        115                 120
```

<210> SEQ ID NO 69
<211> LENGTH: 5
<212> TYPE: PRT
<213> ORGANISM: Artificial Sequence
<220> FEATURE:
<223> OTHER INFORMATION: MF3176 CDR1

<400> SEQUENCE: 69

```
Ser Tyr Ala Met Ser
1               5
```

<210> SEQ ID NO 70
<211> LENGTH: 17
<212> TYPE: PRT
<213> ORGANISM: Artificial Sequence
<220> FEATURE:
<223> OTHER INFORMATION: MF3176 CDR2

-continued

<400> SEQUENCE: 70

Ala Ile Ser Gly Ser Gly Gly Ser Thr Tyr Tyr Ala Asp Ser Val Lys
1               5                   10                  15

Gly

<210> SEQ ID NO 71
<211> LENGTH: 13
<212> TYPE: PRT
<213> ORGANISM: Artificial Sequence
<220> FEATURE:
<223> OTHER INFORMATION: MF3176 CDR3

<400> SEQUENCE: 71

Asp Trp Trp Tyr Pro Pro Tyr Tyr Trp Gly Phe Asp Tyr
1               5                   10

<210> SEQ ID NO 72
<211> LENGTH: 391
<212> TYPE: DNA
<213> ORGANISM: Artificial Sequence
<220> FEATURE:
<223> OTHER INFORMATION: MF3163: heavy chain variable region sequence of
      an erbB-3 binding antibody
<220> FEATURE:
<221> NAME/KEY: CDS
<222> LOCATION: (20)..(391)

<400> SEQUENCE: 72
ggcccagccg gccatggcc cag gtg cag ctg gtg cag tct ggg gct gag gtg      52
                     Gln Val Gln Leu Val Gln Ser Gly Ala Glu Val
                     1               5                   10 aag aag cct ggg gcc tca gtg aag gtc tcc tgc aag gct tct gga tac     100
Lys Lys Pro Gly Ala Ser Val Lys Val Ser Cys Lys Ala Ser Gly Tyr
            15                  20                  25 acc ttc acc ggc tac tat atg cac tgg gtg cga cag gcc cct gga caa     148
Thr Phe Thr Gly Tyr Tyr Met His Trp Val Arg Gln Ala Pro Gly Gln
                30                  35                  40 ggg ctt gag tgg atg gga tgg atc aac cct aac agt ggt ggc aca aac     196
Gly Leu Glu Trp Met Gly Trp Ile Asn Pro Asn Ser Gly Gly Thr Asn
    45                  50                  55 tat gca cag aag ttt cag ggc agg gtc acg atg acc agg gac acg tcc     244
Tyr Ala Gln Lys Phe Gln Gly Arg Val Thr Met Thr Arg Asp Thr Ser
60                  65                  70                  75 atc agc aca gcc tac atg gag ctg agc agg ctg aga tct gac gac acg     292
Ile Ser Thr Ala Tyr Met Glu Leu Ser Arg Leu Arg Ser Asp Asp Thr
                80                  85                  90 gcc gtg tat tac tgt gca aaa gat tct tac tct cgt cat ttc tac tct     340
Ala Val Tyr Tyr Cys Ala Lys Asp Ser Tyr Ser Arg His Phe Tyr Ser
                95                  100                 105 tgg tgg gcc ttt gat tat tgg ggc caa ggt acc ctg gtc acc gtc tcc     388
Trp Trp Ala Phe Asp Tyr Trp Gly Gln Gly Thr Leu Val Thr Val Ser
        110                 115                 120 agt                                                                  391
Ser

<210> SEQ ID NO 73
<211> LENGTH: 124
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Lys Asp Ser Tyr Ser Arg His Phe Tyr Ser Trp Trp Ala Phe Asp
            100                 105                 110

Tyr Trp Gly Gln Gly Thr Leu Val Thr Val Ser Ser
        115                 120

<210> SEQ ID NO 74
<211> LENGTH: 5
<212> TYPE: PRT
<213> ORGANISM: Artificial Sequence
<220> FEATURE:
<223> OTHER INFORMATION: MF3163 CDR1

<400> SEQUENCE: 74

Gly Tyr Tyr Met His
1               5

<210> SEQ ID NO 75
<211> LENGTH: 17
<212> TYPE: PRT
<213> ORGANISM: Artificial Sequence
<220> FEATURE:
<223> OTHER INFORMATION: MF3163 CDR2

<400> SEQUENCE: 75

Trp Ile Asn Pro Asn Ser Gly Gly Thr Asn Tyr Ala Gln Lys Phe Gln
1               5                   10                  15

Gly

<210> SEQ ID NO 76
<211> LENGTH: 15
<212> TYPE: PRT
<213> ORGANISM: Artificial Sequence
<220> FEATURE:
<223> OTHER INFORMATION: MF3163 CDR3

<400> SEQUENCE: 76

Asp Ser Tyr Ser Arg His Phe Tyr Ser Trp Trp Ala Phe Asp Tyr
1               5                   10                  15

<210> SEQ ID NO 77
<211> LENGTH: 382
<212> TYPE: DNA
<213> ORGANISM: Artificial Sequence
<220> FEATURE:
<223> OTHER INFORMATION: MF3099: heavy chain variable region sequence of
      an erbB-3 binding antibody
<220> FEATURE:
<221> NAME/KEY: CDS
<222> LOCATION: (20)..(382)

<400> SEQUENCE: 77

```
ggcccagccg gccatggcc gag gtc cag ctg cag cag cct ggg gct gag ctg      52
                     Glu Val Gln Leu Gln Gln Pro Gly Ala Glu Leu
                      1               5                  10 gtg agg cct ggg act tca gtg aag ttg tcc tgc aag gct tct ggc tac      100
Val Arg Pro Gly Thr Ser Val Lys Leu Ser Cys Lys Ala Ser Gly Tyr
             15                  20                  25 acc ttc acc agc tac tgg atg cac tgg gta aag cag agg cct gga caa      148
Thr Phe Thr Ser Tyr Trp Met His Trp Val Lys Gln Arg Pro Gly Gln
         30                  35                  40 ggc ctt gag tgg atc gga att ctt gat cct tct gat agt tat act acc      196
Gly Leu Glu Trp Ile Gly Ile Leu Asp Pro Ser Asp Ser Tyr Thr Thr
     45                  50                  55 tac aat caa aag ttc aag ggc aag gcc aca tta aca gta gac aca tcc      244
Tyr Asn Gln Lys Phe Lys Gly Lys Ala Thr Leu Thr Val Asp Thr Ser
 60              65                  70                  75 tcc agc ata gcc tac atg cag ctc agc agc ctg aca tct gag gac tct      292
Ser Ser Ile Ala Tyr Met Gln Leu Ser Ser Leu Thr Ser Glu Asp Ser
                 80                  85                  90 gcg ctc tat tac tgt gca aga ggg gga gat tac gac gag gga ggt gct      340
Ala Leu Tyr Tyr Cys Ala Arg Gly Gly Asp Tyr Asp Glu Gly Gly Ala
             95                  100                 105 atg gac tac tgg ggt caa gga acc tcg gtc acc gtc tcc agt             382
Met Asp Tyr Trp Gly Gln Gly Thr Ser Val Thr Val Ser Ser
         110                 115                 120
```

<210> SEQ ID NO 78
<211> LENGTH: 121
<212> TYPE: PRT
<213> ORGANISM: Artificial Sequence
<220> FEATURE:
<223> OTHER INFORMATION: Synthetic Construct

<400> SEQUENCE: 78

```
Glu Val Gln Leu Gln Gln Pro Gly Ala Glu Leu Val Arg Pro Gly Thr
 1               5                  10                  15

Ser Val Lys Leu Ser Cys Lys Ala Ser Gly Tyr Thr Phe Thr Ser Tyr
             20                  25                  30

Trp Met His Trp Val Lys Gln Arg Pro Gly Gln Gly Leu Glu Trp Ile
         35                  40                  45

Gly Ile Leu Asp Pro Ser Asp Ser Tyr Thr Thr Tyr Asn Gln Lys Phe
     50                  55                  60

Lys Gly Lys Ala Thr Leu Thr Val Asp Thr Ser Ser Ser Ile Ala Tyr
 65                  70                  75                  80

Met Gln Leu Ser Ser Leu Thr Ser Glu Asp Ser Ala Leu Tyr Tyr Cys
                 85                  90                  95

Ala Arg Gly Gly Asp Tyr Asp Glu Gly Gly Ala Met Asp Tyr Trp Gly
             100                 105                 110

Gln Gly Thr Ser Val Thr Val Ser Ser
         115                 120
```

<210> SEQ ID NO 79
<211> LENGTH: 5
<212> TYPE: PRT
<213> ORGANISM: Artificial Sequence
<220> FEATURE:
<223> OTHER INFORMATION: MF3099 CDR1

<400> SEQUENCE: 79

Ser Tyr Trp Met His
1               5

<210> SEQ ID NO 80
<211> LENGTH: 17
<212> TYPE: PRT
<213> ORGANISM: Artificial Sequence
<220> FEATURE:
<223> OTHER INFORMATION: MF3099 CDR2

<400> SEQUENCE: 80

Ile Leu Asp Pro Ser Asp Ser Tyr Thr Thr Tyr Asn Gln Lys Phe Lys
1               5                   10                  15
Gly

<210> SEQ ID NO 81
<211> LENGTH: 12
<212> TYPE: PRT
<213> ORGANISM: Artificial Sequence
<220> FEATURE:
<223> OTHER INFORMATION: MF3099 CDR3

<400> SEQUENCE: 81

Gly Gly Asp Tyr Asp Glu Gly Gly Ala Met Asp Tyr
1               5                   10

<210> SEQ ID NO 82
<211> LENGTH: 391
<212> TYPE: DNA
<213> ORGANISM: Artificial Sequence
<220> FEATURE:
<223> OTHER INFORMATION: MF3307: heavy chain variable region sequence of
      an erbB-3 binding antibody
<220> FEATURE:
<221> NAME/KEY: CDS
<222> LOCATION: (20)..(391)

<400> SEQUENCE: 82

```
ggcccagccg gccatggcc cag gtg cag ctg gtg cag tct ggg gct gag gtg         52
                     Gln Val Gln Leu Val Gln Ser Gly Ala Glu Val
                      1               5                  10 aag aag cct ggg gcc tca gtg aag gtc tcc tgc aag gct tct gga tac         100
Lys Lys Pro Gly Ala Ser Val Lys Val Ser Cys Lys Ala Ser Gly Tyr
         15                  20                  25 acc ttc acc ggc tac tat atg cac tgg gtg cga cag gcc cct gga caa         148
Thr Phe Thr Gly Tyr Tyr Met His Trp Val Arg Gln Ala Pro Gly Gln
             30                  35                  40 ggg ctt gag tgg atg gga tgg atc aac cct aac agt ggt ggc aca aac         196
Gly Leu Glu Trp Met Gly Trp Ile Asn Pro Asn Ser Gly Gly Thr Asn
     45                  50                  55 tat gca cag aag ttt cag ggc agg gtc acg atg acc agg gac acg tcc         244
Tyr Ala Gln Lys Phe Gln Gly Arg Val Thr Met Thr Arg Asp Thr Ser
 60                  65                  70                  75 atc agc aca gcc tac atg gag ctg agc agg ctg aga tct gac gac acg         292
Ile Ser Thr Ala Tyr Met Glu Leu Ser Arg Leu Arg Ser Asp Asp Thr
                 80                  85                  90 gcc gtg tat tac tgt gca aga ggt tct cgt aaa cgt ctg tct aac tac         340
Ala Val Tyr Tyr Cys Ala Arg Gly Ser Arg Lys Arg Leu Ser Asn Tyr
             95                 100                 105 ttc aac gcc ttt gat tat tgg ggc caa ggt acc ctg gtc acc gtc tcc         388
Phe Asn Ala Phe Asp Tyr Trp Gly Gln Gly Thr Leu Val Thr Val Ser
         110                 115                 120
``` agt                                                                      391
Ser <210> SEQ ID NO 83
<211> LENGTH: 124
<212> TYPE: PRT
<213> ORGANISM: Artificial Sequence
<220> FEATURE:
<223> OTHER INFORMATION: Synthetic Construct

<400> SEQUENCE: 83

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Ser Arg Lys Arg Leu Ser Asn Tyr Phe Asn Ala Phe Asp
            100                 105                 110

Tyr Trp Gly Gln Gly Thr Leu Val Thr Val Ser Ser
        115                 120

<210> SEQ ID NO 84
<211> LENGTH: 5
<212> TYPE: PRT
<213> ORGANISM: Artificial Sequence
<220> FEATURE:
<223> OTHER INFORMATION: MF3307 CDR1

<400> SEQUENCE: 84

Gly Tyr Tyr Met His
1               5

<210> SEQ ID NO 85
<211> LENGTH: 17
<212> TYPE: PRT
<213> ORGANISM: Artificial Sequence
<220> FEATURE:
<223> OTHER INFORMATION: MF3307 CDR2

<400> SEQUENCE: 85

Trp Ile Asn Pro Asn Ser Gly Gly Thr Asn Tyr Ala Gln Lys Phe Gln
1               5                   10                  15

Gly

<210> SEQ ID NO 86
<211> LENGTH: 15
<212> TYPE: PRT
<213> ORGANISM: Artificial Sequence
<220> FEATURE:
<223> OTHER INFORMATION: MF3307 CDR3

<400> SEQUENCE: 86

Gly Ser Arg Lys Arg Leu Ser Asn Tyr Phe Asn Ala Phe Asp Tyr
1               5                   10                  15

<210> SEQ ID NO 87
<211> LENGTH: 214
<212> TYPE: PRT
<213> ORGANISM: Artificial Sequence
<220> FEATURE:
<223> OTHER INFORMATION: Common Light Chain

<400> SEQUENCE: 87

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 88
<211> LENGTH: 450
<212> TYPE: PRT
<213> ORGANISM: Artificial Sequence
<220> FEATURE:
<223> OTHER INFORMATION: heavy chain for erbB-2 binding

<400> SEQUENCE: 88

```
Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Ala Tyr
            20                  25                  30

Tyr Ile Asn Trp Val Arg Gln Ala Pro Gly Gln Gly Leu Glu Trp Ile
        35                  40                  45

Gly Arg Ile Tyr Pro Gly Ser Gly Tyr Thr Ser Tyr Ala Gln Lys Phe
    50                  55                  60

Gln Gly Arg Ala Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Phe Cys
                85                  90                  95
```

```
Ala Arg Pro Pro Val Tyr Tyr Asp Ser Ala Trp Phe Ala Tyr Trp Gly
            100                 105                 110

Gln Gly Thr Leu Val Thr Val Ser Ala Ser Thr Lys Gly Pro Ser
    115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Asp Pro Pro Ser Arg Glu Glu Met Thr Lys Asn Gln Val Ser
        355                 360                 365

Leu Thr Cys Glu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 89
<211> LENGTH: 453
<212> TYPE: PRT
<213> ORGANISM: Artificial Sequence
<220> FEATURE:
<223> OTHER INFORMATION: heavy chain for erbB-3 binding
```

<400> SEQUENCE: 89

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
        180                 185                 190

Val Thr Val Pro Ser Ser Ser Leu Gly Thr Gln Thr Tyr Ile Cys Asn
            195                 200                 205

Val Asn His Lys Pro Ser Asn Thr Lys Val Asp Lys Arg Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Lys Pro Pro Ser Arg Glu Glu Met Thr Lys Asn
            355                 360                 365

Gln Val Ser Leu Lys Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

```
Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
        435                 440                 445

Ser Leu Ser Pro Gly
    450

<210> SEQ ID NO 90
<211> LENGTH: 379
<212> TYPE: DNA
<213> ORGANISM: Artificial Sequence
<220> FEATURE:
<223> OTHER INFORMATION: MF2889: heavy chain variable region sequence of
      an erbB-2 binding antibody
<220> FEATURE:
<221> NAME/KEY: CDS
<222> LOCATION: (20)..(379)

<400> SEQUENCE: 90
ggcccagccg gccatggcc gag gtc cag ctg cag cag tct gga gct gag ctg         52
                     Glu Val Gln Leu Gln Gln Ser Gly Ala Glu Leu
                      1               5                  10 gta agg cct ggg act tca gtg aag gtg tcc tgc aag gct tct gga tac        100
Val Arg Pro Gly Thr Ser Val Lys Val Ser Cys Lys Ala Ser Gly Tyr
         15                  20                  25 gcc ttc act aat tat ttg ata gag tgg gta aag cag agg cct ggc cag        148
Ala Phe Thr Asn Tyr Leu Ile Glu Trp Val Lys Gln Arg Pro Gly Gln
         30                  35                  40 ggc ctt gag tgg att gga gtg att tat cct gaa ggt ggt ggt act atc        196
Gly Leu Glu Trp Ile Gly Val Ile Tyr Pro Glu Gly Gly Gly Thr Ile
 45                  50                  55 tac aat gag aag ttc aag ggc aag gca aca ctg act gca gac aaa tcc        244
Tyr Asn Glu Lys Phe Lys Gly Lys Ala Thr Leu Thr Ala Asp Lys Ser
 60                  65                  70                  75 tcc agc act gcc tac atg cag ctc agc ggc ctg aca tct gag gac tct        292
Ser Ser Thr Ala Tyr Met Gln Leu Ser Gly Leu Thr Ser Glu Asp Ser
             80                  85                  90 gcg gtc tat ttc tgt gca aga gga gac tat gat tac aaa tat gct atg        340
Ala Val Tyr Phe Cys Ala Arg Gly Asp Tyr Asp Tyr Lys Tyr Ala Met
             95                 100                 105 gac tac tgg ggt caa gga acc tcg gtc acc gtc tcc agt                    379
Asp Tyr Trp Gly Gln Gly Thr Ser Val Thr Val Ser Ser
        110                 115                 120

<210> SEQ ID NO 91
<211> LENGTH: 120
<212> TYPE: PRT
<213> ORGANISM: Artificial Sequence
<220> FEATURE:
<223> OTHER INFORMATION: Synthetic Construct

<400> SEQUENCE: 91

Glu Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asn Tyr
             20                  25                  30

Leu Ile Glu Trp Val Lys Gln Arg Pro Gly Gln Gly Leu Glu Trp Ile
         35                  40                  45
```

```
Gly Val Ile Tyr Pro Glu Gly Gly Thr Ile Tyr Asn Glu Lys Phe
 50                  55                  60

Lys Gly Lys Ala Thr Leu Thr Ala Asp Lys Ser Ser Thr Ala Tyr
 65                  70                  75                  80

Met Gln Leu Ser Gly Leu Thr Ser Glu Asp Ser Ala Val Tyr Phe Cys
                 85                  90                  95

Ala Arg Gly Asp Tyr Asp Tyr Lys Tyr Ala Met Asp Tyr Trp Gly Gln
             100                 105                 110

Gly Thr Ser Val Thr Val Ser Ser
         115                 120

<210> SEQ ID NO 92
<211> LENGTH: 5
<212> TYPE: PRT
<213> ORGANISM: Artificial Sequence
<220> FEATURE:
<223> OTHER INFORMATION: CDR1

<400> SEQUENCE: 92

Asn Tyr Leu Ile Glu
1               5

<210> SEQ ID NO 93
<211> LENGTH: 17
<212> TYPE: PRT
<213> ORGANISM: Artificial Sequence
<220> FEATURE:
<223> OTHER INFORMATION: CDR2

<400> SEQUENCE: 93

Val Ile Tyr Pro Glu Gly Gly Thr Ile Tyr Asn Glu Lys Phe Lys
1               5                   10                  15

Gly

<210> SEQ ID NO 94
<211> LENGTH: 11
<212> TYPE: PRT
<213> ORGANISM: Artificial Sequence
<220> FEATURE:
<223> OTHER INFORMATION: CDR3

<400> SEQUENCE: 94

Gly Asp Tyr Asp Tyr Lys Tyr Ala Met Asp Tyr
1               5                   10

<210> SEQ ID NO 95
<211> LENGTH: 370
<212> TYPE: DNA
<213> ORGANISM: Artificial Sequence
<220> FEATURE:
<223> OTHER INFORMATION: MF2913: heavy chain variable region sequence of
      an erbB-2 binding antibody
<220> FEATURE:
<221> NAME/KEY: CDS
<222> LOCATION: (20)..(370)

<400> SEQUENCE: 95
ggcccagccg gccatggcc gag gtc aag ctg cag cag tct gga cct gag ctg      52
                     Glu Val Lys Leu Gln Gln Ser Gly Pro Glu Leu
                       1               5                  10 gtg aag cct ggc gct tca gtg aag ata tcc tgc aag gct tct ggt tac     100
Val Lys Pro Gly Ala Ser Val Lys Ile Ser Cys Lys Ala Ser Gly Tyr
         15                  20                  25
```

```
tca ttc act gac tac aaa atg gac tgg gtg aag cag agc cat gga aag      148
Ser Phe Thr Asp Tyr Lys Met Asp Trp Val Lys Gln Ser His Gly Lys
         30                  35                  40 agc ctc gaa tgg att gga aat att aat cct aac agt ggt ggt gtt atc      196
Ser Leu Glu Trp Ile Gly Asn Ile Asn Pro Asn Ser Gly Gly Val Ile
 45                  50                  55 tac aac cag aag ttc agg ggc aag gtc aca ttg act gtt gac agg tcc      244
Tyr Asn Gln Lys Phe Arg Gly Lys Val Thr Leu Thr Val Asp Arg Ser
 60                  65                  70                  75 tcc agc gca gcc tac atg gag ctc cgc agc ctg aca tct gag gac act      292
Ser Ser Ala Ala Tyr Met Glu Leu Arg Ser Leu Thr Ser Glu Asp Thr
                 80                  85                  90 gca gtc tat tat tgt tca aga gga ctg tgg gat gct atg gac tcc tgg      340
Ala Val Tyr Tyr Cys Ser Arg Gly Leu Trp Asp Ala Met Asp Ser Trp
                 95                 100                 105 ggt caa gga acc tcg gtc acc gtc tcc agt                              370
Gly Gln Gly Thr Ser Val Thr Val Ser Ser
        110                 115
```

<210> SEQ ID NO 96
<211> LENGTH: 117
<212> TYPE: PRT
<213> ORGANISM: Artificial Sequence
<220> FEATURE:
<223> OTHER INFORMATION: Synthetic Construct

<400> SEQUENCE: 96

```
Glu Val Lys Leu Gln Gln Ser Gly Pro Glu Leu Val Lys Pro Gly Ala
 1               5                  10                  15

Ser Val Lys Ile Ser Cys Lys Ala Ser Gly Tyr Ser Phe Thr Asp Tyr
             20                  25                  30

Lys Met Asp Trp Val Lys Gln Ser His Gly Lys Ser Leu Glu Trp Ile
         35                  40                  45

Gly Asn Ile Asn Pro Asn Ser Gly Gly Val Ile Tyr Asn Gln Lys Phe
     50                  55                  60

Arg Gly Lys Val Thr Leu Thr Val Asp Arg Ser Ser Ser Ala Ala Tyr
 65                  70                  75                  80

Met Glu Leu Arg Ser Leu Thr Ser Glu Asp Thr Ala Val Tyr Tyr Cys
                 85                  90                  95

Ser Arg Gly Leu Trp Asp Ala Met Asp Ser Trp Gly Gln Gly Thr Ser
            100                 105                 110

Val Thr Val Ser Ser
        115
```

<210> SEQ ID NO 97
<211> LENGTH: 16
<212> TYPE: PRT
<213> ORGANISM: Artificial Sequence
<220> FEATURE:
<223> OTHER INFORMATION: CDR1

<400> SEQUENCE: 97

```
Asp Tyr Lys Met Asp Trp Val Lys Gln Ser His Gly Lys Ser Leu Glu
 1               5                  10                  15
```

<210> SEQ ID NO 98
<211> LENGTH: 6
<212> TYPE: PRT
<213> ORGANISM: Artificial Sequence
<220> FEATURE:
<223> OTHER INFORMATION: CDR2

<400> SEQUENCE: 98

Asn Gln Lys Phe Arg Gly
1               5

<210> SEQ ID NO 99
<211> LENGTH: 8
<212> TYPE: PRT
<213> ORGANISM: Artificial Sequence
<220> FEATURE:
<223> OTHER INFORMATION: CDR3

<400> SEQUENCE: 99

Gly Leu Trp Asp Ala Met Asp Ser
1               5

<210> SEQ ID NO 100
<211> LENGTH: 382
<212> TYPE: DNA
<213> ORGANISM: Artificial Sequence
<220> FEATURE:
<223> OTHER INFORMATION: MF1847: heavy chain variable region sequence of
      an erbB-2 binding antibody
<220> FEATURE:
<221> NAME/KEY: CDS
<222> LOCATION: (20)..(382)

<400> SEQUENCE: 100

```
ggcccagccg ccatggcc cag gtg cag ctg gtg gag tct ggg gga ggc gtg        52
                    Gln Val Gln Leu Val Glu Ser Gly Gly Gly Val
                     1               5                  10 gtc cag cct ggg agg tcc ctg aga ctc tcc tgt gca gcc tct gga ttc       100
Val Gln Pro Gly Arg Ser Leu Arg Leu Ser Cys Ala Ala Ser Gly Phe
            15                  20                  25 acc ttc agt agc tat ggc atg cac tgg gtc cgc cag gct cca ggc aag       148
Thr Phe Ser Ser Tyr Gly Met His Trp Val Arg Gln Ala Pro Gly Lys
        30                  35                  40 ggg ctg gag tgg gtg gca gtt ata tca tat gat gga agt aat aaa tac       196
Gly Leu Glu Trp Val Ala Val Ile Ser Tyr Asp Gly Ser Asn Lys Tyr
    45                  50                  55 tat gca gac tcc gtg aag ggc cga ttc acc atc tcc aga gac aat tcc       244
Tyr Ala Asp Ser Val Lys Gly Arg Phe Thr Ile Ser Arg Asp Asn Ser
60                  65                  70                  75 aag aac acg ctg tat ctg caa atg aac agc ctg aga gct gag gac acg       292
Lys Asn Thr Leu Tyr Leu Gln Met Asn Ser Leu Arg Ala Glu Asp Thr
                80                  85                  90 gcc gtg tat tac tgt gca aaa ggt tgg tgg cat ccg ctg ctg tct ggc       340
Ala Val Tyr Tyr Cys Ala Lys Gly Trp Trp His Pro Leu Leu Ser Gly
            95                  100                 105 ttt gat tat tgg ggc caa ggt acc ctg gtc acc gtc tcc agt              382
Phe Asp Tyr Trp Gly Gln Gly Thr Leu Val Thr Val Ser Ser
        110                 115                 120
```

<210> SEQ ID NO 101
<211> LENGTH: 121
<212> TYPE: PRT
<213> ORGANISM: Artificial Sequence
<220> FEATURE:
<223> OTHER INFORMATION: Synthetic Construct

<400> SEQUENCE: 101

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

```
Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Lys Gly Trp Trp His Pro Leu Leu Ser Gly Phe Asp Tyr Trp Gly
            100                 105                 110

Gln Gly Thr Leu Val Thr Val Ser Ser
        115                 120

<210> SEQ ID NO 102
<211> LENGTH: 5
<212> TYPE: PRT
<213> ORGANISM: Artificial Sequence
<220> FEATURE:
<223> OTHER INFORMATION: CDR1

<400> SEQUENCE: 102

Ser Tyr Gly Met His
1               5

<210> SEQ ID NO 103
<211> LENGTH: 17
<212> TYPE: PRT
<213> ORGANISM: Artificial Sequence
<220> FEATURE:
<223> OTHER INFORMATION: CDR2

<400> SEQUENCE: 103

Val Ile Ser Tyr Asp Gly Ser Asn Lys Tyr Tyr Ala Asp Ser Val Lys
1               5                   10                  15

Gly

<210> SEQ ID NO 104
<211> LENGTH: 12
<212> TYPE: PRT
<213> ORGANISM: Artificial Sequence
<220> FEATURE:
<223> OTHER INFORMATION: CDR3

<400> SEQUENCE: 104

Gly Trp Trp His Pro Leu Leu Ser Gly Phe Asp Tyr
1               5                   10

<210> SEQ ID NO 105
<211> LENGTH: 370
<212> TYPE: DNA
<213> ORGANISM: Artificial Sequence
<220> FEATURE:
<223> OTHER INFORMATION: MF3001: heavy chain variable region sequence of
      an erbB-2 binding antibody
<220> FEATURE:
<221> NAME/KEY: CDS
<222> LOCATION: (20)..(370)

<400> SEQUENCE: 105
ggcccagccg gccatggcc gag gtc cag ctg cag cag tct ggg gct gaa ctg      52
                     Glu Val Gln Leu Gln Gln Ser Gly Ala Glu Leu
                      1               5                   10
```

```
gca aaa cct ggg gcc tca gtg aag ctg tcc tgc aag act tct ggc tac      100
Ala Lys Pro Gly Ala Ser Val Lys Leu Ser Cys Lys Thr Ser Gly Tyr
         15                  20                  25 aac ttt cct atc tac tgg atg cac tgg gta aaa cag agg cct gga cgg      148
Asn Phe Pro Ile Tyr Trp Met His Trp Val Lys Gln Arg Pro Gly Arg
         30                  35                  40 ggt ctg gaa tgg att gga tac att aat cct agt act ggt tat att aag      196
Gly Leu Glu Trp Ile Gly Tyr Ile Asn Pro Ser Thr Gly Tyr Ile Lys
 45                  50                  55 aac aat cag aag ttc aag gac aag gcc acc ttg act gca gac aaa tcc      244
Asn Asn Gln Lys Phe Lys Asp Lys Ala Thr Leu Thr Ala Asp Lys Ser
 60                  65                  70                  75 tcc aac aca gcc tac atg cag ctg aac agc ctg aca tat gag gac tct      292
Ser Asn Thr Ala Tyr Met Gln Leu Asn Ser Leu Thr Tyr Glu Asp Ser
                 80                  85                  90 gca gtc tat tac tgt aca aga gaa ggg ata act ggg ttt act tac tgg      340
Ala Val Tyr Tyr Cys Thr Arg Glu Gly Ile Thr Gly Phe Thr Tyr Trp
             95                 100                 105 ggc caa ggg act ctg gtc acc gtc tcc agt                              370
Gly Gln Gly Thr Leu Val Thr Val Ser Ser
             110                 115

<210> SEQ ID NO 106
<211> LENGTH: 117
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Gln Gln Ser Gly Ala Glu Leu Ala Lys Pro Gly Ala
1               5                   10                  15

Ser Val Lys Leu Ser Cys Lys Thr Ser Gly Tyr Asn Phe Pro Ile Tyr
            20                  25                  30

Trp Met His Trp Val Lys Gln Arg Pro Gly Arg Gly Leu Glu Trp Ile
        35                  40                  45

Gly Tyr Ile Asn Pro Ser Thr Gly Tyr Ile Lys Asn Asn Gln Lys Phe
    50                  55                  60

Lys Asp Lys Ala Thr Leu Thr Ala Asp Lys Ser Ser Asn Thr Ala Tyr
65                  70                  75                  80

Met Gln Leu Asn Ser Leu Thr Tyr Glu Asp Ser Ala Val Tyr Tyr Cys
                85                  90                  95

Thr Arg Glu Gly Ile Thr Gly Phe Thr Tyr Trp Gly Gln Gly Thr Leu
            100                 105                 110

Val Thr Val Ser Ser
        115

<210> SEQ ID NO 107
<211> LENGTH: 16
<212> TYPE: PRT
<213> ORGANISM: Artificial Sequence
<220> FEATURE:
<223> OTHER INFORMATION: CDR1

<400> SEQUENCE: 107

Ile Tyr Trp Met His Trp Val Lys Gln Arg Pro Gly Arg Gly Leu Glu
1               5                   10                  15

<210> SEQ ID NO 108
<211> LENGTH: 6
```

```
<212> TYPE: PRT
<213> ORGANISM: Artificial Sequence
<220> FEATURE:
<223> OTHER INFORMATION: CDR2

<400> SEQUENCE: 108

Asn Gln Lys Phe Lys Asp
1               5

<210> SEQ ID NO 109
<211> LENGTH: 8
<212> TYPE: PRT
<213> ORGANISM: Artificial Sequence
<220> FEATURE:
<223> OTHER INFORMATION: CDR3

<400> SEQUENCE: 109

Glu Gly Ile Thr Gly Phe Thr Tyr
1               5

<210> SEQ ID NO 110
<211> LENGTH: 385
<212> TYPE: DNA
<213> ORGANISM: Artificial Sequence
<220> FEATURE:
<223> OTHER INFORMATION: MF1898: heavy chain variable region sequence of
      an erbB-2 binding antibody
<220> FEATURE:
<221> NAME/KEY: CDS
<222> LOCATION: (20)..(385)

<400> SEQUENCE: 110
ggcccagccg gccatggcc cag gtg cag ctg gtg gag tct ggg gga ggc gtg        52
                     Gln Val Gln Leu Val Glu Ser Gly Gly Gly Val
                      1               5                  10 gtc cag cct ggg agg tcc ctg aga ctc tcc tgt gca gcc tct gga ttc        100
Val Gln Pro Gly Arg Ser Leu Arg Leu Ser Cys Ala Ala Ser Gly Phe
         15                  20                  25 acc ttc agt agc tat ggc atg cac tgg gtc cgc cag gct cca ggc aag        148
Thr Phe Ser Ser Tyr Gly Met His Trp Val Arg Gln Ala Pro Gly Lys
     30                  35                  40 ggg ctg gag tgg gtg gca gtt ata tca tat gat gga agt aat aaa tac        196
Gly Leu Glu Trp Val Ala Val Ile Ser Tyr Asp Gly Ser Asn Lys Tyr
 45                  50                  55 tat gca gac tcc gtg aag ggc cga ttc acc atc tcc aga gac aat tcc        244
Tyr Ala Asp Ser Val Lys Gly Arg Phe Thr Ile Ser Arg Asp Asn Ser
 60                  65                  70                  75 aag aac acg ctg tat ctg caa atg aac agc ctg aga gct gag gac acg        292
Lys Asn Thr Leu Tyr Leu Gln Met Asn Ser Leu Arg Ala Glu Asp Thr
                 80                  85                  90 gcc gtg tat tac tgt gca aaa gat ggt ttc cgt cgt act act ctg tct        340
Ala Val Tyr Tyr Cys Ala Lys Asp Gly Phe Arg Arg Thr Thr Leu Ser
             95                 100                 105 ggc ttt gat tat tgg ggc caa ggt acc ctg gtc acc gtc tcc agt            385
Gly Phe Asp Tyr Trp Gly Gln Gly Thr Leu Val Thr Val Ser Ser
         110                 115                 120

<210> SEQ ID NO 111
<211> LENGTH: 122
<212> TYPE: PRT
<213> ORGANISM: Artificial Sequence
<220> FEATURE:
<223> OTHER INFORMATION: Synthetic Construct
```

<400> SEQUENCE: 111

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Phe Arg Arg Thr Thr Leu Ser Gly Phe Asp Tyr Trp
            100                 105                 110

Gly Gln Gly Thr Leu Val Thr Val Ser Ser
        115                 120

<210> SEQ ID NO 112
<211> LENGTH: 5
<212> TYPE: PRT
<213> ORGANISM: Artificial Sequence
<220> FEATURE:
<223> OTHER INFORMATION: CDR1

<400> SEQUENCE: 112

Ser Tyr Gly Met His
1               5

<210> SEQ ID NO 113
<211> LENGTH: 17
<212> TYPE: PRT
<213> ORGANISM: Artificial Sequence
<220> FEATURE:
<223> OTHER INFORMATION: CDR2

<400> SEQUENCE: 113

Val Ile Ser Tyr Asp Gly Ser Asn Lys Tyr Tyr Ala Asp Ser Val Lys
1               5                   10                  15

Gly

<210> SEQ ID NO 114
<211> LENGTH: 13
<212> TYPE: PRT
<213> ORGANISM: Artificial Sequence
<220> FEATURE:
<223> OTHER INFORMATION: CDR3

<400> SEQUENCE: 114

Asp Gly Phe Arg Arg Thr Thr Leu Ser Gly Phe Asp Tyr
1               5                   10

<210> SEQ ID NO 115
<211> LENGTH: 379
<212> TYPE: DNA
<213> ORGANISM: Artificial Sequence
<220> FEATURE:
<223> OTHER INFORMATION: MF3003 heavy chain variable region sequence of
      an erbB-2 binding antibody
<220> FEATURE:
<221> NAME/KEY: CDS
<222> LOCATION: (20)..(379)

<400> SEQUENCE: 115

```
ggcccagccg gccatggcc cag gtg cag ctg aag cag tct gga cct gag ctg        52
                     Gln Val Gln Leu Lys Gln Ser Gly Pro Glu Leu
                      1               5                  10 gtg aag cct ggg gcc tca gtg aag att tcc tgc aag gct tct ggc gac        100
Val Lys Pro Gly Ala Ser Val Lys Ile Ser Cys Lys Ala Ser Gly Asp
             15                  20                  25 gca ttc agt tac tcc tgg atg aac tgg gtg aag cag agg cct gga aag        148
Ala Phe Ser Tyr Ser Trp Met Asn Trp Val Lys Gln Arg Pro Gly Lys
         30                  35                  40 ggt ctt gag tgg att gga cgg att tat cct gga gat gga gat att aac        196
Gly Leu Glu Trp Ile Gly Arg Ile Tyr Pro Gly Asp Gly Asp Ile Asn
     45                  50                  55 tac aat ggg aag ttc aag ggc aag gcc aca ctg act gca gac aaa tcc        244
Tyr Asn Gly Lys Phe Lys Gly Lys Ala Thr Leu Thr Ala Asp Lys Ser
 60                  65                  70                  75 tcc agc aca gcc cac ctg caa ctc aac agc ctg aca tct gag gac tct        292
Ser Ser Thr Ala His Leu Gln Leu Asn Ser Leu Thr Ser Glu Asp Ser
                 80                  85                  90 gcg gtc tac ttc tgt gca aga gga cag ctc gga cta gag gcc tgg ttt        340
Ala Val Tyr Phe Cys Ala Arg Gly Gln Leu Gly Leu Glu Ala Trp Phe
             95                 100                 105 gct tat tgg ggc cag ggg act ctg gtc acc gtc tcc agt                    379
Ala Tyr Trp Gly Gln Gly Thr Leu Val Thr Val Ser Ser
         110                 115                 120
```

<210> SEQ ID NO 116
<211> LENGTH: 120
<212> TYPE: PRT
<213> ORGANISM: Artificial Sequence
<220> FEATURE:
<223> OTHER INFORMATION: Synthetic Construct

<400> SEQUENCE: 116

```
Gln Val Gln Leu Lys Gln Ser Gly Pro Glu Leu Val Lys Pro Gly Ala
 1               5                  10                  15

Ser Val Lys Ile Ser Cys Lys Ala Ser Gly Asp Ala Phe Ser Tyr Ser
             20                  25                  30

Trp Met Asn Trp Val Lys Gln Arg Pro Gly Lys Gly Leu Glu Trp Ile
         35                  40                  45

Gly Arg Ile Tyr Pro Gly Asp Gly Asp Ile Asn Tyr Asn Gly Lys Phe
     50                  55                  60

Lys Gly Lys Ala Thr Leu Thr Ala Asp Lys Ser Ser Ser Thr Ala His
 65                  70                  75                  80

Leu Gln Leu Asn Ser Leu Thr Ser Glu Asp Ser Ala Val Tyr Phe Cys
                 85                  90                  95

Ala Arg Gly Gln Leu Gly Leu Glu Ala Trp Phe Ala Tyr Trp Gly Gln
             100                 105                 110

Gly Thr Leu Val Thr Val Ser Ser
         115                 120
```

<210> SEQ ID NO 117
<211> LENGTH: 16
<212> TYPE: PRT
<213> ORGANISM: Artificial Sequence
<220> FEATURE:
<223> OTHER INFORMATION: CDR1

<400> SEQUENCE: 117

Tyr Ser Trp Met Asn Trp Val Lys Gln Arg Pro Gly Lys Gly Leu Glu
1               5                   10                  15

<210> SEQ ID NO 118
<211> LENGTH: 6
<212> TYPE: PRT
<213> ORGANISM: Artificial Sequence
<220> FEATURE:
<223> OTHER INFORMATION: CDR2

<400> SEQUENCE: 118

Asn Gly Lys Phe Lys Gly
1               5

<210> SEQ ID NO 119
<211> LENGTH: 11
<212> TYPE: PRT
<213> ORGANISM: Artificial Sequence
<220> FEATURE:
<223> OTHER INFORMATION: CDR3

<400> SEQUENCE: 119

Gly Gln Leu Gly Leu Glu Ala Trp Phe Ala Tyr
1               5                   10

<210> SEQ ID NO 120
<211> LENGTH: 391
<212> TYPE: DNA
<213> ORGANISM: Artificial Sequence
<220> FEATURE:
<223> OTHER INFORMATION: MF6058: heavy chain variable region sequence of
      an erbB-3 binding antibody
<220> FEATURE:
<221> NAME/KEY: CDS
<222> LOCATION: (20)..(391)

<400> SEQUENCE: 120
ggcccagccg gccatggcc cag gtg cag ctg gtg cag tct ggg gct gac gtg         52
                     Gln Val Gln Leu Val Gln Ser Gly Ala Asp Val
                      1               5                  10 aag aag cct ggg gcc tca gtg aag gtc acg tgc aag gct tct gga tac         100
Lys Lys Pro Gly Ala Ser Val Lys Val Thr Cys Lys Ala Ser Gly Tyr
             15                  20                  25 acc ttc acc ggc tac tat atg cac tgg gtg cga cag gcc cct gga caa         148
Thr Phe Thr Gly Tyr Tyr Met His Trp Val Arg Gln Ala Pro Gly Gln
         30                  35                  40 gct ctt gag tgg atg gga tgg atc aac cct caa agt ggt ggc aca aac         196
Ala Leu Glu Trp Met Gly Trp Ile Asn Pro Gln Ser Gly Gly Thr Asn
     45                  50                  55 tat gca aag aag ttt cag ggc agg gtc tct atg acc agg gag acg tcc         244
Tyr Ala Lys Lys Phe Gln Gly Arg Val Ser Met Thr Arg Glu Thr Ser
 60                  65                  70                  75 aca agc aca gcc tac atg cag ctg agc agg ctg aga tct gac gac acg         292
Thr Ser Thr Ala Tyr Met Gln Leu Ser Arg Leu Arg Ser Asp Asp Thr
                 80                  85                  90 gct acg tat tac tgt gca aga gat cat ggt tct cgt cat ttc tgg tct         340
Ala Thr Tyr Tyr Cys Ala Arg Asp His Gly Ser Arg His Phe Trp Ser
             95                  100                 105 tac tgg ggc ttt gat tat tgg ggc caa ggt acc ctg gtc acc gtc tcc         388
Tyr Trp Gly Phe Asp Tyr Trp Gly Gln Gly Thr Leu Val Thr Val Ser
         110                 115                 120

```
agt                                                                    391
Ser <210> SEQ ID NO 121
<211> LENGTH: 124
<212> TYPE: PRT
<213> ORGANISM: Artificial Sequence
<220> FEATURE:
<223> OTHER INFORMATION: Synthetic Construct

<400> SEQUENCE: 121

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Gln Ser Gly Gly Thr Asn Tyr Ala Lys Lys Phe
    50                  55                  60

Gln Gly Arg Val Ser Met Thr Arg Glu Thr Ser Thr Ser Thr Ala Tyr
65                  70                  75                  80

Met Gln Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120

<210> SEQ ID NO 122
<211> LENGTH: 5
<212> TYPE: PRT
<213> ORGANISM: Artificial Sequence
<220> FEATURE:
<223> OTHER INFORMATION: CDR1

<400> SEQUENCE: 122

Gly Tyr Tyr Met His
1               5

<210> SEQ ID NO 123
<211> LENGTH: 17
<212> TYPE: PRT
<213> ORGANISM: Artificial Sequence
<220> FEATURE:
<223> OTHER INFORMATION: CDR2

<400> SEQUENCE: 123

Trp Ile Asn Pro Gln Ser Gly Gly Thr Asn Tyr Ala Lys Lys Phe Gln
1               5                   10                  15

Gly

<210> SEQ ID NO 124
<211> LENGTH: 15
<212> TYPE: PRT
<213> ORGANISM: Artificial Sequence
<220> FEATURE:
<223> OTHER INFORMATION: CDR3

<400> SEQUENCE: 124

Asp His Gly Ser Arg His Phe Trp Ser Tyr Trp Gly Phe Asp Tyr
1               5                   10                  15
```

<210> SEQ ID NO 125
<211> LENGTH: 391
<212> TYPE: DNA
<213> ORGANISM: Artificial Sequence
<220> FEATURE:
<223> OTHER INFORMATION: MF6061: heavy chain variable region sequence of an erbB-3 binding antibody
<220> FEATURE:
<221> NAME/KEY: CDS
<222> LOCATION: (20)..(391)

<400> SEQUENCE: 125

```
ggcccagccg gccatggcc cag gtg cag ctg gtg cag tct ggg gct gag gtg        52
                     Gln Val Gln Leu Val Gln Ser Gly Ala Glu Val
                      1               5                  10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
         15                  20                  25 acc ttc acc ggc tac tat atg cac tgg gtg cga cag gcc cct gga caa        148
Thr Phe Thr Gly Tyr Tyr Met His Trp Val Arg Gln Ala Pro Gly Gln
     30                  35                  40 ggg ctt gag tgg atg gga tgg atc aac cct cag agt ggt ggc aca aac        196
Gly Leu Glu Trp Met Gly Trp Ile Asn Pro Gln Ser Gly Gly Thr Asn
 45                  50                  55 tat gca cag aag ttt aag ggc agg gtc acg atg acc agg gac acg tcc        244
Tyr Ala Gln Lys Phe Lys Gly Arg Val Thr Met Thr Arg Asp Thr Ser
60                  65                  70                  75 acc agc aca gcc tac atg gag ctg agc agg ctg aga tct gac gac acg        292
Thr Ser Thr Ala Tyr Met Glu Leu Ser Arg Leu Arg Ser Asp Asp Thr
                 80                  85                  90 gct gtg tat tac tgt gca aga gat cat ggt tct cgt cat ttc tgg tct        340
Ala Val Tyr Tyr Cys Ala Arg Asp His Gly Ser Arg His Phe Trp Ser
             95                 100                 105 tac tgg ggc ttt gat tat tgg ggc caa ggt acc ctg gtc acc gtc tcc        388
Tyr Trp Gly Phe Asp Tyr Trp Gly Gln Gly Thr Leu Val Thr Val Ser
         110                 115                 120 agt                                                                    391
Ser
```

<210> SEQ ID NO 126
<211> LENGTH: 124
<212> TYPE: PRT
<213> ORGANISM: Artificial Sequence
<220> FEATURE:
<223> OTHER INFORMATION: Synthetic Construct

<400> SEQUENCE: 126

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Ile Asn Pro Gln Ser Gly Gly Thr Asn Tyr Ala Gln Lys Phe
     50                  55                  60

Lys Gly Arg Val Thr Met Thr Arg Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp His Gly Ser Arg His Phe Trp Ser Tyr Trp Gly Phe Asp
            100                 105                 110

```
Tyr Trp Gly Gln Gly Thr Leu Val Thr Val Ser Ser
        115                 120

<210> SEQ ID NO 127
<211> LENGTH: 5
<212> TYPE: PRT
<213> ORGANISM: Artificial Sequence
<220> FEATURE:
<223> OTHER INFORMATION: CDR1

<400> SEQUENCE: 127

Gly Tyr Tyr Met His
1               5

<210> SEQ ID NO 128
<211> LENGTH: 17
<212> TYPE: PRT
<213> ORGANISM: Artificial Sequence
<220> FEATURE:
<223> OTHER INFORMATION: CDR2

<400> SEQUENCE: 128

Trp Ile Asn Pro Gln Ser Gly Gly Thr Asn Tyr Ala Gln Lys Phe Lys
1               5                   10                  15

Gly

<210> SEQ ID NO 129
<211> LENGTH: 15
<212> TYPE: PRT
<213> ORGANISM: Artificial Sequence
<220> FEATURE:
<223> OTHER INFORMATION: CDR3

<400> SEQUENCE: 129

Asp His Gly Ser Arg His Phe Trp Ser Tyr Trp Gly Phe Asp Tyr
1               5                   10                  15

<210> SEQ ID NO 130
<211> LENGTH: 391
<212> TYPE: DNA
<213> ORGANISM: Artificial Sequence
<220> FEATURE:
<223> OTHER INFORMATION: MF6065: heavy chain variable region sequence of
      an erbB-3 binding antibody
<220> FEATURE:
<221> NAME/KEY: CDS
<222> LOCATION: (20)..(391)

<400> SEQUENCE: 130
ggcccagccg gccatggcc cag gtg cag ctg gtg cag tct ggg gct gag gtg        52
                     Gln Val Gln Leu Val Gln Ser Gly Ala Glu Val
                      1               5                  10 aag aag cct ggg gcc tca gtg aag gtc tcc tgc aag gct tct gga tac        100
Lys Lys Pro Gly Ala Ser Val Lys Val Ser Cys Lys Ala Ser Gly Tyr
            15                  20                  25 acc ttc acc tct tac tat atg cac tgg gtg cga cag gcc cct gga caa        148
Thr Phe Thr Ser Tyr Tyr Met His Trp Val Arg Gln Ala Pro Gly Gln
        30                  35                  40 ggg ctt gag tgg atg gga tgg atc aac cct cag ggg ggt tct aca aac        196
Gly Leu Glu Trp Met Gly Trp Ile Asn Pro Gln Gly Gly Ser Thr Asn
    45                  50                  55 tat gca cag aag ttt cag ggc agg gtc acg atg acc agg gac acg tcc        244
Tyr Ala Gln Lys Phe Gln Gly Arg Val Thr Met Thr Arg Asp Thr Ser
60                  65                  70                  75
```

```
acc agc aca gtg tac atg gag ctg agc agg ctg aga tct gag gac acg      292
Thr Ser Thr Val Tyr Met Glu Leu Ser Arg Leu Arg Ser Glu Asp Thr
            80                  85                  90 gct gtg tat tac tgt gca aga gat cat ggt tct cgt cat ttc tgg tct      340
Ala Val Tyr Tyr Cys Ala Arg Asp His Gly Ser Arg His Phe Trp Ser
        95                  100                 105 tac tgg ggc ttt gat tat tgg ggc caa ggt acc ctg gtc acc gtc tcc      388
Tyr Trp Gly Phe Asp Tyr Trp Gly Gln Gly Thr Leu Val Thr Val Ser
        110                 115                 120 agt                                                                   391
Ser
```

<210> SEQ ID NO 131
<211> LENGTH: 124
<212> TYPE: PRT
<213> ORGANISM: Artificial Sequence
<220> FEATURE:
<223> OTHER INFORMATION: Synthetic Construct

<400> SEQUENCE: 131

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Gln Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr Val Ser Ser
        115                 120
```

<210> SEQ ID NO 132
<211> LENGTH: 5
<212> TYPE: PRT
<213> ORGANISM: Artificial Sequence
<220> FEATURE:
<223> OTHER INFORMATION: CDR1

<400> SEQUENCE: 132

```
Ser Tyr Tyr Met His
1               5
```

<210> SEQ ID NO 133
<211> LENGTH: 17
<212> TYPE: PRT
<213> ORGANISM: Artificial Sequence
<220> FEATURE:
<223> OTHER INFORMATION: CDR2

<400> SEQUENCE: 133

```
Trp Ile Asn Pro Gln Gly Gly Ser Thr Asn Tyr Ala Gln Lys Phe Gln
1               5                   10                  15

Gly
```

<210> SEQ ID NO 134

<211> LENGTH: 15
<212> TYPE: PRT
<213> ORGANISM: Artificial Sequence
<220> FEATURE:
<223> OTHER INFORMATION: CDR3

<400> SEQUENCE: 134

Asp His Gly Ser Arg His Phe Trp Ser Tyr Trp Gly Phe Asp Tyr
1               5                   10                  15

<210> SEQ ID NO 135
<211> LENGTH: 48
<212> TYPE: PRT
<213> ORGANISM: Artificial Sequence
<220> FEATURE:
<223> OTHER INFORMATION: PG3958 epitope

<400> SEQUENCE: 135

Leu Cys Tyr Gln Asp Thr Ile Leu Trp Lys Asp Ile Phe His Lys Asn
1               5                   10                  15

Asn Gln Leu Ala Leu Thr Leu Ile Asp Thr Asn Arg Ser Arg Ala Cys
            20                  25                  30

His Pro Cys Ser Pro Met Cys Lys Gly Ser Arg Cys Trp Gly Glu Ser
        35                  40                  45

<210> SEQ ID NO 136
<211> LENGTH: 363
<212> TYPE: DNA
<213> ORGANISM: Artificial Sequence
<220> FEATURE:
<223> OTHER INFORMATION: MF6055
<220> FEATURE:
<221> NAME/KEY: CDS
<222> LOCATION: (1)..(363)

<400> SEQUENCE: 136 cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct tct agt ggt ggc aca aac tat gca aag aag ttt     192
Gly Trp Ile Asn Pro Ser Ser Gly Gly Thr Asn Tyr Ala Lys Lys Phe
    50                  55                  60 cag ggc agg gtc acg atg acc agg gag acg tcc aca agc aca gcc tac     240
Gln Gly Arg Val Thr Met Thr Arg Glu Thr Ser Thr Ser Thr Ala Tyr
65                  70                  75                  80 atg gag ctg agc agg ctg aga tct gac gac acg gct acg tat tac tgt     288
Met Glu Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120

<210> SEQ ID NO 137
<211> LENGTH: 121
<212> TYPE: PRT

<213> ORGANISM: Artificial Sequence
<220> FEATURE:
<223> OTHER INFORMATION: Synthetic Construct

<400> SEQUENCE: 137

```
Gln Val Gln Leu Val Gln Ser Gly Ala Asp Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Ala Leu Glu Trp Met
        35                  40                  45
Gly Trp Ile Asn Pro Ser Ser Gly Gly Thr Asn Tyr Ala Lys Lys Phe
    50                  55                  60
Gln Gly Arg Val Thr Met Thr Arg Glu Thr Ser Thr Ser Thr Ala Tyr
65                  70                  75                  80
Met Glu Leu Ser Arg Leu Arg Ser Asp Asp Thr Ala Thr Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 138
<211> LENGTH: 363
<212> TYPE: DNA
<213> ORGANISM: Artificial Sequence
<220> FEATURE:
<223> OTHER INFORMATION: MF6056
<220> FEATURE:
<221> NAME/KEY: CDS
<222> LOCATION: (1)..(363)

<400> SEQUENCE: 138

```
cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac      96
Ser Val Lys Val Thr Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct tct agt ggt ggc aca aac tat gca aag aag ttt     192
Gly Trp Ile Asn Pro Ser Ser Gly Gly Thr Asn Tyr Ala Lys Lys Phe
    50                  55                  60 cag ggc agg gtc tct atg acc agg gag acg tcc aca agc aca gcc tac     240
Gln Gly Arg Val Ser Met Thr Arg Glu Thr Ser Thr Ser Thr Ala Tyr
65                  70                  75                  80 atg cag ctg agc agg ctg aga tct gac gac acg gct acg tat tac tgt     288
Met Gln Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120
```

<210> SEQ ID NO 139
<211> LENGTH: 121
<212> TYPE: PRT

<213> ORGANISM: Artificial Sequence
<220> FEATURE:
<223> OTHER INFORMATION: Synthetic Construct

<400> SEQUENCE: 139

```
Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Ala Leu Glu Trp Met
        35                  40                  45

Gly Trp Ile Asn Pro Ser Ser Gly Gly Thr Asn Tyr Ala Lys Lys Phe
    50                  55                  60

Gln Gly Arg Val Ser Met Thr Arg Glu Thr Ser Thr Ser Thr Ala Tyr
65                  70                  75                  80

Met Gln Leu Ser Arg Leu Arg Ser Asp Asp Thr Ala Thr Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 140
<211> LENGTH: 363
<212> TYPE: DNA
<213> ORGANISM: Artificial Sequence
<220> FEATURE:
<223> OTHER INFORMATION: MF6057
<220> FEATURE:
<221> NAME/KEY: CDS
<222> LOCATION: (1)..(363)

<400> SEQUENCE: 140

```
cag gtg cag ctg gtg cag tct ggg gct gat gtg aag aag cct ggg gcc    48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac    96
Ser Val Lys Val Thr Cys Lys Ala Ser Gly Tyr Thr Phe Thr Gly Tyr
            20                  25                  30 tat atg cac tgg gtg cga cag gcc cct gga caa ggg ctt gag tgg atg   144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt   192
Gly Trp Ile Asn Pro Gln Ser Gly Gly Thr Asn Tyr Ala Gln Lys Phe
    50                  55                  60 cag ggc agg gtc acg atg acc agg gac acg tcc atc agc aca gcc tac   240
Gln Gly Arg Val Thr Met Thr Arg Asp Thr Ser Ile Ser Thr Ala Tyr
65                  70                  75                  80 atg cag ctg agc agg ctg aga tct gac gac acg gct gtg tat tac tgt   288
Met Gln Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat   336
Ala Arg Asp His Gly Ser Arg His Phe Trp Ser Tyr Trp Gly Phe Asp
            100                 105                 110 tat tgg ggc caa ggt acc ctg gtc acc                               363
Tyr Trp Gly Gln Gly Thr Leu Val Thr
        115                 120
```

<210> SEQ ID NO 141
<211> LENGTH: 121
<212> TYPE: PRT

```
<213> ORGANISM: Artificial Sequence
<220> FEATURE:
<223> OTHER INFORMATION: Synthetic Construct

<400> SEQUENCE: 141

Gln Val Gln Leu Val Gln Ser Gly Ala Asp Val Lys Lys Pro Gly Ala
1               5                   10                  15

Ser Val Lys Val Thr Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Gln Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120

<210> SEQ ID NO 142
<211> LENGTH: 363
<212> TYPE: DNA
<213> ORGANISM: Artificial Sequence
<220> FEATURE:
<223> OTHER INFORMATION: MF6058
<220> FEATURE:
<221> NAME/KEY: CDS
<222> LOCATION: (1)..(363)

<400> SEQUENCE: 142 cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc acg tgc aag gct tct gga tac acc ttc acc ggc tac      96
Ser Val Lys Val Thr Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct caa agt ggt ggc aca aac tat gca aag aag ttt     192
Gly Trp Ile Asn Pro Gln Ser Gly Gly Thr Asn Tyr Ala Lys Lys Phe
    50                  55                  60 cag ggc agg gtc tct atg acc agg gag acg tcc aca agc aca gcc tac     240
Gln Gly Arg Val Ser Met Thr Arg Glu Thr Ser Thr Ser Thr Ala Tyr
65                  70                  75                  80 atg cag ctg agc agg ctg aga tct gac gac acg gct acg tat tac tgt     288
Met Gln Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120

<210> SEQ ID NO 143
<211> LENGTH: 121
<212> TYPE: PRT
```

<213> ORGANISM: Artificial Sequence
<220> FEATURE:
<223> OTHER INFORMATION: Synthetic Construct

<400> SEQUENCE: 143

```
Gln Val Gln Leu Val Gln Ser Gly Ala Asp Val Lys Lys Pro Gly Ala
1               5                   10                  15
Ser Val Lys Val Thr Cys Lys Ala Ser Gly Tyr Thr Phe Thr Gly Tyr
            20                  25                  30
Tyr Met His Trp Val Arg Gln Ala Pro Gly Gln Ala Leu Glu Trp Met
        35                  40                  45
Gly Trp Ile Asn Pro Gln Ser Gly Gly Thr Asn Tyr Ala Lys Lys Phe
    50                  55                  60
Gln Gly Arg Val Ser Met Thr Arg Glu Thr Ser Thr Ser Thr Ala Tyr
65                  70                  75                  80
Met Gln Leu Ser Arg Leu Arg Ser Asp Asp Thr Ala Thr Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 144
<211> LENGTH: 363
<212> TYPE: DNA
<213> ORGANISM: Artificial Sequence
<220> FEATURE:
<223> OTHER INFORMATION: MF6059
<220> FEATURE:
<221> NAME/KEY: CDS
<222> LOCATION: (1)..(363)

<400> SEQUENCE: 144

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct ggc agt ggt tct aca aac tat gca cag aag ttt     192
Gly Trp Ile Asn Pro Gly Ser Gly Ser Thr Asn Tyr Ala Gln Lys Phe
    50                  55                  60 cag ggc agg gtc acg atg acc agg gac acg tcc atc agc aca gcc tac     240
Gln Gly Arg Val Thr Met Thr Arg Asp Thr Ser Ile Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120
```

<210> SEQ ID NO 145
<211> LENGTH: 121
<212> TYPE: PRT

<213> ORGANISM: Artificial Sequence
<220> FEATURE:
<223> OTHER INFORMATION: Synthetic Construct

<400> SEQUENCE: 145

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 146
<211> LENGTH: 363
<212> TYPE: DNA
<213> ORGANISM: Artificial Sequence
<220> FEATURE:
<223> OTHER INFORMATION: MF6060
<220> FEATURE:
<221> NAME/KEY: CDS
<222> LOCATION: (1)..(363)

<400> SEQUENCE: 146

```
cag gtg cag ctg gtg cag tct ggg gct gac gtg aag aag cct ggg gcc      48
Gln Val Gln Leu Val Gln Ser Gly Ala Asp Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa gct ctt gag tgg atg     144
Tyr Met His Trp Val Arg Gln Ala Pro Gly Gln Ala Leu Glu Trp Met
        35                  40                  45 gga tgg atc aac cct caa agt ggt ggc aca aac tat gca aag aag ttt     192
Gly Trp Ile Asn Pro Gln Ser Gly Gly Thr Asn Tyr Ala Lys Lys Phe
    50                  55                  60 cag ggc agg gtc acg atg acc agg gag acg tcc aca agc aca gcc tac     240
Gln Gly Arg Val Thr Met Thr Arg Glu Thr Ser Thr Ser Thr Ala Tyr
65                  70                  75                  80 atg gag ctg agc agg ctg aga tct gac gac acg gct acg tat tac tgt     288
Met Glu Leu Ser Arg Leu Arg Ser Asp Asp Thr Ala Thr Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120
```

<210> SEQ ID NO 147
<211> LENGTH: 121
<212> TYPE: PRT

<213> ORGANISM: Artificial Sequence
<220> FEATURE:
<223> OTHER INFORMATION: Synthetic Construct

<400> SEQUENCE: 147

```
Gln Val Gln Leu Val Gln Ser Gly Ala Asp Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Ala Leu Glu Trp Met
        35                  40                  45
Gly Trp Ile Asn Pro Gln Ser Gly Gly Thr Asn Tyr Ala Lys Lys Phe
    50                  55                  60
Gln Gly Arg Val Thr Met Thr Arg Glu Thr Ser Thr Ser Thr Ala Tyr
65                  70                  75                  80
Met Glu Leu Ser Arg Leu Arg Ser Asp Asp Thr Ala Thr Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 148
<211> LENGTH: 363
<212> TYPE: DNA
<213> ORGANISM: Artificial Sequence
<220> FEATURE:
<223> OTHER INFORMATION: MF6061
<220> FEATURE:
<221> NAME/KEY: CDS
<222> LOCATION: (1)..(363)

<400> SEQUENCE: 148

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt     192
Gly Trp Ile Asn Pro Gln Ser Gly Gly Thr Asn Tyr Ala Gln Lys Phe
    50                  55                  60 aag ggc agg gtc acg atg acc agg gac acg tcc acg agc aca gcc tac     240
Lys Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120
```

<210> SEQ ID NO 149
<211> LENGTH: 121
<212> TYPE: PRT

<213> ORGANISM: Artificial Sequence
<220> FEATURE:
<223> OTHER INFORMATION: Synthetic Construct

<400> SEQUENCE: 149

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gln Ser Gly Gly Thr Asn Tyr Ala Gln Lys Phe
    50                  55                  60

Lys Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 150
<211> LENGTH: 363
<212> TYPE: DNA
<213> ORGANISM: Artificial Sequence
<220> FEATURE:
<223> OTHER INFORMATION: MF6062
<220> FEATURE:
<221> NAME/KEY: CDS
<222> LOCATION: (1)..(363)

<400> SEQUENCE: 150

```
cag gtg cag ctg gtg cag tct ggg gct gag gtg aag aag cct ggg gcc     48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac     96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg    144
Tyr Met His Trp Val Arg Gln Ala Pro Gly Gln Gly Leu Glu Trp Met
        35                  40                  45 gga tgg atc aac cct ggc agt ggt tct aca aac tat gca cag aag ttt    192
Gly Trp Ile Asn Pro Gly Ser Gly Ser Thr Asn Tyr Ala Gln Lys Phe
    50                  55                  60 cag ggc agg gtc acg atg acc agg gac acg tcc aca agc aca gcc tac    240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt    288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat    336
Ala Arg Asp His Gly Ser Arg His Phe Trp Ser Tyr Trp Gly Phe Asp
            100                 105                 110 tat tgg ggc caa ggt acc ctg gtc acc                                363
Tyr Trp Gly Gln Gly Thr Leu Val Thr
        115                 120
```

<210> SEQ ID NO 151
<211> LENGTH: 121
<212> TYPE: PRT

<213> ORGANISM: Artificial Sequence
<220> FEATURE:
<223> OTHER INFORMATION: Synthetic Construct

<400> SEQUENCE: 151

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Gly Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 152
<211> LENGTH: 363
<212> TYPE: DNA
<213> ORGANISM: Artificial Sequence
<220> FEATURE:
<223> OTHER INFORMATION: MF6063
<220> FEATURE:
<221> NAME/KEY: CDS
<222> LOCATION: (1)..(363)

<400> SEQUENCE: 152

```
cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct cag agt ggt ggc aca aac tat gca aag aag ttt       192
Gly Trp Ile Asn Pro Gln Ser Gly Gly Thr Asn Tyr Ala Lys Lys Phe
    50                  55                  60 cag ggc agg gtc acg atg acc agg gac acg tcc acg agc aca gcc tac       240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt       288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                    363
Tyr Trp Gly Gln Gly Thr Leu Val Thr
        115                 120
```

<210> SEQ ID NO 153
<211> LENGTH: 121
<212> TYPE: PRT

<213> ORGANISM: Artificial Sequence
<220> FEATURE:
<223> OTHER INFORMATION: Synthetic Construct

<400> SEQUENCE: 153

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Gln Ser Gly Gly Thr Asn Tyr Ala Lys Lys Phe
    50                  55                  60
Gln Gly Arg Val Thr Met Thr Arg Asp Thr Ser Thr Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 154
<211> LENGTH: 363
<212> TYPE: DNA
<213> ORGANISM: Artificial Sequence
<220> FEATURE:
<223> OTHER INFORMATION: MF6064
<220> FEATURE:
<221> NAME/KEY: CDS
<222> LOCATION: (1)..(363)

<400> SEQUENCE: 154

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga aag ggg ctt gag tgg atg     144
Tyr Met His Trp Val Arg Gln Ala Pro Gly Lys Gly Leu Glu Trp Met
        35                  40                  45 gga tgg atc aac cct cag agt ggt ggc aca aac tat gca cag aag ttt     192
Gly Trp Ile Asn Pro Gln Ser Gly Gly Thr Asn Tyr Ala Gln Lys Phe
    50                  55                  60 cag ggc agg gtc acg atg acc agg gac acg tcc acg agc aca gcc tac     240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120
```

<210> SEQ ID NO 155
<211> LENGTH: 121
<212> TYPE: PRT

<213> ORGANISM: Artificial Sequence
<220> FEATURE:
<223> OTHER INFORMATION: Synthetic Construct

<400> SEQUENCE: 155

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Lys Gly Leu Glu Trp Met
        35                  40                  45

Gly Trp Ile Asn Pro Gln Ser Gly Gly Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 156
<211> LENGTH: 363
<212> TYPE: DNA
<213> ORGANISM: Artificial Sequence
<220> FEATURE:
<223> OTHER INFORMATION: MF6065
<220> FEATURE:
<221> NAME/KEY: CDS
<222> LOCATION: (1)..(363)

<400> SEQUENCE: 156

```
cag gtg cag ctg gtg cag tct ggg gct gag gtg aag aag cct ggg gcc     48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc tct tac     96
Ser Val Lys Val Ser Cys Lys Ala Ser Gly Tyr Thr Phe Thr Ser Tyr
            20                  25                  30 tat atg cac tgg gtg cga cag gcc cct gga caa ggg ctt gag tgg atg    144
Tyr Met His Trp Val Arg Gln Ala Pro Gly Gln Gly Leu Glu Trp Met
        35                  40                  45 gga tgg atc aac cct cag ggg ggt tct aca aac tat gca cag aag ttt    192
Gly Trp Ile Asn Pro Gln Gly Gly Ser Thr Asn Tyr Ala Gln Lys Phe
    50                  55                  60 cag ggc agg gtc acg atg acc agg gac acg tcc acg agc aca gtg tac    240
Gln Gly Arg Val Thr Met Thr Arg Asp Thr Ser Thr Ser Thr Val Tyr
65                  70                  75                  80 atg gag ctg agc agg ctg aga tct gag gac acg gct gtg tat tac tgt    288
Met Glu Leu Ser Arg Leu Arg Ser Glu Asp Thr Ala Val Tyr Tyr Cys
                85                  90                  95 gca aga gat cat ggt tct cgt cat ttc tgg tct tac tgg ggc ttt gat    336
Ala Arg Asp His Gly Ser Arg His Phe Trp Ser Tyr Trp Gly Phe Asp
            100                 105                 110 tat tgg ggc caa ggt acc ctg gtc acc                                363
Tyr Trp Gly Gln Gly Thr Leu Val Thr
        115                 120
```

<210> SEQ ID NO 157
<211> LENGTH: 121
<212> TYPE: PRT

<213> ORGANISM: Artificial Sequence
<220> FEATURE:
<223> OTHER INFORMATION: Synthetic Construct

<400> SEQUENCE: 157

```
Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Gln Gly Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Arg Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 158
<211> LENGTH: 363
<212> TYPE: DNA
<213> ORGANISM: Artificial Sequence
<220> FEATURE:
<223> OTHER INFORMATION: MF6066
<220> FEATURE:
<221> NAME/KEY: CDS
<222> LOCATION: (1)..(363)

<400> SEQUENCE: 158

```
cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                  10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct cag agt ggt tct aca aac tat gca cag aag ttt       192
Gly Trp Ile Asn Pro Gln Ser Gly Ser Thr Asn Tyr Ala Gln Lys Phe
    50                  55                  60 cag ggc agg gtc acg atg acc agg gac acg tcc acg agc aca gcc tac       240
Gln Gly Arg Val Thr Met Thr Arg Asp Thr Ser Thr Ser Thr Ala Tyr
65                  70                  75                  80 atg gag ctg agc tct ctg aga tct gag gac acg gct gtg tat tac tgt       288
Met Glu Leu Ser Ser Leu Arg Ser Glu Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                    363
Tyr Trp Gly Gln Gly Thr Leu Val Thr
        115                 120
```

<210> SEQ ID NO 159
<211> LENGTH: 121
<212> TYPE: PRT

```
<213> ORGANISM: Artificial Sequence
<220> FEATURE:
<223> OTHER INFORMATION: Synthetic Construct

<400> SEQUENCE: 159

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Gln Ser Gly Ser Thr Asn Tyr Ala Gln Lys Phe
        50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120

<210> SEQ ID NO 160
<211> LENGTH: 363
<212> TYPE: DNA
<213> ORGANISM: Artificial Sequence
<220> FEATURE:
<223> OTHER INFORMATION: MF6067
<220> FEATURE:
<221> NAME/KEY: CDS
<222> LOCATION: (1)..(363)

<400> SEQUENCE: 160 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
                20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
            35                  40                  45 gga tgg atc aac cct cag agt ggt ggc aca aac tat gca cag aag ttt     192
Gly Trp Ile Asn Pro Gln Ser Gly Gly Thr Asn Tyr Ala Gln Lys Phe
        50                  55                  60 cag ggc agg gtc acg atg acc agg gac acg tcc acg agc aca gtc tac     240
Gln Gly Arg Val Thr Met Thr Arg Asp Thr Ser Thr Ser Thr Val Tyr
65                  70                  75                  80 atg gag ctg agc tct ctg aga tct gac gac acg gct gtg tat tac tgt     288
Met Glu Leu Ser Ser Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120

<210> SEQ ID NO 161
<211> LENGTH: 121
<212> TYPE: PRT
```

<213> ORGANISM: Artificial Sequence
<220> FEATURE:
<223> OTHER INFORMATION: Synthetic Construct

<400> SEQUENCE: 161

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Gln Ser Gly Gly Thr Asn Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Asp Asp Thr Ala Val Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 162
<211> LENGTH: 363
<212> TYPE: DNA
<213> ORGANISM: Artificial Sequence
<220> FEATURE:
<223> OTHER INFORMATION: MF6068
<220> FEATURE:
<221> NAME/KEY: CDS
<222> LOCATION: (1)..(363)

<400> SEQUENCE: 162

```
cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt       192
Gly Trp Ile Asn Pro Gln Ser Gly Gly Thr Asn Tyr Ala Gln Lys Phe
    50                  55                  60 cag ggc agg gtc acg atg acc agg gac acg tcc acg agc aca gcc tac       240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt       288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                   363
Tyr Trp Gly Gln Gly Thr Leu Val Thr
        115                 120
```

<210> SEQ ID NO 163
<211> LENGTH: 121
<212> TYPE: PRT

<213> ORGANISM: Artificial Sequence
<220> FEATURE:
<223> OTHER INFORMATION: Synthetic Construct

<400> SEQUENCE: 163

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Gln Ser Gly Gly Thr Asn Tyr Ala Gln Lys Phe
    50                  55                  60
Gln Gly Arg Val Thr Met Thr Arg Asp Thr Ser Thr Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 164
<211> LENGTH: 363
<212> TYPE: DNA
<213> ORGANISM: Artificial Sequence
<220> FEATURE:
<223> OTHER INFORMATION: MF6069
<220> FEATURE:
<221> NAME/KEY: CDS
<222> LOCATION: (1)..(363)

<400> SEQUENCE: 164

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct cag agt ggt ggc aca aac tat gca cag aag ttt     192
Gly Trp Ile Asn Pro Gln Ser Gly Gly Thr Asn Tyr Ala Gln Lys Phe
    50                  55                  60 cag ggc agg gtc acg atg acc agg gac acg tcc atc agc aca gcc tac     240
Gln Gly Arg Val Thr Met Thr Arg Asp Thr Ser Ile Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120
```

<210> SEQ ID NO 165
<211> LENGTH: 121
<212> TYPE: PRT

<213> ORGANISM: Artificial Sequence
<220> FEATURE:
<223> OTHER INFORMATION: Synthetic Construct

<400> SEQUENCE: 165

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Gln Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 166
<211> LENGTH: 363
<212> TYPE: DNA
<213> ORGANISM: Artificial Sequence
<220> FEATURE:
<223> OTHER INFORMATION: MF6070
<220> FEATURE:
<221> NAME/KEY: CDS
<222> LOCATION: (1)..(363)

<400> SEQUENCE: 166

```
cag gtg cag ctg gtg cag tct ggg gct gag gtg aag aag cct ggg gcc       48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc tct tac       96
Ser Val Lys Val Ser Cys Lys Ala Ser Gly Tyr Thr Phe Thr Ser Tyr
            20                  25                  30 tat atg cac tgg gtg cga cag gcc cct gga caa ggg ctt gag tgg atg      144
Tyr Met His Trp Val Arg Gln Ala Pro Gly Gln Gly Leu Glu Trp Met
        35                  40                  45 gga tgg atc aac cct tct ggg ggt tct aca aac tat gca cag aag ttt      192
Gly Trp Ile Asn Pro Ser Gly Gly Ser Thr Asn Tyr Ala Gln Lys Phe
    50                  55                  60 cag ggc agg gtc acg atg acc agg gac acg tcc acc agc aca gtg tac      240
Gln Gly Arg Val Thr Met Thr Arg Asp Thr Ser Thr Ser Thr Val Tyr
65                  70                  75                  80 atg gag ctg agc agg ctg aga tct gag gac acg gct gtg tat tac tgt      288
Met Glu Leu Ser Arg Leu Arg Ser Glu Asp Thr Ala Val Tyr Tyr Cys
                85                  90                  95 gca aga gat cat ggt tct cgt cat ttc tgg tct tac tgg ggc ttt gat      336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120
```

<210> SEQ ID NO 167
<211> LENGTH: 121
<212> TYPE: PRT

<213> ORGANISM: Artificial Sequence
<220> FEATURE:
<223> OTHER INFORMATION: Synthetic Construct

<400> SEQUENCE: 167

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Trp Ile Asn Pro Ser Gly Gly Ser Thr Asn Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Arg Leu Arg Ser Glu Asp Thr Ala Val Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 168
<211> LENGTH: 363
<212> TYPE: DNA
<213> ORGANISM: Artificial Sequence
<220> FEATURE:
<223> OTHER INFORMATION: MF6071
<220> FEATURE:
<221> NAME/KEY: CDS
<222> LOCATION: (1)..(363)

<400> SEQUENCE: 168

```
cag gtg cag ctg gtg cag tct ggg gct gag gtg aag aag cct ggg gcc        48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac        96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg       144
Tyr Met His Trp Val Arg Gln Ala Pro Gly Gln Gly Leu Glu Trp Met
        35                  40                  45 gga tgg atc aac cct tct agt ggt tct aca aac tat gca cag aag ttt       192
Gly Trp Ile Asn Pro Ser Ser Gly Ser Thr Asn Tyr Ala Gln Lys Phe
    50                  55                  60 cag ggc agg gtc acg atg acc agg gac acg tcc acg agc aca gcc tac       240
Gln Gly Arg Val Thr Met Thr Arg Asp Thr Ser Thr Ser Thr Ala Tyr
65                  70                  75                  80 atg gag ctg agc tct ctg aga tct gag gac acg gct gtg tat tac tgt       288
Met Glu Leu Ser Ser Leu Arg Ser Glu Asp Thr Ala Val Tyr Tyr Cys
                85                  90                  95 gca aga gat cat ggt tct cgt cat ttc tgg tct tac tgg ggc ttt gat       336
Ala Arg Asp His Gly Ser Arg His Phe Trp Ser Tyr Trp Gly Phe Asp
            100                 105                 110 tat tgg ggc caa ggt acc ctg gtc acc                                    363
Tyr Trp Gly Gln Gly Thr Leu Val Thr
        115                 120
```

<210> SEQ ID NO 169
<211> LENGTH: 121
<212> TYPE: PRT

<213> ORGANISM: Artificial Sequence
<220> FEATURE:
<223> OTHER INFORMATION: Synthetic Construct

<400> SEQUENCE: 169

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Ser Thr Asn Tyr Ala Gln Lys Phe
    50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 170
<211> LENGTH: 363
<212> TYPE: DNA
<213> ORGANISM: Artificial Sequence
<220> FEATURE:
<223> OTHER INFORMATION: MF6072
<220> FEATURE:
<221> NAME/KEY: CDS
<222> LOCATION: (1)..(363)

<400> SEQUENCE: 170

```
cag gtg cag ctg gtg cag tct ggg gct gag gtg aag aag cct ggg gcc     48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac     96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg    144
Tyr Met His Trp Val Arg Gln Ala Pro Gly Gln Gly Leu Glu Trp Met
        35                  40                  45 gga tgg atc aac cct tct agt ggt ggc aca aac tat gca cag aag ttt    192
Gly Trp Ile Asn Pro Ser Ser Gly Gly Thr Asn Tyr Ala Gln Lys Phe
    50                  55                  60 cag ggc agg gtc acg atg acc agg gac acg tcc acg agc aca gtc tac    240
Gln Gly Arg Val Thr Met Thr Arg Asp Thr Ser Thr Ser Thr Val Tyr
65                  70                  75                  80 atg gag ctg agc tct ctg aga tct gac gac acg gct gtg tat tac tgt    288
Met Glu Leu Ser Ser Leu Arg Ser Asp Asp Thr Ala Val Tyr Tyr Cys
                85                  90                  95 gca aga gat cat ggt tct cgt cat ttc tgg tct tac tgg ggc ttt gat    336
Ala Arg Asp His Gly Ser Arg His Phe Trp Ser Tyr Trp Gly Phe Asp
            100                 105                 110 tat tgg ggc caa ggt acc ctg gtc acc                                 363
Tyr Trp Gly Gln Gly Thr Leu Val Thr
        115                 120
```

<210> SEQ ID NO 171
<211> LENGTH: 121
<212> TYPE: PRT

<213> ORGANISM: Artificial Sequence
<220> FEATURE:
<223> OTHER INFORMATION: Synthetic Construct

<400> SEQUENCE: 171

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
        115                 120
```

<210> SEQ ID NO 172
<211> LENGTH: 363
<212> TYPE: DNA
<213> ORGANISM: Artificial Sequence
<220> FEATURE:
<223> OTHER INFORMATION: MF6073
<220> FEATURE:
<221> NAME/KEY: CDS
<222> LOCATION: (1)..(363)

<400> SEQUENCE: 172

```
cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac      96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg     144
Tyr Met His Trp Val Arg Gln Ala Pro Gly Gln Gly Leu Glu Trp Met
        35                  40                  45 gga tgg atc aac cct tct agt ggt ggc aca aac tat gca cag aag ttt     192
Gly Trp Ile Asn Pro Ser Ser Gly Gly Thr Asn Tyr Ala Gln Lys Phe
    50                  55                  60 cag ggc agg gtc acg atg acc agg gac acg tcc acg agc aca gcc tac     240
Gln Gly Arg Val Thr Met Thr Arg Asp Thr Ser Thr Ser Thr Ala Tyr
65                  70                  75                  80 atg gag ctg agc agg ctg aga tct gac gac acg gct gtg tat tac tgt     288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat     336
Ala Arg Asp His Gly Ser Arg His Phe Trp Ser Tyr Trp Gly Phe Asp
            100                 105                 110 tat tgg ggc caa ggt acc ctg gtc acc                                  363
Tyr Trp Gly Gln Gly Thr Leu Val Thr
        115                 120
```

<210> SEQ ID NO 173
<211> LENGTH: 121
<212> TYPE: PRT

<213> ORGANISM: Artificial Sequence
<220> FEATURE:
<223> OTHER INFORMATION: Synthetic Construct

<400> SEQUENCE: 173

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Ser Ser Gly Gly Thr Asn Tyr Ala Gln Lys Phe
    50                  55                  60
Gln Gly Arg Val Thr Met Thr Arg Asp Thr Ser Thr Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Asp His Gly Ser Arg His Phe Trp Ser Tyr Trp Gly Phe Asp
            100                 105                 110
Tyr Trp Gly Gln Gly Thr Leu Val Thr
        115                 120
```

<210> SEQ ID NO 174
<211> LENGTH: 363
<212> TYPE: DNA
<213> ORGANISM: Artificial Sequence
<220> FEATURE:
<223> OTHER INFORMATION: MF6074
<220> FEATURE:
<221> NAME/KEY: CDS
<222> LOCATION: (1)..(363)

<400> SEQUENCE: 174

```
cag gtg cag ctg gtg cag tct ggg gct gag gtg aag aag cct ggg gcc    48
Gln Val Gln Leu Val Gln Ser Gly Ala Glu Val Lys Lys Pro Gly Ala
1               5                   10                  15 tca gtg aag gtc tcc tgc aag gct tct gga tac acc ttc acc ggc tac    96
Ser Val Lys Val Ser Cys Lys Ala Ser Gly Tyr Thr Phe Thr Gly Tyr
            20                  25                  30 tat atg cac tgg gtg cga cag gcc cct gga caa ggg ctt gag tgg atg   144
Tyr Met His Trp Val Arg Gln Ala Pro Gly Gln Gly Leu Glu Trp Met
        35                  40                  45 gga tgg atc aac cct tct agt ggt ggc aca aac tat gca cag aag ttt   192
Gly Trp Ile Asn Pro Ser Ser Gly Gly Thr Asn Tyr Ala Gln Lys Phe
    50                  55                  60 cag ggc agg gtc acg atg acc agg gac acg tcc atc agc aca gcc tac   240
Gln Gly Arg Val Thr Met Thr Arg Asp Thr Ser Ile Ser Thr Ala Tyr
65                  70                  75                  80 atg gag ctg agc agg ctg aga tct gac gac acg gct gtg tat tac tgt   288
Met Glu Leu Ser Arg Leu Arg Ser Asp Asp Thr Ala Val Tyr Tyr Cys
                85                  90                  95 gca aga gat cat ggt tct cgt cat ttc tgg tct tac tgg ggc ttt gat   336
Ala Arg Asp His Gly Ser Arg His Phe Trp Ser Tyr Trp Gly Phe Asp
            100                 105                 110 tat tgg ggc caa ggt acc ctg gtc acc                                363
Tyr Trp Gly Gln Gly Thr Leu Val Thr
        115                 120
```

<210> SEQ ID NO 175
<211> LENGTH: 121
<212> TYPE: PRT

<213> ORGANISM: Artificial Sequence
<220> FEATURE:
<223> OTHER INFORMATION: Synthetic Construct

<400> SEQUENCE: 175

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Ser Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp His Gly Ser Arg His Phe Trp Ser Tyr Trp Gly Phe Asp
            100                 105                 110

Tyr Trp Gly Gln Gly Thr Leu Val Thr
            115                 120
```